US008889846B2

(12) United States Patent
Sass et al.

(10) Patent No.: US 8,889,846 B2
(45) Date of Patent: Nov. 18, 2014

(54) **HIGH AFFINITY ANTIBODIES THAT NEUTRALIZE *STAPHYLOCOCCUS* ENTEROTOXIN B**

(75) Inventors: Philip M. Sass, Audubon, PA (US); Nicholas C. Nicolaides, Boothwyn, PA (US); Luigi Grasso, Bala Cynwyd, PA (US); Marc Berger, Yardley, PA (US); Tao Sai, Foster City, CA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 13/540,330

(22) Filed: Jul. 2, 2012

(65) Prior Publication Data
US 2013/0183314 A1 Jul. 18, 2013

Related U.S. Application Data

(62) Division of application No. 11/969,097, filed on Jan. 3, 2008, now Pat. No. 8,236,932.

(60) Provisional application No. 60/883,271, filed on Jan. 3, 2007, provisional application No. 60/888,405, filed on Feb. 6, 2007.

(51) Int. Cl.
*C07H 21/04* (2006.01)
*C12P 21/08* (2006.01)
*C07K 16/12* (2006.01)

(52) U.S. Cl.
CPC ......... *C07K 16/1271* (2013.01); *C07K 2317/21* (2013.01); *C07K 2317/73* (2013.01); *C07K 2317/565* (2013.01); *C07K 2317/92* (2013.01); *C07K 2317/567* (2013.01)
USPC .................. 536/23.53; 530/388.15; 530/388.2

(58) Field of Classification Search
None
See application file for complete search history.

(56) References Cited

U.S. PATENT DOCUMENTS

| 6,713,610 | B1 | 3/2004 | Kucherlapati et al. |
| 7,947,290 | B2 | 5/2011 | Nakashima et al. |
| 8,236,932 | B2 | 8/2012 | Sass et al. |
| 2005/0240009 | A1 | 10/2005 | Carr |
| 2008/0138860 | A1 | 6/2008 | Torikai et al. |

FOREIGN PATENT DOCUMENTS

| EP | 1860120 | 11/2007 |
| JP | 2003-517445 A | 5/2003 |
| JP | 2005-535351 A | 11/2005 |
| WO | WO 00/20598 A1 | 4/2000 |
| WO | WO 03/080672 | 10/2003 |
| WO | WO 2006/085518 | 8/2006 |
| WO | WO 2007/141274 | 12/2007 |

OTHER PUBLICATIONS

Drozdowski et al, "Generation and characterization of high affinity human monoclonal antibodies that neutralize staphylococcal enterotoxin B", Journal of Immune Based Therapies an Vaccines, Dec. 2010, 8(9), 9 pages.
Arad et al., "Superantigen antagonist blocks Th1 cytokine gene induction and lethal shock", Journal Leukoc. Biol., Jun. 2001, 69(6), 921-927.
Bavari et al., "Cross-reactive antibodies prevent the lethal effects of *Staphylococcus aureus* superantigens", Journal Infect. Dis., Oct. 1999, 180(4), 1365-1369.
Boles et al., "Generation of protective immunity by inactivated recombinant staphylococcal enterotoxin B vaccine in nonhuman primates and identification of correlates of immunity," (2003) Clin. Immunol. 108:51-9.
Chiang et al., "PCR detection of Staphylococcal enterotoxins (SEs) N, O, P, Q, R, U, and survey of SE types in *Staphylococcus aureus* isolates from food-poisoning cases in Taiwan", Int. Journal Food Microbiol., Jan. 15, 2008, 121(1), 66-73.
"FY2009 Product Creation Meeting, Dramatic Leap Plan 2011", Eisai Co., Ltd., Power Point Presentation, 121 pages, Dec. 18, 2009.
Holbrook et al., "*Staphylococcus aureus* nasal colonization in HIV-seropositive and HIV-seronegative drug users", Journal Acquir. Immune. Defic. Syndr. Hum. Retrovirol., Dec. 1, 1997, 16(4), 301-306.
LeClaire et al., "Human antibodies to bacterial superantigens and their ability to inhibit T-cell activation and lethality", Antimicrob. Agents Chemother., Feb. 2001, 45(2), 460-463.
LeClaire et al., "Protection against bacterial superantigen staphylococcal enterotoxin B by passive vaccination", Infect. Immun., May 2002, 70(5), 2278-2281.
Li et al., "Human antibodies for immunotherapy development generated via a human B cell hybridoma technology", PNAS USA, Mar. 7, 2006, 103(10), 3557-3562.
Lina et al., "Standard nomenclature for the superantigens expressed by *Staphylococcus* ", Journal Infect. Dis., Jun. 15, 2004, 189(12), 2334-2336.
Lowy, FD, "*Staphylococcus aureus* infections", N. Engl. Journal Med., Aug. 20, 1998, 339(8), 520-532.
Mattix et al., "Aerosolized staphylococcal enterotoxin B-induced pulmonary lesions in rhesus monkeys (*Macaca mulatta*)", Toxicol. Pathol. May-Jun. 1995, 23(3), 262-268.
Miller et al., "*Staphylococcus aureus* in the community: colonization versus infection", PLoS. One., Aug. 20, 2009, 4(8), e6708.
Ono et al., "Identification and characterization of two novel staphylococcal enterotoxins, types S and T", Infect. Immun., Nov. 2008, 76(11), 4999-5005.
Pang et al., "Inhibition of staphylococcal enterotoxin B-induced lymphocyte proliferation and tumor necrosis factor alpha secretion by MAb5, an anti-toxic shock syndrome toxin 1 monoclonal antibody", Infect. Immun., Jun. 2000, 68(6), 3261-3268.
Roy et al., "Human leukocyte antigen-DQ8 transgenic mice: a model to examine the toxicity of aerosolized staphylococcal enterotoxin B", Infect. Immun., Apr. 2005, 73(4), 2452-2460.

(Continued)

*Primary Examiner* — Padma V Baskar
(74) *Attorney, Agent, or Firm* — Baker & Hostetler LLP

(57) ABSTRACT

This invention provides antibodies that specifically bind and neutralize *Staphylococcus* enterotoxin B. In addition, nucleic acids encoding such antibodies, and cells that express such antibodies are provided. Also provided are methods for treating diseases mediated by, and for neutralizing *Staphylococcus* enterotoxin B.

17 Claims, 55 Drawing Sheets

(56) References Cited

OTHER PUBLICATIONS

Ulrich RG., 2007. "Staphylococcal Enterotoxin B and Related Toxins", p. 311-322. In: Medical aspects of chemical and biological warfare.
Visvanathan et al., "Inhibition of bacterial superantigens by peptides and antibodies", Infect. Immun., Feb. 2001, 69(2), 875-884.
Wang et al., "A broad-spectrum inhibitory peptide against staphylococcal enterotoxin superantigen SEA, SEB and SEC", Immunol Lett., Dec. 22, 2008, 121(2), 167-172.
Woody et al., "Staphylococcal enterotoxin B mutants (N23K and F44S): biological effects and vaccine potential in a mouse model", Vaccine, Feb. 1997, 15(2), 133-139.
Yang et al., "Neutralization of multiple staphylococcal superantigens by a single-chain protein consisting of affinity-matured, variable domain repeats", Journal Infect. Dis., Aug. 1, 2008, 198(3), 344-348.
Chothia et al., "Canonical structures for the hypervariable regions of immunoglobulins," (1967) J. Mol. Biol. 196:901-17.
Cline, "Perspectives for Gene Therapy: Inserting New Genetic Information into Mammalian Cells by Physical Techniques and Viral Vectors," (1985) Pharmac Ther. 29:69-92.
Darrenberg et al., "Differences in potency of intravenous poiyspecific inmmunoglobulin G against streptococcal and staphylococcal superantigens: implications for therapy of toxic shock syndrome," (2004) Clin. Infect. Dis. 38:836-42.
Foote et al., "Antibody framework residues affecting the conformation of the hypervariable loops," (1992) I. Mol. Biol. 224:487-99.
Gadi et al., "In vivo sensitization of ovarian tumors to chemotherapy by expression of E. coli purine nucleoside phosphorylase in a small fraction of cells," (2000) Gene Ther. 7:1738-1743.
Grunow et al., "Strategies in the development of human monoclonal antibodies," (1990) Dev. Biol, Stand. 71, 3-7.
Harris et al., "Lack of complete correlation between emetic and T-cell-stimulatory activities of staphylococcal enterotoxins," (1993) Infect. Immun. 61:3175-83.
Jardetzky et al.. "Three-dimensional structure of a human class II histocompatibility molecule complexed with superantigen," (1994) Nature 368:711-8.
Jirholt et al., "Exploiting sequence space; shuffling in vivo formed complementarity determining regions into a master framework," (1998) Gene 215:471-6.
Jones et al., "Replacing the complementarity-determining regions in a human antibody with those from a mouse," (1986) Nature 321:522-5.
Kala et al., "Phage displayed antibodies to heat stable alkaline phosphatase: framework region as a determinant of specificity," (2002) J. Biochem. 132:535-41.
Kappler et al., "V beta-specific stimulation of human T cells by staphylococcal toxins," (1989) Science 244:811-3.
Kolb, "Superantigens of gram-positive bacteria: structure-function analyses and their implications for biological activity," (1998) Curr. Opin. Microbiol 1:56-65.
Krakauer, T. et al., "Dexamethasone Attenuates Staphylococcal Enterotoxin B-Induced Hypthermic Response and Protects Mice from Superantigen-Induced Toxic Shock," Antimicrobial Agents and Chemotherapy, Jan. 2006, 50(1), 391-395.
Leder et al., "A mutational analysis of the binding of staphylococcal enterotoxins B and C3 to the T cell receptor beta chain and major histocompatibility complex class II," (1998) J. Exp. Med. 187:823-33.
Li et al., "Three-dimensional structure of the complex between a T cell receptor beta chain and the superantigen staphylococcal enterotoxin B," (1998) Immunity 9 807-16.
Mantis, N.J., "Vaccines against the category B toxins: Staphylococcal enterotoxin B, epsilon toxin and ricin," (2005) Adv. Drug Del. Rev. 57:1424-39.
Morea et al., "Conformations of the third hypervariable region in the VH domain of immunoglobulins," (1998) J. Mol. Biol. 275:269-94.
Niedbla and Stott, "A comparison of three methods for production of human hybridomas secreting autoantibodies," (1998) Hybridoma 17 (3), 299-304.

Nishi et al., "B cell epitope mapping of the bacterial superantigen staphylococcal enterotoxin B: the dominant epitope region recognized by intravenous IgG," (1997) J. Immunol. 158:247-54.
Okayama and Berg, "A cDNA cloning vector that permits expression of cDNA inserts in mammalian cells," (1983) Mol. Cell. Biol. 3:280.
Olson et al., "Molecular docking of superantigens with class II major histocompatibility complex proteins," (1997) J. Mol. Recognit. 10:277-89.
Panka et al., "Variable region framework differences result in decreased or increased affinity of variant anti-digoxin antibodies," (1988) Proc. Natl. Acad. Sci. USA 85:3080-4.
Presta, "Antibody engineering," (1992) Curr. Op. Stract, Biol. 2:593-6.
Rattan et al., "Protein Synthesis: Posttranslational Modifications and Aging," Ann NY Acad Sci (1992) 663:48-62.
Reichmann et al., "Reshaping human antibodies for therapy," (1988) Nature 332:323-9.
Seifter et al., "Analysis for Protein Modifications and Nonprotein Cofactors," Meth Enzymol (1990) 182:626-646.
Seth, A. et al., "Binary and ternary complexes between T-cell receptor, class II MHC and superantigen in vitro," Nature, May 26, 1994, 369(6478), 324-327.
Soderlind et al., "Recombining germline-derived CDR sequences for creating diverse single-framework antibody libraries," (2000) Nature Biotechnology 18:852-6.
Stiles et al., "Mucosal vaccination with recombinantly attenuated staphylococcal enterotoxin B and protection in a murine model," (2001) Infect. Immun. 69:2031-6.
Swaminathan, S. et al., "Crystal structure of staphylococcal enterotoxin B, a superantigen," Nature, Oct. 29, 1992, 359(6398), 801-806.
Tseng et al., "Humoral immunity to aerosolized staphylococcal enterotoxin B (SEB), a superantigen, in monkeys vaccinated with SEB toxoid-containing microspheres," (1995) Infect. Immun. 63:2880-5.
Ulrich et al. (1997) "Medical Aspects of Chemical and Biological Warfare," Sidell, Takafuj, and Franz, Eds., in Textbook of Military Medicine, Brigadier Gen. Russ Zajtchuk, Eds., Published by the Office of the Surgeon General at TMM Publications, Borden Institute, Walter Reed Army Medical Center, Washington, DC, Chapter 31.
Ulrich et al., "Development of engineered vaccines effective against structurally related bacterial superantigens," (1998) Vaccine 16:1857-64.
Matsubara, K. et al., "Development of serum IgM antibodies against superantigens of *Staphylococcus aureus* and *Streptococcus pyogenes* in Kawasaki disease," Clinical and Experimental Immunology, Mar. 2006, 143(3), 427-434, XP002486131.
Takanori Sasaki et al., "Establishment of Highly Specific and Quantitative Immunoassay Systems for Staphylococcal Enterotoxin A, B, and C Using Newly-Developed Monoclonal Antibodies," Micribiol. Immunol., 2005, 49 (7), 589-597, XP002486132.
Cook, E, et al., "Measurement of Staphylococcal Enterotoxin B in Serum and Culture Supernatant with a Capture Enzyme-Linked Immunosorbent Asay," Clinical and Vaccine Immunology, Sep. 2007, 14(9), 1094-1101.
Metzroth et al, "Concomitant loss of confirmation and superantigenic activity of staphylococcal enterotoxin B deletion mutant proteins", Infection and Immunity, Jun. 1993, 61(6), 2445-2452.
Japanese Patent Application No. 2009-544928: Notice of Reason for Refusal dated Mar. 27, 2013, 6 pages.
Alakhov et al, "Identification Of Functionally Active Fragments Of Staphylococcal Enterotoxin B", Fur. J. Biochem., Nov. 1992, 209, 823-828.
Rudikoff et al, "Single Amino Acid Substitution Altering Antigen-Binding Specificity", Proc. Nat. Acad. Sci. USA, Mar. 1982, 79, 1979-1983.
Tamura et al, "Structural Correlates of an Anticarcinoma Antibody: Identification of Specificity-Determining Residues (SDRs) and Development of a Minimally Immunogenic Antibody Variant by Retention of SDRs Only", J. Immunol. Feb. 1, 2000; 164:1432-1441.

```
1           11          21          31          41          51
  esqpdpkpde  lhksskftgl  menmkvlydd  nhvsainvks  idqflyfdli  ysikdtklgn
  esqpdpkpde  lhksskf     m   mkvlydd nhvsainvks  idqf  yfdli ysikdtklg 61          71          81          91          101         111
  ydnvrvefkn  kdladkykdk  yvdvfganyy  yqcyfskktn  dinshqtdkr  ktcmyggvte
  ydnvrvefkn  kdladkykdk  yvdvfgan       qc  fskktn dinshqtdkr ktcmyggvte 121         131         141         151         161         171
  hngnqldkyr  sitvrvfedg  knllsfdvqt  nkkkvtaqel  dyltrhylvk  nkklyefnns
  hngnqldkyr  sitvrvfedg  knllsfdvqt  nkkkvtaqel  dyltrhylvk  nkklyefnns 181         191         201         211         221         231
  pyetgyikfi  enensfwydm  mpapgdkfdq  skylmmyndn  kmvdskdvki  evylttkkk
  pyetgyikfi  enensfwydm  mpapgdkfd   skylmmyndn  kmvdskdvki  evylttkkk
```

SEB
SEB mutein vaccine
IVIG binding epitopes
TCR-binding H-bonds
TCR-binding Van der Waals contacts

F10: Light Chain Nucleotide Sequence: (SEQ ID NO:27)

GACGTTGAGCTGACCCAGTCTCCTTCCACCCTGTCTGCATCTGTAGGAGACAGAGTC
ACCATCACTTGCCGGGCCAGTCAGAGTATTAGTAGCTGGTTGGCCTGGTATCAGC
AGAAACCAGGGAAAGCCCCTAAGCTCCTGATCTATAAGGCGTCTAGTTTAGAAAG
TGGGGTCCCATCAAGGTTCAGCGGCAGTGGATCTGGGACAGAATTCACTCTCACCAT
CAGCAGCCTGCAGCCTGATGATTTTGCAACTTATTACTGCCAACAGTATAATAGTTA
TCCGTGGACGTTCGGCCAAGGGACCAAGGTGGAAATCAAACGAACTGTGGCTGCA
CCATCTGTCTTCATCTTCCCGCCATCTGATGAGCAGTTGAAATCTGGAACTGCCTCTG
TTGTGTGCCTGCTGAATAACTTCTATCCCAGAGAGGCCAAAGTACAGTGGAAGGTGG
ATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAA
ACACAAAGTCTACGCCTGCGAAGTCACCCATCAGGGCCTGAGCTCGCCCGTCACAA
AGAGCTTCAACAGGGGAGAGTGT

Figure 13B

F10 Light Chain Amino Acid Sequence: (SEQ ID NO: 28)

DVELTQSPSTLSASVGDRVTITCRASQSISSWLAWYQQKPGKAPKLLIYKASSLESGVPS
RFSGSGSGTEFTLTISSLQPDDFATYYCQQYNSYPWTFGQGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

Figure 13C

F10: Heavy Chain Segment Including Variable Domain Nucleotide Sequence: (SEQ ID NO: 29)

CAGGTACAGCTGGTGCAGTCTGGGGGAGGCCTGGTCAAGCCTGGGGGGTCCCTGAG
ACTCTCCTGTGCAGCCTCTGGATTCACCTTCAGTAGCTATAGCATGAACTGGGTCC
GCCAGGCTCCAGGGAAGGGGCTGGAGTGGGTCTCATCCATTAGTAGTAGTAGTAG
TTACATATACTACGCAGACTCAGTGAAGGGCCGATTCACCATCTCCAGAGACAAC
GCCAAGAACTCACTGTATCTGCAAATGAACAGCCTGAGAGCCGAGGACACGGCTGT
GTATTACTGTGCGAGAGGGGGGGTGGCTGGTCGAACCGAAATTTACTACTACTA
CTACGGTATGGACGTCTGGGGCCAAGGGACCACGGTCACCGTCTCCTCAGGGAGT
GCATCCGCCCCAACCCTTTTCCCCCTCGTCTCCTGTGAGAATTCCCCGTCGGATACGA
GCAGCGTGGCCGTTGGCTGCCTCGCACAGGACTTCCTTCCCGACTCCATCACTTTCTC
CTGGAAATACAAGAACAACTCTGACATCAGCAGCACCCGGGGCTTCCCATCAGTCC
TGAGAGGGGGCAAGTACGCAGCCACCTCACAGGTGCTGCTGCCTTCCAAGGACGTC
ATGCAGGGCACAGACGAACACGTGGTGTGCAAAGTCCAGCACCCCAACGGCAACAA
AGAAAAGAACGTGCCTCTTCCA

Figure 13D

F10 Heavy Chain Segment Including Variable Domain Amino Acid Sequence: (SEQ ID NO: 30)

QVQLVQSGGGLVKPGGSLRLSCAASGFTFSSYSMNWVRQAPGKGLEWVSSISSSSSYIY
YADSVKGRFTISRDNAKNSLYLQMNSLRAEDTAVYYCARGGVAGRTEIYYYYGMD
VWGQGTTVTVSSGSASAPTLFPLVSCENSPSDTSSVAVGCLAQDFLPDSITFSWKYKNNS
DISSTRGFPSVLRGGKYAATSQVLLPSKDVMQGTDEHVVCKVQHPNGNKEKNVPLP

Figure 13E

100C9 Light Chain Nucleotide Sequence: (SEQ ID NO: 31)

ATGGGATGGAGCTGTATCATCCTCTTCTTGGTAGCAACAGCTACAGGTGTACACAGC
TCCTATGTGCTGACTCAGCCACCCTCGGTGTCGGTGTCCCCAGGACAGACGGCCAGG
ATCACCTGCTCTGGAGATGCATTGCCAAAGCAATATACTTATTGGTACCAGCAGA
AGCCAGGCCAGGCCCCTGTGGTGGTGATCTATAAAGACAGTGAGAGGCCCTCAGG
GATCCCTGAGCGATTCTCTGGCTCCAGCTCAGGGACAACAGTCACGGTGACCATCAG
TGGAGTCCAGGCAGAAGACGAGGCTGACTATTATTGTCAATCAGCAGACAGCAGT
GGTACTTCCCTGGTGTTCGGCGGAGGGACCAAGCTGACCGTCCTAGGTCAGCCCA
AGGCTGCCCCCTCGGTCACTCTGTTCCCGCCCTCCTCTGAGGAGCTTCAAGCCAACA
AGGCCACACTGGTGTGTCTCATAAGTGACTTCTACCCGGGAGCCGTGACAGTGGCCT
GGAAGGCAGATAGCAGCCCCGTCAAGGCGGGAGTGGAGACCACCACACCCTCCAA
ACAAAGCAACAACAAGTACGCGGCCAGCAGCTACCTGAGCCTGACGCCTGAGCAGT
GGAAGTCCCACAAAAGCTACAGCTGCCAGGTCACGCATGAAGGGAGCACCGTGGAG
AAGACAGTGGCCCCTACAGAATCTTCATAG

Figure 13F

100C9 Light Chain Amino Acid Sequence: (SEQ ID NO: 32)

MGWSCIILFLVATATGVHSSYVLTQPPSVSVSPGQTARITCSGDALPKQVTYWYQQKPG
QAPVVVIYKDSERPSGIPERFSGSSSGTTVTVTISGVQAEDEADYYCQSADSSGTSLVFG
GGTKLTVLGQPKAAPSVTLFPPSSEELQANKATLVCLISDFYPGAVTVAWKADSSPVKA
GVETTTPSKQSNNKYAASSYLSLTPEQWKSHKSYSCQVTHEGSTVEKTVAPTESS*

Figure 13G

100C9 Heavy Chain Nucleotide Sequence: (SEQ ID NO: 33)

ATGGGATGGAGCTGTATCATCCTCTTCTTGGTAGCAACAGCTACAGGTGTACACAGC
GAGGTGCAGCTGGTGGAGTCTGGGGGAGGCTTGGTCCAGCCTGGGGGGTCCCTGAG
ACTCTCCTGTTCAGCCTCTGGTTTCACCTTTAGTAGTTATTGGATGAGCTGGGTCC
GCCAGGCTCCAGGGAAGGGGCTGGAGTGGGTCGCCAACATAATACAAGATGGAAG
TGAGAAATACTATGCGGACTCTGTGAAGGGCCGGCTCACCATCTCCAGAGACAA
CGCCAAGAACTCACTATATCTGCAGATGAACAGCCTGAGAGTCGACGACACGGCTG
TGTATTATTGTGCGAGAGGATATGAGGGGTGTAGTGCAACCAGGTGCTACCTGT
ACTACTTTGACTATTGGGGCCCGGGGACCCTGGTCACCGTCTCCTCAGCCTCCACC
AAGGGCCCATCGGTCTTCCCCCTGGCACCCTCCTCCAAGAGCACCTCTGGGGGCACA
GCGGCCCTGGGCTGCCTGGTCAAGGACTACTTCCCCGAACCGGTGACGGTGTCGTGG
AACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAG
ACCTACATCTGCAACGTGAATCACAAGCCCAGCAACACCAAGGTGGACAAGAGAGT
TGAGCCCAAATCTGGTCCCCCATGCCCACCTTGCCCAGCACCTGAACTCCTGGGGGG
ACCGTCAGTCTTCCTGTTCCCCCCAAAACCCAAGGACACCCTCATGATCTCCCGGAC
CCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAG
GAGCAGTACAACAGCACGTACCGTGTGGTCAGGGTCCTCACCGTCCTGCACCAGGA
CTGGCTGAATGGCAAGGAGTACAAGTGCAAGGTCTCCAACAAAGCCCTCCCGGCCC
CCATCGAGAAAACCATCTCCAAAGCCAAAGGGCAGCCCCGAGAACCACAGGTGTAC
ACCCTGCCCCCATCCCGGGAGGAGATGACCAAGAACCAGGTCAGCCTGACCTGCCT
GGTCAAAGGCTTCTATCCCAGCGACATCGCCGTGGAGTGGGAGAGCAATGGGCAGC
CGGAGGACAACTACAAGACCACGCCTCCCGTGCTGGACTCCGACGGCTCCTTCTTCC
TCTATAGCAAGCTCACCGTGGACAAGAGCAGGTGGCAGCAGGGGAACGTCTTCTCA
TGCTCCGTGATGCATGAGGCTCTGCACAACCACTACACGCAGAAGAGCCTCTCCCTG
TCTCTGGGTAAATGA

Figure 13H

100C9 Heavy Chain Amino Acid Sequence: (SEQ ID NO: 34)

MGWSCIILFLVATATGVHSEVQLVESGGGLVQPGGSLRLSCSASGFTFSSYWMSWVRQ
APGKGLEWVANIIQDGSEKYYADSVKGRLTISRDNAKNSLYLQMNSLRVDDTAVYYC
ARGYEGCSATRCYLYYFDYWGPGTLVTVSSASTKGPSVFPLAPSSKSTSGGTAALGCL
VKDYFPEPVTVSWNSGALTSGVHTFPAVLQSSGLYSLSSVVTVPSSSLGTQTYICNVNHK
PSNTKVDKRVEPKSGPPCPPCPAPELLGGPSVFLFPPKPKDTLMISRTPEVTCVVVDVSHE
DPEVKFNWYVDGVEVHNAKTKPREEQYNSTYRVVRVLTVLHQDWLNGKEYKCKVSN
KALPAPIEKTISKAKGQPREPQVYTLPPSREEMTKNQVSLTCLVKGFYPSDIAVEWESNG
QPEDNYKTTPPVLDSDGSFFLYSKLTVDKSRWQQGNVFSCSVMHEALHNHYTQKSLSL
SLGK*

Figure 13I

79G9 Light Chain Nucleotide Sequence: (SEQ ID NO: 35)

ATGGGATGGAGCTGTATCATCCTCTTCTTGGTAGCAACAGCTACAGGTGTACACAGC
GACATTGAGTTGACCCAGTCTCCATCCTTCCTGTCTGCATCTGTCGGAGACAGAGTC
GCCATCACTTGCCGGGCCAGTCAGGGCATTAGCAATTATTTAGCCTGGTATCAGC
AAAAACCAGGGAAAGCCCCTAAGCTCCTGATCTATGCTGCATTCGTTTTGCAAAG
TGGGGTCCCATCAAGGTTCAGCGGCAGTGGATCTGGGACAGAATTCACTCTCACAAT
CAGTAACCTGCAGCCTGAAGATTTTGCAACTTATTACTGTCAACAACTTAATAGTTA
TCCTCGCGCTTTCGGCCCTGGGACCAAAGTGGATATCAAACGAACTGTGGCTGCAC
CATCTGTCTTCATCTTCCCGCCATCTGATGAGCAGTTGAAATCTGGAACTGCCTCTGT
TGTGTGCCTGCTGAATAACTTCTATCCCAGAGAGGCCAAAGTACAGTGGAAGGTGG
ATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAA
ACACAAAGTCTACGCCTGCGAAGTCACCCATCAGGGCCTGAGCTCGCCCGTCACAA
AGAGCTTCAACAGGGGAGAGTGA

Figure 13J

79G9 Light Chain Amino Acid Sequence: (SEQ ID NO: 36)

MGWSCIILFLVATATGVHSDIELTQSPSFLSASVGDRVAITCRASQGISNYLAWYQQKPG
KAPKLLIYAAFVLQSGVPSRFSGSGSGTEFTLTISNLQPEDFATYYCQQLNSYPRAFGPG
TKVDIKRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGE*

Figure 13K

79G9+ Heavy Chain Nucleotide Sequence: (SEQ ID NO: 37)

ATGGGATGGAGCTGTATCATCCTCTTCTTGGTAGCAACAGCTACAGGTGTACACAGC
GAGGTGCAGCTGTTGCAGTCTGGCGCAGGACTGTTGAAGCCTTCGGAGACCCTGTCC
CTCACCTGCGCTGTCTATGGTGGGTCCTTCAGTGGATACTACTGGAGTTGGATCC
GCCAGGCCCCAGGGAAGGGACTGGAGTGGATTGGGGAAATCGATCATAGTGGAAC
CACCAACTACAACCCGTCCCTCAAGAGTCGGGTCACCATATCAGTAGAGACATCC
AAGAACCAGTTCTCCCTGAGGCTGAGCTCTGTGACCGCCGCGGACTCGGCTGTCTAT
TACTGTGCGAGCAGTGGATATTGTTCTCATGGTTTATGCCCCCAAGAGGACTGG
GGCCAGGGAACCCTGGTCACCGTCTCCTCAGCCTCCACCAAGGGCCCATCGGTCTTC
CCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAG
CAGCGTGGTGACCGTGCCCTCCAGCAGCTTGGGCACCCAGACCTACATCTGCAACGT
GAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTG
AATGGCAAGGAGTACAAGTGCAAGGTCTCCAACAAAGCCCTCCCAGCCCCCATCGA
GAAAACCATCTCCAAAGCCAAAGGGCAGCCCCGAGAACCACAGGTGTACACCCTGC
CCCCATCCCGGGATGAGCTGACCAAGAACCAGGTCAGCCTGACCTGCCTGGTCAAA
GGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGG
GTAAATGA

Figure 13L

79G9+Heavy Chain Amino Acid Sequence: (SEQ ID NO: 38)

MGWSCIILFLVATATGVHSEVQLLQSGAGLLKPSETLSLTCAVYGGSFSGYYWSWIRQA
PGKGLEWIGEIDHSGTTNYNPSLKSRVTISVETSKNQFSLRLSSVTAADSAVYYCASSG
YCSHGLCPQEDWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPEN
NYKTTPPVLDSDGSFFLYSKLTVDKSRWQQGNVFSCSVMHEALHNHYTQKSLSLSPGK*

Figure 13M

79G9 Heavy Chain Nucleotide Sequence: (SEQ ID NO: 119)

ATGGGATGGAGCTGTATCATCCTCTTCTTGGTAGCAACAGCTACAGGTGTCCACTCC
GAGGTACAGCTGGAGGAGTCTGGCGCAGGACTGTTGAAGCCTTCGGAGACCCTGTC
CCTCACCTGCGCTGTCTATGGTGGGTCCTTCAGTGGATACTACTGGAGTTGGATC
CGCCAGGCCCCAGGGAAGGGACTGGAGTGGATTGGGGAAATCGATCATAGTGGAA
CCACCAACTACAACCCGTCCCTCAAGAGTCGGGTCACCATATCAGTAGAGACATC
AAGAACCAGTTCTCCCTGAGGCTGAGCTCTGTGACCGCCGCGGACTCGGCTGTCTA
TTACTGTGCGAGCAGTGGATATTGTTCTCATGGTTTATGCCCCAAGAGGACTGG
GGCCAGGGAACCCTGGTCACCGTCTCCTCAGCCTCCACCAAGGGCCCATCGGTCTTC
CCCCTGGCACCCTCCTCCAAGAGCACCTCTGGGGGCACAGCGGCCCTGGGCTGCCTG
GTCAAGGACTACTTCCCCGAACCGGTGACGGTGTCGTGGAACTCAGGCGCCCTGAC
CAGCGGCGTGCACACCTTCCCGGCTGTCCTACAGTCCTCAGGACTCTACTCCCTCAG
CAGCGTGGTGACCGTGCCCTCCAGCAGCTTGGGCACCCAGACCTACATCTGCAACGT
GAATCACAAGCCCAGCAACACCAAGGTGGACAAGAGAGTTGAGCCCAAATCTTGTG
ACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTG
GTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTG
AATGGCAAGGAGTACAAGTGCAAGGTCTCCAACAAAGCCGTCCCAGCCCCCATCGA
GAAAACCATCTCCAAAGCCAAAGGGCAGCCCCGAGAACCACAGGTGTACACCCTGC
CCCCATCCCGGGAGGAGATGACCAAGAACCAGGTCAGCCTGACCTGCCTGGTCAAA
GGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTATAG
CAAGCTCACCGTGGACAAGAGCAGGTGGCAGCAGGGGAACGTCTTCTCATGCTCCG
TGATGCATGAGGCTCTGCACAACCACTACACGCAGAAGAGCCTCTCCCTGTCTCCGG
GTAAATGA

Figure 13N

79G9 Heavy Chain Amino Acid Sequence: (SEQ ID NO: 126)

MGWSCIILFLVATATGVHSEVQLEESGAGLLKPSETLSLTCAVYGGSFSGYYWSWIRQA
PGKGLEWIGEIDHSGTTNYNPSLKSRVTISVETSKNQFSLRLSSVTAADSAVYYCASSG
YCSHGLCPQEDWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDK
RVEPKSCDKTHTCPPCPAPELLGGPSVFLFPPKPKDTLMISRTPEVTCVVVDVSHEDPEV
KFNWYVDGVEVHNAKTKPREEQYNSTYRVVSVLTVLHQDWLNGKEYKCKVSNKAVP
APIEKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSPGK*

Figure 13O

154G12 Light Chain Nucleotide Sequence (SEQ ID NO: 133)

ATGGGATGGAGCTGTATCATCCTCTTCTTGGTAGCAACAGCTACAGGTGTGCACTCC
CTATGTGCTGACTCAGCCACCCTCAGTGTCAGTGGCCCCAGGAGAGACGGCCAGCA
TTCCTGTGGGGGAAACAACATTGGAACTAAGAGTGTCCACTGGTACCAGCAGAG
GCCAGGCCAGGCCCCTCTACTGGTCCTCTATCATGACACCAGGCGGCCCTCAAGG
ATTCCTGAGCGATTCTCTGGCTCCAACTCTGGAAACACGGCCACCCTGACCATCAGC
AGGGTCGAAGCCGGGGATGAGGCCGACTATTACTGTCAGGTGTGGGATAGTCGAA
GGGTGTTCGGCGGAGGGACCAAGCTGACCGTCCTAGGTCAGCCCAAGGCGGCCCCC
TCGGTCACTCTGTTCCCGCCCTCCTCTGAGGAGCTTCAAGCCAACAAGGCCACACTG
GTGTGTCTCATAAGTGACTTCTACCCGGGAGCCGTGACAGTGGCCTGGAAGGCAGAT
AGCAGCCCCGTCAAGGCGGGAGTGGAGACCACCACACCCTCCAAACAAAGCAACA
ACAAGTACGCGGCCAGCAGCTACCTGAGCCTGACGCCTGAGCAGTGGAAGTCCCAC
AAAAGCTACAGCTGCCAGGTCACGCATGAAGGGAGCACCGTGGAGAAGACAGTGG
CCCCTACAGAATCTTCATGA

Figure 13P

154G12 Light Chain Amino Acid Sequence (SEQ ID NO: 134)

MGWSCIILFLVATATGVHSLCADSATLSVSGPRRDGQHSCGGNNIGTKSVHWYQQRPG
QAPLLVLYHDTRRPSRIPERFSGSNSGNTATLTISRVEAGDEADYYCQVWDSRRVFGG
GTKLTVLGQPKAAPSVTLFPPSSEELQANKATLVCLISDFYPGAVTVAWKADSSPVKAG
VETTTPSKQSNNKYAASSYLSLTPEQWKSHKSYSCQVTHEGSTVEKTVAPTESS*

Figure 13Q

154G12 Heavy Chain Nucleotide Sequence (SEQ ID NO: 141)

ATGGGATGGAGCTGTATCATCCTCTTCTTGGTAGCAACAGCTACAGGTGTCCACTCC
CAGGTGCAGCTGTTGGAGTCAGGGGGAGGCTTGGTCCAGCCGGGGGGGTCCCTGAG
ACTCTCCTGTGCAGCCTCTGGATTCAGCTTTGGCGACTATTGGATGAGTTGGGTC
CGCCAGGCTCCAGGGAAGGGCCTGGAGTGGGTGGCCGACATAAAGCCAGATGG
CAGTGACAAAGACTATGTGGACTCTGTGAAGGGCCGATTCACCATCTCCAGAGA
CAACGCCAAGAACTCACTGTATCTGCAAATGAGCAGCCTGCGAGGCGAAGACACGG
CTGTCTATTATTGTGCGAGAGACTATGTCGTCGTCGCACCATCTCAACCCCCAAA
CATTCACCCTGAATACTTCCAGAACTGGGGCCAGGGCACCCTGGTCATCGTCTCCT
CAGCCTCCACCAAGGGCCCATCGGTCTTCCCCCTGGCACCCTCCTCCAAGAGCACCT
CTGGGGGCACAGCGGCCCTGGGCTGCCTGGTCAAGGACTACTTCCCCGAACCGGTG
ACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGC
TTGGGCACCCAGACCTACATCTGCAACGTGAATCACAAGCCCAGCAACACCAAGGT
GGACAAGAGAGTGAGCTGTGACAAAACTCACACATGCCCACCGTGCCCAGCACCTG
AACTCCTGGGGGGACCGTCAGTCTTCCTCTTCCCCCCAAAACCCAAGGACACCCTCA
TGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGAC
AAAGCCGCGGGAGGAGCAGTACAACAGCACGTACCGTGTGGTCAGCGTCCTCACCG
TCCTGCACCAGGACTGGCTGAATGGCAAGGAGTACAAGTGCAAGGTCTCCAACAAA
GCCCTCCCAGCCCCCATCGAGAAAACCATCTCCAAAGCCAAAGGGCAGCCCCGAGA
ACCACAGGTGTACACCCTGCCCCCATCCCGGGAGGAGATGACCAAGAACCAGGTCA
GCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGA
CGGCTCCTTCTTCCTCTATAGCAAGCTCACCGTGGACAAGAGCAGGTGGCAGCAGG
GGAACGTCTTCTCATGCTCCGTGATGCATGAGGCTCTGCACAACCACTACACGCAGA
AGAGCCTCTCCCTGTCTCCGGGTAAATGA

Figure 13R

154G12 Heavy Chain Amino Acid Sequence (SEQ ID NO: 142)

MGWSCIILFLVATATGVHSQVQLLESGGGLVQPGGSLRLSCAASGFSFGDYWMSWVR
QAPGKGLEWVADIKPDGSDKDYVDSVKGRFTISRDNAKNSLYLQMSSLRGEDTAVYY
CARDYVVAPSQPPNIHPEYFQNWGQGTLVIVSSASTKGPSVFPLAPSSKSTSGGTAAL
GCLVKDYFPEPVTVSWNSGALTSGVHTFPAVLQSSGLYSLSSVVTVPSSSLGTQTYICNV
NHKPSNTKVDKRVSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKC
KVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQK
SLSLSPGK*

Figure 14A

F10 Light Chain Nucleotide Sequences:

FWR1:
GACGTTGAGCTGACCCAGTCTCCTTCCACCCTGTCTGCATCTGTAGGAGACAGAGTC
ACCATCACTTGC (SEQ ID NO:47)

FWR2:
TGGTATCAGCAGAAACCAGGGAAAGCCCCTAAGCTCCTGATCTAT (SEQ ID NO:48)

FWR3:
GGGGTCCCATCAAGGTTCAGCGGCAGTGGATCTGGGACAGAATTCACTCTCACCATC
AGCAGCCTGCAGCCTGATGATTTTGCAACTTATTACTGCCAACAG (SEQ ID NO:49)

CDR1:
CGGGCCAGTCAGAGTATTAGTAGCTGGTTGGCC (SEQ ID NO:50)

CDR2:
AAGGCGTCTAGTTTAGAAAGT (SEQ ID NO:51)

CDR3:
TATAATAGTTATCCGTGGACG (SEQ ID NO:52)

Figure 14B

F10 Light Chain Amino Acid Sequences:

FWR1:
DVELTQSPSTLSASVGDRVTITC (SEQ ID NO:53)

FWR2:
WYQQKPGKAPKLLIY (SEQ ID NO:54)

FWR3:
GVPSRFSGSGSGTEFTLTISSLQPDDFATYYCQQ (SEQ ID NO:55)

CDR1:
RASQSISSWLA (SEQ ID NO:56)

CDR2:
KASSLES (SEQ ID NO:57)

CDR3:
YNSYPWT (SEQ ID NO:58)

Figure 14C

F10 Heavy Chain Nucleotide Sequences

FWR1:
CAGGTACAGCTGGTGCAGTCTGGGGGAGGCCTGGTCAAGCCTGGGGGGTCCCTGAG
ACTCTCCTGTGCAGCCTCTGGA (SEQ ID NO:59)

FWR2:
TGGGTCCGCCAGGCTCCAGGGAAGGGGCTGGAGTGGGTCTCA (SEQ ID NO:60)

FWR3:
CGATTCACCATCTCCAGAGACAACGCCAAGAACTCACTGTATCTGCAAATGAACAG
CCTGAGAGCCGAGGACACGGCTGTGTATTACTGTGCGAGA (SEQ ID NO:61)

CDR1:
TTCACCTTCAGTAGCTATAGCATGAAC (SEQ ID NO:62)

CDR2:
TCCATTAGTAGTAGTAGTAGTTACATATACTACGCAGACTCAGTGAAGGGC (SEQ ID NO:63)

CDR3:
GGGGGGGTGGCTGGTCGAACCGAAATTTACTACTACTACGGTATGGACGTC (SEQ ID NO:64)

Figure 14D

F10 Heavy Chain Amino Acid Sequences:

FWR1:
QVQLVQSGGGLVKPGGSLRLSCAASG (SEQ ID NO:65)

FWR2:
WVRQAPGKGLEWVS (SEQ ID NO:66)

FWR3:
RFTISRDNAKNSLYLQMNSLRAEDTAVYYCAR (SEQ ID NO:67)

CDR1:
FTFSSYSMN (SEQ ID NO:68)

CDR2:
SISSSSSYIYYADSVKG (SEQ ID NO:69)

CDR3:
GGVAGRTEIYYYYYGMDV (SEQ ID NO:70)

Figure 14E

100C9 Light Chain Nucleotide Sequences:

FWR1:
TCCTATGTGCTGACTCAGCCACCCTCGGTGTCGGTGTCCCCAGGACAGACGGCCAGG
ATCACCTGC (SEQ ID NO:71)

FWR2:
TGGTACCAGCAGAAGCCAGGCCAGGCCCTGTGGTGGTGATCTAT (SEQ ID NO:72)

FWR3:
GGGATCCCTGAGCGATTCTCTGGCTCCAGCTCAGGGACAACAGTCACGGTGACCATC
AGTGGAGTCCAGGCAGAAGACGAGGCTGACTATTATTGT (SEQ ID NO:73)

CDR1:
TCTGGAGATGCATTGCCAAAGCAATATACTTAT (SEQ ID NO:74)

CDR2:
AAAGACAGTGAGAGGCCCTCA (SEQ ID NO:75)

CDR3:
CAATCAGCAGACAGCAGTGGTACTTCCCTGGTG (SEQ ID NO:76)

Figure 14F

100C9 Light Chain Amino Acid Sequence

FWR1:
SYVLTQPPSVSVSPGQTARITC (SEQ ID NO:77)

FWR2:
WYQQKPGQAPVVVIY (SEQ ID NO:78)

FWR3:
GIPERFSGSSSGTTVTVTISGVQAEDEADYYC (SEQ ID NO:79)

CDR1:
SGDALPKQYTY (SEQ ID NO:80)

CDR2:
KDSERPS (SEQ ID NO:81)

CDR3:
QSADSSGTSLV (SEQ ID NO:82)

Figure 14G

100C9 Heavy Chain Nucleotide Sequences:

FWR1:
GAGGTGCAGCTGGTGGAGTCTGGGGGAGGCTTGGTCCAGCCTGGGGGGTCCCTGAG
ACTCTCCTGTTCAGCCTCT (SEQ ID NO:83)

FWR2:
TGGGTCCGCCAGGCTCCAGGGAAGGGGCTGGAGTGGGTCGCC (SEQ ID NO:84)

FWR3:
CGGCTCACCATCTCCAGAGACAACGCCAAGAACTCACTATATCTGCAGATGAACAG
CCTGAGAGTCGACGACACGGCTGTGTATTATTGTGCGAGA (SEQ ID NO:85)

CDR1:
GGTTTCACCTTTAGTAGTTATTGGATGAGC (SEQ ID NO:86)

CDR2:
AACATAATACAAGATGGAAGTGAGAAATACTATGCGGACTCTGTGAAGGGC (SEQ
ID NO:87)

CDR3:
GGATATGAGGGGTGTAGTGCAACCAGGTGCTACCTGTACTACTTTGACTAT (SEQ ID
NO:88)

Figure 14H

100C9 Heavy Chain Amino Acid Sequences:

FWR1:
EVQLVESGGGLVQPGGSLRLSCSAS (SEQ ID NO:89)

FWR2:
WVRQAPGKGLEWVA (SEQ ID NO:90)

FWR3:
RLTISRDNAKNSLYLQMNSLRVDDTAVYYCAR (SEQ ID NO:91)

CDR1:
GFTFSSYWMS (SEQ ID NO:92)

CDR2:
NIIQDGSEKYYADSVKG (SEQ ID NO:93)

CDR3:
GYEGCSATRCYLYYFDY (SEQ ID NO:94)

Figure 14I

79G9 Light Chain Nucleotide Sequences:

FWR1:
GACATTGAGTTGACCCAGTCTCCATCCTTCCTGTCTGCATCTGTCGGAGACAGAGTC
GCCATCACTTGC (SEQ ID NO:95)

FWR2:
TGGTATCAGCAAAAACCAGGGAAAGCCCCTAAGCTCCTGATCTAT (SEQ ID NO:96)

FWR3:
GGGGTCCCATCAAGGTTCAGCGGCAGTGGATCTGGGACAGAATTCACTCTCACAATC
AGTAACCTGCAGCCTGAAGATTTTGCAACTTATTACTGT (SEQ ID NO:97)

CDR1:
CGGGCCAGTCAGGGCATTAGCAATTATTTAGCC (SEQ ID NO:98)

CDR2:
GCTGCATTCGTTTTGCAAAGT (SEQ ID NO:99)

CDR3:
CAACAACTTAATAGTTATCCTCGCGCT (SEQ ID NO:100)

Figure 14J

79G9 Light Chain Amino Acid Sequences:

FWR1:
DIELTQSPSFLSASVGDRVAITC (SEQ ID NO:101)

FWR2:
WYQQKPGKAPKLLIY (SEQ ID NO:102)

FWR3:
GVPSRFSGSGSGTEFTLTISNLQPEDFATYYC (SEQ ID NO:103)

CDR1:
RASQGISNYLA (SEQ ID NO:104)

CDR2:
AAFVLQS (SEQ ID NO:105)

CDR3:
QQLNSYPRA (SEQ ID NO:106)

Figure 14K

79G9+ Heavy Chain Nucleotide Sequences:

FWR1:
GAGGTGCAGCTGTTGCAGTCTGGCGCAGGACTGTTGAAGCCTTCGGAGACCCTGTCC
CTCACCTGCGCTGTCTAT (SEQ ID NO:107)

FWR2:
TGGATCCGCCAGGCCCCAGGGAAGGGACTGGAGTGGATTGGG (SEQ ID NO:108)

FWR3:
CGGGTCACCATATCAGTAGAGACATCCAAGAACCAGTTCTCCCTGAGGCTGAGCTCT
GTGACCGCCGCGGACTCGGCTGTCTATTACTGTGCGAGC (SEQ ID NO:109)

CDR1:
GGTGGGTCCTTCAGTGGATACTACTGGAGT (SEQ ID NO:110)

CDR2:
GAAATCGATCATAGTGGAACCACCAACTACAACCCGTCCCTCAAGAGT (SEQ ID NO:111)

CDR3:
AGTGGATATTGTTCTCATGGTTTATGCCCCCAAGAGGAC (SEQ ID NO:112)

Figure 14L

79G9+ Heavy Chain Amino Acid Sequences:

FWR1:
EVQLLQSGAGLLKPSETLSLTCAVY (SEQ ID NO:113)

FWR2:
WIRQAPGKGLEWIG (SEQ ID NO:114)

FWR3:
RVTISVETSKNQFSLRLSSVTAADSAVYYCAS (SEQ ID NO:115)

CDR1:
GGSFSGYYWS (SEQ ID NO:116)

CDR2:
EIDHSGTTNYNPSLKS (SEQ ID NO:117)

CDR3:
SGYCSHGLCPQED (SEQ ID NO:118)

Figure 14M

79G9 Heavy Chain Nucleotide Sequences:

FWR1: (SEQ ID NO: 120)
GAGGTACAGCTGGAGGAGTCTGGCGCAGGACTGTTGAAGCCTTCGGAGACCCTGTCCCTCACCTGCGCTGTCTAT

FWR2: (SEQ ID NO: 121)
TGGATCCGCCAGGCCCCAGGGAAGGGACTGGAGTGGATTGGG

FWR3: (SEQ ID NO: 122)
CGGGTCACCATATCAGTAGAGACATCCAAGAACCAGTTCTCCCTGAGGCTGAGCTCTGTGACCGCCGCGGACTCGGCTGTCTATTACTGTGCGAGC

CDR1: (SEQ ID NO: 123)
GGTGGGTCCTTCAGTGGATACTACTGGAGT

CDR2: (SEQ ID NO: 124)
GAAATCGATCATAGTGGAACCACCAACTACAACCCGTCCCTCAAGAGT

CDR3: (SEQ ID NO: 125)
AGTGGATATTGTTCTCATGGTTTATGCCCCAAGAGGAC

Figure 14N

79G9 Heavy Chain Amino Acid Sequences:

FWR1: (SEQ ID NO: 127)
EVQLEESGAGLLKPSETLSLTCAVY

FWR2: (SEQ ID NO: 128)
WIRQAPGKGLEWIG

FWR3: (SEQ ID NO: 129)
RVTISVETSKNQFSLRLSSVTAADSAVYYCAS

CDR1: (SEQ ID NO: 130)
GGSFSGYYWS

CDR2: (SEQ ID NO: 131)
EIDHSGTTNYNPSLKS

CDR3: (SEQ ID NO: 132)
SGYCSHGLCPQED

Figure 14O

154G12 Light Chain Nucleotide Sequences

FWR1: (SEQ ID NO: 258)
CTATGTGCTGACTCAGCCACCCTCAGTGTCAGTGGCCCCAGGAGAGACGGCCAGCA
TTCCTGT

CRD1: (SEQ ID NO: 259)
GGGGGAAACAACATTGGAACTAAGAGTGTCCAC

FWR2: (SEQ ID NO: 260)
TGGTACCAGCAGAGGCCAGGCCAGGCCCCTCTACTGGTCCTCTAT

CDR2: (SEQ ID NO: 261)
CATGACACCAGGCGGCCCTCA

FWR3: (SEQ ID NO: 262)
TCAAGGATTCCTGAGCGATTCTCTGGCTCCAACTCTGGAAACACGGCCACCCTGACC
ATCAGCAGGGTCGAAGCCGGGGATGAGGCCGACTATTACTGT

CDR3: (SEQ ID NO: 263)
CAGGTGTGGGATAGTCGAAGGGTG

Figure 14P

154G12 Light Chain Amino Acid Sequences

FWR1:
LCADSATLSVSGPRRDGQHSC (SEQ ID NO: 135)

CDR1:
GGNNIGTKSVH (SEQ ID NO: 136)

FWR2:
WYQQRPGQAPLLVLY (SEQ ID NO: 137)

CDR2:
HDTRRPS (SEQ ID NO: 138)

FWR3:
RIPERFSGSNSGNTATLTISRVEAGDEADYYC (SEQ ID NO: 139)

CDR3:
QVWDSRRV (SEQ ID NO: 140)

Figure 14Q

154G12 Heavy Chain Nucleotide Sequences

FWR1: (SEQ ID NO: 252)
CAGGTGCAGCTGTTGGAGTCAGGGGGAGGCTTGGTCCAGCCGGGGGGGTCCCTGAG
ACTCTCCTGTGCAGCCTCT

CDR1: (SEQ ID NO: 253)
GGATTCAGCTTTGGCGACTATTGGATGAGT

FWR2: (SEQ ID NO: 254)
TGGGTCCGCCAGGCTCCA

CDR2: (SEQ ID NO: 255)
GGGAAGGGCCTGGAGTGGGTGGCCGACATAAAGCCAGATGGCAGTGACAAAGACT
ATGTGGACTCTGTGAAGGGC

FWR3: (SEQ ID NO: 256)
CGATTCACCATCTCCAGAGACAACGCCAAGAACTCACTGTATCTGCAAATGAGCAG
CCTGCGAGGCGAAGACACGGCTGTCTATTATTGTGCGAGA

CDR3: (SEQ ID NO: 257)
GACTATGTCGTCGTCGCACCATCTCAACCCCCAAACATTCACCCTGAATACTTCCAG
AAC

Figure 14R

<u>154G12 Heavy Chain Amino Acid Sequences</u>

FWR1:
QVQLLESGGGLVQPGGSLRLSCAAS (SEQ ID NO: 143)

CDR1:
GFSFGDYWMS (SEQ ID NO: 144)

FWR2:
WVRQAPGKGLEWVA (SEQ ID NO: 145)

CDR2:
DIKPDGSDKDYVDSVKG (SEQ ID NO: 146)

FWR3:
RFTISRDNAKNSLYLQMSSLRGEDTAVYYCAR (SEQ ID NO: 147)

CDR3:
DYVVVAPSQPPNIHPEYFQN (SEQ ID NO: 148)

Figure 15A

100C9 Codon Optimized Light Chain Nucleotide Sequence (SEQ ID NO: 149)

ATGGGCTGGTCCTGCATCATCCTGTTTCTGGTGGCCACCGCCACCGGCGTGCACTCC
TCCTACGTGCTGACCCAGCCTCCTTCCGTGTCCGTGTCCCCTGGCCAGACCGCCCGG
ATCACCTGCTCCGGCGACGCCCTGCCTAAGCAGTACACCTACTGGTATCAGCAGA
AGCCCGGCCAGGCCCCTGTGGTGGTGATCTACAAGGACTCCGAGCGGCCTTCCGG
CATCCCTGAGCGGTTCTCCGGCTCCTCCTCCGGCACCACCGTGACCGTGACCATCTC
CGGCGTGCAGGCCGAGGACGAGGCCGACTACTACTGCCAGTCCGCCGACTCCAGC
GGCACCTCCCTGGTGTTTGGCGGCGGAACAAAGCTGACCGTGCTGGGCCAGCCTA
AGGCCGCTCCCTCCGTGACCCTGTTCCCTCCTTCCTCCGAGGAACTGCAGGCCAACA
AGGCCACCCTGGTGTGCCTGATCTCCGACTTCTACCCTGGCGCTGTGACCGTGGCCT
GGAAGGCTGACTCCTCCCCTGTGAAGGCCGGCGTGGAGACAACCACCCCTTCCAAG
CAGTCCAACAACAAGTACGCCGCCTCCTCCTACCTGTCCCTGACCCCTGAGCAGTGG
AAGTCCCACAAGTCCTACAGCTGCCAGGTGACCCACGAGGGCTCCACCGTGGAAAA
GACCGTGGCCCCTACCGAGTCCTCCTGA

Figure 15B

100C9 Codon Optimized Heavy Chain Nucleotide Sequence (SEQ ID NO: 163)

ATGGGCTGGTCCTGCATCATCCTGTTTCTGGTGGCCACCGCCACCGGCGTGCACTCC
GAGGTGCAGCTGGTCGAGTCTGGCGGCGGACTGGTGCAGCCTGGCGGCTCCCTGCG
GCTGTCCTGCTCCGCCTCCGGCTTCACCTTCTCCTCCTACTGGATGTCCTGGGTGC
GGCAGGCTCCTGGCAAGGGCCTGGAGTGGGTGGCCAACATCATCCAGGACGGCTC
CGAGAAGTACTACGCCGACTCCGTGAAGGGCCGGCTGACCATCTCCCGGGACAA
CGCCAAGAACTCCCTGTACCTGCAGATGAACTCCCTGCGGGTGGACGACACCGCG
TGTACTACTGCGCCAGGGGCTACGAGGGCTGCTCCGCCACCCGGTGCTACCTGT
ACTACTTCGACTACTGGGGCCCTGGCACCCTGGTGACCGTGTCCTCCGCCTCCACC
AAGGGCCCTTCCGTGTTCCCTCTGGCCCCTTCCTCCAAGTCCACCTCCGGCGGCACC
GCCGCTCTGGGCTGCCTGGTGAAGGACTACTTCCCTGAGCCTGTGACCGTGAGCTGG
AACTCTGGCGCCCTGACCAGCGGCGTGCACACCTTCCCTGCCGTGCTGCAGTCCTCC
GGCCTGTACTCCCTGTCCTCCGTGGTGACAGTGCCTTCCTCCTCCCTGGGCACCCAG
ACCTACATCTGCAACGTGAACCACAAGCCTTCCAACACCAAGGTGGACAAGCGGGT
GGAGCCTAAGTCCGGCCCTCCTTGCCCTCCCTGCCCTGCCCCTGAGCTGCTGGGCGG
ACCCTCCGTGTTCCTGTTCCCTCCTAAGCCTAAGGACACCCTGATGATCTCCCGGAC
CCCTGAGGTGACCTGCGTGGTGGTGGACGTGTCCCACGAGGATCCTGAGGTGAAGTT
CAATTGGTACGTGGACGGCGTGGAGGTGCACAACGCTAAGACCAAGCCTCGGGAGG
AACAGTACAACTCCACCTACCGGGTGGTGCGGGTGCTGACCGTGCTGCACCAGGAC
TGGCTGAACGGCAAGGAATACAAGTGCAAGGTCTCCAACAAGGCTCTGCCTGCCCC
CATCGAAAAGACCATCTCCAAGGCCAAGGGCCAGCCTCGCGAGCCTCAGGTGTACA
CCCTGCCCCCCAGCCGGGAGGAAATGACCAAGAACCAGGTGTCCCTGACCTGTCTG
GTGAAGGGCTTCTACCCTTCCGATATCGCCGTGGAGTGGGAGTCCAACGGCCAGCCT
GAGGACAACTACAAGACCACCCCTCCTGTGCTGGACTCCGACGGCTCCTTCTTCCTG
TACTCCAAGCTGACCGTGGACAAGTCCCGGTGGCAGCAGGGCAACGTGTTCTCCTGC
TCCGTGATGCACGAGGCCCTGCACAACCACTACACCCAGAAGTCCCTGTCCCTGTCT
CTGGGCAAGTGA

Figure 15C

79G9 Codon Optimized Light Chain Nucleotide Sequence (SEQ ID NO: 177)

ATGGGCTGGTCCTGCATCATCCTGTTTCTGGTGGCCACCGCCACCGGCGTGCACTCC
GACATCGAGCTGACCCAGTCCCCCTCCTTCCTGTCCGCCTCCGTGGGCGACCGGGTG
GCCATCACCTGCCGGGCCTCCCAGGGCATCTCCAACTACCTGGCCTGGTATCAGC
AGAAGCCTGGCAAGGCCCCTAAGCTGCTGATCTACGCCGCCTTCGTGCTGCAGTC
CGGCGTGCCTTCCCGGTTCTCCGGCTCCGGCAGCGGCACCGAGTTCACCCTGACCAT
CTCCAACCTGCAGCCTGAGGACTTCGCCACCTACTACTGCCAGCAGCTGAACTCCT
ACCCCTCGGGCCTTCGGCCCTGGCACCAAGGTGGACATCAAGCGGACCGTGGCCGCT
CCTTCCGTGTTCATCTTCCCTCCCTCCGACGAGCAGCTGAAGTCCGGCACCGCCAGC
GTGGTGTGCCTGCTGAACAACTTCTACCCCCGGGAGGCCAAGGTGCAGTGGAAGGT
GGACAACGCCCTGCAGAGCGGCAACTCCCAGGAATCCGTCACCGAGCAGGACTCCA
AGGACAGCACCTACTCCCTGTCCTCCACCCTGACCCTGTCCAAGGCCGACTACGAGA
AGCACAAGGTGTACGCCTGCGAGGTGACCCACCAGGGCCTGTCCAGCCCTGTGACC
AAGTCCTTCAACCGGGGCGAGTGA

Figure 15D

79G9 Codon Optimized Heavy Chain Nucleotide Sequence (SEQ ID NO: 191)

ATGGGCTGGTCCTGCATCATCCTGTTTCTGGTGGCCACCGCCACCGGCGTGCACTCC
GAGGTGCAGCTGGAGGAATCCGGCGCTGGCCTGCTGAAGCCTTCCGAGACACTGTC
CCTGACCTGCGCCGTGTACGGCGGCTCCTTCTCCGGCTACTACTGGTCCTGGATC
CGGCAGGCTCCTGGCAAGGGCCTGGAGTGGATCGGCGAGATCGACCACTCCGGCA
CCACCAACTACAACCCTTCCCTGAAGTCCCGGGTGACCATCTCCGTGGAGACATC
CAAGAACCAGTTCTCCCTGCGGCTGTCCTCCGTGACCGCCGCTGACTCCGCCGTGTA
CTACTGCGCCTCCAGCGGCTACTGCTCCCACGGCCTGTGCCCTCAGGAAGATTG
GGGCCAGGGCACCCTGGTGACCGTGTCCTCCGCCTCCACCAAGGGCCCTTCCGTGTT
CCCTCTGGCCCCTTCCTCCAAGTCCACCTCCGGCGGCACCGCCGCTCTGGGCTGCCT
GGTGAAGGACTACTTCCCTGAGCCTGTGACCGTGAGCTGGAACTCTGGCGCTCTGAC
CAGCGGCGTGCACACCTTCCCTGCCGTGCTGCAGTCCTCCGGCCTGTACTCCCTGTC
CAGCGTGGTGACAGTGCCTTCCTCCTCCCTGGGCACCCAGACCTACATCTGCAACGT
GAACCACAAGCCTTCCAACACCAAGGTGGACAAGCGGGTGGAGCCTAAGTCCTGCG
ACAAGACCCACACCTGCCCTCCCTGCCCTGCCCCTGAGCTGCTGGGCGGACCCTCCG
TGTTCCTGTTCCCTCCTAAGCCTAAGGACACCCTGATGATCTCCCGGACCCCTGAGG
TGACCTGCGTGGTGGTGGACGTGTCCCACGAGGATCCTGAGGTGAAGTTCAATTGGT
ACGTGGACGGCGTGGAGGTGCACAACGCCAAGACCAAGCCTCGGGAGGAACAGTA
CAACTCCACCTACCGGGTGGTGTCCGTGCTGACCGTGCTGCACCAGGACTGGCTGAA
CGGCAAGGAATACAAGTGCAAGGTCTCCAACAAGGCCGTGCCTGCCCCTATCGAAA
AGACCATCTCCAAGGCCAAGGGCCAGCCTCGCGAGCCTCAGGTGTACACCCTGCCT
CCTAGCCGGGAGGAAATGACCAAGAATCAGGTGTCCCTGACATGTCTGGTGAAGGG
CTTCTACCCTTCCGATATCGCCGTGGAGTGGGAGTCCAACGGCCAGCCTGAGAACAA
CTACAAGACCACCCCTCCTGTGCTGGACTCCGACGGCAGCTTCTTCCTGTACTCCAA
GCTGACCGTGGACAAGTCCCGGTGGCAGCAGGGCAACGTGTTCTCCTGCTCCGTGAT
GCACGAGGCCCTGCACAACCACTACACCCAGAAGTCCCTGTCCCTGTCTCCTGGCAA
GTGA

Figure 15E

154G12 Codon Optimized Light Chain Nucleotide Sequence (SEQ ID NO: 205)

ATGGGCTGGTCCTGCATCATCCTGTTTCTGGTGGCCACCGCCACCGGCGTGCACTCC
CTGTGCGCCGACTCCGCCACCCTGTCCGTGTCCGGCCCTCGGAGGGACGGCCAGCAC
TCCTGCGGCGGCAACAACATCGGCACCAAGTCCGTGCACTGGTATCAGCAGCGG
CCTGGACAGGCCCCTCTGCTGGTGCTGTACCACGACACCAGGCGGCCTTCCCGGA
TCCCTGAGCGGTTCTCCGGCTCCAACTCCGGCAACACCGCTACCCTGACCATCTCCC
GGGTGGAGGCCGGCGACGAGGCCGACTACTACTGCCAGGTGTGGGACTCCAGGC
GGGTGTTCGGCGGAGGAACAAAGCTGACCGTGCTGGGCCAGCCTAAGGCCGCTCCT
TCCGTGACCCTGTTCCCTCCTTCCTCCGAGGAACTGCAGGCCAACAAGGCCACCCTG
GTGTGCCTGATCTCCGACTTCTACCCTGGCGCCGTGACCGTGGCTTGGAAGGCCGAC
TCCTCCCCTGTGAAGGCTGGCGTGGAGACAACCACCCCTTCCAAGCAGTCCAACAAC
AAGTACGCCGCCTCCTCCTACCTGTCCCTGACCCCTGAGCAGTGGAAGTCCCACAAG
TCCTACAGCTGCCAGGTGACCCACGAGGGCTCCACCGTGGAAAAGACCGTGGCCCC
TACCGAGTCCTCCTGA

Figure 15F

154G12 Codon Optimized Heavy Chain Nucleotide Sequence (SEQ ID NO: 219)

ATGGGCTGGTCCTGCATCATCCTGTTTCTGGTGGCCACCGCCACCGGCGTGCACTCC
CAGGTGCAGCTGCTGGAGTCTGGCGGCGGACTGGTGCAGCCTGGCGGCTCCCTGCG
GCTGTCCTGCGCCGCCTCCGGCTTCTCCTTCGGCGACTACTGGATGTCCTGGGTG
CGGCAGGCTCCTGGCAAGGGCCTGGAGTGGGTGGCCGACATCAAGCCTGACGGCA
GCGACAAGGACTACGTGGACTCCGTGAAGGGCCGGTTCACCATCTCCCGGGACA
ACGCCAAGAACTCCCTGTACCTGCAGATGTCCTCCCTGCGGGCGAGGACACCGCC
GTGTACTACTGCGCCAGAGACTACGTGGTGGTGGCCCCTTCCCAGCCTCCTAAC
ATCCACCCTGAGTACTTCCAGAACTGGGGCCAGGGCACCCTGGTGATCGTGTCCT
CCGCCTCCACCAAGGGCCCTTCCGTGTTCCCTCTGGCCCCCTCCTCCAAGTCCACCTC
CGGCGGCACCGCCGCTCTGGGCTGCCTGGTGAAGGACTACTTCCCTGAGCCTGTGAC
CGTGTCCTGGAACTCTGGCGCCCTGACCAGCGGAGTGCACACCTTCCCTGCCGTGCT
GCAGTCCTCCGGCCTGTACTCCCTGTCCTCCGTGGTGACCGTGCCTTCCTCCTCCCTG
GGCACCCAGACCTACATCTGCAACGTGAACCACAAGCCTTCCAACACCAAGGTGGA
CAAGCGGGTGTCCTGCGACAAGACCCACACCTGCCCTCCCTGCCCTGCCCCTGAGCT
GCTGGGCGGACCCTCCGTGTTCCTGTTCCCTCCTAAGCCTAAGGACACCCTGATGAT
CTCCCGGACCCCTGAGGTGACCTGTGTGGTGGTGGACGTGTCCCACGAGGATCCTGA
GGTGAAGTTCAATTGGTACGTGGACGGCGTGGAGGTGCACAACGCTAAGACCAAGC
CTCGGGAGGAACAGTACAACTCCACCTACCGGGTGGTGTCTGTGCTGACCGTGCTGC
ACCAGGACTGGCTGAACGGCAAGGAATACAAGTGCAAGGTCTCCAACAAGGCCCTG
CCCGCTCCCATCGAAAAGACCATCTCCAAGGCCAAGGGCCAGCCTCGCGAGCCTCA
GGTGTACACCCTGCCCCCCAGCCGGGAGGAAATGACCAAGAACCAGGTGTCCCTGA
CCTGTCTGGTGAAGGGCTTCTACCCTTCCGATATCGCCGTGGAGTGGGAGTCCAACG
GCCAGCCTGAGAACAACTACAAGACCACCCCTCCTGTGCTGGACTCCGACGGCTCCT
TCTTCCTGTACTCCAAGCTGACCGTGGACAAGTCCCGGTGGCAGCAGGGCAACGTGT
TCTCCTGCTCCGTGATGCACGAGGCCCTGCACAACCACTACACCCAGAAGTCCCTGT
CCCTGAGCCCTGGCAAGTGA

Figure 16A

100C9 Codon Optimized Light Chain Nucleotide Sequences

FWR1:
TCCTACGTGCTGACCCAGCCTCCTTCCGTGTCCGTGTCCCCTGGCCAGACCGCCCGG
ATCACCTGC (SEQ ID NO:151)

CDR1:
TCCGGCGACGCCCTGCCTAAGCAGTACACCTAC (SEQ ID NO:152)

FWR2:
TGGTATCAGCAGAAGCCCGGCCAGGCCCCTGTGGTGGTGATCTAC (SEQ ID NO:153)

CDR2:
AAGGACTCCGAGCGGCCTTCC (SEQ ID NO:154)

FWR3:
GGCATCCCTGAGCGGTTCTCCGGCTCCTCCTCCGGCACCACCGTGACCGTGACCATC
TCCGGCGTGCAGGCCGAGGACGAGGCCGACTACTACTGC (SEQ ID NO:155)

CDR3:
CAGTCCGCCGACTCCAGCGGCACCTCCCTGGTG (SEQ ID NO:156)

Figure 16B

100C9 Codon Optimized Heavy Chain Nucleotide Sequences

FWR1:
GAGGTGCAGCTGGTCGAGTCTGGCGGCGGACTGGTGCAGCCTGGCGGCTCCCTGCG
GCTGTCCTGCTCCGCCTCC (SEQ ID NO: 165)

CDR1:
GGCTTCACCTTCTCCTCCTACTGGATGTCC (SEQ ID NO: 166)

FWR2:
TGGGTGCGGCAGGCTCCTGGCAAGGGCCTGGAGTGGGTGGCC (SEQ ID NO: 167)

CDR2:
AACATCATCCAGGACGGCTCCGAGAAGTACTACGCCGACTCCGTGAAGGGC (SEQ ID
NO: 168)

FWR3:
CGGCTGACCATCTCCCGGGACAACGCCAAGAACTCCCTGTACCTGCAGATGAACTCC
CTGCGGGTGGACGACACCGCCGTGTACTACTGCGCCAGG (SEQ ID NO: 169)

CDR3:
GGCTACGAGGGCTGCTCCGCCACCCGGTGCTACCTGTACTACTTCGACTAC (SEQ ID
NO: 170)

Figure 16C

79G9 Codon Optimized Light Chain Nucleotide Sequences

FWR1:
GACATCGAGCTGACCCAGTCCCCCTCCTTCCTGTCCGCCTCCGTGGGCGACCGGGTG
GCCATCACCTGC (SEQ ID NO: 179)

CDR1:
CGGGCCTCCCAGGGCATCTCCAACTACCTGGCC (SEQ ID NO: 180)

FWR2:
TGGTATCAGCAGAAGCCTGGCAAGGCCCCTAAGCTGCTGATCTAC (SEQ ID NO:181)

CDR2:
GCCGCCTTCGTGCTGCAGTCC (SEQ ID NO:182)

FWR3:
GGCGTGCCTTCCCGGTTCTCCGGCTCCGGCAGCGGCACCGAGTTCACCCTGACCATC
TCCAACCTGCAGCCTGAGGACTTCGCCACCTACTACTGC (SEQ ID NO:183)

CDR3:
CAGCAGCTGAACTCCTACCCTCGGGCC (SEQ ID NO:184)

Figure 16D

79G9 Codon Optimized Heavy Chain Nucleotide Sequences

FWR1:
GAGGTGCAGCTGGAGGAATCCGGCGCTGGCCTGCTGAAGCCTTCCGAGACACTGTC
CCTGACCTGCGCCGTGTAC (SEQ ID NO:193)

CDR1:
GGCGGCTCCTTCTCCGGCTACTACTGGTCC (SEQ ID NO:194)

FWR2:
TGGATCCGGCAGGCTCCTGGCAAGGGCCTGGAGTGGATCGGC (SEQ ID NO:195)

CDR2:
GAGATCGACCACTCCGGCACCACCAACTACAACCCTTCCCTGAAGTCC (SEQ ID NO:196)

FWR3:
CGGGTGACCATCTCCGTGGAGACATCCAAGAACCAGTTCTCCCTGCGGCTGTCCTCC
GTGACCGCCGCTGACTCCGCCGTGTACTACTGCGCCTCC (SEQ ID NO:197)

CDR3:
AGCGGCTACTGCTCCCACGGCCTGTGCCCTCAGGAAGAT (SEQ ID NO:198)

Figure 16E

154G12 Codon Optimized Light Chain Nucleotide Sequences

FWR1:
CTGTGCGCCGACTCCGCCACCCTGTCCGTGTCCGGCCCTCGGAGGGACGGCCAGCAC
TCCTGC (SEQ ID NO: 207)

CDR1:
GGCGGCAACAACATCGGCACCAAGTCCGTGCAC (SEQ ID NO: 208)

FWR2:
TGGTATCAGCAGCGGCCTGGACAGGCCCCTCTGCTGGTGCTGTAC (SEQ ID NO: 209)

CDR2:
CACGACACCAGGCGGCCTTCC (SEQ ID NO: 210)

FWR3:
CGGATCCCTGAGCGGTTCTCCGGCTCCAACTCCGGCAACACCGCTACCCTGACCATC
TCCCGGGTGGAGGCCGGCGACGAGGCCGACTACTACTGC (SEQ ID NO: 211)

CDR3:
CAGGTGTGGGACTCCAGGCGGGTG (SEQ ID NO: 212)

Figure 16F

154G12 Codon Optimized Heavy Chain Nucleotide Sequences

FWR1:
CAGGTGCAGCTGCTGGAGTCTGGCGGCGGACTGGTGCAGCCTGGCGGCTCCCTGCG
GCTGTCCTGCGCCGCCTCC (SEQ ID NO: 221)

CDR1:
GGCTTCTCCTTCGGCGACTACTGGATGTCC (SEQ ID NO: 222)

FWR2:
TGGGTGCGGCAGGCTCCTGGCAAGGGCCTGGAGTGGGTGGCC (SEQ ID NO: 223)

CDR2:
GACATCAAGCCTGACGGCAGCGACAAGGACTACGTGGACTCCGTGAAGGGC (SEQ ID NO: 224)

FWR3:
CGGTTCACCATCTCCCGGGACAACGCCAAGAACTCCCTGTACCTGCAGATGTCCTCC
CTGCGGGGCGAGGACACCGCCGTGTACTACTGCGCCAGA (SEQ ID NO: 225)

CDR3:
GACTACGTGGTGGTGGCCCCTTCCCAGCCTCCTAACATCCACCCTGAGTACTTCCAG
AAC (SEQ ID NO: 226)

Figure 17A

| Nucleotide | 79G9+ | 79G9 |
|---|---|---|
| 51 | A | C |
| 55 | A | T |
| 56 | G | C |
| 63 | G | A |
| 70 | T | G |
| 71 | T | A |
| 73 | C | G |
| 710 | A | G |
| 1051 | C | G |
| 1137 | T | G |
| 1141 | C | A |
| 1290 | C | T |

Figure 17B

| Amino Acid | 79G9+ | 79G9 |
|---|---|---|
| 24 | L | E |
| 25 | Q | E |
| 237 | K | R |
| 351 | L | V |
| 379 | D | E |
| 381 | L | M |

Figure 18

US 8,889,846 B2

HIGH AFFINITY ANTIBODIES THAT NEUTRALIZE STAPHYLOCOCCUS ENTEROTOXIN B

CROSS-REFERENCE TO RELATED APPLICATIONS

This application is a divisional application of U.S. application Ser. No. 11/969,097, filed Jan. 3, 2008, now U.S. Pat. No. 8,236,932 which claims the benefit of U.S. Provisional Application No. 60/883,271, filed Jan. 3, 2007, and of U.S. Provisional Application No. 60/888,405, filed Feb. 6, 2007. Each of these applications is incorporated by reference herein.

REFERENCE TO GOVERNMENT CONTRACT

This invention was made with government support under Contract No. U01AI075399 awarded by the National Institutes of Health. The government has certain rights in the invention.

FIELD

The invention relates generally to the field of immunotherapeutics. More specifically, the invention relates to monoclonal antibodies that can neutralize bacterial toxins, and methods for using such antibodies to treat subjects exposed to such toxins.

BACKGROUND

Bioterrorism threats have received a great deal of attention at present because of the ease of use of many of these deadly agents as well as accessibility of a largely unprotected populace. There can be significant economic and political ramifications that follow a bioterrorism attack, as was seen in the attacks with anthrax-laden envelopes in Washington, D.C. and New York in 2001 that resulted in disruption of postal service and 18 deaths. Due to the threat from such agents, the Centers for Disease Control established a list of biological agents that can be "weaponized" and have the potential to cause large scale morbidity and mortality. These select agents have been classified into three groups (A, B, and C) based on their potential for wide dissemination in civilian populations. Category B agents are considered to be moderately easy to disseminate and would, if distributed into civilian populations, result in moderate morbidity and mortality. Among the list of Category B agents is the Staphylococcal enterotoxin B (SEB) produced by the microorganism *Staphylococcus aureus* (Mantis, N.J. (2005) Adv. Drug Del. Rev. 57:1424-39). SEB has the potential to cause disease in humans at relatively low doses, in particular when the route of administration occurs by a mucosal surface. Typical routes of administration for SEB are by inhalation as an aerosol or by ingestion of SEB-laden food or water.

There are at least seven antigenically distinct enterotoxins secreted by strains of *S. aureus* (Kotb (1998) Curr. Opin. Microbiol. 1:56-65; Bergdoll (1983) Enterotoxins, in: C. S. F. Easmon, C. Adlam (Eds.), *Staphylococcus* and Staphylococcal Infections, Academic Press, New York, N.Y., pp. 559-598). SEB is a single polypeptide of approximately 28,000 Da molecular mass, and is comprised of two tightly packed domains: a large domain and a small domain (Swaminathan et al. (1992) Nature 359:801-6). Due to the compact tertiary structure of SEB, it is highly resistant to degradation by proteases, including trypsin, chymotrypsin, and papain. It is likely that protease resistance contributes to SEB stability in the intestinal lumen (Mantis (2005)).

Infection of a host organism by pathogenic bacteria such as staphylococci is aided by the production of exotoxins. The SEB produced by *S. aureus* is a protein that is classified as a superantigen (SAg). Superantigens are defined as toxins that can activate T cells by forming a bridge between a MHC II on antigen presenting cells (APCs) and the T cell receptors (TCR) on specific subsets of $CD4^+$ and $CD8^+$ T cells. SEB recognizes one of the seven classes of human $V_\beta^+$ T cell receptors: $V_\beta$3, 12, 13.2, 14, 15, 17, 20 (Jardetzky et al. (1994) Nature 368:711-8; Leder et al. (1998) J. Exp. Med. 187:823-33; Li et al. (1998) Immunity 9:807-16). As a consequence of SEB binding, T cells release massive quantities of cytokines including IL-2, TNF-$\beta$, and interferon-$\gamma$, and undergo hyperproliferation that ultimately results in their depletion (Kappler et al. (1989) Science 244:811-3). MHC II$^+$ APCs respond by producing TNF-$\alpha$ and IL-1 (Krakauer (2003) Methods Mol. Biol. 214:137-49). Two regions of SEB are involved in the interaction with MHC II, including a hydrophobic pocket near L45 and a polar pocket that includes residues Y89, Y115, and E67 (Mantis (2005); Jardetzky et al. (1994); Olson et al, (1997) J. Mol. Recognit. 10:277-89; and, Seth et al. (1994) Nature 369:324-7). It is predicted that obtaining a greater understanding of the molecular interactions between SEB and TCR-MHC II will lead to the development of attenuated SEB vaccine candidates; this prediction has been realized to some extent (Ulrich et al. (1998) Vaccine 16:1857-64).

SEB is a fairly stable protein, although it can be denatured by prolonged boiling. Because it is stable as an aerosol, it is considered a likely candidate for use as a bioterrorist agent. It is an incapacitating toxin, with an $LD_{50}$ (the dose lethal to 50% of the population) by inhalation of 27 µg/kg, and an $ID_{50}$ (the dose infectious to 50% of the population) of only 0.0004 µg/kg. SEB most commonly enters the body by either ingestion or inhalation, thereby leading to two different clinical presentations of SEB food poisoning and SEB respiratory syndrome. On the battlefield it is unlikely that SEB will be ingested, but both routes are possible in a terrorist attack. SEB as a terrorist weapon of mass destruction would most likely be disseminated as an aerosol. (Madsen (2001) Clinics in Laboratory Medicine 21:593-605).

SEB food poisoning is characterized by severe abdominal cramps and usually non-bloody diarrhea, sometimes accompanied by a headache and fever. Symptoms begin suddenly, usually within 2 to 8 hours after ingestion and usually abate in 12 hours or less. Inhalation of aerosolized preformed toxin produces SEB respiratory syndrome, which is characterized by fever, headache, chills, myalagias, nonproductive cough, dyspnea, and retrosternal chest pain. Inadvertent swallowing of the toxin leads to nausea and vomiting, and eye contact may induce conjunctival injection. Fever of 39° C. to 41° C. may last up to 5 days, and cough may persist up to 4 weeks. The mechanism of death in fatal inhalation cases is pulmonary edema (Madsen 2001).

Several potential strategies are under development for the treatment of SEB-infected individuals, although no effective treatment currently exists. The use of intravenous immunoglobulins has been an approach that has met with limited success (Darrenberg et al. (2004) Clin. Infect. Dis. 38:836-42). Another approach under development has recently been reported in a mouse SEB model system (Krakauer et al. (2006) Antimicrob. Agents Chemother. 50:391-5). In mouse SEB model system, mice were exposed to SEB and treated with the anti-inflammatory drug dexamethasone. In an LPS-potentiated model of SEB, toxic shock can be halted if the drug is administered to the mice quickly following SEB treatment (short treatment window). As a practical matter, however, it would be difficult to correctly diagnose exposure to SEB and administer sufficient dexamethasone to quell the SEB-mediated diseases within such a short treatment window.

SEB vaccine research has been primarily carried out by the United States Army Medical Research Institute of Infectious Diseases (USAMRIID). The vaccine development has focused on the use of formalin-inactivated toxin (Tseng et al. (1995) Infect. Immun 63:2880-5). The toxoid vaccine is typically made by prolonged incubation in formalin at pH 7.5. Although the SEB toxoid vaccine was immunogenic and patients did develop an immune reaction to SEB, this vaccine was largely abandoned by USAMRIID in recent years and supplanted by recombinant, site-directed attenuated mutants (Stiles et al. (2001) Infect. Immun. 69:2031-6). Unfortunately, these mutants may not be suitable for use in humans due to retention of emetic activity in primate studies (Harris et al. (1993) Infect. Immun. 61:3175-83).

The SEB work reviewed above suggests that effective methods for combating a terrorist's use of SEB are currently lacking. Therefore, an approach to develop a drug that can neutralize the activity of SEB in vivo would be a valuable human therapeutic for the treatment and prevention of SEB-mediated disease.

SUMMARY

The invention features isolated human antibodies and antigen-binding fragments that specifically bind to, and preferably neutralize *Staphylococcus* enterotoxin B. The antibodies and antigen-binding fragments can comprise a heavy chain CDR3 having SEQ ID NO: 39, 40, 70, 94, 118, 132, or 148. The antibodies and antigen-binding fragments can comprise heavy chain CDR1, CDR2, and CDR3 of SEQ ID NOs: 68, 69, and 70; SEQ ID NOs: 130, 131, and 132; SEQ ID NOs: 92, 93, and 94; or SEQ ID NOs: 144, 146, and 148. In some preferred embodiments, the antibodies and antigen-binding fragments can comprise a heavy chain variable domain of SEQ ID NO: 160, 176, 204, or 230. In some preferred embodiments, the antibodies and antigen-binding fragments can comprise a heavy chain having SEQ ID NO: 30, 34, 126, 142, 216, 232, or 251.

In some preferred embodiments, the antibodies and antigen-binding fragments can comprise light chain CDR1, CDR2, and CDR3 of SEQ ID NOs: 56, 57, and 58; SEQ ID NOs: 104, 105, and 106; SEQ ID NOs: 80, 81, and 82; or SEQ ID NOs: 136, 138, and 140. In some preferred embodiments, the antibodies and antigen-binding fragments can comprise a light chain variable domain of SEQ ID NO: 158, 174, 200, or 228. In some preferred embodiments, the antibodies and antigen-binding fragments can comprise a light chain having SEQ ID NO: 28, 32, 36, 134, 186, 214, or 249.

In some preferred embodiments, the antibodies and antigen-binding fragments can comprise a heavy chain having CDR1 of SEQ ID NO: 68, 92, 130, or 144; CDR2 of SEQ ID NO: 69, 93, 131, or 146; and CDR3 of SEQ ID NO: 70, 94, 132, or 148; and a light chain having CDR1 of SEQ ID NO: 56, 80, 104, or 136; CDR2 of SEQ ID NO: 57, 81, 105, or 138; and CDR3 of SEQ ID NO: 58, 82, 106, or 140. In some preferred embodiments, the antibodies and antigen-binding fragments can comprise a heavy chain variable domain having SEQ ID NO: 160, 176, 204, or 230 and a light chain variable domain having SEQ ID NO: 158, 174, 200, or 228.

In preferred embodiments, the antibodies and antigen-binding fragments of the invention comprise a heavy chain having CDR1 of SEQ ID NO: 68, CDR2 of SEQ ID NO: 69, and CDR3 of SEQ ID NO: 70 and a light chain having CDR1 of SEQ ID NO: 56, CDR2 of SEQ ID NO: 57, and CDR3 of SEQ ID NO: 58. In preferred embodiments, the antibodies and antigen-binding fragments of the invention comprise a heavy chain having a variable domain of SEQ ID NO: 176 and a light chain having a variable domain of SEQ ID NO: 174. In preferred embodiments, the antibodies and antigen-binding fragments of the invention comprise a heavy chain having SEQ ID NO: 30 and a light chain having SEQ ID NO: 28.

In preferred embodiments, the antibodies and antigen-binding fragments of the invention comprise a heavy chain having CDR1 of SEQ ID NO: 130, CDR2 of SEQ ID NO: 131, and CDR3 of SEQ ID NO: 132, and a light chain having CDR1 of SEQ ID NO: 104, CDR2 of SEQ ID NO: 105, and CDR3 of SEQ ID NO: 106. In preferred embodiments, the antibodies and antigen-binding fragments of the invention comprise a heavy chain having a variable domain of SEQ ID NO: 204 and a light chain having a variable domain of SEQ ID NO: 200. In preferred embodiments, the antibodies and antigen-binding fragments of the invention comprise a heavy chain having SEQ ID NO: 232 and a light chain having SEQ ID NO: 186.

In preferred embodiments, the antibodies and antigen-binding fragments of the invention comprise a heavy chain having CDR1 of SEQ ID NO: 92, CDR2 of SEQ ID NO: 93, and CDR3 of SEQ ID NO: 94, and a light chain having CDR1 of SEQ ID NO: 80, CDR2 of SEQ ID NO: 81, and CDR3 of SEQ ID NO: 82. In preferred embodiments, the antibodies and antigen-binding fragments of the invention comprise a heavy chain having a variable domain of SEQ ID NO: 160 and a light chain having a variable domain of SEQ ID NO: 158. In preferred embodiments, the antibodies and antigen-binding fragments of the invention comprise a heavy chain having SEQ ID NO: 251 and a light chain having SEQ ID NO: 249.

In preferred embodiments, the antibodies and antigen-binding fragments of the invention comprise a heavy chain having CDR1 of SEQ ID NO: 144, CDR2 of SEQ ID NO: 146, and CDR3 of SEQ ID NO: 148, and a light chain having CDR1 of SEQ ID NO: 136, CDR2 of SEQ ID NO: 138, and CDR3 of SEQ ID NO: 140. In preferred embodiments, the antibodies and antigen-binding fragments of the invention comprise a heavy chain having a variable domain of SEQ ID NO: 230 and a light chain having a variable domain of SEQ ID NO: 228. In preferred embodiments, the antibodies and antigen-binding fragments of the invention comprise a heavy chain having SEQ ID NO: 216 and a light chain having SEQ ID NO: 214.

The present invention also contemplates antibodies, or antigen-binding fragments thereof, having amino acid sequences that are substantially the same as the previously described amino acid sequences. For example, such antibodies or antigen-binding fragments thereof may include those wherein the heavy chain CDR1, CDR2, and CDR3 are at least 90% identical to the amino acid sequences of SEQ ID NOs: 68, 69, and 70; 92, 93, and 94; 130, 131, and 132; or 144, 146, and 148, respectively. The antibodies or antigen-binding fragments thereof having amino acid sequences that are substantially the same as the previously described amino acid sequences may include those wherein the light chain CDR1, CDR2, and CDR3 are at least 90% identical to the amino acid sequences of SEQ ID NOs: 56, 57, and 58; 80, 81, and 82; 104, 105, and 106; or 136, 138, and 140, respectively. In some embodiments, the antibodies or antigen binding-fragments having amino acid sequences that are substantially the same as the previously described amino acid sequences may include those wherein the heavy chain CDR1, CDR2, and CDR3 are at least 90% identical to the amino acid sequences of SEQ ID NOs: 68, 69, and 70; 92, 93, and 94; 130, 131, and 132; or 144, 146, and 148, respectively, and wherein the light chain CDR1, CDR2, and CDR3 are at least 90% identical to the amino acid sequences of SEQ ID NOs: 56, 57, and 58; 80, 81, and 82; 104, 105, and 106; or 136, 138, and 140, respectively. The antibodies or antigen-binding fragments thereof having amino acid sequences that are substantially the same as the previously described amino acid sequences may include those wherein the heavy chain CDR3 is at least 90% identical to the amino acid sequence of SEQ ID NO: 39, 40, 70, 94, 132, or 148. Such antibodies or antigen-binding fragments thereof may include those wherein the light chain CDR3 is at least 90% identical to the amino acid sequence of SEQ ID NO: 41, 42, 58, 82, 106, or 140.

The antibodies or antigen-binding fragments thereof having amino acid sequences that are substantially the same as the previously described amino acid sequences may include those wherein the heavy chain CDR1, CDR2, and CDR3 and the light chain CDR1, CDR2, and CDR3 are at least 90% identical to the antibody or antigen-binding fragment thereof with a heavy chain having CDR1 of SEQ ID NO: 68, CDR2 of SEQ ID NO: 69, and CDR3 of SEQ ID NO: 70 and a light chain having CDR1 of SEQ ID NO: 56, CDR2 of SEQ ID NO: 57, and CDR3 of SEQ ID NO: 58.

The antibodies or antigen-binding fragments thereof having amino acid sequences that are substantially the same as the previously described amino acid sequences may include those wherein the heavy chain CDR1, CDR2, and CDR3 and the light chain CDR1, CDR2, and CDR3 are at least 90% identical to the antibody or antigen-binding fragment thereof with a heavy chain having CDR1 of SEQ ID NO: 130, CDR2 of SEQ ID NO: 131, and CDR3 of SEQ ID NO: 132, and a light chain having CDR1 of SEQ ID NO: 104, CDR2 of SEQ ID NO: 105, and CDR3 of SEQ ID NO: 106.

The antibodies or antigen-binding fragments thereof having amino acid sequences that are substantially the same as the previously described amino acid sequences may include those wherein the heavy chain CDR1, CDR2, and CDR3 and the light chain CDR1, CDR2, and CDR3 are at least 90% identical to the antibody or antigen-binding fragment thereof with a heavy chain having CDR1 of SEQ ID NO: 92, CDR2 of SEQ ID NO: 93, and CDR3 of SEQ ID NO: 94, and a light chain having CDR1 of SEQ ID NO: 80, CDR2 of SEQ ID NO: 81, and CDR3 of SEQ ID NO: 82.

The antibodies or antigen-binding fragments thereof having amino acid sequences that are substantially the same as the previously described amino acid sequences may include those wherein the heavy chain CDR1, CDR2, and CDR3 and the light chain CDR1, CDR2, and CDR3 are at least 90% identical to the antibody or antigen-binding fragment thereof with a heavy chain having CDR1 of SEQ ID NO: 144, CDR2 of SEQ ID NO: 146, and CDR3 of SEQ ID NO: 148, and a light chain having CDR1 of SEQ ID NO: 136, CDR2 of SEQ ID NO: 138, and CDR3 of SEQ ID NO: 140.

In a further example, antibodies and antigen-binding fragments of the invention comprise a heavy chain having a variable domain at least 90% identical to the amino acid sequence of SEQ ID NO: 176, 160, 204, or 230 and a light chain having a variable domain at least 90% identical to the amino acid sequence of SEQ ID NO: 174, 158, 200, or 228.

The antibodies or antigen-binding fragments thereof having amino acid sequences that are substantially the same as the previously described amino acid sequences may include those having a heavy chain having a variable domain and a light chain having a variable domain at least 90% identical to the amino acid sequence of SEQ ID NO: 176 and SEQ ID NO: 174.

The antibodies or antigen-binding fragments thereof having amino acid sequences that are substantially the same as the previously described amino acid sequences may include those having a heavy chain having a variable domain and a light chain having a variable domain at least 90% identical to the amino acid sequence of SEQ ID NO: 160 and SEQ ID NO: 158.

The antibodies or antigen-binding fragments thereof having amino acid sequences that are substantially the same as the previously described amino acid sequences may include those having a heavy chain having a variable domain and a light chain having a variable domain at least 90% identical to the amino acid sequence of SEQ ID NO: 204 and SEQ ID NO: 200.

The antibodies or antigen-binding fragments thereof having amino acid sequences that are substantially the same as the previously described amino acid sequences may include those having a heavy chain having a variable domain and a light chain having a variable domain at least 90% identical to the amino acid sequence of SEQ ID NO: 230 and SEQ ID NO: 228.

The antibodies and antigen-binding fragments are high affinity antibodies and antigen-binding fragments, and can have an affinity of less than about $1\times10^{-8}$ M, preferably less than about $2\times10^{-8}$ M, and more preferably less than about $3\times10^{-8}$ M. Preferably, the antibodies are monoclonal antibodies, and more preferably, are human monoclonal antibodies. Cells that express such antibodies and antigen-binding fragments, such as hybridoma cells and expression cells, are also provided.

The invention further contemplates antibodies, or antigen-binding fragments thereof, that compete for binding to SEB with antibody 79G9, 154G12, F10, 100C9, F6, E12 or C5.

The invention also contemplates antibodies, or antigen-binding fragments thereof, that bind the same epitope as antibody 79G9, 154G12, F10, 100C9, F6, E12 or C5.

The invention also features polynucleotides that encode antibodies and antigen-binding fragments that specifically bind to *Staphylococcus* enterotoxin B. In some preferred embodiments, the polynucleotides encode an antibody or antigen-binding fragment having heavy chain CDR1, CDR2, and CDR3 of SEQ ID NOs: 68, 69, and 70, respectively. For example, the polynucleotide may comprise SEQ ID NOs: 62, 63, and 64. In some preferred embodiments, the polynucleotides encode an antibody or antigen-binding fragment having heavy chain CDR1, CDR2, and CDR3 of SEQ ID NOs: 130, 131, and 132, respectively. For example, the polynucleotide may comprise SEQ ID NOs: 123 or 194, 124 or 196, and 125 or 198. In some preferred embodiments, the polynucleotides encode an antibody or antigen-binding fragment having heavy chain CDR1, CDR2, and CDR3 of SEQ ID NOs: 92, 93, and 94, respectively. For example, the polynucleotide may comprise SEQ ID NOs: 86 or 166, 87 or 168, and 88 or 170. In some preferred embodiments, the polynucleotides encode an antibody or antigen-binding fragment having heavy chain CDR1, CDR2, and CDR3 of SEQ ID NOs: 144, 146, and 148, respectively. For example, the polynucleotide may comprise SEQ ID NOs: 253 or 222, 255 or 224, and 257 or 226.

In some preferred embodiments, the polynucleotides encode an antibody or antigen-binding fragment having light chain CDR1, CDR2, and CDR3 of SEQ ID NOs: 56, 57, and 58, respectively. For example, the polynucleotide may comprise SEQ ID NOs: 50, 51, and 52. In some preferred embodiments, the polynucleotides encode an antibody or antigen-binding fragment having light chain CDR1, CDR2, and CDR3 of SEQ ID NOs: 104, 105, and 106, respectively. For example, the polynucleotide may comprise SEQ ID NOs: 98 or 180, 99 or 182, and 100 or 184. In some preferred embodiments, the polynucleotides encode an antibody or antigen-binding fragment having light chain CDR1, CDR2, and CDR3 of SEQ ID NOs: 80, 81, and 82, respectively. For example, the polynucleotide may comprise SEQ ID NOs: 74 or 152, 75 or 154, and 76 or 156. In some preferred embodiments, the polynucleotides encode an antibody or antigen-binding fragment having light chain CDR1, CDR2, and CDR3 of SEQ ID NOs: 136, 138, and 140, respectively. For example, the polynucleotide may comprise SEQ ID NOs: 259 or 208, 261 or 210, and 263 or 212.

In some preferred embodiments, the antibody or antigen-binding fragment heavy chain variable domain is encoded by a polynucleotide comprising SEQ ID NO: 159, 164, 172, 175, 192, 203, or 229. In some preferred embodiments, the heavy chain sequence is encoded by a polynucleotide comprising SEQ ID NO: 29, 33, 119, 141, 162, 163, 190, 191, 215, 218, 219, 231, or 250. In some preferred embodiments, the polynucleotides encode an antibody or antigen-binding fragment having heavy chain variable domain of SEQ ID NO: 160. For example, the polynucleotide may comprise SEQ ID NO: 159 or 164. In some preferred embodiments, the polynucleotides encode an antibody or antigen-binding fragment having heavy chain variable domain of SEQ ID NO: 176. For example, the polynucleotide may comprise SEQ ID NO: 175. In some preferred embodiments, the polynucleotides encode an antibody or antigen-binding fragment having heavy chain variable domain of SEQ ID NO: 204. For example the polynucleotide may comprise SEQ ID NO: 172 or 203. In some preferred embodiments, the polynucleotides encode an antibody or antigen-binding fragment having heavy chain variable domain of SEQ ID NO: 230. For example the polynucleotide may comprise SEQ ID NO: 192 or 229.

In some preferred embodiments, the antibody and antigen-binding fragment light chain CDR1, CDR2, and CDR3 are encoded by polynucleotides comprising SEQ ID NOs: 50, 51, and 52; SEQ ID NOs: 98, 99, and 100; SEQ ID NOs: 74, 75, and 76; SEQ ID NOs: 259, 261, and 263; SEQ ID NOs: 180, 182, and 184; SEQ ID NOs: 152, 154, and 156; or SEQ ID NOs: 208, 210, and 212, respectively. In some preferred embodiments, the antibody and antigen-binding fragment light chain variable domain is encoded by a polynucleotide comprising SEQ ID NO: 150, 157, 171, 173, 178, 199, or 227.

In some preferred embodiments, the polynucleotides of the invention encode an antibody or antigen-binding fragment having a light chain variable domain of SEQ ID NO: 158. For example, the polynucleotides may comprise SEQ ID NO: 150 or 157. In some preferred embodiments, the polynucleotides encode an antibody or antigen-binding fragment having a light chain variable domain of SEQ ID NO: 174. For example, the polynucleotide may comprise SEQ ID NO: 173. In some preferred embodiments, the polynucleotides encode an antibody or antigen-binding fragment having a light chain variable domain of SEQ ID NO: 200. For example, the polynucleotide may comprise SEQ ID NO: 171 or 199. In some preferred embodiments, the polynucleotides encode an antibody or antigen-binding fragment having a light chain variable domain of SEQ ID NO: 228. For example the polynucleotide may comprise SEQ ID NO: 178 or 227. In some preferred embodiments, the antibody and antigen-binding fragment light chain sequence is encoded by a polynucleotide comprising SEQ ID NO: 27, 31, 35, 133, 149, 161, 177, 185, 189, 205, 213, 217, or 248.

In some preferred embodiments, the polynucleotides encode an antibody or antigen-binding fragment having heavy chain CDR1, CDR2, and CDR3; and light chain CDR1, CDR2, and CDR3 of SEQ ID NOs: 68, 69, and 70; and 56, 57, and 58, respectively. For example, the polynucleotide may comprise SEQ ID NOs: 62, 63, and 64; and 50, 51, and 52. In some preferred embodiments, the polynucleotides encode an antibody or antigen-binding fragment having heavy chain CDR1, CDR2, and CDR3; and light chain CDR1, CDR2, and CDR3 of SEQ ID NOs: 130, 131, and 132; and 104, 105, and 106, respectively. For example, the polynucleotide may comprise SEQ ID NOs: 123 or 194, 124 or 196, and 125 or 198; and 98 or 180, 99 or 182, and 100 or 184. In some preferred embodiments, the polynucleotides encode an antibody or antigen-binding fragment having heavy chain CDR1, CDR2, and CDR3; and light chain CDR1, CDR2, and CDR3 of SEQ ID NOs: 92, 93, and 94; and 80, 81, and 82, respectively. For example, the polynucleotide may comprise SEQ ID NOs: 86 or 166, 87 or 168, and 88 or 170; and 74 or 152, 75 or 154, and 76 or 156. In some preferred embodiments, the polynucleotides encode an antibody or antigen-binding fragment having heavy chain CDR1, CDR2, and CDR3; and light chain CDR1, CDR2, and CDR3 of SEQ ID NOs: 144, 146, and 148; and 136, 138, and 140, respectively. For example, the polynucleotide may comprise SEQ ID NOs: 253 or 222, 255 or 224, and 257 or 226; and 259 or 208, 261 or 210, and 263 or 212.

In some preferred embodiments, the polynucleotides encode an antibody or antigen-binding fragment having a heavy chain variable domain and a light chain variable domain of SEQ ID NOs: 176 and 174. For example, the polynucleotide may comprise SEQ ID NO: 175 and 173. In some preferred embodiments, the polynucleotides encode an antibody or antigen-binding fragment having a heavy chain variable domain and a light chain variable domain of SEQ ID NOs: 204 and 200. For example, the polynucleotide may comprise SEQ ID NO: 203 or 172 and 199 or 171. In some preferred embodiments, the polynucleotides encode an antibody or antigen-binding fragment having a heavy chain variable domain and a light chain variable domain of SEQ ID NOs: 160 and 158. For example, the polynucleotide may comprise SEQ ID NO: 159 or 164 and 157 or 150. In some preferred embodiments, the polynucleotides encode an antibody or antigen-binding fragment having a heavy chain variable domain and a light chain variable domain of SEQ ID NOs: 230 and 228. For example, the polynucleotide may comprise SEQ ID NO: 229 or 192 and 227 or 178.

In some preferred embodiments, the polynucleotide encoding the antibodies and antigen-binding fragments can comprise a heavy chain having CDR1 of SEQ ID NO: 62, 86, 123, 166, 194, 222, or 253; CDR2 of SEQ ID NO: 63, 87, 124, 168, 196, 224, or 255; and CDR3 of SEQ ID NO: 64, 88, 125, 170, 198, 212, or 257; and a light chain having CDR1 of SEQ ID NO: 50, 74, 98, 152, 180, 208, or 259; CDR2 of SEQ ID NO: 51, 75, 99, 154, 182, 210, or 261; and CDR3 of SEQ ID NO: 52, 76, 100, 156, 184, 212, or 263. In some preferred embodiments, the polynucleotide encoding the antibodies and antigen-binding fragments can comprise a heavy chain variable domain having SEQ ID NO: 159, 164, 172, 175, 192, 203, or 229 and a light chain variable domain having SEQ ID NO: 150, 157, 171, 173, 178, 199, or 227. In some preferred embodiments, the polynucleotide encoding the antibodies and antigen-binding fragments can comprise a heavy chain sequence of SEQ ID NO: 29, 33, 119, 141, 162, 163, 190, 191, 215, 218, 219, 231, or 250 and a light chain sequence of SEQ ID NO: 27, 31, 35, 133, 149, 161, 177, 185, 189, 205, 213, 217, or 248. Vectors comprising such polynucleotides are also provided.

The invention also features methods for treating or preventing a *Staphylococcus* enterotoxin B-mediated disease in a subject in need of such treatment. The methods comprise administering to the subject a composition comprising a pharmaceutically acceptable carrier and at least one antibody that specifically binds to *Staphylococcus* enterotoxin B in an amount effective to treat or prevent a *Staphylococcus* enterotoxin B-mediated disease. The invention also features methods for neutralizing *Staphylococcus* enterotoxin B in subjects in need thereof. The methods comprise administering to the subject at least one inventive antibody that specifically binds to and neutralizes *Staphylococcus* enterotoxin B in an amount effective to neutralize *Staphylococcus* enterotoxin B.

Also featured are methods for making antibodies and antigen-binding fragments that specifically bind to *Staphylococcus* enterotoxin B. In some embodiments, the methods comprise culturing bone marrow or peripheral blood cells isolated from an animal with the *Staphylococcus* enterotoxin B or antigenic fragment thereof, isolating B cells that express an antibody that specifically binds to *Staphylococcus* enterotoxin B, and isolating antibodies produced by said B cells. In some embodiments, the animal is immunized with *Staphylococcus* enterotoxin B or antigenic fragment thereof prior to isolation of the bone marrow or peripheral blood cells. It is preferable, but not required, that the animal be a mammal, and more preferable, that the animal is a human.

BRIEF DESCRIPTION OF THE DRAWINGS

FIG. 1 shows the amino acid sequence of Staphylococcal enterotoxin B (SEB) from *S. aureus* strain ATCC14458 (bold type) (SEQ ID NO: 46). A parallel SEB amino acid sequence is provided (italics) showing differences in the amino acid sequence between SEB and the SEB mutein vaccine (STEB) (dark highlight) (SEQ ID NO: 45) (Boles et al. (2003) Clin. Immunol. 108:51-9), and also showing WIG binding epitopes (single underline) (Nishi et al. (1997) J. Immunol. 158:247-54), T-cell receptor-binding H-bonds (double underline) (Li et al. (1998) Immunity 9:807-16), and T-cell receptor-binding Van der Waals contacts (light highlight).

FIGS. 13A-R shows the nucleic acid and amino acid sequences of the H and L chains of antibodies F10 (SEQ ID NOS:27-30, 173-176), 100C9 (SEQ ID NOS:31-34, 157-160, 248-251), 79G9+ (SEQ ID NOS:37-38, 187-188, 201-202), 79G9 (SEQ ID NOS:35-36, 119, 126, 185-186, 199-200, 203-204, 231-232), and 154G12 (SEQ ID NOS:133-134, 141-142, 213-216, 227-230). The bolded regions of the sequences highlight the CDRs, the underlined segment denotes a leader sequence added by PCR, and the shaded regions indicate the variable domain.

FIGS. 14A-R shows the CDR and FWR regions of antibodies F10 (SEQ ID NOS:47-70), 100C9 (SEQ ID NOS:71-94), 79G9+ (SEQ ID NOS:107-118), 79G9 (SEQ ID NOS: 95-106, 120-125, 127-132), and 154G12 (SEQ ID NOS:135-140, 143-148, 252-263).

FIG. 15 shows the codon optimized nucleic acid sequences of the H and/or L chains of antibodies 100C9 (SEQ ID NO:149-150, 161-164), 79G9 (SEQ ID NOS:171-172, 177, 189-191), and 154G12 (SEQ ID NOS:178, 192, 205, 217-219). The bolded regions of the sequences highlight the CDRs, the underlined segment denotes a leader sequence added by PCR, and the shaded regions indicate the variable domain.

FIG. 16 shows the codon optimized nucleic acid sequences for the CDR and FWR regions of antibodies 100C9 (SEQ ID NOS:151-156, 165-170), 79G9 (SEQ ID NOS:179-184, 193-198), and 154G12 (SEQ ID NOS:207-212, 221-226).

FIG. 17 illustrates sequence differences between 79G9 and 79G9+. FIG. 17A shows differences in the nucleotide sequences of 79G9 (SEQ ID NO: 119) and 79G9+ (SEQ ID NO: 37). FIG. 17B shows differences in the amino acid sequences of 79G9 (SEQ ID NO: 126) and 79G9+ (SEQ ID NO: 38). Cells producing antibodies comprising the 79G9 heavy chain nucleic acid sequence and 79G9 light chain nucleic acid sequence were deposited with the American Type Culture Collection on Jan. 3, 2007.

FIG. 18 shows binding of antibodies 79G9, 100C9, and 154G12 to *Staphylococcus* enterotoxins SEA, SED, SEC1, SEC2, and TSST-1; Streptococcal pyrogenic exotoxins SPE-A, SPE-B; and Tetanus toxoid. Hashed bars illustrate binding of control antibodies specific for either TSST-1 or Tetanus toxoid.

DETAILED DESCRIPTION

Figure 2:
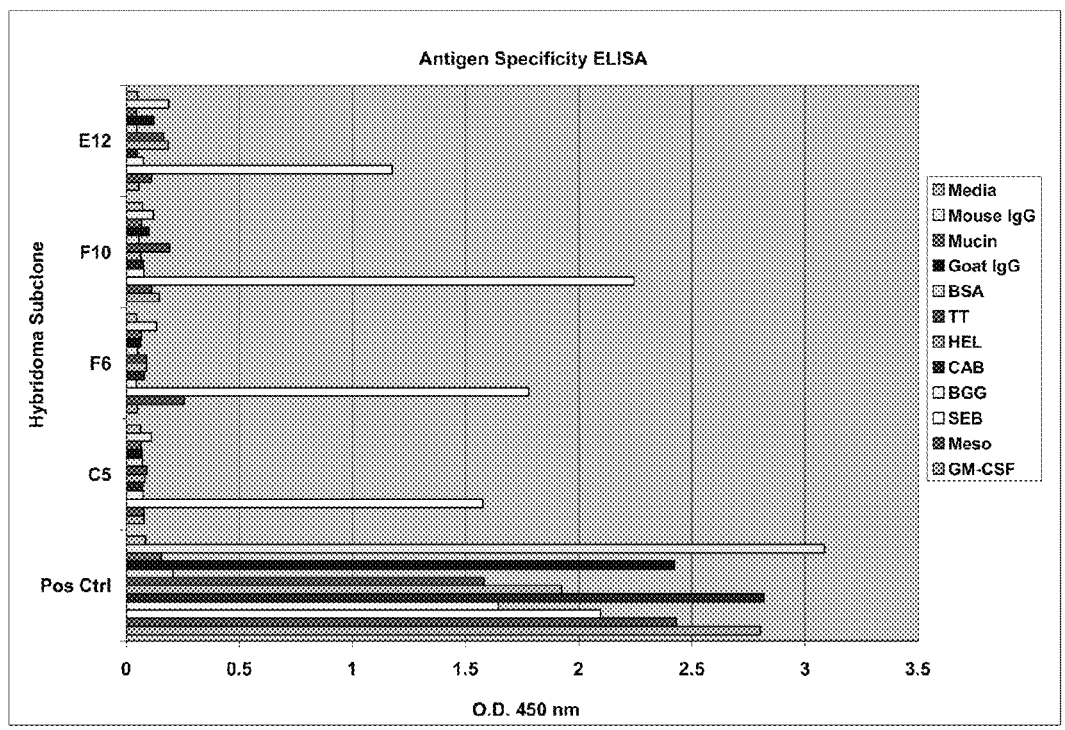
FIG. 2 shows an antigen panel ELISA for selection of antigen-specific human mAbs E12, F6, F10, and C5. Antibodies were screened for binding to mucin, goat IgG, BSA, TT, HEL, CAB, BGG, SEB, mesothelin, and GM-CSF. Antibodies with known reactivity against the various antigens were used as positive controls. The murine antibody S5 was used as a positive control to show reactivity with SEB. The E12, F6, F10, and C5 antibodies were specific for SEB, and did not cross react with any of the other antigens in the panel. The figure legend identifies the antigens tested and provides the order for the bars on the graph that correspond to the listed antigens.

For convenience, Table 1 lists each SEQ ID NO and the name of the corresponding sequence.

TABLE 1

Sequence ID numbers

| SEQ ID NO | Sequence Description |
|---|---|
| 1 | Primer 390 |
| 2 | Primer 391 |
| 3 | Primer 883 |
| 4 | Primer 974 |
| 5 | Primer 975 |
| 6 | Primer 1463 |
| 7 | Primer 882 |
| 8 | Primer 885 |
| 9 | Primer 888 |
| 10 | Primer 900 |
| 11 | Primer 1017 |
| 12 | Primer 1018 |
| 13 | Primer 1019 |
| 14 | Primer 1024 |
| 15 | Primer 1040 |
| 16 | Primer 1500 |
| 17 | Primer 1550 |
| 18 | Primer 1551 |
| 19 | Primer 1552 |
| 20 | Primer 1553 |
| 21 | Leader 2 Nucleotide Sequence |
| 22 | Primer 1557 |
| 23 | Primer 1559 |
| 24 | Primer 1560 |
| 25 | Primer 1570 |
| 26 | Primer 996 |
| 27 | F10: Light Chain Nucleotide Sequence |
| 28 | F10 Light Chain Amino Acid Sequence |
| 29 | F10: Heavy Chain Segment Including Variable Domain Nucleotide Sequence |
| 30 | F10 Heavy Chain Segment Including Variable Domain Amino Acid Sequence |
| 31 | 100C9 Light Chain Nucleotide Sequence |
| 32 | 100C9 Light Chain Amino Acid Sequence |
| 33 | 100C9 Heavy Chain Nucleotide Sequence |
| 34 | 100C9 Heavy Chain Amino Acid Sequence |
| 35 | 79G9 Light Chain Nucleotide Sequence |
| 36 | 79G9 Light Chain Amino Acid Sequence |
| 37 | 79G9+ Heavy Chain Nucleotide Sequence |
| 38 | 79G9+ Heavy Chain Amino Acid Sequence |
| 39 | C5 Heavy Chain Variable Domain CDR3 Amino Acid Sequence |
| 40 | F6 Heavy Chain Variable Domain CDR3 Amino Acid Sequence |
| 41 | C5 Light Chain Variable Domain CDR3 Amino Acid Sequence |
| 42 | F6 Light Chain Variable Domain CDR3 Amino Acid Sequence |
| 43 | Leader 1 Nucleotide Sequence |
| 44 | Leader Amino Acid Sequence |
| 45 | STEB |
| 46 | SEB |
| 47 | F10 Light Chain FWR1 Nucleotide Sequence |
| 48 | F10 Light Chain FWR2 Nucleotide Sequence |
| 49 | F10 Light Chain FWR3 Nucleotide Sequence |
| 50 | F10 Light Chain CDR1 Nucleotide Sequence |
| 51 | F10 Light Chain CDR2 Nucleotide Sequence |
| 52 | F10 Light Chain CDR3 Nucleotide Sequence |
| 53 | F10 Light Chain FWR1 Amino Acid Sequence |
| 54 | F10 Light Chain FWR2 Amino Acid Sequence |

TABLE 1-continued

Sequence ID numbers

| SEQ ID NO | Sequence Description |
|---|---|
| 55 | F10 Light Chain FWR3 Amino Acid Sequence |
| 56 | F10 Light Chain CDR1 Amino Acid Sequence |
| 57 | F10 Light Chain CDR2 Amino Acid Sequence |
| 58 | F10 Light Chain CDR3 Amino Acid Sequence |
| 59 | F10 Heavy Chain FWR1 Nucleotide Sequence |
| 60 | F10 Heavy Chain FWR2 Nucleotide Sequence |
| 61 | F10 Heavy Chain FWR3 Nucleotide Sequence |
| 62 | F10 Heavy Chain CDR1 Nucleotide Sequence |
| 63 | F10 Heavy Chain CDR2 Nucleotide Sequence |
| 64 | F10 Heavy Chain CDR3 Nucleotide Sequence |
| 65 | F10 Heavy Chain FWR1 Amino Acid Sequence |
| 66 | F10 Heavy Chain FWR2 Amino Acid Sequence |
| 67 | F10 Heavy Chain FWR3 Amino Acid Sequence |
| 68 | F10 Heavy Chain CDR1 Amino Acid Sequence |
| 69 | F10 Heavy Chain CDR2 Amino Acid Sequence |
| 70 | F10 Heavy Chain CDR3 Amino Acid Sequence |
| 71 | 100C9 Light Chain FWR1 Nucleotide Sequence |
| 72 | 100C9 Light Chain FWR2 Nucleotide Sequence |
| 73 | 100C9 Light Chain FWR3 Nucleotide Sequence |
| 74 | 100C9 Light Chain CDR1 Nucleotide Sequence |
| 75 | 100C9 Light Chain CDR2 Nucleotide Sequence |
| 76 | 100C9 Light Chain CDR3 Nucleotide Sequence |
| 77 | 100C9 Light Chain FWR1 Amino Acid Sequence |
| 78 | 100C9 Light Chain FWR2 Amino Acid Sequence |
| 79 | 100C9 Light Chain FWR3 Amino Acid Sequence |
| 80 | 100C9 Light Chain CDR1 Amino Acid Sequence |
| 81 | 100C9 Light Chain CDR2 Amino Acid Sequence |
| 82 | 100C9 Light Chain CDR3 Amino Acid Sequence |
| 83 | 100C9 Heavy Chain FWR1 Nucleotide Sequence |
| 84 | 100C9 Heavy Chain FWR2 Nucleotide Sequence |
| 85 | 100C9 Heavy Chain FWR3 Nucleotide Sequence |
| 86 | 100C9 Heavy Chain CDR1 Nucleotide Sequence |
| 87 | 100C9 Heavy Chain CDR2 Nucleotide Sequence |
| 88 | 100C9 Heavy Chain CDR3 Nucleotide Sequence |
| 89 | 100C9 Heavy Chain FWR1 Amino Acid Sequence |
| 90 | 100C9 Heavy Chain FWR2 Amino Acid Sequence |
| 91 | 100C9 Heavy Chain FWR3 Amino Acid Sequence |
| 92 | 100C9 Heavy Chain CDR1 Amino Acid Sequence |
| 93 | 100C9 Heavy Chain CDR2 Amino Acid Sequence |
| 94 | 100C9 Heavy Chain CDR3 Amino Acid Sequence |
| 95 | 79G9 Light Chain FWR1 Nucleotide Sequence |
| 96 | 79G9 Light Chain FWR2 Nucleotide Sequence |
| 97 | 79G9 Light Chain FWR3 Nucleotide Sequence |
| 98 | 79G9 Light Chain CDR1 Nucleotide Sequence |
| 99 | 79G9 Light Chain CDR2 Nucleotide Sequence |
| 100 | 79G9 Light Chain CDR3 Nucleotide Sequence |
| 101 | 79G9 Light Chain FWR1 Amino Acid Sequence |
| 102 | 79G9 Light Chain FWR2 Amino Acid Sequence |
| 103 | 79G9 Light Chain FWR3 Amino Acid Sequence |
| 104 | 79G9 Light Chain CDR1 Amino Acid Sequence |
| 105 | 79G9 Light Chain CDR2 Amino Acid Sequence |
| 106 | 79G9 Light Chain CDR3 Amino Acid Sequence |
| 107 | 79G9+ Heavy Chain FWR1 Nucleotide Sequence |
| 108 | 79G9+ Heavy Chain FWR2 Nucleotide Sequence |
| 109 | 79G9+ Heavy Chain FWR3 Nucleotide Sequence |
| 110 | 79G9+ Heavy Chain CDR1 Nucleotide Sequence |
| 111 | 79G9+ Heavy Chain CDR2 Nucleotide Sequence |
| 112 | 79G9+ Heavy Chain CDR3 Nucleotide Sequence |
| 113 | 79G9+ Heavy Chain FWR1 Amino Acid Sequence |
| 114 | 79G9+ Heavy Chain FWR2 Amino Acid Sequence |
| 115 | 79G9+ Heavy Chain FWR3 Amino Acid Sequence |
| 116 | 79G9+ Heavy Chain CDR1 Amino Acid Sequence |
| 117 | 79G9+ Heavy Chain CDR2 Amino Acid Sequence |
| 118 | 79G9+ Heavy Chain CDR3 Amino Acid Sequence |
| 119 | 79G9 Heavy Chain Nucleotide Sequence |
| 120 | 79G9 Heavy Chain FWR1 Nucleotide Sequence |
| 121 | 79G9 Heavy Chain FWR2 Nucleotide Sequence |
| 122 | 79G9 Heavy Chain FWR3 Nucleotide Sequence |
| 123 | 79G9 Heavy Chain CDR1 Nucleotide Sequence |
| 124 | 79G9 Heavy Chain CDR2 Nucleotide Sequence |
| 125 | 79G9 Heavy Chain CDR3 Nucleotide Sequence |
| 126 | 79G9 Heavy Chain Amino Acid Sequence |
| 127 | 79G9 Heavy Chain FWR1 Amino Acid Sequence |
| 128 | 79G9 Heavy Chain FWR2 Amino Acid Sequence |
| 129 | 79G9 Heavy Chain FWR3 Amino Acid Sequence |

TABLE 1-continued

Sequence ID numbers

| SEQ ID NO | Sequence Description |
|---|---|
| 130 | 79G9 Heavy Chain CDR1 Amino Acid Sequence |
| 131 | 79G9 Heavy Chain CDR2 Amino Acid Sequence |
| 132 | 79G9 Heavy Chain CDR3 Amino Acid Sequence |
| 133 | 154G12 Light Chain Nucleotide Sequence |
| 134 | 154G12 Light Chain Amino Acid Sequence |
| 135 | 154G12 Light Chain FWR1 Amino Acid Sequence |
| 136 | 154G12 Light Chain CDR1 Amino Acid Sequence |
| 137 | 154G12 Light Chain FWR2 Amino Acid Sequence |
| 138 | 154G12 Light Chain CDR2 Amino Acid Sequence |
| 139 | 154G12 Light Chain FWR3 Amino Acid Sequence |
| 140 | 154G12 Light Chain CDR3 Amino Acid Sequence |
| 141 | 154G12 Heavy Chain Nucleotide Sequence |
| 142 | 154G12 Heavy Chain Amino Acid Sequence |
| 143 | 154G12 Heavy Chain FWR1 Amino Acid Sequence |
| 144 | 154G12 Heavy Chain CDR1 Amino Acid Sequence |
| 145 | 154G12 Heavy Chain FWR2 Amino Acid Sequence |
| 146 | 154G12 Heavy Chain CDR2 Amino Acid Sequence |
| 147 | 154G12 Heavy Chain FWR3 Amino Acid Sequence |
| 148 | 154G12 Heavy Chain CDR3 Amino Acid Sequence |
| 149 | 100C9 Codon Optimized Light Chain Nucleotide Sequence |
| 150 | 100C9 Codon Optimized Light Chain Variable Domain Nucleotide Sequence |
| 151 | 100C9 Codon Optimized Light Chain FWR1 Nucleotide Sequence |
| 152 | 100C9 Codon Optimized Light Chain CDR1 Nucleotide Sequence |
| 153 | 100C9 Codon Optimized Light Chain FWR2 Nucleotide Sequence |
| 154 | 100C9 Codon Optimized Light Chain CDR2 Nucleotide Sequence |
| 155 | 100C9 Codon Optimized Light Chain FWR3 Nucleotide Sequence |
| 156 | 100C9 Codon Optimized Light Chain CDR3 Nucleotide Sequence |
| 157 | 100C9 Light Chain Variable Domain Nucleotide Sequence |
| 158 | 100C9 Light Chain Variable Domain Amino Acid Sequence |
| 159 | 100C9 Heavy Chain Variable Domain Nucleotide Sequence |
| 160 | 100C9 Heavy Chain Variable Domain Amino Acid Sequence |
| 161 | 100C9 Codon Optimized Light Chain Nucleotide Sequence (Minus Leader Sequence) |
| 162 | 100C9 Codon Optimized Heavy Chain Nucleotide Sequence (Minus Leader Sequence) |
| 163 | 100C9 Codon Optimized Heavy Chain Nucleotide Sequence |
| 164 | 100C9 Codon Optimized Heavy Chain Variable Domain Nucleotide Sequence |
| 165 | 100C9 Codon Optimized Heavy Chain FWR1 Nucleotide Sequence |
| 166 | 100C9 Codon Optimized Heavy Chain CDR1 Nucleotide Sequence |
| 167 | 100C9 Codon Optimized Heavy Chain FWR2 Nucleotide Sequence |
| 168 | 100C9 Codon Optimized Heavy Chain CDR2 Nucleotide Sequence |
| 169 | 100C9 Codon Optimized Heavy Chain FWR3 Nucleotide Sequence |
| 170 | 100C9 Codon Optimized Heavy Chain CDR3 Nucleotide Sequence |
| 171 | 79G9 Codon Optimized Light Chain Variable Domain Nucleotide Sequence |
| 172 | 79G9 Codon Optimized Heavy Chain Variable Domain Nucleotide Sequence |
| 173 | F10: Light Chain Variable Domain Nucleotide Sequence |
| 174 | F10 Light Chain Variable Domain Amino Acid Sequence |
| 175 | F10: Heavy Chain Variable Domain Nucleotide Sequence |
| 176 | F10 Heavy Chain Variable Domain Amino Acid Sequence |
| 177 | 79G9 Codon Optimized Light Chain Nucleotide Sequence |
| 178 | 154G12 Codon Optimized Light Chain Variable Domain Nucleotide Sequence |
| 179 | 79G9 Codon Optimized Light Chain FWR1 Nucleotide Sequence |
| 180 | 79G9 Codon Optimized Light Chain CDR1 Nucleotide Sequence |
| 181 | 79G9 Codon Optimized Light Chain FWR2 Nucleotide Sequence |
| 182 | 79G9 Codon Optimized Light Chain CDR2 Nucleotide Sequence |
| 183 | 79G9 Codon Optimized Light Chain FWR3 Nucleotide Sequence |
| 184 | 79G9 Codon Optimized Light Chain CDR3 Nucleotide Sequence |
| 185 | 79G9 Light Chain Nucleotide Sequence (Minus Leader Sequence) |
| 186 | 79G9 Light Chain Amino Acid Sequence (Minus Leader Sequence) |
| 187 | 79G9+ Heavy Chain Nucleotide Sequence (Minus Leader Sequence) |
| 188 | 79G9+ Heavy Chain Amino Acid Sequence (Minus Leader Sequence) |
| 189 | 79G9 Codon Optimized Light Chain Nucleotide Sequence (Minus Leader Sequence) |
| 190 | 79G9 Codon Optimized Heavy Chain Nucleotide Sequence (Minus Leader Sequence) |
| 191 | 79G9 Codon Optimized Heavy Chain Nucleotide Sequence |
| 192 | 154G12 Codon Optimized Heavy Chain Variable Domain Nucleotide Sequence |
| 193 | 79G9 Codon Optimized Heavy Chain FWR1 Nucleotide Sequence |
| 194 | 79G9 Codon Optimized Heavy Chain CDR1 Nucleotide Sequence |
| 195 | 79G9 Codon Optimized Heavy Chain FWR2 Nucleotide Sequence |
| 196 | 79G9 Codon Optimized Heavy Chain CDR2 Nucleotide Sequence |
| 197 | 79G9 Codon Optimized Heavy Chain FWR3 Nucleotide Sequence |
| 198 | 79G9 Codon Optimized Heavy Chain CDR3 Nucleotide Sequence |
| 199 | 79G9 Light Chain Variable Domain Nucleotide Sequence |
| 200 | 79G9 Light Chain Variable Domain Amino Acid Sequence |
| 201 | 79G9+ Heavy Chain Variable Domain Nucleotide Sequence |
| 202 | 79G9+ Heavy Chain Variable Domain Amino Acid Sequence |
| 203 | 79G9 Heavy Chain Variable Domain Nucleotide Sequence |
| 204 | 79G9 Heavy Chain Variable Domain Amino Acid Sequence |
| 205 | 154G12 Codon Optimized Light Chain Nucleotide Sequence |
| 206 | Leader 3 Nucleotide Sequence |
| 207 | 154G12 Codon Optimized Light Chain FWR1 Nucleotide Sequence |
| 208 | 154G12 Codon Optimized Light Chain CDR1 Nucleotide Sequence |
| 209 | 154G12 Codon Optimized Light Chain FWR2 Nucleotide Sequence |
| 210 | 154G12 Codon Optimized Light Chain CDR2 Nucleotide Sequence |
| 211 | 154G12 Codon Optimized Light Chain FWR3 Nucleotide Sequence |
| 212 | 154G12 Codon Optimized Light Chain CDR3 Nucleotide Sequence |
| 213 | 154G12 Light Chain Nucleotide Sequence (Minus Leader Sequence) |
| 214 | 154G12 Light Chain Amino Acid Sequence (Minus Leader Sequence) |
| 215 | 154G12 Heavy Chain Nucleotide Sequence (Minus Leader Sequence) |
| 216 | 154G12 Heavy Chain Amino Acid Sequence (Minus Leader Sequence) |
| 217 | 154G12 Codon Optimized Light Chain Nucleotide Sequence (Minus Leader Sequence) |
| 218 | 154G12 Codon Optimized Heavy Chain Nucleotide Sequence (Minus Leader Sequence) |
| 219 | 154G12 Codon Optimized Heavy Chain Nucleotide Sequence |
| 220 | Leader 4 Nucleotide Sequence |
| 221 | 154G12 Codon Optimized Heavy Chain FWR1 Nucleotide Sequence |
| 222 | 154G12 Codon Optimized Heavy Chain CDR1 Nucleotide Sequence |
| 223 | 154G12 Codon Optimized Heavy Chain FWR2 Nucleotide Sequence |
| 224 | 154G12 Codon Optimized Heavy Chain CDR2 Nucleotide Sequence |

TABLE 1-continued

Sequence ID numbers

| SEQ ID NO | Sequence Description |
| --- | --- |
| 225 | 154G12 Codon Optimized Heavy Chain FWR3 Nucleotide Sequence |
| 226 | 154G12 Codon Optimized Heavy Chain CDR3 Nucleotide Sequence |
| 227 | 154G12 Light Chain Variable Domain Nucleotide Sequence |
| 228 | 154G12 Light Chain Variable Domain Amino Acid Sequence |
| 229 | 154G12 Heavy Chain Variable Domain Nucleotide Sequence |
| 230 | 154G12 Heavy Chain Variable Domain Amino Acid Sequence |
| 231 | 79G9 Heavy Chain Nucleotide Sequence (Minus Leader Sequence) |
| 232 | 79G9 Heavy Chain Amino Acid Sequence (Minus Leader Sequence) |
| 233 | Primer 1015 |
| 234 | Primer 1020 |
| 235 | Primer 1321 |
| 236 | Primer 1461 |
| 237 | Primer 1530 |
| 238 | Primer 1578 |
| 239 | Primer 1582 |
| 240 | Primer 1730 |
| 241 | Primer 1731 |
| 242 | Primer 1732 |
| 243 | Primer 1733 |
| 244 | Primer 1734 |
| 245 | Primer 1735 |
| 246 | Primer 1736 |
| 247 | Primer 1737 |
| 248 | 100C9 Light Chain Nucleotide Sequence (Minus Leader Sequence) |
| 249 | 100C9 Light Chain Amino Acid Sequence (Minus Leader Sequence) |
| 250 | 100C9 Heavy Chain Nucleotide Sequence (Minus Leader Sequence) |
| 251 | 100C9 Heavy Chain Amino Acid Sequence (Minus Leader Sequence) |
| 252 | 154G12 Heavy Chain FWR1 Nucleotide Sequence |
| 253 | 154G12 Heavy Chain CDR1 Nucleotide Sequence |
| 254 | 154G12 Heavy Chain FWR2 Nucleotide Sequence |
| 255 | 154G12 Heavy Chain CDR2 Nucleotide Sequence |
| 256 | 154G12 Heavy Chain FWR3 Nucleotide Sequence |
| 257 | 154G12 Heavy Chain CDR3 Nucleotide Sequence |
| 258 | 154G12 Light Chain FWR1 Nucleotide Sequence |
| 259 | 154G12 Light Chain CDR1 Nucleotide Sequence |
| 260 | 154G12 Light Chain FWR2 Nucleotide Sequence |
| 261 | 154G12 Light Chain CDR2 Nucleotide Sequence |
| 262 | 154G12 Light Chain FWR3 Nucleotide Sequence |
| 263 | 154G12 Light Chain CDR3 Nucleotide Sequence |
| 264 | Primer 1577 |
| 265 | Primer 1584 |

Various terms relating to the methods and other aspects of the present invention are used throughout the specification and claims. Such terms are to be given their ordinary meaning in the art unless otherwise indicated. Other specifically defined terms are to be construed in a manner consistent with the definitions provided herein.

The following abbreviations are used throughout the specification. SEB, *staphylococcus* enterotoxin B; PBMC, peripheral blood mononuclear cells; BSA, bovine serum albumin; TT, tetanus toxoid; HEL, hen egg lysozyme; CAB, chicken albumin; BGG, bovine gamma globulin; TCR, T-cell receptor; CDR, complementarity determining region; FWR, framework region.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Substantially the same" with respect to nucleic acid or amino acid sequences, means at least about 65% identity between two or more sequences. Preferably, the term refers to at least about 70% identity between two or more sequences, more preferably at least about 75% identity, more preferably at least about 80% identity, more preferably at least about 85% identity, more preferably at least about 90% identity, more preferably at least about 91% identity, more preferably at least about 92% identity, more preferably at least about 93% identity, more preferably at least about 94% identity, more preferably at least about 95% identity, more preferably at least about 96% identity, more preferably at least about 97% identity, more preferably at least about 98% identity, and more preferably at least about 99% or greater identity.

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

A cell has been "transformed" or "transfected" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62.

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody can be within the cytoplasm of the cell, and/or into the extracellular milieu such as the growth medium of a cell culture.

The terms "treating" or "treatment" refer to any success or indicia of success in the attenuation or amelioration of an injury, pathology or condition, including any objective or subjective parameter such as abatement, remission, diminishing of symptoms or making the injury, pathology, or condition more tolerable to the patient, slowing in the rate of degeneration or decline, making the final point of degeneration less debilitating, improving a subject's physical or mental well-being, or prolonging the length of survival. The treatment or amelioration of symptoms can be based on objective or subjective parameters; including the results of a physical examination, neurological examination, and/or psychiatric evaluations.

"Effective amount" and "therapeutically effective amount" are used interchangeably herein, and refer to an amount of an antibody or composition, as described herein effective to achieve a particular biological result such as, but not limited to, biological results disclosed, described, or exemplified herein. Such results may include, but are not limited to, the treatment of disease mediated by exposure to *Staphylococcus* enterotoxin B, as determined by any means suitable in the art.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "inhibition of mitogenesis in vitro" means a decrease in the number of cells, in culture, by about 5%, preferably about 10%, more preferably about 20%, more preferably about 30%, more preferably about 40%, more preferably about 50%, more preferably about 60%, more preferably about 70%, more preferably about 80%, more preferably about 90%, and most preferably about 100%. In vitro inhibition of mitogenic cell growth may be measured by assays known in the art.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting.

*Staphylococcus* toxins are a major virulence factor for infections with *Staphylococcus* bacteria. Exposure to such toxins, whether by ingestion of contaminated food or water, or by inhalation, for example, by means of a terrorist attack, can produce rapid-onset debilitating illness. To date, effective treatments for exposure to *Staphylococcus* toxins have been slow in coming. It has been discovered in accordance with the present invention that toxins such as *Staphylococcus* enterotoxin B can be neutralized with antibodies.

Accordingly, in one aspect, the invention features isolated antibodies and antigen-binding fragments thereof that specifically bind to *Staphylococcus* enterotoxins, and more specifically, to *Staphylococcus* enterotoxin B. The antibodies can be polyclonal or monoclonal, or can be derivatives or fragments of antibodies that retain specificity for Staphylococcal enterotoxins. The general structure of an antibody molecule comprises an antigen binding domain, which includes heavy and light chains, and the Fc domain, which serves a variety of functions, including complement fixation.

There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM isotypes, respectively. The inventive antibodies include all isotypes and synthetic multimers of the four-chain immunoglobulin structure. The inventive antibodies also include the IgY isotype generally found in hen or turkey serum and hen or turkey egg yolk. Antibodies noncovalently, specifically, and reversibly bind an antigen.

Antigen-binding fragments comprise portions of intact antibodies that retain antigen-binding specificity of the parent antibody molecule. For example, antigen-binding fragments can comprise at least one variable region (either a heavy chain or light chain variable region). Examples of suitable antigen-binding fragments include, without limitation antibodies with polyepitopic specificity, bispecific antibodies, diabodies, and single-chain molecules, as well as Fab, F(ab')2, Fd, Fabc, and Fv molecules, single chain (Sc) antibodies, individual antibody light chains, individual antibody heavy chains, chimeric fusions between antibody chains and other molecules, heavy chain monomers or dimers, light chain monomers or dimers, dimers consisting of one heavy and one light chain, and the like. All antibody isotypes can be used to produce antigen-binding fragments. Antigen-binding fragments can be recombinantly produced.

The antibodies and antigen-binding fragments of the invention can be derived from any species. For example, the antibodies and antigen-binding fragments can be mouse, rat, goat, horse, swine, bovine, chicken, rabbit, donkey, human, and the like. For use in the treatment of humans, non-human derived antibodies and antigen-binding fragments can be structurally altered to be less antigenic upon administration to a human patient.

In some embodiments of the invention, the antibodies are chimeric antibodies. Chimeric antibodies and methods to produce them are well known and established in the art. As used herein, the term "chimeric antibody" means an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a mouse antigen binding domain with a human Fc or other such structural domain.

In some embodiments, the antibodies are humanized antibodies. Humanized antibodies can be chimeric immunoglobulins, immunoglobulin chains or fragments thereof (such as Fv, Fab, Fab', F(ab')2 or other antigen-binding subsequences of antibodies) that contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FWR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FWR regions are those of a human immunoglobulin sequence. The humanized antibody optimally also will comprise at least a portion of an immunoglobulin constant region (Fc), typically that of a human immunoglobulin. For further details, see Jones et al. (1986) Nature 321:522-5; Reichmann et al. (1988) Nature 332:323-9; and, Presta (1992) Curr. Op. Struct. Biol. 2:593-6.

In preferred aspects of the invention, the antibodies are fully human. As used herein, the term "human antibody" means that the antibody is either solely from human origin or any antibody in which the variable and constant domain sequences are human sequences. The term encompasses antibodies with sequences derived from (i.e., that utilize) human genes, but which have been changed, e.g., to decrease possible immunogenicity, increase affinity, eliminate cysteines that may cause undesirable folding, etc. The term encompasses such antibodies produced recombinantly in non-human cells, which may impart glycosylation not typical of human cells.

The antibodies of the invention can be labeled or otherwise conjugated to various chemical or biomolecule moieties, for example, for therapeutic or diagnostic applications. The moieties can be cytotoxic, for example, bacterial toxins, viral toxins, radioisotopes, and the like. The moieties can be detectable labels, for example, fluorescent labels, radiolabels, biotin, and the like.

Those of skill in the art will recognize that antibody specificity is primarily determined by the six CDR regions, especially H chain CDR3 (Kala et al. (2002) J. Biochem. 132:535-41; Morea et al. (1998) J. Mol. Biol. 275:269-94; and, Chothia et al. (1987) J. Mol. Biol. 196:901-17). Antibody framework regions, however, can play a role in antigen-antibody interactions (Panka et al. (1988) Proc. Natl. Acad. Sci. USA 85:3080-4), particularly with respect to their role in conformation of CDR loops (Foote et al. (1992) J. Mol. Biol. 224:487-99). Thus, the inventive antibodies can comprise any combination of H or L chain CDR or FWR regions that confer antibody specificity for SEB. Domain shuffling experiments, which are routinely carried out in the art (Jirholt et al. (1998) Gene 215:471-6; Soderlind et al. (2000) Nature Biotechnology 18:852-6), can be employed to generate antibodies that specifically bind SEB according to the specifications described and exemplified herein. Antibodies generated by such domain shuffling experiments are within the scope of the present invention.

Accordingly, in some embodiments, the antibodies comprise a heavy chain CDR1 amino acid sequence substantially the same as or identical to SEQ ID NO: 68, 92, 116, 130, or 144. In some embodiments, the antibodies comprise a heavy chain CDR2 amino acid sequence substantially the same as or identical to SEQ ID NO: 69, 93, 117, 131, or 146. In some particularly preferred embodiments, the antibodies comprise a heavy chain CDR3 amino acid sequence substantially the same as or identical to SEQ ID NO: 39, 40, 70, 94, 118, 132, or 148. In some embodiments, the antibodies comprise a light chain CDR1 amino acid sequence substantially the same as or identical to SEQ ID NO: 56, 80, 104, or 136. In some embodiments, the antibodies comprise a light chain CDR2 amino acid sequence substantially the same as or identical to SEQ ID NO: 57, 81, 105, or 138. In some embodiments, the antibodies comprise a light chain CDR3 amino acid sequence substantially the same as or identical to SEQ ID NO: 58, 82, 106, or 140. In some embodiments, the antibodies comprise a heavy chain FWR1 amino acid sequence substantially the same as or identical to SEQ ID NO: 65, 89, 113, 127, or 143. In some embodiments, the antibodies comprise a heavy chain FWR2 amino acid sequence substantially the same as or identical to SEQ ID NO: 66, 90, 114, 128, or 145. In some embodiments, the antibodies comprise a heavy chain FWR3 amino acid sequence substantially the same as or identical to SEQ ID NO: 67, 91, 115, 129, or 147. In some embodiments, the antibodies comprise a light chain FWR1 amino acid sequence substantially the same as or identical to SEQ ID NO: 53, 77, 101, or 135. In some embodiments, the antibodies comprise a light chain FWR2 amino acid sequence substantially the same as or identical to SEQ ID NO: 54, 78, 102, or 137. In some embodiments, the antibodies comprise a light chain FWR3 amino acid sequence substantially the same as or identical to SEQ ID NO: 55, 79, 103, or 139. FIGS. 14 and 16 show examples of nucleic acid sequences that can encode the heavy and light chain CDR1-3 and FWR1-3 described in this paragraph.

The inventive antibodies can comprise a heavy chain that comprises the amino acid sequence of SEQ ID NO: 30. This heavy chain can be encoded by the nucleic acid sequence that comprises SEQ ID NO: 29. The inventive antibodies can comprise a heavy chain that comprises the amino acid sequence of SEQ ID NO: 251. This heavy chain can be encoded by a nucleic acid sequence that comprises SEQ ID NO: 250 or 162. The inventive antibodies can comprise a heavy chain that comprises the amino acid sequence of SEQ ID NO: 188. This heavy chain can be encoded by the nucleic acid sequence that comprises SEQ ID NO: 37. The inventive antibodies can comprise a heavy chain that comprises the amino acid sequence of SEQ ID NO: 232. This heavy chain can be encoded by a nucleic acid sequence that comprises SEQ ID NO: 231 or 190. The inventive antibodies can comprise a heavy chain that comprises the amino acid sequence of SEQ ID NO: 216. This heavy chain can be encoded by a nucleic acid sequence that comprises SEQ ID NO: 215 or 218.

The invention features isolated human antibodies and antigen-binding fragments that specifically bind to, and preferably neutralize *Staphylococcus* enterotoxin B. The antibodies and antigen-binding fragments can comprise a heavy chain CDR3 having SEQ ID NO: 39, 40, 70, 94, 118, 132, or 148. The antibodies and antigen-binding fragments can comprise heavy chain CDR1, CDR2, and CDR3 of SEQ ID NOs: 68, 69, and 70; SEQ ID NOs: 116, 117, and 118; SEQ ID NOs: 130, 131, and 132; SEQ ID NOs: 92, 93, and 94; or SEQ ID NOs: 144, 146, and 148. In some preferred embodiments, the antibodies and antigen-binding fragments can comprise a heavy chain variable domain of SEQ ID NO: 160, 176, 202, 204, or 230. In some preferred embodiments, the antibodies and antigen-binding fragments can comprise a heavy chain having SEQ ID NO: 30, 34, 38, 126, 142, 216, 232, or 251.

In some preferred embodiments, the antibodies and antigen-binding fragments can comprise light chain CDR1, CDR2, and CDR3 of SEQ ID NOs: 56, 57, and 58; SEQ ID NOs: 104, 105, and 106; SEQ ID NOs: 80, 81, and 82; or SEQ ID NOs: 136, 138, and 140. In some preferred embodiments, the antibodies and antigen-binding fragments can comprise a light chain variable domain of SEQ ID NO: 158, 174, 200, or 228. In some preferred embodiments, the antibodies and antigen-binding fragments can comprise a light chain having SEQ ID NO: 28, 32, 36, 134, 186, 214, or 249.

In some preferred embodiments, the antibodies and antigen-binding fragments can comprise a heavy chain having CDR1 of SEQ ID NO: 68, 92, 116, 130, or 144; CDR2 of SEQ ID NO: 69, 93, 117, 131, or 146; and CDR3 of SEQ ID NO: 70, 94, 118, 132, or 148; and a light chain having CDR1 of SEQ ID NO: 56, 80, 104, or 136; CDR2 of SEQ ID NO: 57, 81, 105, or 138; and CDR3 of SEQ ID NO: 58, 82, 106, or 140. In some preferred embodiments, the antibodies and antigen-binding fragments can comprise a heavy chain variable domain having SEQ ID NO: 160, 176, 202, 204, or 230 and a light chain variable domain having SEQ ID NO: 158, 174, 200, 228.

In preferred embodiments, the antibodies and antigen-binding fragments of the invention comprise a heavy chain having CDR1 of SEQ ID NO: 68, CDR2 of SEQ ID NO: 69, and CDR3 of SEQ ID NO: 70 and a light chain having CDR1 of SEQ ID NO: 56, CDR2 of SEQ ID NO: 57, and CDR3 of SEQ ID NO: 58. In preferred embodiments, the antibodies and antigen-binding fragments of the invention comprise a heavy chain having a variable domain of SEQ ID NO: 176 and a light chain having a variable domain of SEQ ID NO: 174. In preferred embodiments, the antibodies and antigen-binding fragments of the invention comprise a heavy chain having SEQ ID NO: 30 and a light chain having SEQ ID NO: 28.

In preferred embodiments, the antibody and antigen-binding fragments of the invention comprise a heavy chain having CDR1 of SEQ ID NO: 116, CDR2 of SEQ ID NO: 117, and CDR3 of SEQ ID NO: 118, and a light chain having CDR1 of SEQ ID NO: 104, CDR2 of SEQ ID NO: 105, and CDR3 of SEQ ID NO: 106. In preferred embodiments, the antibodies and antigen-binding fragments of the invention comprise a heavy chain having a variable domain of SEQ ID NO: 202 and a light chain having a variable domain of SEQ ID NO: 200. In preferred embodiments, the antibodies and antigen-binding fragments of the invention comprise a heavy chain having SEQ ID NO: 188 and a light chain having SEQ ID NO: 186.

In preferred embodiments, the antibodies and antigen-binding fragments of the invention comprise a heavy chain having CDR1 of SEQ ID NO: 130, CDR2 of SEQ ID NO: 131, and CDR3 of SEQ ID NO: 132, and a light chain having CDR1 of SEQ ID NO: 104, CDR2 of SEQ ID NO: 105, and CDR3 of SEQ ID NO: 106. In preferred embodiments, the antibodies and antigen-binding fragments of the invention comprise a heavy chain having a variable domain of SEQ ID NO: 204 and a light chain having a variable domain of SEQ ID NO: 200. In preferred embodiments, the antibodies and antigen-binding fragments of the invention comprise a heavy chain having SEQ ID NO: 232 and a light chain having SEQ ID NO: 186.

In preferred embodiments, the antibodies and antigen-binding fragments of the invention comprise a heavy chain having CDR1 of SEQ ID NO: 92, CDR2 of SEQ ID NO: 93, and CDR3 of SEQ ID NO: 94, and a light chain having CDR1 of SEQ ID NO: 80, CDR2 of SEQ ID NO: 81, and CDR3 of SEQ ID NO: 82. In preferred embodiments, the antibodies and antigen-binding fragments of the invention comprise a heavy chain having a variable domain of SEQ ID NO: 160 and a light chain having a variable domain of SEQ ID NO: 158. In preferred embodiments, the antibodies and antigen-binding fragments of the invention comprise a heavy chain having SEQ ID NO: 251 and a light chain having SEQ ID NO: 249.

In preferred embodiments, the antibodies and antigen-binding fragments of the invention comprise a heavy chain having CDR1 of SEQ ID NO: 144, CDR2 of SEQ ID NO: 146, and CDR3 of SEQ ID NO: 148, and a light chain having CDR1 of SEQ ID NO: 136, CDR2 of SEQ ID NO: 138, and CDR3 of SEQ ID NO: 140. In preferred embodiments, the antibodies and antigen-binding fragments of the invention comprise a heavy chain having a variable domain of SEQ ID NO: 230 and a light chain having a variable domain of SEQ ID NO: 228. In preferred embodiments, the antibodies and antigen-binding fragments of the invention comprise a heavy chain having SEQ ID NO: 216 and a light chain having SEQ ID NO: 214.

The antibodies and antigen-binding fragments are high affinity antibodies and antigen-binding fragments, and can have an affinity of less than about $1\times10^{-8}$ M, preferably less than about $2\times10^{-8}$ M, and more preferably less than about $3\times10^{-8}$ M. Preferably, the antibodies are monoclonal antibodies, and more preferably, are human monoclonal antibodies. Cells that express such antibodies and antigen-binding fragments, such as hybridoma cells and expression cells, are also provided.

The inventive antibodies can comprise a light chain that comprises the amino acid sequence of SEQ ID NO: 28. This light chain can be encoded by the nucleic acid sequence that comprises SEQ ID NO: 27. The inventive antibodies can comprise a light chain that comprises the amino acid sequence of SEQ ID NO: 249. This light chain can be encoded by a nucleic acid sequence that comprises SEQ ID NO: 31, 248, 161, or 149. The inventive antibodies can comprise a light chain that comprises the amino acid sequence of SEQ ID NO: 186. This light chain can be encoded by a nucleic acid sequence that comprises SEQ ID NO: 185 or 189. The inventive antibodies can comprise a light chain that comprises the amino acid sequence of SEQ ID NO: 214. This light chain can be encoded by a nucleotide sequence comprising SEQ ID NO: 213 or 217.

It is to be understood that, because of the natural sequence variation likely to exist among heavy and light chains and the genes encoding them, one skilled in the art would expect to find some level of variation within the amino acid sequences or the genes encoding them, while still maintaining the unique binding properties (e.g., specificity and affinity) of the antibodies of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The antibodies of the invention thus include variants having single or multiple amino acid substitutions, deletions, additions, or replacements that retain the biological properties (e.g., binding affinity or immune effector activity) of the antibodies of the invention.

The skilled person can produce variants having single or multiple amino acid substitutions, deletions, additions or replacements. These variants may include, inter alias (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies of the invention may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

In some preferred embodiments, the antibodies can comprise a heavy chain that comprises the amino acid sequence of SEQ ID NO: 30 and a light chain that comprises the amino acid sequence of SEQ ID NO: 28. In some preferred embodiments, the antibodies can comprise a heavy chain that comprises the amino acid sequence of SEQ ID NO: 251 and a light chain that comprises the amino acid sequence of SEQ ID NO: 249. In some preferred embodiments, the antibodies can comprise a heavy chain that comprises the amino acid sequence of SEQ ID NO: 188 and a light chain that comprises the amino acid sequence of SEQ ID NO: 186. In some preferred embodiments, the antibodies can comprise a heavy chain that comprises the amino acid sequence of SEQ ID NO: 232 and a light chain that comprises the amino acid sequence of SEQ ID NO: 186. In some preferred embodiments, the antibodies can comprise a heavy chain that comprises the amino acid sequence of SEQ ID NO: 216 and a light chain that comprises the amino acid sequence of SEQ ID NO: 214. Those of skill in the art will recognize, however, that in some cases, the pairing of a given heavy with various light chains, or the pairing of a given light chain with various heavy chains will produce antibodies with the same or better specificity and/or affinity than the native combination. Accordingly, the invention is not limited to the preferred combinations of H and L chain pairs, and the inventive antibodies thus encompass different combinations of H and L chain pairs, including without limitation, the H and L chains described herein, or other H or L chains that would be known to those of skill in the art, or otherwise experimentally determined to be compatible with the H and L chains described herein in order to obtain specific and high affinity binding to SEB.

The antibodies of the invention have binding affinities (in M) for target antigen that include a dissociation constant ($K_D$) of less than $1\times10^{-2}$. In some embodiments, the $K_D$ is less than $1\times10^{-3}$. In other embodiments, the $K_D$ is less than $1\times10^{-4}$. In some embodiments, the $K_D$ is less than $1\times10^{-5}$. In still other embodiments, the $K_D$ is less than $1\times10^{-6}$. In other embodiments, the $K_D$ is less than $1\times10^{-7}$. In other embodiments, the $K_D$ is less than $1\times10^{-8}$, $2\times10^{-8}$, or $3\times10^{-8}$. In other embodiments, the $K_D$ is less than $1\times10^{-9}$. In other embodiments, the $K_D$ is less than $1\times10^{-10}$, $2\times10^{-10}$, or $3\times10^{-10}$. In still other embodiments, the $K_D$ is less than $1\times10^{-11}$. In some embodiments, the $K_D$ is less than $1\times10^{-12}$. In other embodiments, the $K_D$ is less than $1\times10^{-13}$. In other embodiments, the $K_D$ is less than $1\times10^{-14}$. In still other embodiments, the $K_D$ is less than $1\times10^{-15}$.

The inventive antibodies can be modified, e.g., by the covalent attachment of any type of molecule to the antibody such that covalent attachment does not prevent the antibody from binding to its epitope. Examples of suitable modifications include, but are not limited to glycosylation, acetylation, pegylation, phosphorylation, amidation, and the like. The antibodies of the invention may themselves be derivatized by known protecting/blocking groups, proteolytic cleavage, linkage to a cellular ligand or other proteins, and the like. The antibodies of the invention may have post-translational moieties that improve upon antibody activity or stability. These moieties include sulfur, methyl, carbohydrate, phosphorus as well as other chemical groups commonly found on immunoglobulin molecules. Furthermore, the antibodies of the invention may contain one or more non-classical amino acids.

Nucleotide sequences that encode antibodies of the invention are provided. Nucleic acids of the invention include but are not limited to genomic DNA, DNA, cDNA, RNA, double- and single-stranded nucleic acids, and complementary sequences thereof.

Preferred polynucleotides of the invention include nucleic acid sequences encoding the heavy chain amino acid sequence of SEQ ID NO: 30, 34, 38, 126, 142, 216, 232, or 251. The nucleic acid sequences encoding the light chain amino acid sequence of SEQ ID NO: 28, 32, 36, 134, 186, 214, or 249. Other preferred polynucleotides of the invention include nucleic acid sequences encoding the heavy chain variable domain amino acid sequence of SEQ ID NO: 160, 176, 202, 204, or 230. The nucleic acid sequences encoding the light chain variable domain amino acid sequence of SEQ ID NO: 158, 174, 200, or 228. Other preferred polynucleotides include nucleic acid sequences encoding the antibody CDR3 domains of SEQ ID NOs: 39, 40, 41, 42, 58, 70, 82, 94, 106, 118, 132, 140, or 148; CDR2 domains of SEQ ID NO: 57, 69, 81, 93, 105, 117, 131, 138, or 146. and CDR1 domains of SEQ ID NO: 56, 68, 80, 92, 104, 116, 130, 136, and 144.

Some preferred examples of polynucleotides encoding the amino acid sequences of the invention include heavy chain polynucleotides of SEQ ID NOs: 29, 33, 37, 119, 141, 162, 163, 190, 191, 215, 218, 219, 231, and 250; and light chain polynucleotides of SEQ ID NOs: 27, 31, 35, 133, 149, 161, 177, 185, 189, 205, 213, 217, and 248. Other preferred examples of polynucleotides encoding the amino acid sequences of the invention include heavy chain variable domains of SEQ ID NOs: 159, 164, 172, 175, 192, 201, 203, and 229; and light chain variable domains of SEQ ID NOs: 150, 157, 171, 173, 178, 199, and 227. Other preferred examples of polynucleotides encoding the amino acid sequences of the invention include heavy chain CDR1 domains of SEQ ID NOs: 62, 86, 110, 123, 166, 194, 222, and 253; CDR2 domains of SEQ ID NO: 63, 87, 111, 124, 168, 196, 224, and 255; and CDR3 domains of SEQ ID NO: 64, 88, 112, 125, 170, 198, 212, and 257; and light chain CDR1 domains of SEQ ID NO: 50, 74, 98, 152, 180, 208, and 259; CDR2 domains of SEQ ID NO: 51, 75, 99, 154, 182, 210, and 261; and CDR3 domains of SEQ ID NO: 52, 76, 100, 156, 184, 212, and 263. While the polynucleotide sequences described here and elsewhere in the specification provide examples of preferred embodiments of the invention, those of skill in the art will recognize that the degenerate nature of the genetic code provides numerous polynucleotides that will encode the antibodies and antibody fragments of the invention. The invention also features polynucleotides that encode antibodies and antigen-binding fragments that specifically bind to *Staphylococcus* enterotoxin B. In some preferred embodiments, the polynucleotides encode an antibody or antigen-binding fragment having heavy chain CDR1, CDR2, and CDR3 of SEQ ID NOs: 68, 69, and 70. For example, the polynucleotide may comprise SEQ ID NOs: 62, 63, and 64. In some preferred embodiments, the polynucleotides encode an antibody or antigen-binding fragment having heavy chain CDR1, CDR2, and CDR3 of SEQ ID NOs: 116, 117, and 118. For example, the polynucleotide may comprise SEQ ID NOs: 110, 111, and 112. In some preferred embodiments, the polynucleotides encode an antibody or antigen-binding fragment having heavy chain CDR1, CDR2, and CDR3 of SEQ ID NOs: 130, 131, and 132. For example, the polynucleotide may comprise SEQ ID NOs: 123 or 194, 124 or 196, and 125 or 198. In some preferred embodiments, the polynucleotides encode an antibody or antigen-binding fragment having heavy chain CDR1, CDR2, and CDR3 of SEQ ID NOs: 92, 93, and 94. For example, the polynucleotide may comprise SEQ ID NOs: 86 or 166, 87 or 168, and 88 or 170. In some preferred embodiments, the polynucleotides encode an antibody or antigen-binding fragment having heavy chain CDR1, CDR2, and CDR3 of SEQ ID NOs: 144, 146, and 148. For example, the polynucleotide may comprise SEQ ID NOs: 253 or 222, 255 or 224, and 257 or 226.

In some preferred embodiments, the polynucleotides encode an antibody or antigen-binding fragment having light chain CDR1, CDR2, and CDR3 of SEQ ID NOs: 56, 57, and 58. For example, the polynucleotide may comprise SEQ ID NOs: 50, 51, and 52. In some preferred embodiments, the polynucleotides encode an antibody or antigen-binding fragment having light chain CDR1, CDR2, and CDR3 of SEQ ID NOs: 104, 105, and 106. For example, the polynucleotide may comprise SEQ ID NOs: 98 or 180, 99 or 182, and 100 or 184. In some preferred embodiments, the polynucleotides encode an antibody or antigen-binding fragment having light chain CDR1, CDR2, and CDR3 of SEQ ID NOs: 80, 81, and 82. For example, the polynucleotide may comprise SEQ ID NOs: 74 or 152, 75 or 154, and 76 or 156. In some preferred embodiments, the polynucleotides encode an antibody or antigen-binding fragment having light chain CDR1, CDR2, and CDR3 of SEQ ID NOs: 136, 138, and 140. For example, the polynucleotide may comprise SEQ ID NOs: 259 or 208, 261 or 210, and 263 or 212.

In some preferred embodiments, the antibody or antigen-binding fragment heavy chain variable domain is encoded by a polynucleotide comprising SEQ ID NO: 159, 164, 172, 175, 192, 201, 203, or 229. In some preferred embodiments, the heavy chain sequence is encoded by a polynucleotide comprising SEQ ID NO: 29, 33, 37, 119, 141, 162, 163, 190, 191, 215, 218, 219, 231, or 250. In some preferred embodiments, the polynucleotides encode an antibody or antigen-binding fragment having heavy chain variable domain of SEQ ID NO: 160. For example, the polynucleotide may comprise SEQ ID NO: 159 or 164. In some preferred embodiments, the polynucleotides encode an antibody or antigen-binding fragment having heavy chain variable domain of SEQ ID NO: 176. For example, the polynucleotide may comprise SEQ ID NO: 175. In some preferred embodiments, the polynucleotides encode an antibody or antigen-binding fragment having heavy chain variable domain of SEQ ID NO: 202. For example, the polynucleotide may comprise SEQ ID NO: 201. In some preferred embodiments, the polynucleotides encode an antibody or antigen-binding fragment having heavy chain variable domain of SEQ ID NO: 204. For example the polynucleotide may comprise SEQ ID NO: 172 or 203. In some preferred embodiments, the polynucleotides encode an antibody or antigen-binding fragment having heavy chain variable domain of SEQ ID NO: 230. For example the polynucleotide may comprise SEQ ID NO: 192 or 229.

In some preferred embodiments, the antibody and antigen-binding fragment light chain CDR1, CDR2, and CDR3 are encoded by polynucleotides comprising SEQ ID NOs: 50, 51, and 52; SEQ ID NOs: 98, 99, and 100; SEQ ID NOs: 74, 75, and 76; SEQ ID NOs: 259, 261, and 263; SEQ ID NOs: 180, 182, and 184; SEQ ID NOs: 152, 154, and 156; or SEQ ID NOs: 208, 210, and 212. In some preferred embodiments, the antibody and antigen-binding fragment light chain variable domain is encoded by a polynucleotide comprising SEQ ID NO: 150, 157, 171, 173, 178, 199, or 227.

In some preferred embodiments, the polynucleotides encode an antibody or antigen-binding fragment having a light chain variable domain of SEQ ID NO: 158. For example, the polynucleotide may comprise SEQ ID NO: 150 or 157. In some preferred embodiments, the polynucleotides encode an antibody or antigen-binding fragment having a light chain variable domain of SEQ ID NO: 174. For example, the polynucleotide may comprise SEQ ID NO: 173. In some preferred embodiments, the polynucleotides encode an antibody or antigen-binding fragment having a light chain variable domain of SEQ ID NO: 200. For example, the polynucleotide may comprise SEQ ID NO: 171 or 199. In some preferred embodiments, the polynucleotides encode an antibody or antigen-binding fragment having a light chain variable domain of SEQ ID NO: 228. For example the polynucleotide may comprise SEQ ID NO: 178 or 227. In some preferred embodiments, the antibody and antigen-binding fragment light chain sequence is encoded by a polynucleotide comprising SEQ ID NO: 27, 31, 35, 133, 149, 161, 177, 185, 189, 205, 213, 217, or 248.

In some preferred embodiments, the polynucleotides encode an antibody or antigen-binding fragment having heavy chain CDR1, CDR2, and CDR3; and light chain CDR1, CDR2, and CDR3 of SEQ ID NOs: 68, 69, and 70; and 56, 57, and 58; respectively. For example, the polynucleotide may comprise SEQ ID NOs: 62, 63, and 64; and 50, 51, and 52; respectively. In some preferred embodiments, the polynucleotides encode an antibody or antigen-binding fragment having heavy chain CDR1, CDR2, and CDR3; and light chain CDR1, CDR2, and CDR3 of SEQ ID NOs: 116, 117, and 118; and 104, 105, and 106; respectively. For example, the polynucleotide may comprise SEQ ID NOs: 110, 111, and 112; and 98 or 180, 99 or 182, and 100 or 184; respectively. In some preferred embodiments, the polynucleotides encode an antibody or antigen-binding fragment having heavy chain CDR1, CDR2, and CDR3; and light chain CDR1, CDR2, and CDR3 of SEQ ID NOs: 130, 131, and 132; and 104, 105, and 106; respectively. For example, the polynucleotide may comprise SEQ ID NOs: 123 or 194, 124 or 196, and 125 or 198; and 98 or 180, 99 or 182, and 100 or 184; respectively. In some preferred embodiments, the polynucleotides encode an antibody or antigen-binding fragment having heavy chain CDR1, CDR2, and CDR3; and light chain CDR1, CDR2, and CDR3 of SEQ ID NOs: 92, 93, and 94; and 80, 81, and 82; respectively. For example, the polynucleotide may comprise SEQ ID NOs: 86 or 166, 87 or 168, and 88 or 170; and 74 or 152, 75 or 154, and 76 or 156; respectively. In some preferred embodiments, the polynucleotides encode an antibody or antigen-binding fragment having heavy chain CDR1, CDR2, and CDR3; and light chain CDR1, CDR2, and CDR3 of SEQ ID NOs: 144, 146, and 148; and 136, 138, and 140; respectively. For example, the polynucleotide may comprise SEQ ID NOs: 253 or 222, 255 or 224, and 257 or 226; and 259 or 208, 261 or 210, and 263 or 212; respectively.

In some preferred embodiments, the polynucleotides encode an antibody or antigen-binding fragment having a heavy chain variable domain and a light chain variable domain of SEQ ID NOs: 176 and 174. For example, the polynucleotide may comprise SEQ ID NO: 175 and 173. In some preferred embodiments, the polynucleotides encode an antibody or antigen-binding fragment having a heavy chain variable domain and a light chain variable domain of SEQ ID NOs: 202 and 200. For example, the polynucleotide may comprise SEQ ID NO: 201 and 199 or 171. In some preferred embodiments, the polynucleotides encode an antibody or antigen-binding fragment having a heavy chain variable domain and a light chain variable domain of SEQ ID NOs: 204 and 200. For example, the polynucleotide may comprise SEQ ID NO: 203 or 172 and 199 or 171. In some preferred embodiments, the polynucleotides encode an antibody or antigen-binding fragment having a heavy chain variable domain and a light chain variable domain of SEQ ID NOs: 160 and 158. For example, the polynucleotide may comprise SEQ ID NO: 159 or 164 and 157 or 150. In some preferred embodiments, the polynucleotides encode an antibody or antigen-binding fragment having a heavy chain variable domain and a light chain variable domain of SEQ ID NOs: 230 and 228. For example, the polynucleotide may comprise SEQ ID NO: 229 or 192 and 227 or 178.

In some preferred embodiments, the polynucleotide encoding the antibodies and antigen-binding fragments can comprise a heavy chain having CDR1 of SEQ ID NO: 62, 86, 110, 123, 166, 194, 222, or 253; CDR2 of SEQ ID NO: 63, 87, 111, 124, 168, 196, 224, or 255; and CDR3 of SEQ ID NO: 64, 88, 112, 125, 170, 198, 212, or 257; and a light chain having CDR1 of SEQ ID NO: 50, 74, 98, 152, 180, 208, or 259; CDR2 of SEQ ID NO: 51, 75, 99, 154, 182, 210, or 261; and CDR3 of SEQ ID NO: 52, 76, 100, 156, 184, 212, or 263. In some preferred embodiments, the polynucleotide encoding the antibodies and antigen-binding fragments can comprise a heavy chain variable domain having SEQ ID NO: 159, 164, 172, 175, 192, 201, 203, or 229 and a light chain variable domain having SEQ ID NO: 150, 157, 171, 173, 178, 199, or 227. In some preferred embodiments, the polynucleotide encoding the antibodies and antigen-binding fragments can comprise a heavy chain sequence of SEQ ID NO: 29, 33, 37, 119, 141, 162, 163, 190, 191, 215, 218, 219, 231, or 250 and a light chain sequence of SEQ ID NO: 27, 31, 35, 133, 149, 161, 177, 185, 189, 205, 213, 217, or 248. Vectors comprising such polynucleotides are also provided.

In some embodiments, polynucleotides of the invention (and the peptides they encode) include a leader sequence. Any leader sequence known in the art may be employed. The leader sequence may include but is not limited to a restriction site and/or a translation start site. In some preferred embodiments, the leader sequence has the nucleic acid sequence

```
                                          (SEQ ID NO: 43)
ATGGGATGGAGCTGTATCATCCTCTTCTTGGTAGCAACAGCTACAGGTGT

ACACAGC,
                                         (SEQ ID NO: 206)
ATGGGCTGGTCCTGCATCATCCTGTTTCTGGTGGCCACCGCCACCGGCGT

GCACTCC,
                                         (SEQ ID NO: 220)
ATGGGATGGAGCTGTATCATCCTCTTCTTGGTAGCAACAGCTACAGGTGT

CCACTCC, or
                                          (SEQ ID NO: 21)
ATGGGATGGAGCTGTATCATCCTCTTCTTGGTAGCAACAGCTACAGGTGT

GCACTCC.
```

In some preferred embodiments, the leader sequence encodes the amino acid sequence MGWSCIILFLVATATGVHS (SEQ ID NO: 44).

Also encompassed within the present invention are vectors comprising the polynucleotides of the invention. The vectors can be expression vectors. Recombinant expression vectors containing a sequence encoding a polypeptide of interest are thus provided. The expression vector may contain one or more additional sequences such as but not limited to regulatory sequences (e.g., promoter, enhancer), a selection marker, and a polyadenylation signal. Vectors for transforming a wide variety of host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors of the invention include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors can be constructed as described in Okayama and Berg (1983) *Mol. Cell. Biol.* 3:280.

In some embodiments, the antibody coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use in the present invention. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. Other promoters are known to those of ordinary skill in the art. In one embodiment, the antibody coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like. Other suitable inducible promoters will be known to those of skill in the art.

Vectors of the invention may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFS), or positioned in another way. Regulatory elements, such as the IRES motif, can also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), HSV-TK, HSV-TK derivatives for ganciclovir selection, or bacterial purine nucleoside phosphorylase gene for 6-methylpurine selection (Gadi et al. (2000) *Gene Ther.* 7:1738-1743). A nucleic acid sequence encoding a selection marker or the cloning site may be upstream or downstream of a nucleic acid sequence encoding a polypeptide of interest or cloning site.

The vectors of the invention can be used to transform various cells with the genes encoding the various antibodies of the invention. For example, the vectors may be used to generate antibody-producing cells. Thus, another aspect of the invention features host cells transformed with vectors comprising a nucleic acid sequence encoding an antibody that specifically binds SEB, such as the antibodies described and exemplified herein.

Numerous techniques are known in the art for the introduction of foreign genes into cells and may be used to construct the recombinant cells for purposes of carrying out the inventive methods, in accordance with the various embodiments of the invention. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline (1985) *Pharmac. Ther.* 29:69-92). Calcium phosphate precipitation and polyethylene glycol (PEG)-induced fusion of bacterial protoplasts with mammalian cells can also be used to transform cells.

Cells transfected with expression vectors of the invention can be selected under positive selection conditions and/or screened for recombinant expression of the antibodies. Recombinant-positive cells are expanded and screened for subclones exhibiting a desired phenotype, such as high level expression, enhanced growth properties, and/or the ability to yield proteins with desired biochemical characteristics, for example, due to protein modification and/or altered post-translational modifications. These phenotypes may be due to inherent properties of a given subclone or to mutagenesis. Mutagenesis can be effected through the use of chemicals, UV-wavelength light, radiation, viruses, insertional mutagens, defective DNA repair, or a combination of such methods.

Cells suitable for use in the invention for the expression of antibodies are preferably eukaryotic cells, more preferably cells of plant, rodent, or human origin, for example but not limited to NSO, CHO, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. Highly preferred cells for expression of antibodies are hybridoma cells. Methods for producing hybridomas are well established in the art.

Once a cell expressing the desired protein is identified, it can be expanded and selected. Transfected cells may be selected in a number of ways. For example, cells may be selected for expression of the polypeptide of interest. For cells in which the vector also contains an antibiotic resistance gene, the cells may be selected for antibiotic resistance, which positively selects for cells containing the vector. In other embodiments, the cells may be allowed to grow under selective conditions.

The invention also features compositions comprising at least one inventive antibody and a pharmaceutically acceptable carrier. Such compositions are useful, for example, for administration to patients to treat or prevent SEB-mediated diseases, such as those described and exemplified herein. The compositions can be formulated as any of various preparations that are known and suitable in the art, including those described and exemplified herein.

In some embodiments, the compositions are aqueous formulations. Aqueous solutions can be prepared by admixing the antibodies in water or suitable physiologic buffer, and optionally adding suitable colorants, flavors, preservatives, stabilizing and thickening agents and the like as desired. Aqueous suspensions can also be made by dispersing the antibodies in water or physiologic buffer with viscous material, such as natural or synthetic gums, resins, methylcellulose, sodium carboxymethylcellulose, and other well-known suspending agents.

Also included are liquid formulations and solid form preparations which are intended to be converted, shortly before use, to liquid form preparations. Such liquid forms include solutions, suspensions, syrups, slurries, and emulsions. Liquid preparations may be prepared by conventional means with pharmaceutically acceptable additives such as suspending agents (e.g., sorbitol syrup, cellulose derivatives or hydrogenated edible fats or oils); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). These preparations may contain, in addition to the active agent, colorants, flavors, stabilizers, buffers, artificial and natural sweeteners, dispersants, thickeners, solubilizing agents, and the like. The compositions may be in powder or lyophilized form for constitution with a suitable vehicle such as sterile water, physiological buffer, saline solution, or alcohol, before use.

The compositions can be formulated for injection into a subject. For injection, the compositions of the invention can be formulated in aqueous solutions such as water or alcohol, or in physiologically compatible buffers such as Hanks's solution, Ringer's solution, or physiological saline buffer. The solution may contain formulatory agents such as suspending, stabilizing and/or dispersing agents. Injection formulations may also be prepared as solid form preparations which are intended to be converted, shortly before use, to liquid form preparations suitable for injection, for example, by constitution with a suitable vehicle, such as sterile water, saline solution, or alcohol, before use.

The compositions can be formulated in sustained release vehicles or depot preparations. Such long acting formulations may be administered by implantation (for example subcutaneously or intramuscularly) or by intramuscular injection. Thus, for example, the compositions may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well-known examples of delivery vehicles suitable for use as carriers for hydrophobic drugs.

The invention also features methods for treating or preventing diseases mediated by SEB in subjects in need of such treatment or prevention. In some aspects, the methods can comprise identifying a subject in need of treatment or prevention for SEB-mediated disease. In one embodiment, the methods comprise administering to the subject a composition, such as those described and exemplified herein, the composition comprising a pharmaceutically acceptable carrier and at least one antibody that specifically binds to, and preferably neutralizes, Staphylococcus enterotoxin B, in an amount effective to treat or prevent diseases mediated by SEB. In one embodiment, the methods comprise administering to the subject at least one antibody, such as the antibodies described and exemplified herein, that specifically binds to, and preferably neutralizes, Staphylococcus enterotoxin B, in an amount effective to treat or prevent diseases mediated by SEB.

As those of skill in the art will understand, SEB is a virulence factor for Staphylococcus bacteria that can be produced in individuals with Staphylococcus spp. infection. Thus, a subject in need of treatment with SEB-neutralizing antibodies can have an infection with Staphylococcus bacteria. The infection can be anywhere in or on the body of the subject, and can be at any stage of infection such as incipient, advanced, or chronic infection such as those observed in patients with implanted medical devices. In addition, as described herein, SEB itself can cause various diseases in patients. SEB can be present apart from the bacteria that produce it, for example, in contaminated food or beverage, or if dispersed in the form of a biological terrorist attack. Accordingly, a subject in need of treatment with SEB-neutralizing antibodies can be exposed to SEB, and not necessarily in conjunction with the bacteria or other cells that express the toxin.

SEB mediates a variety of disease states in subjects exposed to the toxin. Non-limiting examples of diseases mediated by SEB that can be effectively treated with the inventive methods and inventive SEB-neutralizing antibodies include fever, myalgia, respiratory distress, dyspnea, pleurisy, headache, nausea, vomiting, anorexia, hepatomegaly, and leukocytosis (see, e.g., Ulrich et al. (1997) Medical Aspects of Chemical and Biological Warfare, Sidell, Takafuj, and Franz, Eds., in Textbook of Military Medicine, Brigadier Gen. Russ Zajtchuk, Eds., Published by the Office of the Surgeon General at TMM Publications, Borden Institute, Walter Reed Army Medical Center, Washington, D.C.). Those of skill in the art will know other diseases and complications mediated by SEB that could be treated according to the inventive methods.

The subject can be any animal, and preferably is a mammal such as a mouse, rat, hamster, guinea pig, rabbit, cat, dog, monkey, donkey, cow, horse, pig, and the like. Most preferably, the mammal is a human.

In the inventive methods, the at least one antibody is preferably an antibody of the invention. For example, the at least one antibody can comprise a heavy chain having CDR1 of SEQ ID NO: 68, 92, 116, 130, or 144; CDR2 of SEQ ID NO: 69, 93, 117, 131, or 146; and CDR3 of SEQ ID NO: 70, 94, 118, 132, or 148; and a light chain having CDR1 of SEQ ID NO: 56, 80, 104, or 136; CDR2 of SEQ ID NO: 57, 81, 105, or 138; and CDR3 of SEQ ID NO: 58, 82, 106, or 140. In some preferred embodiments, the at least one antibody can comprise a heavy chain variable domain having SEQ ID NO: 160, 176, 202, 204, or 230 and a light chain variable domain having SEQ ID NO: 158, 174, 200, 228.

In preferred embodiments, the at least one antibody can comprise a heavy chain having CDR1 of SEQ ID NO: 68, CDR2 of SEQ ID NO: 69, and CDR3 of SEQ ID NO: 70 and a light chain having CDR1 of SEQ ID NO: 56, CDR2 of SEQ ID NO: 57, and CDR3 of SEQ ID NO: 58. In preferred embodiments, the at least one antibody can comprise a heavy chain having a variable domain of SEQ ID NO: 176 and a light chain having a variable domain of SEQ ID NO: 174. In preferred embodiments, the at least one antibody can comprise a heavy chain having SEQ ID NO: 30 and a light chain having SEQ ID NO: 28.

In preferred embodiments, the antibody and antigen-binding fragments of the invention comprise a heavy chain having CDR1 of SEQ ID NO: 116, CDR2 of SEQ ID NO: 117, and CDR3 of SEQ ID NO: 118, and a light chain having CDR1 of SEQ ID NO: 104, CDR2 of SEQ ID NO: 105, and CDR3 of SEQ ID NO: 106. In preferred embodiments, the at least one antibody can comprise a heavy chain having a variable domain of SEQ ID NO: 202 and a light chain having a variable domain of SEQ ID NO: 200. In preferred embodiments, the at least one antibody can comprise a heavy chain having SEQ ID NO: 188 and a light chain having SEQ ID NO: 186.

In preferred embodiments, the at least one antibody can comprise a heavy chain having CDR1 of SEQ ID NO: 130, CDR2 of SEQ ID NO: 131, and CDR3 of SEQ ID NO: 132, and a light chain having CDR1 of SEQ ID NO: 104, CDR2 of SEQ ID NO: 105, and CDR3 of SEQ ID NO: 106. In preferred embodiments, the at least one antibody can comprise a heavy chain having a variable domain of SEQ ID NO: 204 and a light chain having a variable domain of SEQ ID NO: 200. In preferred embodiments, the at least one antibody can comprise a heavy chain having SEQ ID NO: 232 and a light chain having SEQ ID NO: 186.

In preferred embodiments, the at least one antibody can comprise a heavy chain having CDR1 of SEQ ID NO: 92, CDR2 of SEQ ID NO: 93, and CDR3 of SEQ ID NO: 94, and a light chain having CDR1 of SEQ ID NO: 80, CDR2 of SEQ ID NO: 81, and CDR3 of SEQ ID NO: 82. In preferred embodiments, the at least one antibody can comprise a heavy chain having a variable domain of SEQ ID NO: 160 and a light chain having a variable domain of SEQ ID NO: 158. In preferred embodiments, the at least one antibody can comprise a heavy chain having SEQ ID NO: 251 and a light chain having SEQ ID NO: 249.

In preferred embodiments, the at least one antibody can comprise a heavy chain having CDR1 of SEQ ID NO: 144, CDR2 of SEQ ID NO: 146, and CDR3 of SEQ ID NO: 148, and a light chain having CDR1 of SEQ ID NO: 136, CDR2 of SEQ ID NO: 138, and CDR3 of SEQ ID NO: 140. In preferred embodiments, the at least one antibody can comprise a heavy chain having a variable domain of SEQ ID NO: 230 and a light chain having a variable domain of SEQ ID NO: 228. In preferred embodiments, the at least one antibody can comprise a heavy chain having SEQ ID NO: 216 and a light chain having SEQ ID NO: 214.

In highly preferred embodiments, the at least one antibody neutralizes SEB. In some aspects of the method, the at least one antibody preferably has an affinity for *Staphylococcus* enterotoxin B of less than about $1 \times 10^{-8}$ M, preferably less than about $3 \times 10^{-8}$ M, more preferably has an affinity for *Staphylococcus* enterotoxin B of less than about $1 \times 10^{-9}$ M, and more preferably has an affinity for *Staphylococcus* enterotoxin B of less than about $1 \times 10^{-10}$ M, and preferably less than about $3 \times 10^{-10}$ M.

Administration of the compositions can be by infusion or injection (intravenously, intramuscularly, intracutaneously, subcutaneously, intrathecal, intraduodenally, intraperitoneally, and the like). The compositions can also be administered intranasally, vaginally, rectally, orally, or transdermally. Preferably, the compositions are administered orally. Administration can be at the direction of a physician.

Various alternative pharmaceutical delivery systems may be employed. Non-limiting examples of such systems include liposomes and emulsions. Certain organic solvents such as dimethylsulfoxide also may be employed. Additionally, the compositions may be delivered using a sustained-release system, such as semipermeable matrices of solid polymers containing the therapeutic antibodies. The various sustained-release materials available are well known by those skilled in the art. Sustained-release capsules may, depending on their chemical nature, release the antibodies over a range of several days to several weeks to several months.

To treat a subject afflicted with SEB-mediated disease, a therapeutically effective amount of the composition is administered to the subject. A therapeutically effective amount will provide a clinically significant abatement in at least one disease mediated by SEB, which can be, but are not limited to, those described and exemplified herein.

The effective amount of the composition may be dependent on any number of variables, including without limitation, the species, breed, size, height, weight, age, overall health of the subject, the type of formulation, the mode or manner or administration, or the severity of the disease in the subject caused by SEB. The appropriate effective amount can be routinely determined by those of skill in the art using routine optimization techniques and the skilled and informed judgment of the practitioner and other factors evident to those skilled in the art. Preferably, a therapeutically effective dose of the compounds described herein will provide therapeutic benefit without causing substantial toxicity to the subject.

Toxicity and therapeutic efficacy of agents or compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents or compositions which exhibit large therapeutic indices are preferred. The data obtained from cell culture assays and animal studies can be used in formulating a range of dosage for use in the subject. The dosage of such agents or compositions lies preferably within a range of circulating concentrations that include the $ED_{50}$ with little or no toxicity. The dosage may vary within this range depending upon the dosage form employed and the route of administration utilized.

For any composition used in the methods of the invention, the therapeutically effective dose can be estimated initially from in vitro assays such as cell culture assays. For example, a dose can be formulated in animal models to achieve a circulating plasma concentration range that includes the $IC_{50}$ as determined in cell culture (i.e., the concentration of the composition which achieves a half-maximal inhibition of the osteoclast formation or activation). Such information can be used to more accurately determine useful doses in a specified subject such as a human. The treating physician can terminate, interrupt, or adjust administration due to toxicity, or to organ dysfunctions, and can adjust treatment as necessary if the clinical response were not adequate in order to improve the response. The magnitude of an administered dose in the management of the disorder of interest will vary with the severity of the condition to be treated and to the route of administration. The severity of the condition may, for example, be evaluated, in part, by standard prognostic evaluation methods.

In one aspect of the inventive methods, the compositions comprise a concentration of at least one anti-SEB antibody in a range of about 0.01% to about 90% of the dry matter weight of the composition. In some embodiments, the at least one anti-SEB antibody comprises up to about 50% of the dry matter weight of the composition. In some embodiments, the at least one anti-SEB antibody comprises up to about 40% of the dry matter weight of the composition. In some embodiments, the at least one anti-SEB antibody comprises up to about 30% of the dry matter weight of the composition. In some embodiments, the at least one anti-SEB antibody comprises up to about 25% of the dry matter weight of the composition. In some embodiments, the at least one anti-SEB antibody comprises up to about 20% of the dry matter weight of the composition. In some embodiments, the at least one anti-SEB antibody comprises up to about 15% of the dry matter weight of the composition. In some embodiments, the at least one anti-SEB antibody comprises up to about 10% of the dry matter weight of the composition.

In some embodiments, subjects can be administered at least one anti-SEB antibody in a daily dose range of about 0.01 mg to about 500 mg of antibody per kg of the weight of the subject. The dose administered to the subject can also be measured in terms of total amount of the at least one anti-SEB antibody administered per day. In some embodiments, a subject is administered about 5 to about 5000 milligrams of at least one anti-SEB per day. In some embodiments, a subject is administered up to about 10 milligrams of at least one anti-SEB per day. In some embodiments, a subject is administered up to about 100 milligrams of at least one anti-SEB per day. In some embodiments, a subject is administered up to about 250 milligrams of at least one anti-SEB per day. In some embodiments, a subject is administered up to about 500 milligrams of at least one anti-SEB per day. In some embodiments, a subject is administered up to about 750 milligrams of at least one anti-SEB per day. In some embodiments, a subject is administered up to about 1000 milligrams of at least one anti-SEB per day. In some embodiments, a subject is administered up to about 1500 milligrams of at least one anti-SEB per day. In some embodiments, a subject is administered up to about 2000 milligrams of at least one anti-SEB per day. In some embodiments, a subject is administered up to about 2500 milligrams of at least one anti-SEB per day. In some embodiments, a subject is administered up to about 3000 milligrams of at least one anti-SEB per day. In some embodiments, a subject is administered up to about 3500 milligrams of at least one anti-SEB per day. In some embodiments, a subject is administered up to about 4000 milligrams of at least one anti-SEB per day. In some embodiments, a subject is administered up to about 4500 milligrams of at least one anti-SEB per day. In some embodiments, a subject is administered up to about 5000 milligrams of at least one anti-SEB per day.

Treatment can be initiated with smaller dosages that are less than the optimum dose of the at least one anti-SEB, followed by an increase in dosage over the course of the treatment until the optimum effect under the circumstances is reached. If needed, the total daily dosage may be divided and administered in portions throughout the day.

For effective treatment of SEB-mediated diseases, one skilled in the art may recommend a dosage schedule and dosage amount adequate for the subject being treated. It may be preferred that dosing occur one to four or more times daily for as long as needed. The dosing may occur less frequently if the compositions are formulated in sustained delivery vehicles. The dosage schedule may also vary depending on the active drug concentration, which may depend on the needs of the subject.

The compositions of the invention for treating SEB-mediated diseases may also be co-administered with other well known therapeutic agents that are selected for their particular usefulness against the condition that is being treated. For example, such therapeutic agents can be pain relievers, fever reducers, stomach antacids, compounds which lessen untoward effects of the compositions, or other known agents that treat SEB-mediated diseases.

The administration of these additional compounds may be simultaneous with the administration of the at least one anti-SEB antibody, or may be administered in tandem, either before or after the administration of the at least one anti-SEB antibody, as necessary. Any suitable protocol may be devised whereby the various compounds to be included in the combination treatment are administered within minutes, hours, days, or weeks of each other. Repeated administration in a cyclic protocol is also contemplated to be within the scope of the present invention.

The invention also features methods for making an antibody that specifically binds to *Staphylococcus* enterotoxin B. In some embodiments, the methods comprise isolating bone marrow or peripheral blood cells from an animal, culturing such cells with the *Staphylococcus* enterotoxin B or an antigenic fragment thereof, isolating B cells from the culture that express an antibody that specifically binds to *Staphylococcus* enterotoxin B, and isolating antibodies produced by the B cells. Optionally, the B cells can be fused with donor cells to form a hybridoma, according to any methods that are known in the art. The animal from which bone marrow cells or peripheral blood cells are isolated can be immunized with *Staphylococcus* enterotoxin B or antigenic fragment thereof prior to isolation of the bone marrow or peripheral blood cells. Any animal can be used in the methods. Preferably, the animals are mammals, and more preferably are humans. In some embodiments, the *Staphylococcus* enterotoxin B used to immunize the animal, and/or used in the culture with the isolated bone marrow or peripheral blood cells is STEB. STEB has the following amino acid sequence, with residues that differ from SEB underlined: ESQPDPKPDELH-KSSKFTGLMENMKVLYDDNHVSAINVKS IDQF RYFDLIYSIKDTKLGNYDNVRVEFKNKDLADKYKD KYVDVFGANAYY QC AFSKKTNDINSHQTDKRKTCMYGGVTEHNGNQLDK YRSITVRVFEDG KNLLSFDVQTNKKKVTAQELDYLT-RHYLVKNKKLYEFNNS PYETGYIKFI ENENSFWYDM MPAPGDKFDQSKYLMMYNDNKMVDSKD-VKIEVYLTTKKK (SEQ ID NO: 45). For comparison, SEB has the following amino acid sequence: ESQPDPKPDELH-KSSKFTGLMENMKVLYDDNHVSAINVKS IDQFLY-FDLIYSIKDTKLGNYDNVRVEFKNKD-LADKYKDKYVDVFGANYYY QCYFSKKTNDINSHQTDKRKTCMYG-GVTEHNGNQLDKYRSITVRVFEDG KNLLSFDVQT-NKKKVTAQELDYLTRHYLVKNKKLYEFNNS PYET-GYIKFI ENENSFWYDM MPAPGDKFDQSKYLMMYNDNKMVDSKD-VKIEVYLTTKKK (SEQ ID NO: 46).

In some embodiments, the methods for making an antibody that specifically binds to *Staphylococcus* enterotoxin B comprise comprising culturing a host cell under conditions suitable to produce the antibody, and recovering the antibody from the cell culture. In some embodiments, the host cell can be any cell transformed with a vector comprising the inventive polynucleotides that encode the inventive antibodies and antigen-binding fragments thereof.

The following examples are provided to describe the invention in greater detail. They are intended to illustrate, not to limit, the invention.

EXAMPLE 1

Generation of Antigen-Specific Fully Human Hybridoma Cell Lines

Healthy human donors were pre-screened for serum titers to SEB. SEB-specific ELISA were performed by coating TPP Immunomini ELISA plates with 1 μg/ml STEB (SEB vaccine) dissolved in bicarbonate coating buffer (pH 9.6) (Sigma) overnight at 4° C. The plates were then washed three times with washing buffer (containing 0.5% tween-20), and then blocked with 1× assay buffer for 2 h at room temperature. The blocked plates were incubated at room temperature for 1 h with serial dilutions of normal human plasma (1:100, 1:300, 1:900, 1;2,700, 1:8, 100 and 1:24,300) from different donors as well as positive controls (mouse anti-SEB mAb 15D2-1-1 and rabbit anti-SEB PAb FT1009). After incubation with serum, the plates were washed, and incubated with HRP-labeled goat anti-human IgG (H+L) (1:10,000 diluted), HRP-labeled goat anti-mouse IgG (H+L) (1:10,000 diluted) and HRP-labeled goat anti-rabbit IgG (H+L) (1:10,000 diluted) for 1 h at room temperature with shaking. The plates were then washed, and developed with 100 µl TMB substrate per well, and the reaction was stopped by adding 50 µl stop solution (1M $H_2SO_4$). Developed plates were read at 450 nm on a microtiter plate reader.

To obtain SEB-reactive B cells, leukopacks were obtained from SEB-positive donors. PBMCs were purified by Ficoll-Paque (GE Healthcare, Piscataway, N.J.) density gradient centrifugation. $CD_2O$-positive B cells were isolated from PBMCs by negative selection using the EasySep® Human B Cell Enrichment Kit (StemCell Technologies, Vancouver, BC). The enriched B cells were stimulated and expanded using the CD40 culture system.

B cells were resuspended to a final concentration of $0.2\times10^6$ cells/ml in IMDM (Gibco) supplemented with 10% heat-inactivated human AB serum (Nabi Pharmaceuticals, FL, USA), 4 mM L-glutamine, 10 μg/ml gentamicin (Gibco), 50 μg/mltransferrin (Sigma Chemical Co., ST. Louis, Mo.) and 5 μg/ml insulin (Sigma Chemical Co.). Enriched B cells were activated via CD40 using CD40 ligand (CD40L) transfected CHO feeder cells. For the co-culture, CD40L-CHO cells were γ-irradiated (96 Gy) and $0.4\times10^5$ cells were plated in 6-well plates. The feeder cells were allowed to adhere overnight at 37° C. A total of 4 ml ($0.8\times10^6$) isolated B cells were co-cultured at 37° C. for seven to fourteen days with the γ-irradiated CD40L-CHO in the presence of 100 U/ml recombinant human IL-4 (PeproTech) and 0.55 μM CsA (Sigma Chemical Co.).

Expanded B cells were fused with a myeloma fusion partner via electro-fusion using the CytoPulse CEEF-50 at a 1:1 B cell:myeloma cell ratio. Clones E12, F10, F6, C5, 79G9, and 100C9 were fused with K6H6/B5 myeloma cells (ATCC) and seeded in flat-bottomed 96-well plates in RPMI 1640 (Invitrogen, Carlsbad, Calif.) supplemented with 10% heat-inactivated FBS (JRH Biosciences, KS, USA), 2 mM L-glutamine, 0.1 mM non-essential amino acids, 1 mM sodium pyruvate, 55 μM 2-Mercaptoethanol, and 1×HAT (100 μM hypoxanthine, 0.4 μM aminopterin and 16 μM thymidine. Clone 154G12 was fused with CBF7 myeloma cells (Grunow et al. (1990) Dev. Biol. Stand. 71, 3-7; Niedbla and Stott (1998) Hybridoma 17 (3), 299-304) and seeded in flat-bottomed 96-well plates in IMDM (Gibco) supplemented with 10% heat-inactivated human AB serum (Nabi Pharmaceuticals, FL, USA), 4 mM L-glutamine, 10 mg/ml gentamicin (Gibco), 50 mg/ml transferrin (Sigma Chemical Co., ST. Louis, Mo.) and 5 mg/ml insulin (Sigma Chemical Co.).

Following cell fusion, culture medium was replaced weekly and HAT selection continued during the antigen-reactivity screening process. Approximately 90% of seeded wells exhibited viable hybridoma cell growth. Hybridomas were screened by ELISA using an attenuated form of recombinant SEB (STEB). Hybridoma clones with SEB reactivity were tested again by ELISA to confirm reactivity and specificity by demonstrating binding to SEB but not to tetanus toxoid (TT). Clones E12, F10, F6, C5, 79G9, 100C9, and 154G12 were highly reactive with SEB but not with TT. Each clone was then subcloned followed by ELISA screening to confirm retention of SEB specificity.

EXAMPLE 2

Characterization of Antibody Specificity

To further characterize the anti-SEB antibodies, antigen specificity ELISAs were performed using a panel of antigens: SEB, STEB, BGG, CAB, HEL, TT, BSA, human mesothelin, human GM-CSF, human mucin, goat IgG and mouse IgG.

Antigen-specific ELISA were performed by coating TPP Immunomini ELISA plates with 1 mg/ml STEB (SEB vaccine), 0.5 mg/ml SEB, 2 mg/mlBGG, 2 mg/ml CAB, 2 mg/ml HEL, 1:500 dilution TT, 1% BSA, 0.2 mg/ml human Mesothelin, 2 mg/ml human mucin, 1 mg/ml human GM-CSF, 2 mg/ml goat IgG, 2 mg/ml mouse IgG dissolved in bicarbonate coating buffer (pH 9.6) (Sigma) overnight at 4° C. The plates were then washed three times with washing buffer (containing 0.5% Tween-20), and then blocked with 1× assay buffer for 2 h at room temperature. The blocked plates were incubated at room temperature for 1 h with hybridoma supernatant as well as positive controls. After incubation, the plates were washed, and incubated with HRP-labeled goat anti-human IgG (H+L) (1:10,000 diluted), HRP-labeled goat anti-mouse IgG (H+L) (1:10,000 diluted) or HRP-labeled goat anti-rabbit IgG (H+L) (1:10,000 diluted) for 1 h at room temperature with shaking. The plates were then washed, and developed with 100 μl TMB substrate per well, and the reaction was stopped by adding 50 μl stop solution (1M $H_2SO_4$). Developed plates were read at 450 nm on a microtiter plate reader. FIGS. 2 and 6 provide the results of these experiments.

FIG. 2 shows that antibodies E12, F10, F6, and C5 specifically recognize SEB, and show no cross reactivity with the other antigens in the panel. Positive control antibodies for each of the different antibodies were screened in parallel. The positive control antibodies are as follows: Mouse IgG: Goat anti-mouse IgG (Jackson Immunoresearch, Media, PA); Goat IgG: Donkey anti-goat IgG (Jackson Immunoresearch,); BSA, donor serum (prepared in house); TT, donor serum (prepared in house); HEL, rabbit anti-HEL (Fitzgerald Industries International); CAB, mouse anti-chicken egg albumin (Sigma); BGG, rabbit anti-bovine IgG (AbD Serotec, Oxford, UK); mesothelin (anti-mesothelin, prepared in house); GM-CSF (anti-GM-CSF, prepared in house).

FIG. 6 shows that antibodies 100C9 and 79G9 recognize SEB and the vaccine variant of SEB, STEB. The antibodies demonstrated no cross-reactivity with the other antigens in the panel.

EXAMPLE 3

Characterization of Antibody Isotype

The isotype of each antibody subclone was determined by a standard ELISA using anti-human IgG, IgG1, IgG2, IgG3, IgM, Lk and Ll. Isotype ELISA were performed by coating TPP Immunomini ELISA plates with 2.5 ng/ml Goat anti-human IgG+M (H+L) (from Jackson Immunoresearch) dissolved in bicarbonate coating buffer (pH 9.6) (Sigma) overnight at 4° C. The plates were then washed three times with washing buffer (containing 0.5% Tween-20), and then blocked with 1× assay buffer for 2 h at room temperature. The blocked plates were incubated at room temperature for 1 h with hybridoma supernatant. After incubation, the plates were washed, and incubated with HRP-labeled goat anti-human IgG Fcγ (1:10,000 diluted, from Jackson Immunoresearch), HRP-labeled goat anti-human IgM 5μ (1:10,000 diluted, from Jackson Immunoresearch), HRP-labeled mouse anti-human light chain κ (1:10,000 diluted, from Southern-Biotech) or HRP-labeled mouse anti-human light chain λ (1:10,000 diluted, from SouthernBiotech) for 1 h at room temperature with shaking. The plates were then washed, and developed with 100 µl TMB substrate per well, and the reaction was stopped by adding 50 µl stop solution (1M $H_2SO_4$). Developed plates were read at 450 nm on a microtiter plate reader.) The results are presented in FIGS. 3 and 5.

Figure 3:
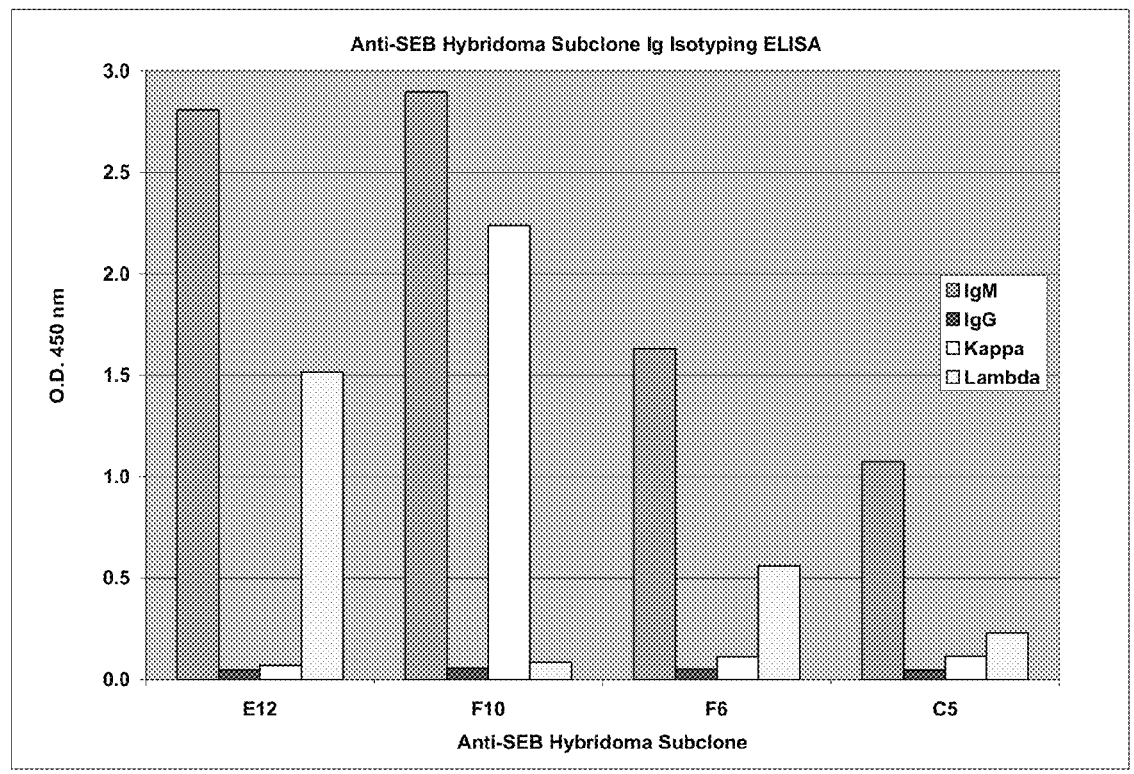
FIG. 3 shows isotype determination of SEB-specific antibodies E12, F10, F6, and C5. Each antibody was shown to be IgM. E12, F6, and C5 were shown to have a lambda light chain, and F10 was shown to have a kappa light chain.
Figure 5:
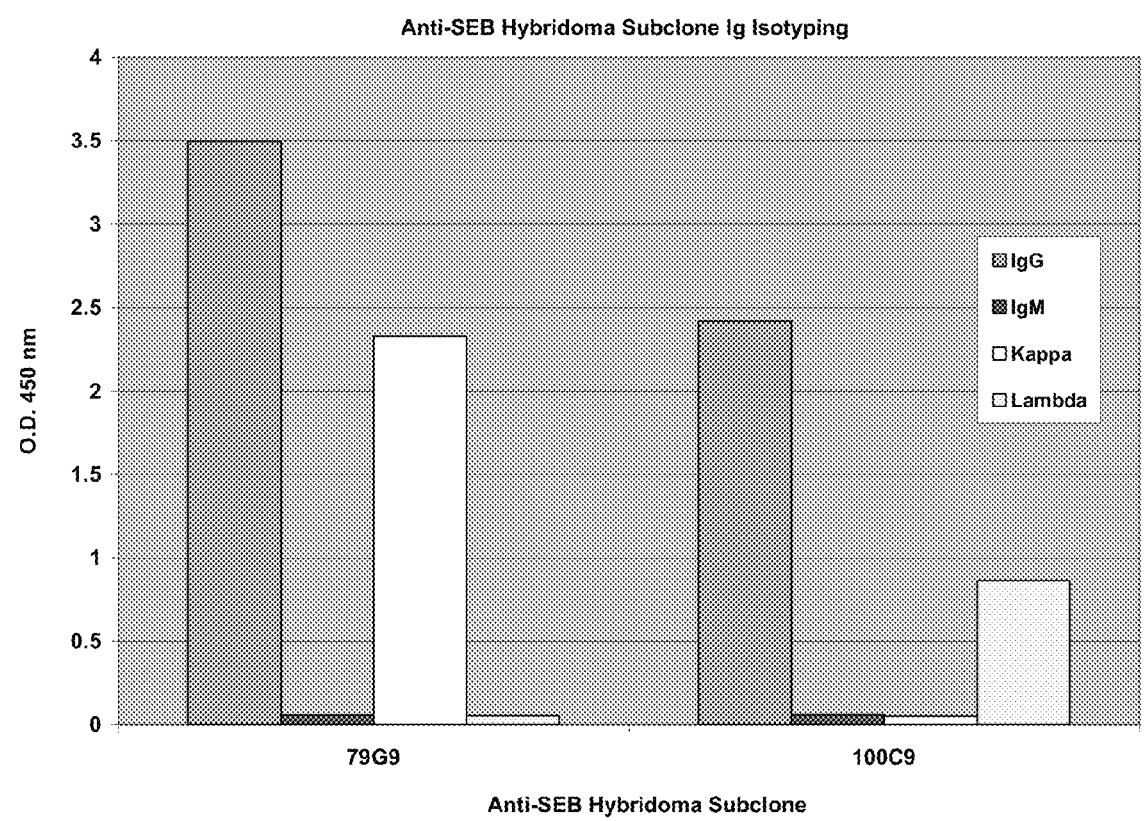
FIG. 5 shows isotype determination of SEB-specific antibodies 79G9 and 100C9. Both antibodies were shown to be IgG. 79G9 has a kappa light chain, and 100C9 has a lambda light chain.
Figure 6:
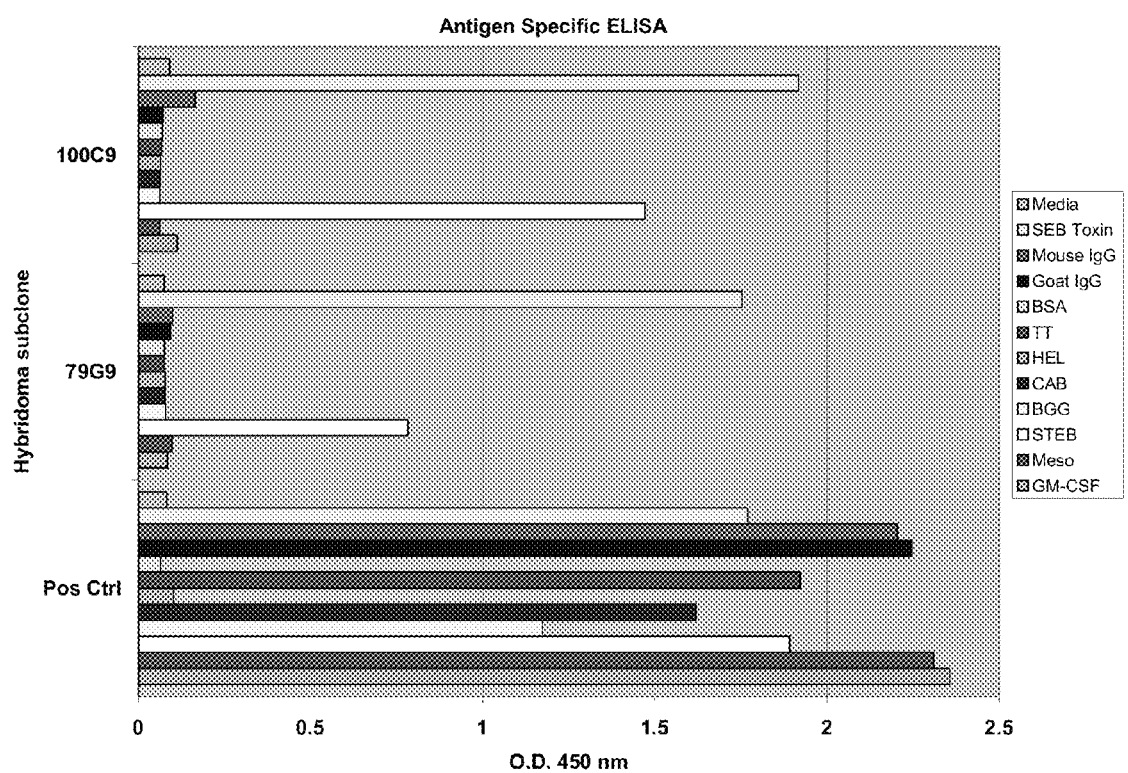
FIG. 6 shows an antigen panel ELISA for selection of antigen-specific human MAbs 79G9 and 100C9. Antibodies were screened for binding to mucin, goat IgG, BSA, TT, HEL, CAB, BGG, SEB, mesothelin, and GM-CSF. Antibodies with known reactivity against the various antigens were used as positive controls. The murine antibody S5 was used as a positive control to show reactivity with SEB. 79G9 and 100C9 reacted with SEB and the SEB vaccine STEB. No cross-reactivity was observed with the other antigens in the panel. The figure legend identifies the antigens tested and provides the order for the bars on the graph that correspond to the listed antigens.

FIG. 3 shows that antibodies E12, F10, F6, and C5 are IgM antibodies. Antibody F10 has a Kappa light chain, and antibodies E12, F6, and C5 have Lambda light chains. FIG. 5 shows that antibodies 79G9 and 100C9 are IgG. Antibody 79G9 has a Kappa light chain, and antibody 100C9 has a Lambda light chain.

EXAMPLE 4

Antibody Inhibition of SEB-Mediated PBMC Proliferation

Human PBMCs from healthy donors were obtained from leukopacks by Ficoll-Paque density gradient centrifugation. Cells were washed three times in complete RPMI. PBMCs were resuspended to $10^6$/ml in RPMI 1640 supplemented with 10% fetal bovine serum, 2 mM L-glutamine and 1% penicillin-streptomycin (all purchased from Gibco). One hundred microliters ($10^5$ cells) were added to the wells of 96 well, flat-bottomed plates in the presence SEB (Toxin Technology, Inc., Sarasota, Fla.).

A dose-response curve for SEB was established to determine the appropriate toxin concentration for the neutralization studies. To evaluate neutralization activity, 100 µl of SEB (50 pg/ml) was incubated for 1 hour at 37° C. with culture supernatants from SEB-reactive human B cell hybridomas prior to the addition of PBMCs. Murine anti-SEB monoclonal antibody clone S5 (Fitzgerald Industries International, Inc., Concord, Mass.) was used as a positive control for the inhibition of SEB mediated stimulation. The cultures were incubated at 37° C. for three days, followed by another 24 hours of culture in the presence of 5-bromo-2'-deoxyuridine (BrdU). Cell proliferation was assessed by measuring BrdU incorporation by ELISA (Roche Applied Science, Indianapolis, Ind.). Percent inhibition was calculated according to the formula 100–[O.D. with anti-SEB Ig/O.D. with SEB only]×100.

Figure 4:
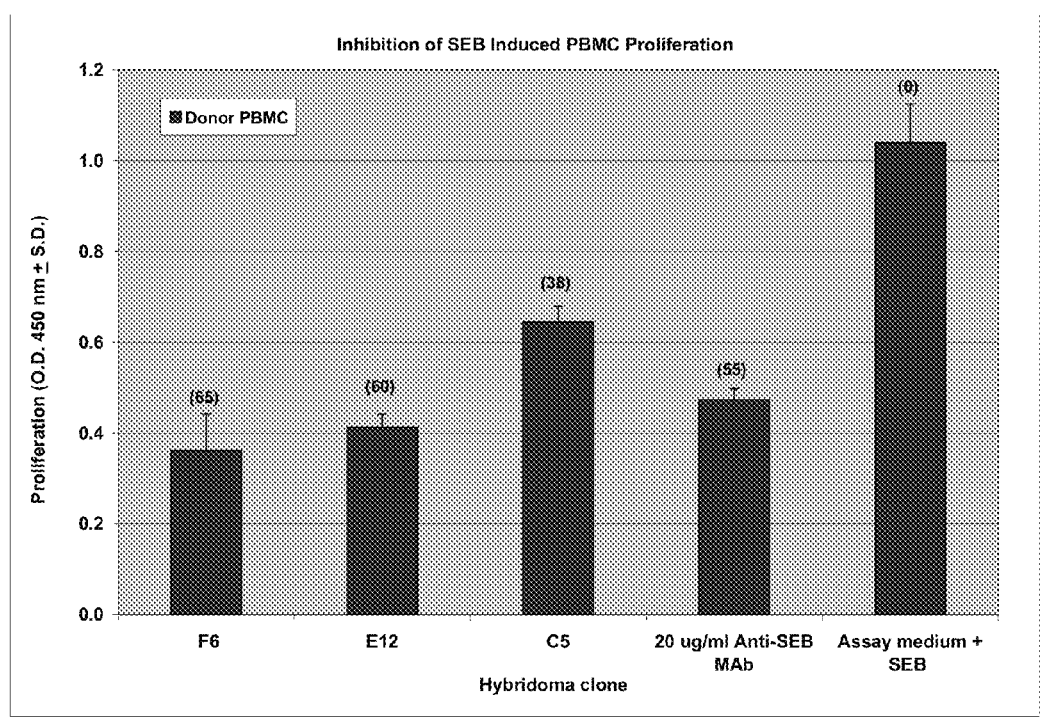
FIG. 4 shows SEB-dependent proliferation of PBMC with fully human mAbs F6, E12, and C5. The positive control designated as anti-SEB MAb is murine S5. Each antibody induced PBMC proliferation upon neutralization of SEB. Assay medium alone is shown in parallel to demonstrate lack of proliferation.

FIG. 4 demonstrates inhibition of SEB mediated PBMC proliferation with fully human mAbs F6, E12, and C5. Murine anti-SEB antibody S5 was screened in parallel as a positive control. The three antibodies were able to significantly inhibit SEB-induced PBMC proliferation at levels comparable to the control antibody.

Figure 7:
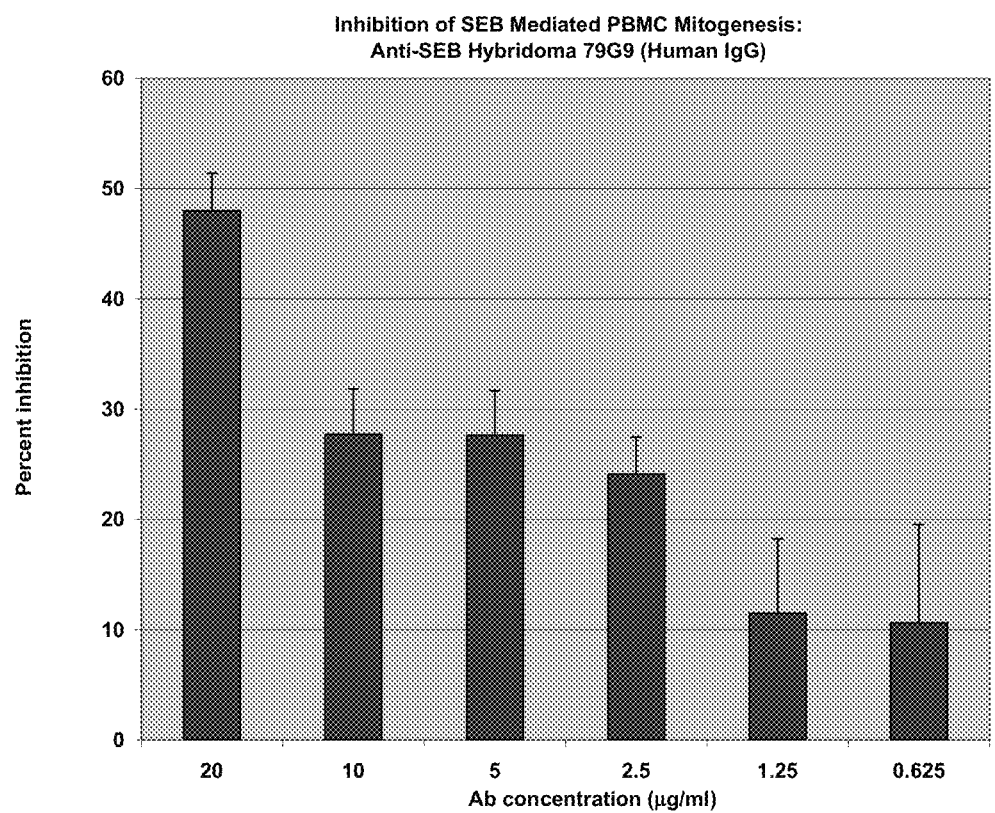
FIG. 7 shows inhibition of SEB-mediated PBMC mitogenesis by clone 79G9. Increasing concentration of antibody provided increased inhibition of mitogenesis.
Figure 8:
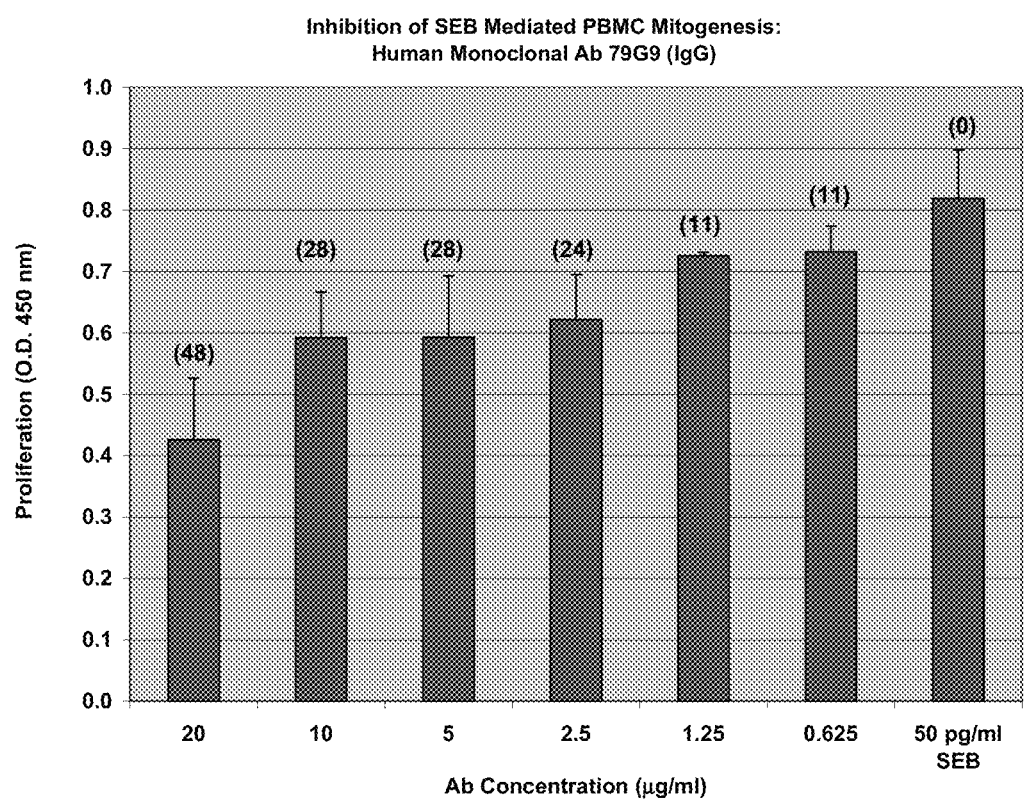
FIG. 8 shows dose-dependent inhibition of SEB-mediated PBMC mitogenesis by human monoclonal antibody 79G9.

FIG. 7 demonstrates that antibody 79G9 inhibited SEB-mediated PBMC mitogenesis. Increasing concentrations of 79G9 increased the percent inhibition of the mitogenesis. FIG. 8 demonstrates inhibition of SEB mediated PBMC proliferation with antibody 79G9. Increasing concentrations of the antibody increased the level of inhibition of the proliferation.

EXAMPLE 5

Cytokine Bioassays

The ability of the human antibodies to inhibit SEB-induced proinflammatory cytokine production was studied with human PBMCs as follows. A dose-response curve for SEB (Toxin Technology, Inc.) was first determined Fresh human PBMC were obtained from healthy adult donors and purified by Ficoll-Paque Plus (Amersham-Pharmacia). Approximately $1 \times 10^5$ cells in 200 µl of cIMDM medium supplemented with 10% heat-inactivated fetal bovine serum (Gibco BRL), 2 mM L-glutamine (Gibco BRL) were cultured in 96-well flat-bottom tissue culture plates (Falcon Labware) and incubated with various concentrations of SEB for 18-22 hrs at 37° C. in 5% $CO_2$. Culture supernatants were transferred to IFN-γ and TNF-α coated plates (75 µl/well) and assayed using ELISA kit (R&D System) according to manufacture protocols. SEB $EC_{50}$ values were calculated using graph package Prism4 (GraphPad Software). For neutralization studies, various concentrations of antibodies were preincubated with SEB (at either 4× or 1×$EC_{50}$) for 1 h at 37° C. prior to the addition of cells. The sensitivity limit of the IFN-γ and TNF-α assay were 16 pg/ml.

Figure 9:
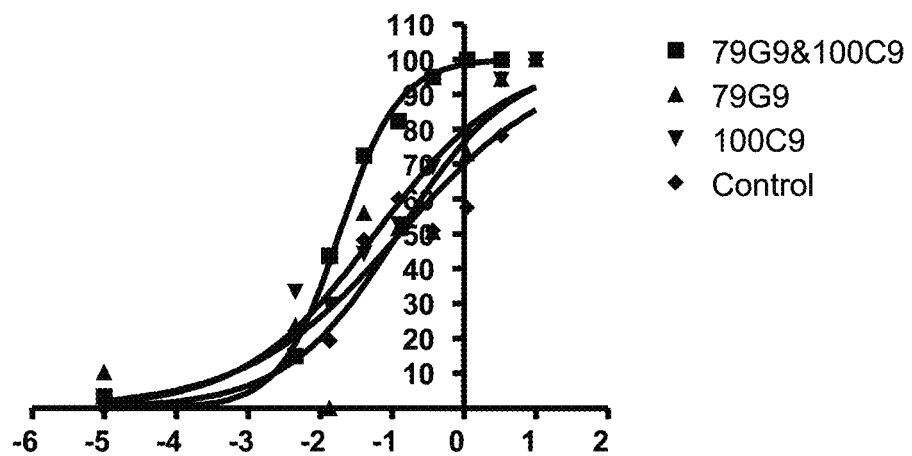
FIG. 9 shows inhibition of SEB-induced IFN-γ production by antibodies 79G9 and 100C9. When the antibodies were used together, a synergistic or additive effect of inhibition of SEB-induced IFN-γ production was observed. The murine antibody S5 was used as a positive control.
Figure 10:
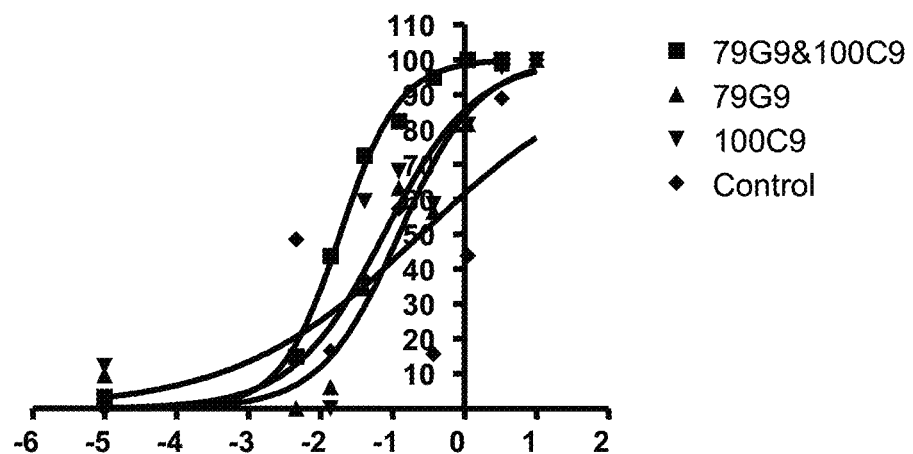
FIG. 10 shows inhibition of SEB induced TNF-α production by antibodies 79G9 and 100C9. When the antibodies were used together, a synergistic or additive effect of inhibition of SEB-induced TNF-α production was observed. The murine antibody S5 was used as a positive control.
Figure 11:
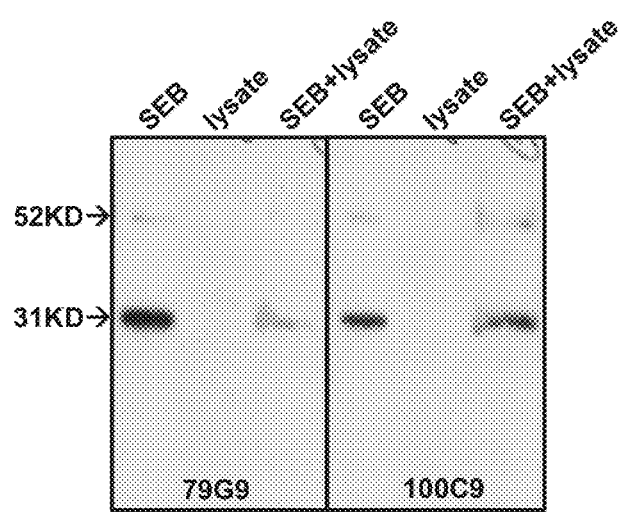
FIG. 11 shows an immunoblot demonstrating that human antibodies 79G9 and 100C9 bind to SEB, but not to other human proteins that are present in whole-cell lysate.
Figure 12:
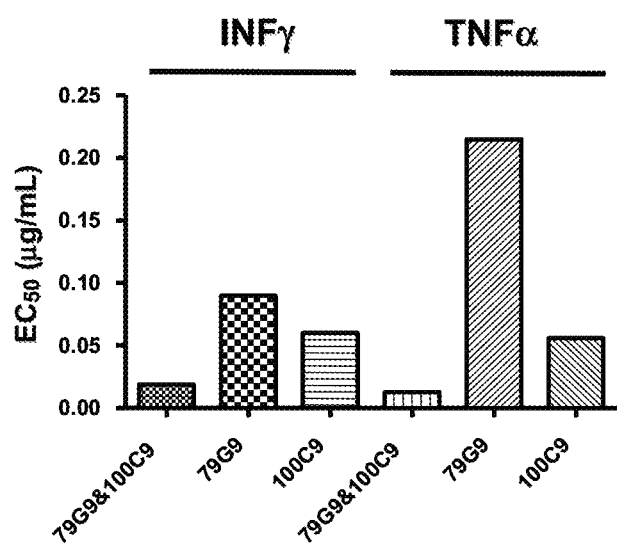
FIG. 12 shows that human antibodies 79G9 and 100C9 inhibit IFN-γ and TNF-α production by human T-cells. A synergistic or additive effect is observed when the antibodies are used in tandem.

Table 2 shows the raw data of IFN-γ inhibition by the antibody, 79G9. 79G9 at 2.5 mg/ml inhibits SEB induced IFN-γ production to below detection. FIG. 9 shows the converted data where percentage of inhibition was graphed using graph package Prism4 (GraphPad Software). The data show that either 79G9 or 100C9 alone could block SEB-induced abnormal secretion of IFN-γ, to the same extent, or even more effectively than the positive control anti-SEB mouse antibody S5 ($EC_{50}$ of 0.125 mg/ml and 0.07665 mg/ml vs. 0.2517 mg/ml). In addition, when the two antibodies 79G9 and 100C9 were used in combination, a synergistic or additive effect of SEB neutralization was observed, with the antibodies exhibiting a combined $EC_{50}$ of 0.0188 mg/ml. FIG. 10 shows that similar results are obtained in an assay for TNF-α inhibition. As observed for IFN-γ, 79G9 and 100C9 were found to inhibit TNF-α production at or above levels inhibited by S5. Similarly, a synergistic or additive effect for 79G9 and 100C9 was also observed for TNF-α inhibition. FIG. 12 shows a graph of calculated $EC_{50}$ values for TNF-α and IFN-γ inhibition. The synergistic or additive effect of 79G9 and 100C9 is shown in the graph.

TABLE 2

| Production of IFN-γ with 79G9 cytokine bioassay. ||
|---|---|
| 79G9 Concentration (µg/ml) | IFN-γ (pg/ml) |
| 20 | <16 |
| 10 | <16 |
| 5 | <16 |
| 2.5 | <16 |
| 1.25 | 21 |
| 0.625 | 20 |
| 0.313 | 28 |
| 0.156 | 24 |
| 0.078 | 38 |
| 0.039 | 37 |
| No Ab (Cells + SEB) | 59 |

EXAMPLE 6

Analysis of Anti-SEB Antibodies Binding Kinetics and Antibody Competition

SEB was diluted in sodium acetate buffer, pH 5.0, to a concentration of 5 µg/ml and coupled to a CM5 chip using standard amine chemistry with 1-ethyl-3-(3-dimethylaminopropyl) carbodiimide hydrochloride (EDC) and N-hydroxysuccinimide (NHS) to a level of 10.8 RU bound on a BIAcore® 3000 instrument running BIAcore® 3000 Control software, version 3.2. The remaining active sites were quenched with 1M ethanolamine A reference flow cell was prepared as a control by activation with EDC and NHS and subsequent quenching with ethanolamine without the administration of SEB ligand. A surface-performance analysis was performed on the chip using 500 nM 100C9 antibody and 10 mM HCl as regeneration solution to confirm stable response and baseline. Mass transport effects were evaluated by analyzing association and dissociation of selected anti-SEB antibodies at flow rates of 10 μl/min, 45 μl/min, and 70 μl/min. Rates varied by less than 10% over the range of flow rates tested, indicating little or no mass transport limitations.

To analyze antibody binding kinetics, purified anti-SEB monoclonal antibodies were diluted to 1000 nM, 333.3 nM, 111.1 nM, 37.0 nM, 12.3 nM, 4.1 nM, 1.4 nM, 0.46 nM, and 0 nM in HBS-EP buffer (BIAcore®). Samples were randomly injected at a flow rate of 30 μL/min (total injected volume was 250 μL) first over the reference cell then the SEB-coupled cell. Dissociation was observed for 30 minutes. Regeneration of the chip following each cycle was accomplished by two 50 μl injections of 10 mM HCl at a flow rate of 100 μl/min. All subsequent data analysis was performed in BIAevaluation software, version 4.1. Sensograms were first normalized by subtraction of data from blank injections to remove bulk effects and instrument noise. Association ($k_{a1}$) and dissociation ($k_{d1}$) rate constants for the binding reaction A+B=AB (where A is anti-SEB analyte and B is SEB ligand) were determined simultaneously by global fit of the data for each antibody analyzed to a bivalent analyte binding model. A steady state binding constant ($K_{D1}$) for the above interaction was determined by the relationship $K_{D1}=k_{d1}/k_{a1}$ (Table 3).

TABLE 3

Binding kinetics for anti-SEB antibodies 79G9, 100C9, and 154G12.

| Anti-SEB Antibody | $k_{a1}$ (×10$^3$ M$^{-1}$sec$^{-1}$) | $k_{d1}$ (×10$^{-4}$ sec$^{-1}$) | $K_{D1}$ (nM) |
|---|---|---|---|
| 79G9 | 9.56 | 2.39 | 25.00 |
| 100C9 | 159.0 | 15.5 | 9.75 |
| 154G12 | 93 | 0.271 | 0.29 |

To determine whether binding competition occurred, anti-SEB monoclonal antibodies were injected at a concentration of 1 μM onto the ligand-bound chip, as described above. This concentration was chosen because, for all antibodies, this was 10- to 100-fold greater than the $K_{D1}$. Under these conditions, all, or nearly all, of the available binding sites should be occupied. This was followed by a second injection of the same antibody to confirm equilibrium state had been reached. A third, non-similar antibody was then injected at a concentration of 1 μM. The chip was subsequently regenerated with two 50 μl, injections of 10 mM HCl. The degree of binding ($R_{eq'}$) of the second antibody was compared with the level of binding achieved on an unoccupied chip ($R_{eq}$). The ratio of $R_{eq'}/R_{eq}$ was then calculated; a ratio close to or equal to 1 indicated that the antibodies do not compete and bind independently to SEB, while a ratio of much less than 1 indicated significant overlap in binding sites (Table 4).

TABLE 4

Binding competition for anti-SEB antibodies 79G9, 100C9, and 154G12.

| 1st mAb | 2nd mAb | $R_{eq}$ | $R_{eq'}$ | $R_{eq'}/R_{eq}$ |
|---|---|---|---|---|
| 154G12 | 79G9 | 19.4 | 16.8 | 0.87 |
| 154G12 | 100C9 | 22.2 | 0 | 0.00 |
| 79G9 | 154G12 | 33 | 27.3 | 0.83 |
| 79G9 | 100C9 | 22 | 14.9 | 0.68 |

The results shown in Table 4 indicate that 79G9 and 154G12 do not compete, and that they can bind independent of one another and do not have overlapping epitopes. However, these data also indicate that 154G12 and 100C9 do compete highly with one another and thus have overlapping epitopes. 79G9 slightly inhibits subsequent binding of 100C9, and thus these two antibodies may have neighboring epitopes. Due to the rapid dissociation rate of 100C9 and the difficulty of assessing effects on binding of a subsequent antibody, 100C9 was not tested as the first antibody.

EXAMPLE 7

Human Anti-SEB Antibodies Neutralize SEB Activity In Vitro and In Vivo

Human anti-SEB monoclonal antibodies 79G9 and 100C9 are two independent human IgG4 highly specific to SEB that were derived as follows. Human B-cells from healthy donors were immunized ex vivo with SEB-derived peptides and fused to a cell partner to derive >2,000 hybridomas. Clones secreting SEB-specific mAbs were identified robotically using an ELISA method employing SEB-coated plates. Lead hybridomas secreting mAbs for which specific binding was confirmed by subsequent analyses were further expanded and characterized.

FIG. 6 shows that 79G9 and 100C9 specifically bound purified SEB and STEB (the USAMRIID's vaccine candidate) and did not cross-react with other unrelated purified proteins tested. When used for immunoblotting, antibodies only reacted to SEB and showed no crossreactivity to the thousands of proteins present in a human cell lysate (FIG. 11). 100C9 binds to SEB more strongly relative to 79G9 as determined by ELISA (data not shown).

To determine biological activity of 79G9 and 100C9 in vivo, Balb/C mice were challenged with SEB and treated with 79G9 alone or in combination with 100C9. Because in this model mice are fairly insensitive to the toxin, lipopolysaccaride (LPS) needs to be injected to boost the animal response to SEB. The SEB challenge corresponded to approximately 10 (Study 1) or 25 (Study 2) 50% lethal dose ($LD_{50}$), or 2-5 ng of SEB/mouse delivered i.p. Based on the in vitro data, it was estimated that a Antibody:SEB molar ratio around 100:1 would be sufficient (molecular weights for antibodies and SEB are approximately 150 and 30 kD, respectively) and therefore antibody dose did not exceed 1 mg/mouse (1,000 ng antibody:2 ng SEB:5 [weight difference]=100). In Study 1 (Table 5), a 79G9:SEB molar ratio of 100:1 protected 100% of the mice (5 of 5 animals) compared to no survivors (0 in 4) in the untreated group. SEB or LPS alone did not cause lethality.

TABLE 5

Survival of mice exposed to SEB and treated with Anti-SEB antibodies, Study 1.
Balb/C SEB/LPS challenge model

| | | | | Survivors/Total Mice | |
|---|---|---|---|---|---|
| Group | SEB LD$_{50}$ | Treatment | Dose (µg) | 18 Hours | 72 Hours |
| 1 | 0 (no LPS) | — | — | 2/2 | 2/2 |
| 2 | 0 (with LPS) | — | — | 4/4 | 4/4 |
| 3 | 10 | — | — | 2/4 | 0/4 |
| 4 | 10 | 79G9 | 1 mg | 5/5 | 5/5 |

SEB exposure was increased to 25 LD$_{50}$ in Study 2 (Table 6). No treatment or control human IgG were unable to rescue mice from SEB toxicity. By contrast, 3 of 5 mice survived the SEB exposure either when mice were treated with 79G9 alone (1 mg) at a 79G9:SEB ratio of 40:1, or when treated with a combination of 79G9 and 100C9 (0.1 mg each) with a combined Antibody:SEB ratio of just 8:1. This combination led to 100% survival (5 of 5 mice) using a Antibody:SEB ratio of 40:1 (0.5 mg of each antibody).

TABLE 6

Survival of mice exposed to SEB and treated with Anti-SEB antibodies, Study 2.
Balb/C SEB/LPS challenge model

| | SEB | | | Survivors/Total Mice | |
|---|---|---|---|---|---|
| Group | LD$_{50}$ | Treatment | Dose (µg) | 18 Hours | 72 Hours |
| 1 | 25 | — | — | 1/3 | 0/3 |
| 2 | 25 | Control Human IgG | 1 mg | 1/3 | 0/3 |
| 3 | 25 | 79G9 | 1 mg | 5/5 | 3/5 |
| 4 | 25 | 79G9 + 100C9 | 0.1 + 0.1 mg | 5/5 | 3/5 |
| 5 | 25 | 79G9 + 100C9 | 0.5 + 0.5 mg | 5/5 | 5/5 |

EXAMPLE 8

Nucleotide and Amino Acids Sequences Encoding Fully Human Anti-SEB Antibodies F10, 79G9 and 100C9

Nucleotide and amino acid sequences for fully human anti-SEB antibodies were obtained by standard molecular biology methods. Briefly, total RNA was isolated from hybridomas F10, 79G9, and 100C9 using Trizol reagent (Invitrogen, Carlsbad, Calif.) according to the manufacturer's instructions. The message was synthesized to cDNA using Superscript II reverse transcriptase (Invitrogen) according to the manufacturer's instructions.

To amplify the light and heavy chain variable regions, PCR reactions were carried out with Herculase DNA polymerase (Stratagene, La Jolla, Calif.). Primers used for the heavy and light chain amplification for each antibody are set forth in Table 7 below.

TABLE 7

PCR primers for Amplification of Nucleotide Sequences for Antibodies to SEB

| Primer | Sequence (5'-3') | SEQ ID NO: |
|---|---|---|
| 390 | CCCAGTCACGACGTTGTAAAACG | 1 |
| 391 | AGCGGATAACAATTTCACACAGG | 2 |
| 883 | TGGAAGAGGCACGTTCTTTTCTTT | 3 |
| 974 | AGGTRCAGCTGBWGSAGTCDG | 4 |
| 975 | GAHRTYSWGHTGACBCAGTCTCC | 5 |
| 1463 | GATCGAATTCTTAACACTCTCCCCTGTTGAAGCTCTTTGTGACGGGCGAGCTCAGGCC | 6 |
| 882 | GTCCACCTTGGTGTTGCTGGGCTT | 7 |
| 885 | TGAAGATTCTGTAGGGGCCACTGTCTT | 8 |
| 888 | GAGGTGCAGCTGGTGGAGTCTGG | 9 |
| 900 | TCCTATGTGCTGACTCAGCCACC | 10 |
| 1017 | TGCAAGGTCTCCAACAAAGC | 11 |
| 1018 | CCTGGTTCTTGGTCAGCTCA | 12 |
| 1019 | GGCACGGTGGGCATGTGTGA | 13 |
| 1024 | ACCAAGGGCCCATCGGTCTT | 14 |
| 1040 | GCAACACCAAGGTGGACAAG | 15 |
| 1500 | GGTTCAGGGGGAGGTGTGGGAGGT | 16 |
| 1550 | GGGAAGCTTGCCGCCACCATGGGATGGAGCTGTATCATCCTCTTCTTGGTAGCAACAGCTACAGGTGTACACAGCTCCTATGTGCTGACTCAGCCACC | 17 |
| 1551 | CCCGAATTCCTATGAAGATTCTGTAGGGGCCACTGTCTT | 18 |
| 1552 | GGGAAGCTTGCCGCCACCATGGGATGGAGCTGTATCATCCTCTTCTTGGTAGCAACAGCTACAGGTGTACACAGCGAGGTGCAGCTGGTGGAGTCTGGG | 19 |
| 1553 | CCCGAATTCTCATTTACCCAGAGACAGGGAGAGGCTCTTCTG | 20 |
| 1557 | GGGAAGCTTGCCGCCACCATGGGATGGAGCTGTATCATCCTCTTCTTGGTAGCAACAGCTACAGGTGTACACAGCGACATTGAGTTGACCCAGTCTCCA | 22 |
| 1559 | GGGAAGCTTGCCGCCACCATGGGATGGAGCTGTATCATCCTCTTCTTGGTAGCAACAGCTACAGGTGTACACAGCGTACAGCTGTTGGAGTCTGGCGCA | 23 |
| 1560 | CCCTTCGAATTAATCACTCTCCCCTGTTGAAGCTCTTTG | 24 |
| 1570 | GGGAAGCTTGCCGCCACCATGGGATGGAGCTGTATCATCCTCTTCTTGGTAGCAACAGCTACAGGTGTACACAGCGAGGTACAGCTGTTGGAGTCTGGCGCA | 25 |
| 996 | GATCGAATTCTCATTTCCCGGGAGACAGGGAGAGG | 26 |

TABLE 7-continued

| PCR primers for Amplification of Nucleotide Sequences for Antibodies to SEB | | |
|---|---|---|
| Primer | Sequence (5'-3') | SEQ ID NO: |
| 1015 | GGTTCGCTTATTGGGGCCAA | 233 |
| 1020 | CGGTGTCTTCGGGTCTCAGG | 234 |
| 1321 | GGAGGGCAGTGTAGTCTGAG | 235 |
| 1461 | CCTCTACAAATGTGGTATGGCTGATTATG | 236 |
| 1530 | GGGAACGGTGCATTGGAACG | 237 |
| 1577 | CCCAAGCTTGCCGCCACCATGGGATGGAGCTGTATC ATCCTCTTCTTGGTAGCAACAGCTACAGGTGTCCAC TCCSAGGTRCAGCTGBWGSAGTCDG | 264 |
| 1578 | CCCAAGCTTGCCGCCACCATGGGATGGAGCTGTATC ATCCTCTTCTTGGTAGCAACAGCTACAGGTGTCCAC TCCGAHRTYSWGHTGACBCAGTCTCC | 238 |
| 1582 | CCCGAATTCTCATGAAGATTCTGTAGGGGCCACTGT CTT | 239 |
| 1584 | CCCGAATTCTCATTTACCCGGAGACAGGGAGAGGCT CTTC | 265 |
| 1730 | ACGCCGTCCACGTACCAATT | 240 |
| 1731 | AAGCCCTTCACCAGACAGGT | 241 |
| 1732 | TGGTGGACGTGTCCCACG | 242 |
| 1733 | GGAAGGGCCCTTGGTGGA | 243 |
| 1734 | ACCGTGGCCGCTCCTTCC | 244 |
| 1735 | TGCAGGGCGTTGTCCACC | 245 |
| 1736 | AGGCCGCTCCCTCCGTGA | 246 |
| 1737 | TTCACAGGGGAGGAGTCAG | 247 |

In the above table, R = A or G; B = C or G or T; W = A or T; S = C or G; D = A or G or T; H = A or C or T; Y = C or T.

PCR products were cloned into pCR4-TOPO vector (Invitrogen), transformed into *E. coli* Mach1 cells and transformants were selected on LB-Kanamycin plates. Colonies were screened for inserts using the same primer pairs used for PCR amplification, and four positive colonies each were used to generate template DNA for DNA sequence determination, using TempliPhi reagent (GE Healthcare).

DNA inserts were sequenced using primers SEQ ID NO: 1 and 2, with Beckman Coulter DTCS sequencing reagent, followed by data acquisition and analysis on a Beckman Coulter CEQ2000. To add a leader peptide sequence to the light chain, a positive clone was re-amplified with primers SEQ ID NOs:17 and 18 (for 100C9), and SEQ ID NOs 22 and 24 (for 79G9) using Herculase DNA polymerase. To generate a full length heavy chain including a leader peptide sequence, PCR was carried out with primers SEQ ID NOs 19 and 20 (for 100C9), and SEQ ID NOs: 25 and 26 (for 79G9) using the original cDNA as template. The resulting PCR product was TA cloned, transformed into Mach1 cells and positive clones were identified as described above.

Full length heavy chain cDNA was sequenced using primers SEQ ID NOs: 1, 2, 11, 12, 13, 14, 15, 16, 19, and 20 (for 100C9), and SEQ ID NOs: 1, 2, 11, 12, 13, 14, and 15 (for 79G9) using template DNA generated with TempliPhi reagent. The resulting DNA sequences for the full length heavy chain variable regions are as follows: F10 (SEQ ID NO: 29); 100C9 (SEQ ID NO: 250); 79G9+ (SEQ ID NO: 201); 79G9 (SEQ ID NO: 231). It should be pointed out that the heavy chain nucleic acid sequence for 79G9 represents a corrected nucleic acid sequence for 79G9+ (FIG. 17). The resulting DNA sequences for the full length light chain variable regions are follows: F10 (SEQ ID NO: 173); 100C9 (SEQ ID NO: 248); 79G9 (SEQ ID NO: 185). The predicted amino acid sequences derived from the heavy chain nucleic acid sequences are as follows: F10 (SEQ ID NO: 30); 100C9 (SEQ ID NO: 251); 79G9+ (SEQ ID NO: 188); 79G9 (SEQ ID NO: 232). The predicted amino acid sequences derived from the light chain nucleic acid sequences are as follows: F10 (SEQ ID NO: 28); 100C9 (SEQ ID NO: 249); 79G9 (SEQ ID NO: 186).

The nucleic acid and amino acid sequences for each of these antibodies is presented in FIG. 13 A-N. The underlined portions of the sequence represent the leader sequence added by PCR. The bolded regions of the sequences highlight the CDRs. The shaded regions indicate the variable domain. FIG. 14 A-N provides the sequences for CDR and FWR regions for antibodies F10, 100C9, and 79G9.

The VH and VL CDR3 region sequences were additionally obtained for hybridomas C5 and F6. Total RNA was isolated from hybridomas C5 and F6 using Trizol reagent (Invitrogen) according to the manufacturer's instructions. cDNA was synthesized using Superscript II reverse transcriptase (Invitrogen) according to the manufacturer's instructions. To amplify the light and heavy chain variable regions, PCR reactions were carried out with Herculase DNA polymerase (Stratagene) using Morphotek primers #885 (SEQ ID NO: 8) and #900 (SEQ ID NO: 10) for the light chains and #974 (SEQ ID NO: 4) and #883 (SEQ ID NO: 3) for the heavy chains. PCR products were cloned into pCR4-TOPO vector (Invitrogen), transformed into *E. coli* Mach1 cells and transformants were selected on LB Kanamycin plates. Colonies were screened for inserts with the same primer pairs as above and 4 positive colonies each were used to generate template DNA for DNA sequence determination, using TempliPhi reagent (GE Healthcare). DNA inserts were sequenced with Morphotek primers #390 (SEQ ID NO: 1) and #391 (SEQ ID NO: 2) using Beckman Coulter DTCS sequencing reagent followed by data acquisition and analysis on a Beckman Coulter CEQ2000. The predicted CDR3 translated amino acid sequences are shown below in Table 8.

TABLE 8

| Variable region sequences for IgM hybridoma subclones C5, and F6. | | | |
|---|---|---|---|
| Hybridoma | | Closests Germline Match (VH) | SEQ ID NO: |
| | VH CDR3 Sequence | | |
| C5 | CSAAGTVDYWGQG | VH3-30 | 39 |
| F6 | CTTMRNWGQG | VH3-15 | 40 |
| | VL CDR3 Sequence | | |
| C5 | CQSADSSGTYVFGTG | V2-17 | 41 |
| F6 | CQSADSSGTYVVFGGG | V2-17 | 42 |

EXAMPLE 9

Cloning and Sequencing of Human IgG Anti-SEB Antibody 154G12

Nucleotide and amino acid sequences for human IgG anti-SEB antibody 154G12 was obtained by standard molecular biology methods. Total RNA was isolated from hybridoma 154G12 using Trizol® reagent (Invitrogen) according to the manufacturer's instructions. Superscript II reverse transcriptase (Invitrogen) was used to synthesize 154G12 cDNA from the isolated total RNA according to the manufacturer's instructions.

To amplify the light and heavy chain nucleic acid sequences, PCR was carried out with Herculase® DNA polymerase (Stratagene) using primers #1578 (SEQ ID NO: 238) and #1582 (SEQ ID NO: 239) for the light chain, and #1584 (SEQ ID NO: 265) and #1577 (SEQ ID NO: 264) for the heavy chain (Table 7). The 5' primers for both chain amplifications contain leader peptides for eukaryotic expression.

The resulting PCR products were cloned into pCR4-TOPO vector (Invitrogen), transformed into *E. coli* Mach1 cells, plated on LB Kanamycin agar plates, and selected for Kanamycin resistance. Colonies were screened for inserts using primers #1578 (SEQ ID NO: 238) and #1582 (SEQ ID NO: 239) for the light chain, and #1584 (SEQ ID NO: 265) and #1577 (SEQ ID NO: 264) for the heavy chain (Table 7). Four positive colonies each were used to generate template DNA for DNA sequence determination, using TempliPhi reagent (GE Healthcare).

Light chain DNA inserts were sequenced with primers #1321 (SEQ ID NO: 235), 1461 (SEQ ID NO: 236), 1500 (SEQ ID NO: 16), 1551 (SEQ ID NO: 18), and 1552 (SEQ ID NO: 19) (Table 7) using Beckman Coulter DTCS sequencing reagent followed by data acquisition and analysis on a Beckman Coulter CEQ2000. Full length 154G12 heavy chain cDNA was sequenced with primers #996 (SEQ ID NO: 26), 1015 (SEQ ID NO: 233), 1017 (SEQ ID NO: 11), 1018 (SEQ ID NO: 12), 1019 (SEQ ID NO: 13), 1020 (SEQ ID NO: 234), 1040 (SEQ ID NO: 15), and 1530 (SEQ ID NO: 237) (Table 7) using template DNA generated with TempliPhi reagent.

The nucleic acid and amino acid sequences for the antibody are provided in FIG. 13 O-R, where the bolded regions of the sequences highlight the CDRs, the underlined segment denotes a leader sequence added by PCR, and the shaded regions indicate the variable domain. The bolded regions of the sequences highlight the CDRs. FIG. 14 O-R provides the nucleic acid and amino acid sequences for CDR and FWR regions for the antibody.

EXAMPLE 10

Development of Codon Optimized Fully Human IgG Anti-SEB Antibodies 79G9, 100C9, and 154G12

The complete open reading frames for the heavy and/or light chains of the fully human IgG anti-SEB antibodies 79G9, 100C9, and 154G12 were submitted to GeneArt AG (Regensburg, Germany) for codon usage optimization. Optimized forms of all three antibody (heavy and light chains) were sequenced. Light and heavy chain DNA inserts were sequenced with the following clone-specific sequencing primers listed in Table 7: 79G9 light chain—#1734 (SEQ ID NO: 244) and #1735 (SEQ ID NO: 245); 100C9 and 154G12 light chains—#1736 (SEQ ID NO: 246) and #1737 (SEQ ID NO: 247); 79G9, 100C9, and 154G12 heavy chains—#1730 (SEQ ID NO: 240), #1731 (SEQ ID NO: 241), #1732 (SEQ ID NO: 242), and #1733 (SEQ ID NO: 243). Sequencing was carried out using Beckman Coulter DTCS sequencing reagent followed by data acquisition and analysis on a Beckman Coulter CEQ2000.

The nucleic acid sequences for these antibodies are provided in FIG. 15, where the bolded regions of the sequences highlight the CDRs, the underlined segment denotes a leader sequence added by PCR, and the shaded regions indicate the antibody variable domain. FIG. 16 provides the nucleic acid sequences for CDR and FWR regions for these antibodies.

EXAMPLE 11

Assessment of Anti-SEB Antibody-Mediated Inhibition of SEB-Induced T-Cell Cytokine Production Human peripheral blood mononuclear cells (PBMCs) were used to determine the ability of the anti-SEB antibodies to inhibit SEB-induced T-cell cytokine production and measure their in vitro $EC_{50}$ values. Approximately $1 \times 10^5$ PBMCs were cultured at 37° C. in 5% $CO_2$ in 96-well flat-bottom tissue culture plates. Anti-SEB antibodies 79G9, 154G12, or a mixture of thereof, at 4× concentrations, were incubated with SEB (4× its in vitro $ED_{50}$) for 1 hour. The mixture was then added to the PBMCs (1× final concentration for both anti-SEB antibody and SEB) and incubated for 18-22 hours. To determine whether cytokine production occurred, supernatants were transferred to anti-IFN-γ and anti-TNF-α absorbed ELISA plates and assayed using an ELISA kit (R&D System) following the manufacturer's recommended procedure. $EC_{50}$ calculations of anti-SEB antibody were performed using Prism4 (GraphPad Software). The sensitivity limit of the IFN-γ and TNF-α ELISA is 16 pg/mL. Results are shown in Table 9.

TABLE 9

$EC_{50}$ values for Anti-SEB antibodies 154G12 and 79G9

| Antibody (:g/ml) | IFN-( | | TNF-∀ | |
|---|---|---|---|---|
| | $EC_{50}$ (ng/ml) | Std. Dev. | $EC_{50}$ (ng/ml) | Std. Dev. |
| 154G12 (1) | 0.60 | 0.07 | 0.96 | 0.49 |
| 79G9 (10) | 158.39 | 174.82 | 216.87 | 257.76 |
| 154G12 (1), 79G9 (1) | 0.90 | 0.21 | 1.23 | 0.52 |

EXAMPLE 12

Figure 18:
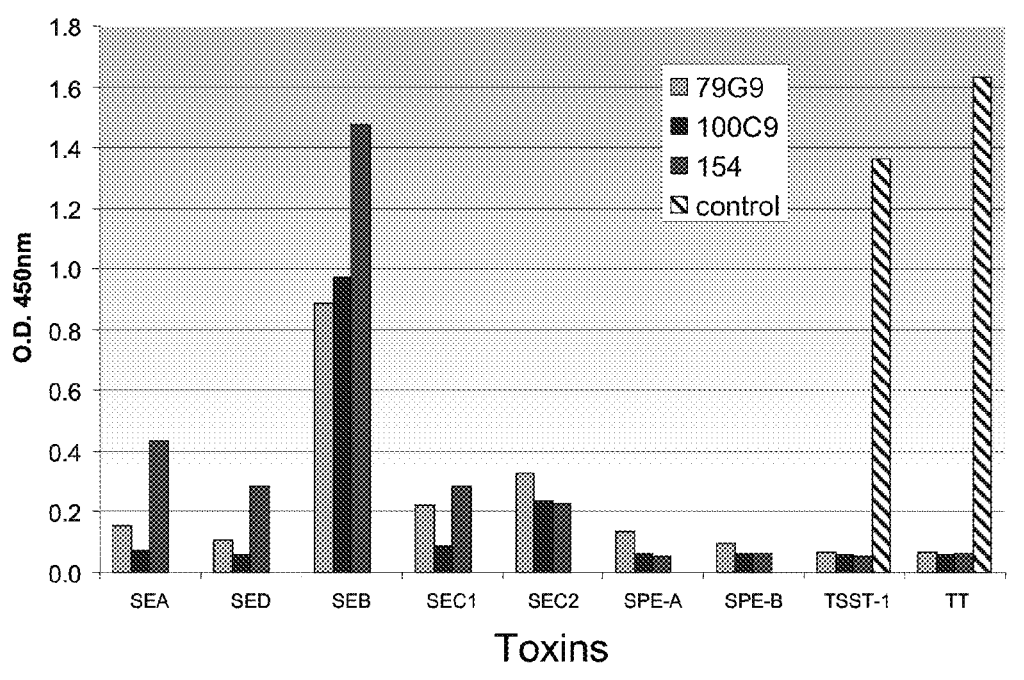

Reactivity of SEB-Specific Antibodies 79G9, 100C9, and 154G12 to SEB-Related Toxins To determine the SEB-specificity of antibodies 79G9, 100C9, and 154G12, these antibodies were examined for cross-reactivity to SEB-related *Staphylococcus* enterotoxins SEA, SED, SEC1, SEC2, and TSST-1; Streptococcal pyrogenic exotoxins SPE-A, SPE-B (each purchased from Toxin Technologies); and Tetanus toxoid (TT, purchased from Cylex Inc.). Each of the toxins was diluted to 0.5 μg/ml in coating buffer (50 mM carbonate-bicarbonate, pH 9.4 (Sigma)) and absorbed onto ELISA plates overnight at 4° C. The ELISA plates were blocked with assay buffer (PBS (Cell-Gro) containing 1% BSA (Sigma) and 0.05% Tween 20 (Bio-Rad)) for 2 hours at room temperature. The ELISA plates were washed once with washing buffer (PBS containing 0.05% Tween 20). Purified antibodies 79G9, 100C9, and 154G12; control mouse anti-TSST-1 (Hycult); and control mouse anti-TT (Abcam), each at a concentration of 2.5 μg/ml, were transferred into the ELISA plates at 100 p. 1 per well and incubated at room temperature for 1 hour. Subsequently, plates were washed four times. Antibody binding was determined by adding 100 µl per well of horseradish peroxidase-conjugated goat anti-human IgG+M (H+L) (Jackson ImmunoResearch) diluted 1:10,000 in binding buffer was for antibodies 79G9, 100C9, and 154G12, while horseradish peroxidase-conjugated goat anti-mouse IgG (H+L) was used to detect control antibodies. Once added to the ELISA plates, horseradish peroxidase-conjugated antibodies were incubated at room temperature for 1 hour. Plates were washed four times and SureBlue substrate (Kirkegaard & Perry Laboratories) was added (100 µl/well) for 10 min. Reactions were stopped by adding 1 N sulfuric acid (50 µl/well), and the absorbance was determined at 450 nm. Results are shown in FIG. 18.

Biological Deposit of Antibody-Producing Cells: Consistent with the detailed description and the written examples provided herein, examples of antibody-producing cells of the invention were deposited with the Amer. Type Cult. Coll. (10801 University Blvd., Manassas, Va. 20110-2209). Hybridoma cell lines producing antibodies 100C9 and 79G9 were deposited Jan. 3, 2007 and have been assigned ATCC accession numbers PTA-8115 and PTA-8116, respectively. Additionally, cells producing antibodies F10, F6, E12, C5, and 154G12 were deposited on Dec. 19, 2007 and have been assigned ATCC Access. Nos. PTA-8849, PTA-8848, PTA-8847, PTA-8846, and PTA-8850, respectively.

The present invention is not limited to the embodiments described and exemplified above, but is capable of variation and modification within the scope of the appended claims.

What is claimed:

1. An isolated vector comprising a polynucleotide encoding an antibody heavy chain comprising a heavy chain CDR1 comprising the amino acid sequence of SEQ ID NO: 68, a heavy chain CDR2 comprising the amino acid sequence of SEQ ID NO: 69, and a heavy chain CDR3 comprising the amino acid sequence of SEQ ID NO: 70.

2. The vector of claim 1, said polynucleotide further encoding an antibody light chain comprising a light chain CDR1 comprising the amino acid sequence of SEQ ID NO: 56, a light chain CDR2 comprising the amino acid sequence of SEQ ID NO: 57, and a light chain CDR3 comprising the amino acid sequence of SEQ ID NO: 58.

3. An isolated vector comprising a polynucleotide encoding an antibody light chain comprising a light chain CDR1 comprising the amino acid sequence of SEQ ID NO: 56, a light chain CDR2 comprising the amino acid sequence of SEQ ID NO: 57, and a light chain CDR3 comprising the amino acid sequence of SEQ ID NO: 58.

4. An isolated vector comprising a polynucleotide encoding an antibody heavy chain comprising a heavy chain CDR1 comprising the amino acid sequence of SEQ ID NO: 130, a heavy chain CDR2 comprising the amino acid sequence of SEQ ID NO: 131, and a heavy chain CDR3 comprising the amino acid sequence of SEQ ID NO: 132.

5. The vector of claim 4, said polynucleotide further encoding an antibody light chain comprising a light chain CDR1 comprising the amino acid sequence of SEQ ID NO: 104, a light chain CDR2 comprising the amino acid sequence of SEQ ID NO: 105, and a light chain CDR3 comprising the amino acid sequence of SEQ ID NO: 106.

6. An isolated vector comprising a polynucleotide encoding an antibody light chain comprising a light chain CDR1 comprising the amino acid sequence of SEQ ID NO: 104, a light chain CDR2 comprising the amino acid sequence of SEQ ID NO: 105, and a light chain CDR3 comprising the amino acid sequence of SEQ ID NO: 106.

7. An isolated vector comprising a polynucleotide encoding an antibody heavy chain comprising a heavy chain CDR1 comprising the amino acid sequence of SEQ ID NO: 92, a heavy chain CDR2 comprising the amino acid sequence of SEQ ID NO: 93, and a heavy chain CDR3 comprising the amino acid sequence of SEQ ID NO: 94.

8. The vector of claim 7, said polynucleotide further encoding an antibody light chain comprising a light chain CDR1 comprising the amino acid sequence of SEQ ID NO: 80, a light chain CDR2 comprising the amino acid sequence of SEQ ID NO: 81, and a light chain CDR3 comprising the amino acid sequence of SEQ ID NO: 82.

9. An isolated vector comprising a polynucleotide encoding an antibody light chain comprising a light chain CDR1 comprising the amino acid sequence of SEQ ID NO: 80, a light chain CDR2 comprising the amino acid sequence of SEQ ID NO: 81, and a light chain CDR3 comprising the amino acid sequence of SEQ ID NO: 82.

10. An isolated vector comprising a polynucleotide encoding an antibody heavy chain comprising a heavy chain CDR1 comprising the amino acid sequence of SEQ ID NO: 144, a heavy chain CDR2 comprising the amino acid sequence of SEQ ID NO: 146, and a heavy chain CDR3 comprising the amino acid sequence of SEQ ID NO: 148.

11. The vector of claim 10, said polynucleotide further encoding an antibody light chain comprising a light chain CDR1 comprising the amino acid sequence of SEQ ID NO: 136, a light chain CDR2 comprising the amino acid sequence of SEQ ID NO: 138, and a light chain CDR3 comprising the amino acid sequence of SEQ ID NO: 140.

12. An isolated vector comprising a polynucleotide encoding an antibody light chain comprising a light chain CDR1 comprising the amino acid sequence of SEQ ID NO: 136, a light chain CDR2 comprising the amino acid sequence of SEQ ID NO: 138, and a light chain CDR3 comprising the amino acid sequence of SEQ ID NO: 140.

13. The vector of any one of claims 1 to 12 wherein said polynucleotide is a cDNA.

14. A cell that expresses a vector comprising a polynucleotide encoding an antibody, or antigen-binding fragment thereof, that binds to *Staphylococcus* enterotoxin B, said antibody comprising:
   a. a heavy chain CDR1 comprising the amino acid sequence of SEQ ID NO: 68, a heavy chain CDR2 comprising the amino acid sequence of SEQ ID NO: 69, and a heavy chain CDR3 comprising the amino acid sequence of SEQ ID NO: 70, a light chain CDR1 comprising the amino acid sequence of SEQ ID NO: 56, a light chain CDR2 comprising the amino acid sequence of SEQ ID NO: 57, and a light chain CDR3 comprising the amino acid sequence of SEQ ID NO: 58;
   b. a heavy chain CDR1 comprising the amino acid sequence of SEQ ID NO: 130, a heavy chain CDR2 comprising the amino acid sequence of SEQ ID NO: 131, and a heavy chain CDR3 comprising the amino acid sequence of SEQ ID NO: 132, a light chain CDR1 comprising the amino acid sequence of SEQ ID NO: 104, a light chain CDR2 comprising the amino acid sequence of SEQ ID NO: 105, and a light chain CDR3 comprising the amino acid sequence of SEQ ID NO: 106;
   c. a heavy chain CDR1 comprising the amino acid sequence of SEQ ID NO: 92, a heavy chain CDR2 comprising the amino acid sequence of SEQ ID NO: 93, and a heavy chain CDR3 comprising the amino acid sequence of SEQ ID NO: 94, a light chain CDR1 comprising the amino acid sequence of SEQ ID NO: 80, a light chain CDR2 comprising the amino acid sequence of SEQ ID NO: 81, and a light chain CDR3 comprising the amino acid sequence of SEQ ID NO: 82; or
   d. a heavy chain CDR1 comprising the amino acid sequence of SEQ ID NO: 144, a heavy chain CDR2 comprising the amino acid sequence of SEQ ID NO: 146, and a heavy chain CDR3 comprising the amino acid sequence of SEQ ID NO: 148, a light chain CDR1 comprising the amino acid sequence of SEQ ID NO: 136, a light chain CDR2 comprising the amino acid sequence of SEQ ID NO: 138, and a light chain CDR3 comprising the amino acid sequence of SEQ ID NO: 140.

15. A hybridoma cell that expresses a polynucleotide encoding an antibody, or antigen-binding fragment thereof, that binds to *Staphylococcus* enterotoxin B, said antibody comprising:
   a. a heavy chain CDR1 comprising the amino acid sequence of SEQ ID NO: 68, a heavy chain CDR2 comprising the amino acid sequence of SEQ ID NO: 69, and a heavy chain CDR3 comprising the amino acid sequence of SEQ ID NO: 70, a light chain CDR1 comprising the amino acid sequence of SEQ ID NO: 56, a light chain CDR2 comprising the amino acid sequence of SEQ ID NO: 57, and a light chain CDR3 comprising the amino acid sequence of SEQ IDNO: 58;
   b. a heavy chain CDR1 comprising the amino acid sequence of SEQ ID NO: 130, a heavy chain CDR2 comprising the amino acid sequence of SEQ ID NO: 131, and a heavy chain CDR3 comprising the amino acid sequence of SEQ ID NO: 132, a light chain CDR1 comprising the amino acid sequence of SEQ ID NO: 104, a light chain CDR2 comprising the amino acid sequence of SEQ ID NO: 105, and a light chain CDR3 comprising the amino acid sequence of SEQ ID NO: 106;
   c. a heavy chain CDR1 comprising the amino acid sequence of SEQ ID NO: 92, a heavy chain CDR2 comprising the amino acid sequence of SEQ ID NO: 93, and a heavy chain CDR3 comprising the amino acid sequence of SEQ ID NO: 94, a light chain CDR1 comprising the amino acid sequence of SEQ ID NO: 80, a light chain CDR2 comprising the amino acid sequence of SEQ ID NO: 81, and a light chain CDR3 comprising the amino acid sequence of SEQ ID NO: 82; or
   d. a heavy chain CDR1 comprising the amino acid sequence of SEQ ID NO: 144, a heavy chain CDR2 comprising the amino acid sequence of SEQ ID NO: 146, and a heavy chain CDR3 comprising the amino acid sequence of SEQ ID NO: 148, a light chain CDR1 comprising the amino acid sequence of SEQ ID NO: 136, a light chain CDR2 comprising the amino acid sequence of SEQ ID NO: 138, and a light chain CDR3 comprising the amino acid sequence of SEQ ID NO: 140.

16. A method of making an antibody or antigen-binding fragment thereof, comprising culturing the cell of claim 14 or 15 under conditions suitable to produce the antibody or an antigen-binding fragment, and recovering the antibody or antigen-binding fragment from the cell culture.

17. An immortalized cell that expresses a polynucleotide encoding an antibody, or antigen-binding fragment thereof, that binds to *Staphylococcus* enterotoxin B, said antibody comprising:
   a. a heavy chain CDR1 comprising the amino acid sequence of SEQ ID NO: 68, a heavy chain CDR2 comprising the amino acid sequence of SEQ ID NO: 69, and a heavy chain CDR3 comprising the amino acid sequence of SEQ ID NO: 70, a light chain CDR1 comprising the amino acid sequence of SEQ ID NO: 56, a light chain CDR2 comprising the amino acid sequence of SEQ ID NO: 57, and a light chain CDR3 comprising the amino acid sequence of SEQ ID NO: 58;
   b. a heavy chain CDR1 comprising the amino acid sequence of SEQ ID NO: 130, a heavy chain CDR2 comprising the amino acid sequence of SEQ ID NO: 131, and a heavy chain CDR3 comprising the amino acid sequence of SEQ ID NO: 132, a light chain CDR1 comprising the amino acid sequence of SEQ ID NO: 104, a light chain CDR2 comprising the amino acid sequence of SEQ ID NO: 105, and a light chain CDR3 comprising the amino acid sequence of SEQ ID NO: 106;
   c. a heavy chain CDR1 comprising the amino acid sequence of SEQ ID NO: 92, a heavy chain CDR2 comprising the amino acid sequence of SEQ ID NO: 93, and a heavy chain CDR3 comprising the amino acid sequence of SEQ ID NO: 94, a light chain CDR1 comprising the amino acid sequence of SEQ ID NO: 80, a light chain CDR2 comprising the amino acid sequence of SEQ ID NO: 81, and a light chain CDR3 comprising the amino acid sequence of SEQ ID NO: 82; or d. a heavy chain CDR1 comprising the amino acid sequence of SEQ ID NO: 144, a heavy chain CDR2 comprising the amino acid sequence of SEQ ID NO: 146, and a heavy chain CDR3 comprising the amino acid sequence of SEQ ID NO: 148, a light chain CDR1 comprising the amino acid sequence of SEQ ID NO: 136, a light chain CDR2 comprising the amino acid sequence of SEQ ID NO: 138, and a light chain CDR3 comprising the amino acid sequence of SEQ ID NO: 140.

* * * * *

```
                             SEQUENCE LISTING

<160> NUMBER OF SEQ ID NOS: 265

<210> SEQ ID NO 1
<211> LENGTH: 23
<212> TYPE: DNA
<213> ORGANISM: Homo Sapiens

<400> SEQUENCE: 1
cccagtcacg acgttgtaaa acg                                               23

<210> SEQ ID NO 2
<211> LENGTH: 23
<212> TYPE: DNA
<213> ORGANISM: Homo Sapiens

<400> SEQUENCE: 2
agcggataac aatttcacac agg                                               23

<210> SEQ ID NO 3
<211> LENGTH: 24
<212> TYPE: DNA
<213> ORGANISM: Homo Sapiens

<400> SEQUENCE: 3
tggaagaggc acgttctttt cttt                                              24

<210> SEQ ID NO 4
<211> LENGTH: 21
<212> TYPE: DNA
<213> ORGANISM: Homo Sapiens
<220> FEATURE:
<221> NAME/KEY: misc_feature
<222> LOCATION: (5)..(5)
<223> OTHER INFORMATION: R = A or G
<220> FEATURE:
<221> NAME/KEY: misc_feature
<222> LOCATION: (12)..(12)
<223> OTHER INFORMATION: B = C or G or T
<220> FEATURE:
<221> NAME/KEY: misc_feature
<222> LOCATION: (13)..(13)
<223> OTHER INFORMATION: W = A or T
<220> FEATURE:
<221> NAME/KEY: misc_feature
<222> LOCATION: (15)..(15)
<223> OTHER INFORMATION: S =  C or G
<220> FEATURE:
<221> NAME/KEY: misc_feature
<222> LOCATION: (20)..(20)
<223> OTHER INFORMATION: D = A or G or T
```

<400> SEQUENCE: 4
aggtrcagct gbwgsagtcd g                                      21

<210> SEQ ID NO 5
<211> LENGTH: 23
<212> TYPE: DNA
<213> ORGANISM: Homo Sapiens
<220> FEATURE:
<221> NAME/KEY: misc_feature
<222> LOCATION: (3)..(3)
<223> OTHER INFORMATION: H = A or C or T
<220> FEATURE:
<221> NAME/KEY: misc_feature
<222> LOCATION: (4)..(4)
<223> OTHER INFORMATION: R = A or G
<220> FEATURE:
<221> NAME/KEY: misc_feature
<222> LOCATION: (6)..(6)
<223> OTHER INFORMATION: Y = C or T
<220> FEATURE:
<221> NAME/KEY: misc_feature
<222> LOCATION: (7)..(7)
<223> OTHER INFORMATION: S = C or G
<220> FEATURE:
<221> NAME/KEY: misc_feature
<222> LOCATION: (8)..(8)
<223> OTHER INFORMATION: W = A or T
<220> FEATURE:
<221> NAME/KEY: misc_feature
<222> LOCATION: (10)..(10)
<223> OTHER INFORMATION: H = A or C or T
<220> FEATURE:
<221> NAME/KEY: misc_feature
<222> LOCATION: (15)..(15)
<223> OTHER INFORMATION: B = C or G or T

<400> SEQUENCE: 5
gahrtyswgh tgacbcagtc tcc                                    23

<210> SEQ ID NO 6
<211> LENGTH: 58
<212> TYPE: DNA
<213> ORGANISM: Homo Sapiens

<400> SEQUENCE: 6
gatcgaattc ttaacactct cccctgttga agctctttgt gacgggcgag ctcaggcc   58

<210> SEQ ID NO 7
<211> LENGTH: 24
<212> TYPE: DNA
<213> ORGANISM: Homo Sapiens

<400> SEQUENCE: 7
gtccaccttg gtgttgctgg gctt                                   24

<210> SEQ ID NO 8
<211> LENGTH: 27
<212> TYPE: DNA
<213> ORGANISM: Homo Sapiens

<400> SEQUENCE: 8
tgaagattct gtaggggcca ctgtctt                                27

<210> SEQ ID NO 9
<211> LENGTH: 23
<212> TYPE: DNA
<213> ORGANISM: Homo Sapiens

<400> SEQUENCE: 9

```
gaggtgcagc tggtggagtc tgg                                            23

<210> SEQ ID NO 10
<211> LENGTH: 23
<212> TYPE: DNA
<213> ORGANISM: Homo Sapiens

<400> SEQUENCE: 10
tcctatgtgc tgactcagcc acc                                            23

<210> SEQ ID NO 11
<211> LENGTH: 20
<212> TYPE: DNA
<213> ORGANISM: Homo Sapiens

<400> SEQUENCE: 11
tgcaaggtct ccaacaaagc                                                20

<210> SEQ ID NO 12
<211> LENGTH: 20
<212> TYPE: DNA
<213> ORGANISM: Homo Sapiens

<400> SEQUENCE: 12
cctggttctt ggtcagctca                                                20

<210> SEQ ID NO 13
<211> LENGTH: 20
<212> TYPE: DNA
<213> ORGANISM: Homo Sapiens

<400> SEQUENCE: 13
ggcacggtgg gcatgtgtga                                                20

<210> SEQ ID NO 14
<211> LENGTH: 20
<212> TYPE: DNA
<213> ORGANISM: Homo Sapiens

<400> SEQUENCE: 14
accaagggcc catcggtctt                                                20

<210> SEQ ID NO 15
<211> LENGTH: 20
<212> TYPE: DNA
<213> ORGANISM: Homo Sapiens

<400> SEQUENCE: 15
gcaacaccaa ggtggacaag                                                20

<210> SEQ ID NO 16
<211> LENGTH: 24
<212> TYPE: DNA
<213> ORGANISM: Homo Sapiens

<400> SEQUENCE: 16
ggttcagggg gaggtgtggg aggt                                           24

<210> SEQ ID NO 17
<211> LENGTH: 98
<212> TYPE: DNA
<213> ORGANISM: Homo Sapiens
```

<400> SEQUENCE: 17
gggaagcttg ccgccaccat gggatggagc tgtatcatcc tcttcttggt agcaacagct    60
acaggtgtac acagctccta tgtgctgact cagccacc                            98

<210> SEQ ID NO 18
<211> LENGTH: 39
<212> TYPE: DNA
<213> ORGANISM: Homo Sapiens

<400> SEQUENCE: 18
cccgaattcc tatgaagatt ctgtagggc cactgtctt                            39

<210> SEQ ID NO 19
<211> LENGTH: 99
<212> TYPE: DNA
<213> ORGANISM: Homo Sapiens

<400> SEQUENCE: 19
gggaagcttg ccgccaccat gggatggagc tgtatcatcc tcttcttggt agcaacagct    60
acaggtgtac acagcgaggt gcagctggtg gagtctggg                           99

<210> SEQ ID NO 20
<211> LENGTH: 42
<212> TYPE: DNA
<213> ORGANISM: Homo Sapiens

<400> SEQUENCE: 20
cccgaattct catttaccca gagacaggga gaggctcttc tg                       42

<210> SEQ ID NO 21
<211> LENGTH: 57
<212> TYPE: DNA
<213> ORGANISM: Artificial Sequence
<220> FEATURE:
<223> OTHER INFORMATION: Polynucleotide

<400> SEQUENCE: 21
atgggatgga gctgtatcat cctcttcttg gtagcaacag ctacaggtgt gcactcc       57

<210> SEQ ID NO 22
<211> LENGTH: 99
<212> TYPE: DNA
<213> ORGANISM: Homo Sapiens

<400> SEQUENCE: 22
gggaagcttg ccgccaccat gggatggagc tgtatcatcc tcttcttggt agcaacagct    60
acaggtgtac acagcgacat tgagttgacc cagtctcca                           99

<210> SEQ ID NO 23
<211> LENGTH: 99
<212> TYPE: DNA
<213> ORGANISM: Homo Sapiens

<400> SEQUENCE: 23
gggaagcttg ccgccaccat gggatggagc tgtatcatcc tcttcttggt agcaacagct    60
acaggtgtac acagcgtaca gctgttggag tctggcgca                           99

<210> SEQ ID NO 24
<211> LENGTH: 39
<212> TYPE: DNA

```
<400> SEQUENCE: 24
cccttcgaat taatcactct ccctgttga agctctttg                                39

<210> SEQ ID NO 25
<211> LENGTH: 102
<212> TYPE: DNA
<213> ORGANISM: Homo Sapiens

<400> SEQUENCE: 25
gggaagcttg ccgccaccat gggatggagc tgtatcatcc tcttcttggt agcaacagct       60
acaggtgtac acagcgaggt acagctgttg gagtctggcg ca                          102

<210> SEQ ID NO 26
<211> LENGTH: 35
<212> TYPE: DNA
<213> ORGANISM: Homo Sapiens

<400> SEQUENCE: 26
gatcgaattc tcatttcccg ggagacaggg agagg                                  35

<210> SEQ ID NO 27
<211> LENGTH: 642
<212> TYPE: DNA
<213> ORGANISM: Homo Sapiens

<400> SEQUENCE: 27
gacgttgagc tgacccagtc tccttccacc ctgtctgcat ctgtaggaga cagagtcacc       60
atcacttgcc gggccagtca gagtattagt agctggttgg cctggtatca gcagaaacca     120
gggaaagccc ctaagctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacag tataatagtt atccgtggac gttcggccaa     300
gggaccaagg tggaaatcaa acgaactgtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga aaacacaaa gtctacgcct gcgaagtcac ccatcagggc      600
ctgagctcgc ccgtcacaaa gagcttcaac aggggagagt gt                         642

<210> SEQ ID NO 28
<211> LENGTH: 214
<212> TYPE: PRT
<213> ORGANISM: Homo Sapiens

<400> SEQUENCE: 28

Asp Val Glu Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Asp Asp Phe Ala Thr Tyr Tyr Cys Gln Gln Tyr Asn Ser Tyr Pro Trp
                85                   90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 29
<211> LENGTH: 693
<212> TYPE: DNA
<213> ORGANISM: Homo Sapiens

<400> SEQUENCE: 29
caggtacagc tggtgcagtc tggggggaggc ctggtcaagc ctgggggggtc cctgagactc      60 tcctgtgcag cctctggatt caccttcagt agctatagca tgaactgggt ccgccaggct     120
ccagggaagg gctggagtg gtctcatcc attagtagta gtagtagtta catatactac      180
gcagactcag tgaagggccg attcaccatc tccagagaca cgccaagaa ctcactgtat      240 ctgcaaatga acagcctgag agccgaggac acggctgtgt attactgtgc gagagggggg      300
gtggctggtc gaaccgaaat ttactactac tactacggta tggacgtctg gggccaaggg      360
accacggtca ccgtctcctc agggagtgca tccgccccaa cccttttccc cctcgtctcc      420
tgtgagaatt ccccgtcgga tacgagcagc gtggccgttg gctgcctcgc acaggacttc      480
cttcccgact ccatcacttt ctcctggaaa tacaagaaca actctgacat cagcagcacc      540
cggggcttcc catcagtcct gagagggggc aagtacgcag ccacctcaca ggtgctgctg      600
ccttccaagg acgtcatgca gggcacagac gaacacgtgg tgtgcaaagt ccagcacccc      660
aacggcaaca agaaaagaa cgtgcctctt cca                                    693

<210> SEQ ID NO 30
<211> LENGTH: 231
<212> TYPE: PRT
<213> ORGANISM: Homo Sapiens

<400> SEQUENCE: 30

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Ala Gly Arg Thr Glu Ile Tyr Tyr Tyr Tyr Tyr
            100                 105                 110

Gly Met Asp Val Trp Gly Gln Gly Thr Thr Val Thr Val Ser Ser Gly
        115                 120                 125

Ser Ala Ser Ala Pro Thr Leu Phe Pro Leu Val Ser Cys Glu Asn Ser
    130                 135                 140

Pro Ser Asp Thr Ser Ser Val Ala Val Gly Cys Leu Ala Gln Asp Phe
145                 150                 155                 160

Leu Pro Asp Ser Ile Thr Phe Ser Trp Lys Tyr Lys Asn Asn Ser Asp
                165                 170                 175

Ile Ser Ser Thr Arg Gly Phe Pro Ser Val Leu Arg Gly Gly Lys Tyr
            180                 185                 190

Ala Ala Thr Ser Gln Val Leu Leu Pro Ser Lys Asp Val Met Gln Gly
        195                 200                 205

Thr Asp Glu His Val Val Cys Lys Val Gln His Pro Asn Gly Asn Lys
    210                 215                 220

Glu Lys Asn Val Pro Leu Pro
225                 230

<210> SEQ ID NO 31
<211> LENGTH: 702
<212> TYPE: DNA
<213> ORGANISM: Homo Sapiens

<400> SEQUENCE: 31
atgggatgga gctgtatcat cctcttcttg gtagcaacag ctacaggtgt acacagctcc      60
tatgtgctga ctcagccacc ctcggtgtcg gtgtcccag  acagacggc  caggatcacc     120 tgctctggag atgcattgcc aaagcaatat acttattggt accagcagaa gccaggccag     180
gcccctgtgg tggtgatcta taaagacagt gagaggccct cagggatccc tgagcgattc     240
tctggctcca gctcagggac aacagtcacg gtgaccatca gtggagtcca ggcagaagac     300
gaggctgact attattgtca atcagcagac agcagtggta cttccctggt gttcggcgga     360
gggaccaagc tgaccgtcct aggtcagccc aaggctgccc cctcggtcac tctgttcccg     420
ccctcctctg aggagcttca agccaacaag gccacactgg tgtgtctcat aagtgacttc     480
tacccgggag ccgtgacagt ggcctggaag gcagatagca gccccgtcaa ggcgggagtg     540
gagaccacca cacctccaa  acaaagcaac aacaagtacg cggccagcag ctacctgagc     600
ctgacgcctg agcagtggaa gtcccacaaa agctacagct gccaggtcac gcatgaaggg     660
agcaccgtgg agaagacagt ggcccctaca gaatcttcat ag                        702

<210> SEQ ID NO 32
<211> LENGTH: 233
<212> TYPE: PRT
<213> ORGANISM: Homo Sapiens

<400> SEQUENCE: 32

Met Gly Trp Ser Cys Ile Ile Leu Phe Leu Val Ala Thr Ala Thr Gly
1               5                   10                  15

Val His Ser Ser Tyr Val Leu Thr Gln Pro Pro Ser Val Ser Val Ser
            20                  25                  30

Pro Gly Gln Thr Ala Arg Ile Thr Cys Ser Gly Asp Ala Leu Pro Lys
            35                  40                  45
Gln Tyr Thr Tyr Trp Tyr Gln Gln Lys Pro Gly Gln Ala Pro Val Val
        50                  55                  60
Val Ile Tyr Lys Asp Ser Glu Arg Pro Ser Gly Ile Pro Glu Arg Phe
65                  70                  75                  80
Ser Gly Ser Ser Ser Gly Thr Thr Val Thr Val Thr Ile Ser Gly Val
                85                  90                  95
Gln Ala Glu Asp Glu Ala Asp Tyr Tyr Cys Gln Ser Ala Asp Ser Ser
            100                 105                 110
Gly Thr Ser Leu Val Phe Gly Gly Gly Thr Lys Leu Thr Val Leu Gly
        115                 120                 125
Gln Pro Lys Ala Ala Pro Ser Val Thr Leu Phe Pro Pro Ser Ser Glu
    130                 135                 140
Glu Leu Gln Ala Asn Lys Ala Thr Leu Val Cys Leu Ile Ser Asp Phe
145                 150                 155                 160
Tyr Pro Gly Ala Val Thr Val Ala Trp Lys Ala Asp Ser Ser Pro Val
                165                 170                 175
Lys Ala Gly Val Glu Thr Thr Thr Pro Ser Lys Gln Ser Asn Asn Lys
            180                 185                 190
Tyr Ala Ala Ser Ser Tyr Leu Ser Leu Thr Pro Glu Gln Trp Lys Ser
        195                 200                 205
His Lys Ser Tyr Ser Cys Gln Val Thr His Glu Gly Ser Thr Val Glu
    210                 215                 220
Lys Thr Val Ala Pro Thr Glu Ser Ser
225                 230

<210> SEQ ID NO 33
<211> LENGTH: 1419
<212> TYPE: DNA
<213> ORGANISM: Homo Sapiens

<400> SEQUENCE: 33
atgggatgga gctgtatcat cctcttcttg gtagcaacag ctacaggtgt acacagcgag     60
gtgcagctgg tggagtctgg gggaggcttg gtccagcctg gggggtccct gagactctcc    120
tgttcagcct ctggtttcac ctttagtagt tattggatga gctgggtccg ccaggctcca    180
gggaaggggc tggagtgggt cgccaacata atacaagatg aagtgagaaa atactatgcg    240
gactctgtga aggccggct caccatctcc agagacaacg ccaagaactc actatatctg    300
cagatgaaca gcctgagagt cgacgacacg gctgtgtatt attgtgcgag aggatatgag    360
gggtgtagtg caaccaggtg ctacctgtac tactttgact attggggccc ggggaccctg    420
gtcaccgtct cctcagcctc caccaagggc ccatcggtct tccccctggc accctcctcc    480
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgaccgtgcc ctccagcagc    660
ttgggcaccc agacctacat ctgcaacgtg aatcacaagc ccagcaacac caaggtggac    720
aagagagttg agcccaaatc ttgtgacaaa actcacacat gcccaccgtg cccagcacct    780
gaactcctgg ggggaccgtc agtcttcctg ttccccccaa aacccaagga caccctcat gatctcccgg    840 acccctgagg tcacatgcgt ggtggtggac gtgagccacg aagaccctga ggtcaagttc    900
aactggtacg tggacggcgt ggaggtgcat aatgccaaga caaagccgcg ggaggagcag    960

```
tacaacagca cgtaccgtgt ggtcagggtc ctcaccgtcc tgcaccagga ctggctgaat    1020
ggcaaggagt acaagtgcaa ggtctccaac aaagccctcc cggcccccat cgagaaaacc    1080
atctccaaag ccaaagggca gccccgagaa ccacaggtgt acaccctgcc cccatcccgg    1140
gaggagatga ccaagaacca ggtcagcctg acctgcctgg tcaaaggctt ctatcccagc    1200
gacatcgccg tggagtggga gagcaatggg cagccggagg acaactacaa gaccacgcct    1260
cccgtgctgg actccgacgg ctccttcttc ctctatagca agctcaccgt ggacaagagc    1320
aggtggcagc aggggaacgt cttctcatgc tccgtgatgc atgaggctct gcacaaccac    1380
tacacgcaga agagcctctc cctgtctctg ggtaaatga                          1419
```

<210> SEQ ID NO 34
<211> LENGTH: 472
<212> TYPE: PRT
<213> ORGANISM: Homo Sapiens

<400> SEQUENCE: 34

```
Met Gly Trp Ser Cys Ile Ile Leu Phe Leu Val Ala Thr Ala Thr Gly
1               5                   10                  15

Val His Ser Glu Val Gln Leu Val Glu Ser Gly Gly Gly Leu Val Gln
            20                  25                  30

Pro Gly Gly Ser Leu Arg Leu Ser Cys Ser Ala Ser Gly Phe Thr Phe
        35                  40                  45

Ser Ser Tyr Trp Met Ser Trp Val Arg Gln Ala Pro Gly Lys Gly Leu
    50                  55                  60

Glu Trp Val Ala Asn Ile Ile Gln Asp Gly Ser Glu Lys Tyr Tyr Ala
65                  70                  75                  80

Asp Ser Val Lys Gly Arg Leu Thr Ile Ser Arg Asp Asn Ala Lys Asn
                85                  90                  95

Ser Leu Tyr Leu Gln Met Asn Ser Leu Arg Val Asp Asp Thr Ala Val
            100                 105                 110

Tyr Tyr Cys Ala Arg Gly Tyr Glu Gly Cys Ser Ala Thr Arg Cys Tyr
        115                 120                 125

Leu Tyr Tyr Phe Asp Tyr Trp Gly Pro Gly Thr Leu Val Thr Val Ser
    130                 135                 140

Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Gly Pro Pro Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285
```

```
Val Asp Val Ser His Glu Asp Pro Glu Val Lys Phe Asn Trp Tyr Val
    290                 295                 300
Asp Gly Val Glu Val His Asn Ala Lys Thr Lys Pro Arg Glu Glu Gln
305                 310                 315                 320
Tyr Asn Ser Thr Tyr Arg Val Val Arg Val Leu Thr Val Leu His Gln
                325                 330                 335
Asp Trp Leu Asn Gly Lys Glu Tyr Lys Cys Lys Val Ser Asn Lys Ala
            340                 345                 350
Leu Pro Ala Pro Ile Glu Lys Thr Ile Ser Lys Ala Lys Gly Gln Pro
        355                 360                 365
Arg Glu Pro Gln Val Tyr Thr Leu Pro Pro Ser Arg Glu Glu Met Thr
370                 375                 380
Lys Asn Gln Val Ser Leu Thr Cys Leu Val Lys Gly Phe Tyr Pro Ser
385                 390                 395                 400
Asp Ile Ala Val Glu Trp Glu Ser Asn Gly Gln Pro Glu Asp Asn Tyr
                405                 410                 415
Lys Thr Thr Pro Pro Val Leu Asp Ser Asp Gly Ser Phe Phe Leu Tyr
            420                 425                 430
Ser Lys Leu Thr Val Asp Lys Ser Arg Trp Gln Gln Gly Asn Val Phe
        435                 440                 445
Ser Cys Ser Val Met His Glu Ala Leu His Asn His Tyr Thr Gln Lys
450                 455                 460
Ser Leu Ser Leu Ser Leu Gly Lys
465                 470

<210> SEQ ID NO 35
<211> LENGTH: 699
<212> TYPE: DNA
<213> ORGANISM: Homo Sapiens

<400> SEQUENCE: 35
atgggatgga gctgtatcat cctcttcttg gtagcaacag ctacaggtgt acacagcgac      60
attgagttga cccagtctcc atccttcctg tctgcatctg tcggagacag agtcgccatc     120
acttgccggg ccagtcaggg cattagcaat tatttagcct ggtatcagca aaaaccaggg     180
aaagccccta agctcctgat ctatgctgca ttcgttttgc aaagtggggt cccatcaagg     240
ttcagcggca gtggatctgg gacagaattc actctcacaa tcagtaacct gcagcctgaa     300
gattttgcaa cttattactg tcaacaactt aatagttatc ctcgcgcttt cggccctggg     360
accaaagtgg atatcaaacg aactgtggct gcaccatctg tcttcatctt cccgccatct     420
gatgagcagt tgaaatctgg aactgcctct gttgtgtgcc tgctgaataa cttctatccc     480
agagaggcca agtacagtg gaaggtggat aacgccctcc aatcgggtaa ctcccaggag     540
agtgtcacag agcaggacag caaggacagc acctacagcc tcagcagcac cctgacgctg     600
agcaaagcag actacgagaa acacaaagtc tacgcctgcg aagtcacccc tcagggcctg     660
agctcgcccg tcacaaagag cttcaacagg ggagagtga                          699

<210> SEQ ID NO 36
<211> LENGTH: 232
<212> TYPE: PRT
<213> ORGANISM: Homo Sapiens

<400> SEQUENCE: 36

Met Gly Trp Ser Cys Ile Ile Leu Phe Leu Val Ala Thr Ala Thr Gly
1               5                   10                  15
```

Val His Ser Asp Ile Glu Leu Thr Gln Ser Pro Ser Phe Leu Ser Ala
            20                  25                  30

Ser Val Gly Asp Arg Val Ala Ile Thr Cys Arg Ala Ser Gln Gly Ile
        35                  40                  45

Ser Asn Tyr Leu Ala Trp Tyr Gln Gln Lys Pro Gly Lys Ala Pro Lys
    50                  55                  60

Leu Leu Ile Tyr Ala Ala Phe Val Leu Gln Ser Gly Val Pro Ser Arg
65                  70                  75                  80

Phe Ser Gly Ser Gly Ser Gly Thr Glu Phe Thr Leu Thr Ile Ser Asn
                85                  90                  95

Leu Gln Pro Glu Asp Phe Ala Thr Tyr Tyr Cys Gln Gln Leu Asn Ser
            100                 105                 110

Tyr Pro Arg Ala Phe Gly Pro Gly Thr Lys Val Asp Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu
225                 230

<210> SEQ ID NO 37
<211> LENGTH: 1413
<212> TYPE: DNA
<213> ORGANISM: Homo Sapiens

<400> SEQUENCE: 37
atgggatgga gctgtatcat cctcttcttg gtagcaacag ctacaggtgt acacagcgag      60
gtgcagctgt tgcagtctgg cgcaggactg ttgaagcctt cggagaccct gtccctcacc     120
tgcgctgtct atggtgggtc cttcagtgga tactactgga gttggatccg ccaggcccca     180
gggaagggac tggagtggat tgggaaatc gatcatagtg aaccaccaa ctacaacccg       240 tccctcaaga gtcgggtcac catatcagta gagacatcca agaaccagtt ctccctgagg     300
ctgagctctg tgaccgccgc ggactcggct gtctattact gtgcgagcag tggatattgt     360
tctcatggtt tatgccccca agaggactgg ggccagggaa ccctggtcac cgtctcctca     420
gcctccacca agggcccatc ggtcttcccc ctggcaccct cctccaagag cacctctggg     480
ggcacagcgg ccctgggctg cctggtcaag gactacttcc ccgaaccggt gacggtgtcg     540
tggaactcag gcgccctgac cagcggcgtg cacaccttcc cggctgtcct acagtcctca     600
ggactctact ccctcagcag cgtggtgacc gtgccctcca gcagcttggg cacccagacc     660
tacatctgca acgtgaatca caagcccagc aacaccaagg tggacaagaa agttgagccc     720
aaatcttgtg acaaaactca cacatgccca ccgtgcccag cacctgaact cctgggggga     780
ccgtcagtct tcctcttccc cccaaaaccc aaggacaccc tcatgatctc ccggaccct      840 gaggtcacat gcgtggtggt ggacgtgagc cacgaagacc ctgaggtcaa gttcaactgg     900

```
tacgtggacg gcgtggaggt gcataatgcc aagacaaagc cgcgggagga gcagtacaac    960
agcacgtacc gtgtggtcag cgtcctcacc gtcctgcacc aggactggct gaatggcaag   1020
gagtacaagt gcaaggtctc caacaaagcc ctcccagccc ccatcgagaa aaccatctcc   1080
aaagccaaag ggcagccccg agaaccacag gtgtacaccc tgcccccatc ccgggatgag   1140
ctgaccaaga accaggtcag cctgacctgc ctggtcaaag gcttctatcc cagcgacatc   1200
gccgtggagt gggagagcaa tgggcagccg gagaacaact acaagaccac gcctcccgtg   1260
ctggactccg acggctcctt cttcctctac agcaagctca ccgtggacaa gagcaggtgg   1320
cagcagggga acgtcttctc atgctccgtg atgcatgagg ctctgcacaa ccactacacg   1380
cagaagagcc tctccctgtc tccgggtaaa tga                                1413

<210> SEQ ID NO 38
<211> LENGTH: 470
<212> TYPE: PRT
<213> ORGANISM: Homo Sapiens

<400> SEQUENCE: 38

Met Gly Trp Ser Cys Ile Ile Leu Phe Leu Val Ala Thr Ala Thr Gly
1               5                   10                  15

Val His Ser Glu Val Gln Leu Leu Gln Ser Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ala Pro Gly Lys Gly Leu
    50                  55                  60

Glu Trp Ile Gly Glu Ile Asp His Ser Gly Thr Thr Asn Tyr Asn Pro
65                  70                  75                  80

Ser Leu Lys Ser Arg Val Thr Ile Ser Val Glu Thr Ser Lys Asn Gln
                85                  90                  95

Phe Ser Leu Arg Leu Ser Ser Val Thr Ala Ala Asp Ser Ala Val Tyr
            100                 105                 110

Tyr Cys Ala Ser Ser Gly Tyr Cys Ser His Gly Leu Cys Pro Gln Glu
        115                 120                 125

Asp Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
```

```
                275                 280                 285
Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 39
<211> LENGTH: 13
<212> TYPE: PRT
<213> ORGANISM: Homo Sapiens

<400> SEQUENCE: 39

Cys Ser Ala Ala Gly Thr Val Asp Tyr Trp Gly Gln Gly
1               5                   10

<210> SEQ ID NO 40
<211> LENGTH: 10
<212> TYPE: PRT
<213> ORGANISM: Homo Sapiens

<400> SEQUENCE: 40

Cys Thr Thr Met Arg Asn Trp Gly Gln Gly
1               5                   10

<210> SEQ ID NO 41
<211> LENGTH: 15
<212> TYPE: PRT
<213> ORGANISM: Homo Sapiens

<400> SEQUENCE: 41

Cys Gln Ser Ala Asp Ser Ser Gly Thr Tyr Val Phe Gly Thr Gly
1               5                   10                  15

<210> SEQ ID NO 42
<211> LENGTH: 16
<212> TYPE: PRT
<213> ORGANISM: Homo Sapiens

<400> SEQUENCE: 42
```

Cys Gln Ser Ala Asp Ser Ser Gly Thr Tyr Val Val Phe Gly Gly Gly
1               5                   10                  15

<210> SEQ ID NO 43
<211> LENGTH: 57
<212> TYPE: DNA
<213> ORGANISM: Artificial Sequence
<220> FEATURE:
<223> OTHER INFORMATION: Polynucleotide

<400> SEQUENCE: 43
atgggatgga gctgtatcat cctcttcttg gtagcaacag ctacaggtgt acacagc        57

<210> SEQ ID NO 44
<211> LENGTH: 19
<212> TYPE: PRT
<213> ORGANISM: Artificial Sequence
<220> FEATURE:
<223> OTHER INFORMATION: Synthetic construct

<400> SEQUENCE: 44

Met Gly Trp Ser Cys Ile Ile Leu Phe Leu Val Ala Thr Ala Thr Gly
1               5                   10                  15

Val His Ser

<210> SEQ ID NO 45
<211> LENGTH: 239
<212> TYPE: PRT
<213> ORGANISM: Artificial Sequence
<220> FEATURE:
<223> OTHER INFORMATION: Synthetic construct

<400> SEQUENCE: 45

Glu Ser Gln Pro Asp Pro Lys Pro Asp Glu Leu His Lys Ser Ser Lys
1               5                   10                  15

Phe Thr Gly Leu Met Glu Asn Met Lys Val Leu Tyr Asp Asp Asn His
                20                  25                  30

Val Ser Ala Ile Asn Val Lys Ser Ile Asp Gln Phe Arg Tyr Phe Asp
            35                  40                  45

Leu Ile Tyr Ser Ile Lys Asp Thr Lys Leu Gly Asn Tyr Asp Asn Val
        50                  55                  60

Arg Val Glu Phe Lys Asn Lys Asp Leu Ala Asp Lys Tyr Lys Asp Lys
65                  70                  75                  80

Tyr Val Asp Val Phe Gly Ala Asn Ala Tyr Tyr Gln Cys Ala Phe Ser
                85                  90                  95

Lys Lys Thr Asn Asp Ile Asn Ser His Gln Thr Asp Lys Arg Lys Thr
            100                 105                 110

Cys Met Tyr Gly Gly Val Thr Glu His Asn Gly Asn Gln Leu Asp Lys
        115                 120                 125

Tyr Arg Ser Ile Thr Val Arg Val Phe Glu Asp Gly Lys Asn Leu Leu
130                 135                 140

Ser Phe Asp Val Gln Thr Asn Lys Lys Lys Val Thr Ala Gln Glu Leu
145                 150                 155                 160

Asp Tyr Leu Thr Arg His Tyr Leu Val Lys Asn Lys Lys Leu Tyr Glu
                165                 170                 175

Phe Asn Asn Ser Pro Tyr Glu Thr Gly Tyr Ile Lys Phe Ile Glu Asn
            180                 185                 190

Glu Asn Ser Phe Trp Tyr Asp Met Met Pro Ala Pro Gly Asp Lys Phe
        195                 200                 205

Asp Gln Ser Lys Tyr Leu Met Met Tyr Asn Asp Asn Lys Met Val Asp
    210                 215                 220
Ser Lys Asp Val Lys Ile Glu Val Tyr Leu Thr Thr Lys Lys Lys
225                 230                 235

<210> SEQ ID NO 46
<211> LENGTH: 239
<212> TYPE: PRT
<213> ORGANISM: Staphylococcus aureus

<400> SEQUENCE: 46

Glu Ser Gln Pro Asp Pro Lys Pro Asp Glu Leu His Lys Ser Ser Lys
1               5                   10                  15
Phe Thr Gly Leu Met Glu Asn Met Lys Val Leu Tyr Asp Asp Asn His
            20                  25                  30
Val Ser Ala Ile Asn Val Lys Ser Ile Asp Gln Phe Leu Tyr Phe Asp
        35                  40                  45
Leu Ile Tyr Ser Ile Lys Asp Thr Lys Leu Gly Asn Tyr Asp Asn Val
    50                  55                  60
Arg Val Glu Phe Lys Asn Lys Asp Leu Ala Asp Lys Tyr Lys Asp Lys
65                  70                  75                  80
Tyr Val Asp Val Phe Gly Ala Asn Tyr Tyr Gln Cys Tyr Phe Ser
                85                  90                  95
Lys Lys Thr Asn Asp Ile Asn Ser His Gln Thr Asp Lys Arg Lys Thr
            100                 105                 110
Cys Met Tyr Gly Gly Val Thr Glu His Asn Gly Asn Gln Leu Asp Lys
        115                 120                 125
Tyr Arg Ser Ile Thr Val Arg Val Phe Glu Asp Gly Lys Asn Leu Leu
    130                 135                 140
Ser Phe Asp Val Gln Thr Asn Lys Lys Lys Val Thr Ala Gln Glu Leu
145                 150                 155                 160
Asp Tyr Leu Thr Arg His Tyr Leu Val Lys Asn Lys Lys Leu Tyr Glu
                165                 170                 175
Phe Asn Asn Ser Pro Tyr Glu Thr Gly Tyr Ile Lys Phe Ile Glu Asn
            180                 185                 190
Glu Asn Ser Phe Trp Tyr Asp Met Met Pro Ala Pro Gly Asp Lys Phe
        195                 200                 205
Asp Gln Ser Lys Tyr Leu Met Met Tyr Asn Asp Asn Lys Met Val Asp
    210                 215                 220
Ser Lys Asp Val Lys Ile Glu Val Tyr Leu Thr Thr Lys Lys Lys
225                 230                 235

<210> SEQ ID NO 47
<211> LENGTH: 69
<212> TYPE: DNA
<213> ORGANISM: Homo Sapiens

<400> SEQUENCE: 47
gacgttgagc tgacccagtc tccttccacc ctgtctgcat ctgtaggaga cagagtcacc    60
atcacttgc                                                            69

<210> SEQ ID NO 48
<211> LENGTH: 45
<212> TYPE: DNA
<213> ORGANISM: Homo Sapiens

<400> SEQUENCE: 48
tggtatcagc agaaaccagg gaaagcccct aagctcctga tctat          45

<210> SEQ ID NO 49
<211> LENGTH: 102
<212> TYPE: DNA
<213> ORGANISM: Homo Sapiens

<400> SEQUENCE: 49
ggggtcccat caaggttcag cggcagtgga tctgggacag aattcactct caccatcagc    60
agcctgcagc ctgatgattt tgcaacttat tactgccaac ag                     102

<210> SEQ ID NO 50
<211> LENGTH: 33
<212> TYPE: DNA
<213> ORGANISM: Homo Sapiens

<400> SEQUENCE: 50
cgggccagtc agagtattag tagctggttg gcc                               33

<210> SEQ ID NO 51
<211> LENGTH: 21
<212> TYPE: DNA
<213> ORGANISM: Homo Sapiens

<400> SEQUENCE: 51
aaggcgtcta gtttagaaag t                                            21

<210> SEQ ID NO 52
<211> LENGTH: 21
<212> TYPE: DNA
<213> ORGANISM: Homo Sapiens

<400> SEQUENCE: 52
tataatagtt atccgtggac g                                            21

<210> SEQ ID NO 53
<211> LENGTH: 23
<212> TYPE: PRT
<213> ORGANISM: Homo Sapiens

<400> SEQUENCE: 53

Asp Val Glu Leu Thr Gln Ser Pro Ser Thr Leu Ser Ala Ser Val Gly
1               5                   10                  15

Asp Arg Val Thr Ile Thr Cys
            20

<210> SEQ ID NO 54
<211> LENGTH: 15
<212> TYPE: PRT
<213> ORGANISM: Homo Sapiens

<400> SEQUENCE: 54

Trp Tyr Gln Gln Lys Pro Gly Lys Ala Pro Lys Leu Leu Ile Tyr
1               5                   10                  15

<210> SEQ ID NO 55
<211> LENGTH: 34
<212> TYPE: PRT
<213> ORGANISM: Homo Sapiens

<400> SEQUENCE: 55

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr Cys
            20                  25                  30

Gln Gln

<210> SEQ ID NO 56
<211> LENGTH: 11
<212> TYPE: PRT
<213> ORGANISM: Homo Sapiens

<400> SEQUENCE: 56

Arg Ala Ser Gln Ser Ile Ser Ser Trp Leu Ala
1               5                   10

<210> SEQ ID NO 57
<211> LENGTH: 7
<212> TYPE: PRT
<213> ORGANISM: Homo Sapiens

<400> SEQUENCE: 57

Lys Ala Ser Ser Leu Glu Ser
1               5

<210> SEQ ID NO 58
<211> LENGTH: 7
<212> TYPE: PRT
<213> ORGANISM: Homo Sapiens

<400> SEQUENCE: 58

Tyr Asn Ser Tyr Pro Trp Thr
1               5

<210> SEQ ID NO 59
<211> LENGTH: 78
<212> TYPE: DNA
<213> ORGANISM: Homo Sapiens

<400> SEQUENCE: 59
caggtacagc tggtgcagtc tgggggaggc ctggtcaagc ctgggggtc cctgagactc      60 tcctgtgcag cctctgga                                                   78

<210> SEQ ID NO 60
<211> LENGTH: 42
<212> TYPE: DNA
<213> ORGANISM: Homo Sapiens

<400> SEQUENCE: 60
tgggtccgcc aggctccagg gaaggggctg gagtgggtct ca                         42

<210> SEQ ID NO 61
<211> LENGTH: 96
<212> TYPE: DNA
<213> ORGANISM: Homo Sapiens

<400> SEQUENCE: 61
cgattcacca tctccagaga caacgccaag aactcactgt atctgcaaat gaacagcctg      60
agagccgagg acacggctgt gtattactgt gcgaga                                96

<210> SEQ ID NO 62
<211> LENGTH: 27
<212> TYPE: DNA
<213> ORGANISM: Homo Sapiens -continued

<400> SEQUENCE: 62
ttcaccttca gtagctatag catgaac					27

<210> SEQ ID NO 63
<211> LENGTH: 51
<212> TYPE: DNA
<213> ORGANISM: Homo Sapiens

<400> SEQUENCE: 63
tccattagta gtagtagtag ttacatatac tacgcagact cagtgaaggg c				51

<210> SEQ ID NO 64
<211> LENGTH: 54
<212> TYPE: DNA
<213> ORGANISM: Homo Sapiens

<400> SEQUENCE: 64 ggggggtgg ctggtcgaac cgaaattac tactactact acggtatgga cgtc				54

<210> SEQ ID NO 65
<211> LENGTH: 26
<212> TYPE: PRT
<213> ORGANISM: Homo Sapiens

<400> SEQUENCE: 65

Gln Val Gln Leu Val Gln Ser Gly Gly Gly Leu Val Lys Pro Gly Gly
1               5                   10                  15

Ser Leu Arg Leu Ser Cys Ala Ala Ser Gly
            20                  25

<210> SEQ ID NO 66
<211> LENGTH: 14
<212> TYPE: PRT
<213> ORGANISM: Homo Sapiens

<400> SEQUENCE: 66

Trp Val Arg Gln Ala Pro Gly Lys Gly Leu Glu Trp Val Ser
1               5                   10

<210> SEQ ID NO 67
<211> LENGTH: 32
<212> TYPE: PRT
<213> ORGANISM: Homo Sapiens

<400> SEQUENCE: 67

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 68
<211> LENGTH: 9
<212> TYPE: PRT
<213> ORGANISM: Homo Sapiens

<400> SEQUENCE: 68

Phe Thr Phe Ser Ser Tyr Ser Met Asn
1               5

<210> SEQ ID NO 69
<211> LENGTH: 17
<212> TYPE: PRT
<213> ORGANISM: Homo Sapiens

<400> SEQUENCE: 69

Ser Ile Ser Ser Ser Ser Ser Tyr Ile Tyr Tyr Ala Asp Ser Val Lys
1               5                   10                  15
Gly

<210> SEQ ID NO 70
<211> LENGTH: 18
<212> TYPE: PRT
<213> ORGANISM: Homo Sapiens

<400> SEQUENCE: 70

Gly Gly Val Ala Gly Arg Thr Glu Ile Tyr Tyr Tyr Tyr Gly Met
1               5                   10                  15
Asp Val

<210> SEQ ID NO 71
<211> LENGTH: 66
<212> TYPE: DNA
<213> ORGANISM: Homo Sapiens

<400> SEQUENCE: 71
tcctatgtgc tgactcagcc accctcggtg tcggtgtccc caggacagac ggccaggatc      60
acctgc                                                                66

<210> SEQ ID NO 72
<211> LENGTH: 45
<212> TYPE: DNA
<213> ORGANISM: Homo Sapiens

<400> SEQUENCE: 72
tggtaccagc agaagccagg ccaggcccct gtggtggtga tctat                     45

<210> SEQ ID NO 73
<211> LENGTH: 96
<212> TYPE: DNA
<213> ORGANISM: Homo Sapiens

<400> SEQUENCE: 73
gggatccctg agcgattctc tggctccagc tcagggacaa cagtcacggt gaccatcagt      60
ggagtccagg cagaagacga ggctgactat tattgt                                96

<210> SEQ ID NO 74
<211> LENGTH: 33
<212> TYPE: DNA
<213> ORGANISM: Homo Sapiens

<400> SEQUENCE: 74
tctggagatg cattgccaaa gcaatatact tat                                  33

<210> SEQ ID NO 75
<211> LENGTH: 21
<212> TYPE: DNA
<213> ORGANISM: Homo Sapiens

<400> SEQUENCE: 75
aaagacagtg agaggccctc a                                               21

<210> SEQ ID NO 76
<211> LENGTH: 33
<212> TYPE: DNA

<213> ORGANISM: Homo Sapiens

<400> SEQUENCE: 76
caatcagcag acagcagtgg tacttccctg gtg                33

<210> SEQ ID NO 77
<211> LENGTH: 22
<212> TYPE: PRT
<213> ORGANISM: Homo Sapiens

<400> SEQUENCE: 77

Ser Tyr Val Leu Thr Gln Pro Pro Ser Val Ser Val Ser Pro Gly Gln
1               5                   10                  15

Thr Ala Arg Ile Thr Cys
            20

<210> SEQ ID NO 78
<211> LENGTH: 15
<212> TYPE: PRT
<213> ORGANISM: Homo Sapiens

<400> SEQUENCE: 78

Trp Tyr Gln Gln Lys Pro Gly Gln Ala Pro Val Val Val Ile Tyr
1               5                   10                  15

<210> SEQ ID NO 79
<211> LENGTH: 32
<212> TYPE: PRT
<213> ORGANISM: Homo Sapiens

<400> SEQUENCE: 79

Gly Ile Pro Glu Arg Phe Ser Gly Ser Ser Ser Gly Thr Thr Val Thr
1               5                   10                  15

Val Thr Ile Ser Gly Val Gln Ala Glu Asp Glu Ala Asp Tyr Tyr Cys
            20                  25                  30

<210> SEQ ID NO 80
<211> LENGTH: 11
<212> TYPE: PRT
<213> ORGANISM: Homo Sapiens

<400> SEQUENCE: 80

Ser Gly Asp Ala Leu Pro Lys Gln Tyr Thr Tyr
1               5                   10

<210> SEQ ID NO 81
<211> LENGTH: 7
<212> TYPE: PRT
<213> ORGANISM: Homo Sapiens

<400> SEQUENCE: 81

Lys Asp Ser Glu Arg Pro Ser
1               5

<210> SEQ ID NO 82
<211> LENGTH: 11
<212> TYPE: PRT
<213> ORGANISM: Homo Sapiens

<400> SEQUENCE: 82

Gln Ser Ala Asp Ser Ser Gly Thr Ser Leu Val
1               5                   10

<210> SEQ ID NO 83
<211> LENGTH: 75
<212> TYPE: DNA
<213> ORGANISM: Homo Sapiens

<400> SEQUENCE: 83

```
gaggtgcagc tggtggagtc tgggggaggc ttggtccagc ctggggggtc cctgagactc    60
tcctgttcag cctct                                                    75
```

<210> SEQ ID NO 84
<211> LENGTH: 42
<212> TYPE: DNA
<213> ORGANISM: Homo Sapiens

<400> SEQUENCE: 84

```
tgggtccgcc aggctccagg gaaggggctg gagtgggtcg cc                      42
```

<210> SEQ ID NO 85
<211> LENGTH: 96
<212> TYPE: DNA
<213> ORGANISM: Homo Sapiens

<400> SEQUENCE: 85

```
cggctcacca tctccagaga caacgccaag aactcactat atctgcagat gaacagcctg    60
agagtcgacg acacggctgt gtattattgt gcgaga                             96
```

<210> SEQ ID NO 86
<211> LENGTH: 30
<212> TYPE: DNA
<213> ORGANISM: Homo Sapiens

<400> SEQUENCE: 86

```
ggtttcacct ttagtagtta ttggatgagc                                    30
```

<210> SEQ ID NO 87
<211> LENGTH: 51
<212> TYPE: DNA
<213> ORGANISM: Homo Sapiens

<400> SEQUENCE: 87

```
aacataatac aagatggaag tgagaaatac tatgcggact ctgtgaaggg c             51
```

<210> SEQ ID NO 88
<211> LENGTH: 51
<212> TYPE: DNA
<213> ORGANISM: Homo Sapiens

<400> SEQUENCE: 88

```
ggatatgagg ggtgtagtgc aaccaggtgc tacctgtact actttgacta t             51
```

<210> SEQ ID NO 89
<211> LENGTH: 25
<212> TYPE: PRT
<213> ORGANISM: Homo Sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ser Ala Ser
            20                  25

<210> SEQ ID NO 90

```
<211> LENGTH: 14
<212> TYPE: PRT
<213> ORGANISM: Homo Sapiens

<400> SEQUENCE: 90

Trp Val Arg Gln Ala Pro Gly Lys Gly Leu Glu Trp Val Ala
1               5                   10

<210> SEQ ID NO 91
<211> LENGTH: 32
<212> TYPE: PRT
<213> ORGANISM: Homo Sapiens

<400> SEQUENCE: 91

Arg Leu Thr Ile Ser Arg Asp Asn Ala Lys Asn Ser Leu Tyr Leu Gln
1               5                   10                  15

Met Asn Ser Leu Arg Val Asp Asp Thr Ala Val Tyr Tyr Cys Ala Arg
            20                  25                  30

<210> SEQ ID NO 92
<211> LENGTH: 10
<212> TYPE: PRT
<213> ORGANISM: Homo Sapiens

<400> SEQUENCE: 92

Gly Phe Thr Phe Ser Ser Tyr Trp Met Ser
1               5                   10

<210> SEQ ID NO 93
<211> LENGTH: 17
<212> TYPE: PRT
<213> ORGANISM: Homo Sapiens

<400> SEQUENCE: 93

Asn Ile Ile Gln Asp Gly Ser Glu Lys Tyr Tyr Ala Asp Ser Val Lys
1               5                   10                  15

Gly

<210> SEQ ID NO 94
<211> LENGTH: 17
<212> TYPE: PRT
<213> ORGANISM: Homo Sapiens

<400> SEQUENCE: 94

Gly Tyr Glu Gly Cys Ser Ala Thr Arg Cys Tyr Leu Tyr Tyr Phe Asp
1               5                   10                  15

Tyr

<210> SEQ ID NO 95
<211> LENGTH: 69
<212> TYPE: DNA
<213> ORGANISM: Homo Sapiens

<400> SEQUENCE: 95
gacattgagt tgacccagtc tccatccttc ctgtctgcat ctgtcggaga cagagtcgcc    60
atcacttgc                                                           69

<210> SEQ ID NO 96
<211> LENGTH: 45
<212> TYPE: DNA
<213> ORGANISM: Homo Sapiens

<400> SEQUENCE: 96
```

```
tggtatcagc aaaaaccagg gaaagcccct aagctcctga tctat          45
```

<210> SEQ ID NO 97
<211> LENGTH: 96
<212> TYPE: DNA
<213> ORGANISM: Hpmo Sapiens

<400> SEQUENCE: 97

```
ggggtcccat caaggttcag cggcagtgga tctgggacag aattcactct cacaatcagt   60
aacctgcagc ctgaagattt tgcaacttat tactgt                             96
```

<210> SEQ ID NO 98
<211> LENGTH: 33
<212> TYPE: DNA
<213> ORGANISM: Homo Sapiens

<400> SEQUENCE: 98

```
cgggccagtc agggcattag caattattta gcc                       33
```

<210> SEQ ID NO 99
<211> LENGTH: 21
<212> TYPE: DNA
<213> ORGANISM: Homo Sapiens

<400> SEQUENCE: 99

```
gctgcattcg ttttgcaaag t                                    21
```

<210> SEQ ID NO 100
<211> LENGTH: 27
<212> TYPE: DNA
<213> ORGANISM: Homo Sapiens

<400> SEQUENCE: 100

```
caacaactta atagttatcc tcgcgct                              27
```

<210> SEQ ID NO 101
<211> LENGTH: 23
<212> TYPE: PRT
<213> ORGANISM: Homo Sapiens

<400> SEQUENCE: 101

Asp Ile Glu Leu Thr Gln Ser Pro Ser Phe Leu Ser Ala Ser Val Gly
1               5                   10                  15

Asp Arg Val Ala Ile Thr Cys
            20

<210> SEQ ID NO 102
<211> LENGTH: 15
<212> TYPE: PRT
<213> ORGANISM: Homo Sapiens

<400> SEQUENCE: 102

Trp Tyr Gln Gln Lys Pro Gly Lys Ala Pro Lys Leu Leu Ile Tyr
1               5                   10                  15

<210> SEQ ID NO 103
<211> LENGTH: 32
<212> TYPE: PRT
<213> ORGANISM: Homo Sapiens

<400> SEQUENCE: 103

Gly Val Pro Ser Arg Phe Ser Gly Ser Gly Ser Gly Thr Glu Phe Thr

```
                1               5                  10                 15
             Leu Thr Ile Ser Asn Leu Gln Pro Glu Asp Phe Ala Thr Tyr Tyr Cys
                            20                  25                  30

<210> SEQ ID NO 104
<211> LENGTH: 11
<212> TYPE: PRT
<213> ORGANISM: Homo Sapiens

<400> SEQUENCE: 104

Arg Ala Ser Gln Gly Ile Ser Asn Tyr Leu Ala
1               5                   10

<210> SEQ ID NO 105
<211> LENGTH: 7
<212> TYPE: PRT
<213> ORGANISM: Homo Sapiens

<400> SEQUENCE: 105

Ala Ala Phe Val Leu Gln Ser
1               5

<210> SEQ ID NO 106
<211> LENGTH: 9
<212> TYPE: PRT
<213> ORGANISM: Homo Sapiens

<400> SEQUENCE: 106

Gln Gln Leu Asn Ser Tyr Pro Arg Ala
1               5

<210> SEQ ID NO 107
<211> LENGTH: 75
<212> TYPE: DNA
<213> ORGANISM: Homo Sapiens

<400> SEQUENCE: 107
gaggtgcagc tgttgcagtc tggcgcagga ctgttgaagc cttcggagac cctgtccctc    60
acctgcgctg tctat                                                    75

<210> SEQ ID NO 108
<211> LENGTH: 42
<212> TYPE: DNA
<213> ORGANISM: Homo Sapiens

<400> SEQUENCE: 108
tggatccgcc aggccccagg gaagggactg gagtggattg gg                      42

<210> SEQ ID NO 109
<211> LENGTH: 96
<212> TYPE: DNA
<213> ORGANISM: Homo Sapiens

<400> SEQUENCE: 109
cgggtcacca tatcagtaga gacatccaag aaccagttct ccctgaggct gagctctgtg    60
accgccgcgg actcggctgt ctattactgt gcgagc                             96

<210> SEQ ID NO 110
<211> LENGTH: 30
<212> TYPE: DNA
<213> ORGANISM: Homo Sapiens

<400> SEQUENCE: 110
```

```
ggtgggtcct tcagtggata ctactggagt                                    30
```

<210> SEQ ID NO 111
<211> LENGTH: 48
<212> TYPE: DNA
<213> ORGANISM: Homo Sapiens

<400> SEQUENCE: 111

```
gaaatcgatc atagtggaac caccaactac aacccgtccc tcaagagt               48
```

<210> SEQ ID NO 112
<211> LENGTH: 39
<212> TYPE: DNA
<213> ORGANISM: Homo Sapiens

<400> SEQUENCE: 112

```
agtggatatt gttctcatgg tttatgcccc caagaggac                          39
```

<210> SEQ ID NO 113
<211> LENGTH: 25
<212> TYPE: PRT
<213> ORGANISM: Homo Sapiens

<400> SEQUENCE: 113

Glu Val Gln Leu Leu Gln Ser Gly Ala Gly Leu Leu Lys Pro Ser Glu
1               5                   10                  15

Thr Leu Ser Leu Thr Cys Ala Val Tyr
            20                  25

<210> SEQ ID NO 114
<211> LENGTH: 14
<212> TYPE: PRT
<213> ORGANISM: Homo Sapiens

<400> SEQUENCE: 114

Trp Ile Arg Gln Ala Pro Gly Lys Gly Leu Glu Trp Ile Gly
1               5                   10

<210> SEQ ID NO 115
<211> LENGTH: 32
<212> TYPE: PRT
<213> ORGANISM: Homo Sapiens

<400> SEQUENCE: 115

Arg Val Thr Ile Ser Val Glu Thr Ser Lys Asn Gln Phe Ser Leu Arg
1               5                   10                  15

Leu Ser Ser Val Thr Ala Ala Asp Ser Ala Val Tyr Tyr Cys Ala Ser
            20                  25                  30

<210> SEQ ID NO 116
<211> LENGTH: 10
<212> TYPE: PRT
<213> ORGANISM: Homo Sapiens

<400> SEQUENCE: 116

Gly Gly Ser Phe Ser Gly Tyr Tyr Trp Ser
1               5                   10

<210> SEQ ID NO 117
<211> LENGTH: 16
<212> TYPE: PRT
<213> ORGANISM: Homo Sapiens

<400> SEQUENCE: 117

Glu Ile Asp His Ser Gly Thr Thr Asn Tyr Asn Pro Ser Leu Lys Ser
1               5                   10                  15

<210> SEQ ID NO 118
<211> LENGTH: 13
<212> TYPE: PRT
<213> ORGANISM: Homo Sapiens

<400> SEQUENCE: 118

Ser Gly Tyr Cys Ser His Gly Leu Cys Pro Gln Glu Asp
1               5                   10

<210> SEQ ID NO 119
<211> LENGTH: 1413
<212> TYPE: DNA
<213> ORGANISM: Homo Sapiens

<400> SEQUENCE: 119

| | |
|---|---:|
| atgggatgga gctgtatcat cctcttcttg gtagcaacag ctacaggtgt ccactccgag | 60 |
| gtacagctgg aggagtctgg cgcaggactg ttgaagcctt cggagaccct gtccctcacc | 120 |
| tgcgctgtct atggtgggtc cttcagtgga tactactgga gttggatccg ccaggcccca | 180 |
| gggaagggac tggagtggat tgggaaatc gatcatagtg aaccaccaa ctacaacccg | 240 |
| tccctcaaga gtcgggtcac catatcagta gagacatcca agaaccagtt ctccctgagg | 300 |
| ctgagctctg tgaccgccgc ggactcggct gtctattact gtgcgagcag tggatattgt | 360 |
| tctcatggtt tatgccccca agaggactgg ggccagggaa ccctggtcac cgtctcctca | 420 |
| gcctccacca agggcccatc ggtcttcccc ctggcaccct cctccaagag cacctctggg | 480 |
| ggcacagcgg ccctgggctg cctggtcaag gactacttcc ccgaaccggt gacggtgtcg | 540 |
| tggaactcag gcgccctgac cagcggcgtg cacaccttcc cggctgtcct acagtcctca | 600 |
| ggactctact ccctcagcag cgtggtgacc gtgccctcca gcagcttggg cacccagacc | 660 |
| tacatctgca acgtgaatca caagcccagc aacaccaagg tggacaagag agttgagccc | 720 |
| aaatcttgtg acaaaactca cacatgccca ccgtgcccag cacctgaact cctgggggga | 780 |
| ccgtcagtct tcctcttccc cccaaaaccc aaggacaccc tcatgatctc ccggacccct | 840 |
| gaggtcacat gcgtggtggt ggacgtgagc cacgaagacc ctgaggtcaa gttcaactgg | 900 |
| tacgtggacg gcgtggaggt gcataatgcc aagacaaagc cgcgggagga gcagtacaac | 960 |
| agcacgtacc gtgtggtcag cgtcctcacc gtcctgcacc aggactggct gaatggcaag | 1020 |
| gagtacaagt gcaaggtctc caacaaagcc gtcccagccc ccatcgagaa aaccatctcc | 1080 |
| aaagccaaag gcagccccg agaaccacag gtgtacaccc tgcccccatc ccgggaggag | 1140 |
| atgaccaaga accaggtcag cctgacctgc ctggtcaaag gcttctatcc cagcgacatc | 1200 |
| gccgtggagt gggagagcaa tgggcagccg gagaacaact acaagaccac gcctcccgtg | 1260 |
| ctggactccg acggctcctt cttcctctat agcaagctca ccgtggacaa gagcaggtgg | 1320 |
| cagcagggga acgtcttctc atgctccgtg atgcatgagg ctctgcacaa ccactacacg | 1380 |
| cagaagagcc tctccctgtc tccgggtaaa tga | 1413 |

<210> SEQ ID NO 120
<211> LENGTH: 75
<212> TYPE: DNA
<213> ORGANISM: Homo Sapiens

<400> SEQUENCE: 120

-continued gaggtacagc tggaggagtc tggcgcagga ctgttgaagc cttcggagac cctgtccctc     60
acctgcgctg tctat                                                     75

<210> SEQ ID NO 121
<211> LENGTH: 42
<212> TYPE: DNA
<213> ORGANISM: Homo Sapiens

<400> SEQUENCE: 121
tggatccgcc aggcccagg gaagggactg gagtggattg gg                        42

<210> SEQ ID NO 122
<211> LENGTH: 96
<212> TYPE: DNA
<213> ORGANISM: Homo Sapiens

<400> SEQUENCE: 122
cgggtcacca tatcagtaga gacatccaag aaccagttct ccctgaggct gagctctgtg     60
accgccgcgg actcggctgt ctattactgt gcgagc                              96

<210> SEQ ID NO 123
<211> LENGTH: 30
<212> TYPE: DNA
<213> ORGANISM: Homo Sapiens

<400> SEQUENCE: 123
ggtgggtcct tcagtggata ctactggagt                                     30

<210> SEQ ID NO 124
<211> LENGTH: 48
<212> TYPE: DNA
<213> ORGANISM: Homo Sapiens

<400> SEQUENCE: 124
gaaatcgatc atagtggaac caccaactac aacccgtccc tcaagagt                 48

<210> SEQ ID NO 125
<211> LENGTH: 39
<212> TYPE: DNA
<213> ORGANISM: Homo Sapiens

<400> SEQUENCE: 125
agtggatatt gttctcatgg tttatgcccc caagaggac                           39

<210> SEQ ID NO 126
<211> LENGTH: 470
<212> TYPE: PRT
<213> ORGANISM: Homo Sapiens

<400> SEQUENCE: 126

Met Gly Trp Ser Cys Ile Ile Leu Phe Leu Val Ala Thr Ala Thr Gly
1               5                   10                  15

Val His Ser Glu Val Gln Leu Glu Glu Ser Gly Ala Gly Leu Leu Lys
            20                  25                  30

Pro Ser Glu Thr Leu Ser Leu Thr Cys Ala Val Tyr Gly Gly Ser Phe
        35                  40                  45

Ser Gly Tyr Tyr Trp Ser Trp Ile Arg Gln Ala Pro Gly Lys Gly Leu
    50                  55                  60

Glu Trp Ile Gly Glu Ile Asp His Ser Gly Thr Thr Asn Tyr Asn Pro
65                  70                  75                  80

```
Ser Leu Lys Ser Arg Val Thr Ile Ser Val Glu Thr Ser Lys Asn Gln
                85                  90                  95

Phe Ser Leu Arg Leu Ser Ser Val Thr Ala Ala Asp Ser Ala Val Tyr
            100                 105                 110

Tyr Cys Ala Ser Ser Gly Tyr Cys Ser His Gly Leu Cys Pro Gln Glu
        115                 120                 125

Asp Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Val Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 127
<211> LENGTH: 25
```

```
<212> TYPE: PRT
<213> ORGANISM: Homo Sapiens

<400> SEQUENCE: 127

Glu Val Gln Leu Glu Glu Ser Gly Ala Gly Leu Leu Lys Pro Ser Glu
1               5                   10                  15

Thr Leu Ser Leu Thr Cys Ala Val Tyr
            20                  25

<210> SEQ ID NO 128
<211> LENGTH: 14
<212> TYPE: PRT
<213> ORGANISM: Homo Sapiens

<400> SEQUENCE: 128

Trp Ile Arg Gln Ala Pro Gly Lys Gly Leu Glu Trp Ile Gly
1               5                   10

<210> SEQ ID NO 129
<211> LENGTH: 32
<212> TYPE: PRT
<213> ORGANISM: Homo Sapiens

<400> SEQUENCE: 129

Arg Val Thr Ile Ser Val Glu Thr Ser Lys Asn Gln Phe Ser Leu Arg
1               5                   10                  15

Leu Ser Ser Val Thr Ala Ala Asp Ser Ala Val Tyr Tyr Cys Ala Ser
            20                  25                  30

<210> SEQ ID NO 130
<211> LENGTH: 10
<212> TYPE: PRT
<213> ORGANISM: Homo Sapiens

<400> SEQUENCE: 130

Gly Gly Ser Phe Ser Gly Tyr Tyr Trp Ser
1               5                   10

<210> SEQ ID NO 131
<211> LENGTH: 16
<212> TYPE: PRT
<213> ORGANISM: Homo Sapiens

<400> SEQUENCE: 131

Glu Ile Asp His Ser Gly Thr Thr Asn Tyr Asn Pro Ser Leu Lys Ser
1               5                   10                  15

<210> SEQ ID NO 132
<211> LENGTH: 13
<212> TYPE: PRT
<213> ORGANISM: Homo Sapiens

<400> SEQUENCE: 132

Ser Gly Tyr Cys Ser His Gly Leu Cys Pro Gln Glu Asp
1               5                   10

<210> SEQ ID NO 133
<211> LENGTH: 690
<212> TYPE: DNA
<213> ORGANISM: Homo Sapiens

<400> SEQUENCE: 133
atgggatgga gctgtatcat cctcttcttg gtagcaacag ctacaggtgt gcactcccta      60
```

-continued

```
tgtgctgact cagccaccct cagtgtcagt ggccccagga gagacggcca gcattcctgt    120
gggggaaaca acattggaac taagagtgtc cactggtacc agcagaggcc aggccaggcc    180
cctctactgg tcctctatca tgacaccagg cggccctcaa ggattcctga gcgattctct    240
ggctccaact ctggaaacac ggccaccctg accatcagca ggtcgaagc cggggatgag     300 gccgactatt actgtcaggt gtgggatagt cgaagggtgt tcggcggagg gaccaagctg    360
accgtcctag gtcagcccaa ggcggccccc tcggtcactc tgttcccgcc ctcctctgag    420
gagcttcaag ccaacaaggc cacactggtg tgtctcataa gtgacttcta cccgggagcc    480
gtgacagtgg cctggaaggc agatagcagc cccgtcaagg cgggagtgga gaccaccaca    540
ccctccaaac aaagcaacaa caagtacgcg gccagcagct acctgagcct gacgcctgag    600
cagtggaagt cccacaaaag ctacagctgc caggtcacgc atgaaggag caccgtggag     660 aagacagtgg cccctacaga atcttcatga                                      690
```

<210> SEQ ID NO 134
<211> LENGTH: 229
<212> TYPE: PRT
<213> ORGANISM: Homo Sapiens

<400> SEQUENCE: 134

```
Met Gly Trp Ser Cys Ile Ile Leu Phe Leu Val Ala Thr Ala Thr Gly
1               5                   10                  15

Val His Ser Leu Cys Ala Asp Ser Ala Thr Leu Ser Val Ser Gly Pro
            20                  25                  30

Arg Arg Asp Gly Gln His Ser Cys Gly Gly Asn Asn Ile Gly Thr Lys
        35                  40                  45

Ser Val His Trp Tyr Gln Gln Arg Pro Gly Gln Ala Pro Leu Leu Val
    50                  55                  60

Leu Tyr His Asp Thr Arg Arg Pro Ser Arg Ile Pro Glu Arg Phe Ser
65                  70                  75                  80

Gly Ser Asn Ser Gly Asn Thr Ala Thr Leu Thr Ile Ser Arg Val Glu
                85                  90                  95

Ala Gly Asp Glu Ala Asp Tyr Tyr Cys Gln Val Trp Asp Ser Arg Arg
            100                 105                 110

Val Phe Gly Gly Gly Thr Lys Leu Thr Val Leu Gly Gln Pro Lys Ala
        115                 120                 125

Ala Pro Ser Val Thr Leu Phe Pro Pro Ser Ser Glu Glu Leu Gln Ala
    130                 135                 140

Asn Lys Ala Thr Leu Val Cys Leu Ile Ser Asp Phe Tyr Pro Gly Ala
145                 150                 155                 160

Val Thr Val Ala Trp Lys Ala Asp Ser Ser Pro Val Lys Ala Gly Val
                165                 170                 175

Glu Thr Thr Thr Pro Ser Lys Gln Ser Asn Asn Lys Tyr Ala Ala Ser
            180                 185                 190

Ser Tyr Leu Ser Leu Thr Pro Glu Gln Trp Lys Ser His Lys Ser Tyr
        195                 200                 205

Ser Cys Gln Val Thr His Glu Gly Ser Thr Val Glu Lys Thr Val Ala
    210                 215                 220

Pro Thr Glu Ser Ser
225
```

<210> SEQ ID NO 135
<211> LENGTH: 21
<212> TYPE: PRT

<213> ORGANISM: Homo Sapiens

<400> SEQUENCE: 135

Leu Cys Ala Asp Ser Ala Thr Leu Ser Val Ser Gly Pro Arg Arg Asp
1               5                   10                  15

Gly Gln His Ser Cys
            20

<210> SEQ ID NO 136
<211> LENGTH: 11
<212> TYPE: PRT
<213> ORGANISM: Homo Sapiens

<400> SEQUENCE: 136

Gly Gly Asn Asn Ile Gly Thr Lys Ser Val His
1               5                   10

<210> SEQ ID NO 137
<211> LENGTH: 15
<212> TYPE: PRT
<213> ORGANISM: Homo Sapiens

<400> SEQUENCE: 137

Trp Tyr Gln Gln Arg Pro Gly Gln Ala Pro Leu Leu Val Leu Tyr
1               5                   10                  15

<210> SEQ ID NO 138
<211> LENGTH: 7
<212> TYPE: PRT
<213> ORGANISM: Homo Sapiens

<400> SEQUENCE: 138

His Asp Thr Arg Arg Pro Ser
1               5

<210> SEQ ID NO 139
<211> LENGTH: 32
<212> TYPE: PRT
<213> ORGANISM: Homo Sapiens

<400> SEQUENCE: 139

Arg Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
                20                  25                  30

<210> SEQ ID NO 140
<211> LENGTH: 8
<212> TYPE: PRT
<213> ORGANISM: Homo Sapiens

<400> SEQUENCE: 140

Gln Val Trp Asp Ser Arg Arg Val
1               5

<210> SEQ ID NO 141
<211> LENGTH: 1428
<212> TYPE: DNA
<213> ORGANISM: Homo Sapiens

<400> SEQUENCE: 141
atgggatgga gctgtatcat cctcttcttg gtagcaacag ctacaggtgt ccactcccag      60
gtgcagctgt tggagtcagg gggaggcttg gtccagccgg ggggtccct gagactctcc     120

```
tgtgcagcct ctggattcag ctttggcgac tattggatga gttgggtccg ccaggctcca     180 ggaagggcc tggagtgggt ggccgacata aagccagatg cagtgacaa agactatgtg      240 gactctgtga agggccgatt caccatctcc agagacaacg ccaagaactc actgtatctg    300
caaatgagca gcctgcgagg cgaagacacg gctgtctatt attgtgcgag agactatgtc    360
gtcgtcgcac catctcaacc cccaaacatt caccctgaat acttccagaa ctggggccag    420
ggcaccctgg tcatcgtctc ctcagcctcc accaagggcc catcggtctt ccccctggca    480
ccctcctcca gagcacctc tgggggcaca gcggccctgg gctgcctggt caaggactac     540
ttccccgaac cggtgacggt gtcgtggaac tcaggcgccc tgaccagcgg cgtgcacacc    600
ttcccggctg tcctacagtc ctcaggactc tactccctca gcagcgtggt gaccgtgccc    660
tccagcagct gggcaccca gacctacatc tgcaacgtga atcacaagcc cagcaacacc     720
aaggtggaca gagagtgag ctgtgacaaa actcacacat gcccaccgtg cccagcacct     780
gaactcctgg gggaccgtc agtcttcctc ttcccccca aacccaagga caccctcatg      840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac    1020
tggctgaatg gcaaggagta caagtgcaag gtctccaaca aagccctccc agcccccatc    1080
gagaaaacca tctccaaagc caaagggcag ccccgagaac acaggtgta caccctgccc    1140 ccatcccggg aggagatgac caagaaccag gtcagcctga cctgcctggt caaaggcttc    1200
tatcccagcg acatcgccgt ggagtgggag agcaatgggc agccggagaa caactacaag    1260
accacgcctc ccgtgctgga ctccgacggc tccttcttcc tctatagcaa gctcaccgtg    1320
gacaagagca ggtggcagca ggggaacgtc ttctcatgct ccgtgatgca tgaggctctg    1380
cacaaccact acacgcagaa gagcctctcc ctgtctccgg gtaaatga                 1428
```

<210> SEQ ID NO 142
<211> LENGTH: 475
<212> TYPE: PRT
<213> ORGANISM: Homo Sapiens

<400> SEQUENCE: 142

```
Met Gly Trp Ser Cys Ile Ile Leu Phe Leu Val Ala Thr Ala Thr Gly
1               5                   10                  15

Val His Ser Gln Val Gln Leu Leu Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Gly Asp Tyr Trp Met Ser Trp Val Arg Gln Ala Pro Gly Lys Gly Leu
    50                  55                  60

Glu Trp Val Ala Asp Ile Lys Pro Asp Gly Ser Asp Lys Asp Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Ser Ser Leu Arg Gly Glu Asp Thr Ala Val
            100                 105                 110

Tyr Tyr Cys Ala Arg Asp Tyr Val Val Ala Pro Ser Gln Pro Pro
        115                 120                 125

Asn Ile His Pro Glu Tyr Phe Gln Asn Trp Gly Gln Gly Thr Leu Val
    130                 135                 140
```

Ile Val Ser Ser Ala Ser Thr Lys Gly Pro Ser Val Phe Pro Leu Ala
145                 150                 155                 160

Pro Ser Ser Lys Ser Thr Ser Gly Gly Thr Ala Ala Leu Gly Cys Leu
            165                 170                 175

Val Lys Asp Tyr Phe Pro Glu Pro Val Thr Val Ser Trp Asn Ser Gly
        180                 185                 190

Ala Leu Thr Ser Gly Val His Thr Phe Pro Ala Val Leu Gln Ser Ser
            195                 200                 205

Gly Leu Tyr Ser Leu Ser Ser Val Val Thr Val Pro Ser Ser Ser Leu
        210                 215                 220

Gly Thr Gln Thr Tyr Ile Cys Asn Val Asn His Lys Pro Ser Asn Thr
225                 230                 235                 240

Lys Val Asp Lys Arg Val Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 143
<211> LENGTH: 25
<212> TYPE: PRT
<213> ORGANISM: Homo Sapiens

<400> SEQUENCE: 143

Gln Val Gln Leu Leu Glu Ser Gly Gly Gly Leu Val Gln Pro Gly Gly
1               5                   10                  15

Ser Leu Arg Leu Ser Cys Ala Ala Ser
            20                  25

```
<210> SEQ ID NO 144
<211> LENGTH: 10
<212> TYPE: PRT
<213> ORGANISM: Homo Sapiens

<400> SEQUENCE: 144

Gly Phe Ser Phe Gly Asp Tyr Trp Met Ser
1               5                   10

<210> SEQ ID NO 145
<211> LENGTH: 14
<212> TYPE: PRT
<213> ORGANISM: Homo Sapiens

<400> SEQUENCE: 145

Trp Val Arg Gln Ala Pro Gly Lys Gly Leu Glu Trp Val Ala
1               5                   10

<210> SEQ ID NO 146
<211> LENGTH: 17
<212> TYPE: PRT
<213> ORGANISM: Homo Sapiens

<400> SEQUENCE: 146

Asp Ile Lys Pro Asp Gly Ser Asp Lys Asp Tyr Val Asp Ser Val Lys
1               5                   10                  15

Gly

<210> SEQ ID NO 147
<211> LENGTH: 32
<212> TYPE: PRT
<213> ORGANISM: Homo Sapiens

<400> SEQUENCE: 147

Arg Phe Thr Ile Ser Arg Asp Asn Ala Lys Asn Ser Leu Tyr Leu Gln
1               5                   10                  15

Met Ser Ser Leu Arg Gly Glu Asp Thr Ala Val Tyr Tyr Cys Ala Arg
            20                  25                  30

<210> SEQ ID NO 148
<211> LENGTH: 20
<212> TYPE: PRT
<213> ORGANISM: Homo Sapiens

<400> SEQUENCE: 148

Asp Tyr Val Val Val Ala Pro Ser Gln Pro Pro Asn Ile His Pro Glu
1               5                   10                  15

Tyr Phe Gln Asn
            20

<210> SEQ ID NO 149
<211> LENGTH: 702
<212> TYPE: DNA
<213> ORGANISM: Homo Sapiens

<400> SEQUENCE: 149
atgggctggt cctgcatcat cctgtttctg gtggccaccg ccaccggcgt gcactcctcc      60
tacgtgctga cccagcctcc ttccgtgtcc gtgtccctg gccagaccgc ccggatcacc     120
tgctccggcg acgccctgcc taagcagtac acctactggt atcagcagaa gcccggccag     180
gcccctgtgg tggtgatcta caaggactcc gagcggcctt ccggcatccc tgagcggttc     240
tccggctcct cctccggcac caccgtgacc gtgaccatct ccggcgtgca ggccgaggac     300
```

```
gaggccgact actactgcca gtccgccgac tccagcggca cctccctggt gtttggcggc    360
ggaacaaagc tgaccgtgct gggccagcct aaggccgctc cctccgtgac cctgttccct    420
ccttcctccg aggaactgca ggccaacaag gccaccctgg tgtgcctgat ctccgacttc    480
taccctggcg ctgtgaccgt ggcctggaag gctgactcct cccctgtgaa ggccggcgtg    540
gagacaacca ccccttccaa gcagtccaac aacaagtacg ccgcctcctc ctacctgtcc    600
ctgacccctg agcagtggaa gtcccacaag tcctacagct gccaggtgac ccacgagggc    660
tccaccgtgg aaaagaccgt ggcccctacc gagtcctcct ga                       702

<210> SEQ ID NO 150
<211> LENGTH: 294
<212> TYPE: DNA
<213> ORGANISM: Homo Sapiens

<400> SEQUENCE: 150
tcctacgtgc tgacccagcc tccttccgtg tccgtgtccc ctggccagac cgcccggatc     60
acctgctccg gcgacgccct gcctaagcag tacacctact ggtatcagca gaagcccggc    120
caggcccctg tggtggtgat ctacaaggac tccgagcggc cttccggcat ccctgagcgg    180
ttctccggct cctcctccgg caccaccgtg accgtgacca tctccggcgt gcaggccgag    240
gacgaggccg actactactg ccagtccgcc gactccagcg gcacctccct ggtg          294

<210> SEQ ID NO 151
<211> LENGTH: 66
<212> TYPE: DNA
<213> ORGANISM: Homo Sapiens

<400> SEQUENCE: 151
tcctacgtgc tgacccagcc tccttccgtg tccgtgtccc ctggccagac cgcccggatc     60
acctgc                                                                66

<210> SEQ ID NO 152
<211> LENGTH: 33
<212> TYPE: DNA
<213> ORGANISM: Homo Sapiens

<400> SEQUENCE: 152
tccggcgacg ccctgcctaa gcagtacacc tac                                  33

<210> SEQ ID NO 153
<211> LENGTH: 45
<212> TYPE: DNA
<213> ORGANISM: Homo Sapiens

<400> SEQUENCE: 153
tggtatcagc agaagcccgg ccaggcccct gtggtggtga tctac                     45

<210> SEQ ID NO 154
<211> LENGTH: 21
<212> TYPE: DNA
<213> ORGANISM: Homo Sapiens

<400> SEQUENCE: 154
aaggactccg agcggccttc c                                               21

<210> SEQ ID NO 155
<211> LENGTH: 96
<212> TYPE: DNA
```

<213> ORGANISM: Homo Sapiens

<400> SEQUENCE: 155

```
ggcatccctg agcggttctc cggctcctcc tccggcacca ccgtgaccgt gaccatctcc    60
ggcgtgcagg ccgaggacga ggccgactac tactgc                              96
```

<210> SEQ ID NO 156
<211> LENGTH: 33
<212> TYPE: DNA
<213> ORGANISM: Homo Sapiens

<400> SEQUENCE: 156

```
cagtccgccg actccagcgg cacctccctg gtg                                 33
```

<210> SEQ ID NO 157
<211> LENGTH: 294
<212> TYPE: DNA
<213> ORGANISM: Homo Sapiens

<400> SEQUENCE: 157

```
tcctatgtgc tgactcagcc accctcggtg tcggtgtccc caggacagac ggccaggatc    60
acctgctctg gagatgcatt gccaaagcaa tatacttatt ggtaccagca gaagccaggc   120
caggcccctg tggtggtgat ctataaagac agtgagaggc cctcagggat ccctgagcga   180
ttctctggct ccagctcagg gacaacagtc acggtgacca tcagtggagt ccaggcagaa   240
gacgaggctg actattattg tcaatcagca gacagcagtg gtacttccct ggtg         294
```

<210> SEQ ID NO 158
<211> LENGTH: 98
<212> TYPE: PRT
<213> ORGANISM: Homo Sapiens

<400> SEQUENCE: 158

```
Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Pro Gly Gln Ala Pro Val Val Val Ile Tyr
        35                  40                  45

Lys Asp Ser Glu Arg Pro Ser Gly Ile Pro Glu Arg Phe Ser Gly Ser
    50                  55                  60

Ser Ser Gly Thr Thr Val Thr Val Thr Ile Ser Gly Val Gln Ala Glu
65                  70                  75                  80

Asp Glu Ala Asp Tyr Tyr Cys Gln Ser Ala Asp Ser Ser Gly Thr Ser
                85                  90                  95

Leu Val
```

<210> SEQ ID NO 159
<211> LENGTH: 345
<212> TYPE: DNA
<213> ORGANISM: Homo Sapiens

<400> SEQUENCE: 159

```
gaggtgcagc tggtggagtc tgggggaggc ttggtccagc ctggggggtc cctgagactc    60
tcctgttcag cctctggttt cacctttagt agttattgga tgagctgggt ccgccaggct   120
ccagggaagg ggctggagtg ggtcgccaac ataatacaag atggaagtga aaaatactat   180
gcggactctg tgaagggccg gctcaccatc tccagagaca acgccaagaa ctcactatat   240
```

```
ctgcagatga acagcctgag agtcgacgac acggctgtgt attattgtgc gagaggatat    300
gaggggtgta gtgcaaccag gtgctacctg tactactttg actat                    345
```

<210> SEQ ID NO 160
<211> LENGTH: 115
<212> TYPE: PRT
<213> ORGANISM: Homo Sapiens

<400> SEQUENCE: 160

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Ile Gln Asp Gly Ser Glu Lys Tyr Tyr Ala Asp Ser Val
    50                  55                  60

Lys Gly Arg Leu Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
                85                  90                  95

Ala Arg Gly Tyr Glu Gly Cys Ser Ala Thr Arg Cys Tyr Leu Tyr Tyr
            100                 105                 110

Phe Asp Tyr
        115
```

<210> SEQ ID NO 161
<211> LENGTH: 645
<212> TYPE: DNA
<213> ORGANISM: Homo Sapiens

<400> SEQUENCE: 161

```
tcctacgtgc tgacccagcc tccttccgtg tccgtgtccc ctggccagac cgcccggatc     60
acctgctccg gcgacgccct gcctaagcag tacacctact ggtatcagca gaagcccggc    120
caggcccctg tggtggtgat ctacaaggac tccgagcggc cttccggcat ccctgagcgg    180
ttctccggct cctcctccgg caccaccgtg accgtgacca tctccggcgt gcaggccgag    240
gacgaggcca actactactg ccagtccgcc gactccagcg gcacctccct ggtgtttggc    300
ggcggaacaa agctgaccgt gctgggccag cctaaggccg ctcccctccgt gaccctgttc    360 cctccttcct ccgaggaact gcaggccaac aaggccaccc tggtgtgcct gatctccgac    420
ttctaccctg gcgctgtgac cgtggcctgg aaggctgact cctcccctgt gaaggccggc    480
gtggagacaa ccaccccttc caagcagtcc aacaacaagt acgccgcctc ctcctacctg    540
tccctgaccc ctgagcagtg gaagtcccac aagtcctaca gctgccaggt gacccacgag    600
ggctccaccg tggaaaagac cgtggcccct accgagtcct cctga                   645
```

<210> SEQ ID NO 162
<211> LENGTH: 1362
<212> TYPE: DNA
<213> ORGANISM: Homo Sapiens

<400> SEQUENCE: 162

```
gaggtgcagc tggtcgagtc tggcggcgga ctggtgcagc ctggcggctc cctgcggctg     60
tcctgctccg cctccggctt caccttctcc tcctactgga tgtcctgggt gcggcaggct    120
```

-continued

```
cctggcaagg gcctggagtg ggtggccaac atcatccagg acggctccga gaagtactac        180
gccgactccg tgaagggccg gctgaccatc tcccgggaca cgccaagaa ctccctgtac          240
ctgcagatga actccctgcg ggtggacgac accgccgtgt actactgcgc cagggggctac       300
gagggctgct ccgccacccg gtgctacctg tactacttcg actactgggg ccctggcacc        360
ctggtgaccg tgtcctccgc ctccaccaag ggcccttccg tgttccctct ggccccttcc        420
tccaagtcca cctccggcgg caccgccgct ctgggctgcc tggtgaagga ctacttccct       480
gagcctgtga ccgtgagctg gaactctggc gccctgacca gcggcgtgca caccttccct       540
gccgtgctgc agtcctccgg cctgtactcc ctgtcctccg tggtgacagt gccttcctcc       600
tccctgggca cccagaccta catctgcaac gtgaaccaca agccttccaa caccaaggtg       660
gacaagcggg tggagcctaa gtccggccct ccttgccctc cctgccctgc ccctgagctg       720
ctgggcggac cctccgtgtt cctgttccct cctaagccta aggacaccct gatgatctcc       780
cggacccctg aggtgacctg cgtggtggtg gacgtgtccc acgaggatcc tgaggtgaag       840
ttcaattggt acgtggacgg cgtggaggtg cacaacgcta agaccaagcc tcgggaggaa       900
cagtacaact ccacctaccg ggtggtgcgg gtgctgaccg tgctgcacca ggactggctg       960
aacggcaagg aatacaagtg caaggtctcc aacaaggctc tgcctgcccc catcgaaaag      1020
accatctcca aggccaaggg ccagcctcgc gagcctcagg tgtacaccct gcccccagc       1080
cgggaggaaa tgaccaagaa ccaggtgtcc ctgacctgtc tggtgaaggg cttctaccct      1140
tccgatatcg ccgtggagtg ggagtccaac ggccagcctg aggacaacta caagaccacc     1200
cctcctgtgc tggactccga cggctccttc ttcctgtact ccaagctgac cgtggacaag     1260
tcccggtggc agcagggcaa cgtgttctcc tgctccgtga tgcacgaggc cctgcacaac     1320
cactacaccc agaagtccct gtccctgtct ctgggcaagt ga                        1362
```

<210> SEQ ID NO 163  
<211> LENGTH: 1419  
<212> TYPE: DNA  
<213> ORGANISM: Homo Sapiens

<400> SEQUENCE: 163

```
atgggctggt cctgcatcat cctgtttctg gtggccaccg ccaccggcgt gcactccgag         60
gtgcagctgg tcgagtctgg cggcggactg gtgcagcctg gcggctccct gcggctgtcc        120
tgctccgcct ccggcttcac cttctcctcc tactggatgt cctgggtgcg gcaggctcct       180
ggcaagggcc tggagtgggt ggccaacatc atccaggacg gctccgagaa gtactacgcc       240
gactccgtga agggccggct gaccatctcc cgggacaacg ccaagaactc cctgtacctg       300
cagatgaact ccctgcgggt ggacgacacc gccgtgtact actgcgccag gggctacgag       360
ggctgctccg ccacccggtg ctacctgtac tacttcgact actggggccc tggcaccctg       420
gtgaccgtgt cctccgcctc caccaagggc ccttccgtgt tccctctggc ccttcctcc        480
aagtccacct ccggcggcac cgccgctctg ggctgcctgg tgaaggacta cttccctgag       540
cctgtgaccg tgagctggaa ctctggcgcc ctgaccagcg gcgtgcacac cttccctgcc       600
gtgctgcagt cctccggcct gtactccctg tcctccgtgg tgacagtgcc ttcctcctcc       660
ctgggcaccc agacctacat ctgcaacgtg aaccacaagc cttccaacac caaggtggac      720
aagcgggtgg agcctaagtc cggccctcct tgccctccct gccctgcccc tgagctgctg      780
ggcggacccc ccgtgttcct gttccctcct aagcctaagg acaccctgat gatctcccgg      840
accccctgagg tgacctgcgt ggtggtggac gtgtcccacg aggatcctga ggtgaagttc     900
```

```
aattggtacg tggacggcgt ggaggtgcac aacgctaaga ccaagcctcg ggaggaacag     960
tacaactcca cctaccgggt ggtgcgggtg ctgaccgtgc tgcaccagga ctggctgaac    1020
ggcaaggaat acaagtgcaa ggtctccaac aaggctctgc ctgcccccat cgaaaagacc    1080
atctccaagg ccaagggcca gcctcgcgag cctcaggtgt acaccctgcc ccccagccgg    1140
gaggaaatga ccaagaacca ggtgtccctg acctgtctgg tgaagggctt ctacccttcc    1200
gatatcgccg tggagtggga gtccaacggc agcctgagg acaactacaa gaccaccccct   1260 cctgtgctgg actccgacgg ctccttcttc ctgtactcca agctgaccgt ggacaagtcc    1320
cggtggcagc agggcaacgt gttctcctgc tccgtgatgc acgaggccct gcacaaccac    1380
tacacccaga agtccctgtc cctgtctctg ggcaagtga                          1419
```

<210> SEQ ID NO 164
<211> LENGTH: 345
<212> TYPE: DNA
<213> ORGANISM: Homo Sapiens

<400> SEQUENCE: 164

```
gaggtgcagc tggtcgagtc tggcggcgga ctggtgcagc ctggcggctc cctgcggctg     60
tcctgctccg cctccggctt caccttctcc tcctactgga tgtcctgggt gcggcaggct    120
cctggcaagg gcctggagtg ggtggccaac atcatccagg acggctccga gaagtactac    180
gccgactccg tgaagggccg gctgaccatc tcccgggaca cgccaagaa ctccctgtac     240 ctgcagatga actccctgcg ggtggacgac accgccgtgt actactgcgc caggggctac    300
gagggctgct ccgccacccg gtgctacctg tactacttcg actac                    345
```

<210> SEQ ID NO 165
<211> LENGTH: 75
<212> TYPE: DNA
<213> ORGANISM: Homo Sapiens

<400> SEQUENCE: 165

```
gaggtgcagc tggtcgagtc tggcggcgga ctggtgcagc ctggcggctc cctgcggctg     60
tcctgctccg cctcc                                                      75
```

<210> SEQ ID NO 166
<211> LENGTH: 30
<212> TYPE: DNA
<213> ORGANISM: Homo Sapiens

<400> SEQUENCE: 166

```
ggcttcacct tctcctccta ctggatgtcc                                      30
```

<210> SEQ ID NO 167
<211> LENGTH: 42
<212> TYPE: DNA
<213> ORGANISM: Homo Sapiens

<400> SEQUENCE: 167

```
tgggtgcggc aggctcctgg caagggcctg gagtgggtgg cc                        42
```

<210> SEQ ID NO 168
<211> LENGTH: 51
<212> TYPE: DNA
<213> ORGANISM: Homo Sapiens

<400> SEQUENCE: 168
```

```
aacatcatcc aggacggctc cgagaagtac tacgccgact ccgtgaaggg c           51
```

<210> SEQ ID NO 169
<211> LENGTH: 96
<212> TYPE: DNA
<213> ORGANISM: Homo Sapiens

<400> SEQUENCE: 169

```
cggctgacca tctcccggga caacgccaag aactccctgt acctgcagat gaactccctg   60
cgggtggacg acaccgccgt gtactactgc gccagg                            96
```

<210> SEQ ID NO 170
<211> LENGTH: 51
<212> TYPE: DNA
<213> ORGANISM: Homo Sapiens

<400> SEQUENCE: 170

```
ggctacgagg gctgctccgc cacccggtgc tacctgtact acttcgacta c           51
```

<210> SEQ ID NO 171
<211> LENGTH: 291
<212> TYPE: DNA
<213> ORGANISM: Homo Sapiens

<400> SEQUENCE: 171

```
gacatcgagc tgacccagtc cccctccttc ctgtccgcct ccgtgggcga ccgggtggcc   60
atcacctgcc gggcctccca gggcatctcc aactacctgg cctggtatca gcagaagcct  120
ggcaaggccc ctaagctgct gatctacgcc gccttcgtgc tgcagtccgg cgtgccttcc  180
cggttctccg gctccggcag cggcaccgag ttcaccctga ccatctccaa cctgcagcct  240
gaggacttcg ccacctacta ctgccagcag ctgaactcct accctcgggc c           291
```

<210> SEQ ID NO 172
<211> LENGTH: 330
<212> TYPE: DNA
<213> ORGANISM: Homo Sapiens

<400> SEQUENCE: 172

```
gaggtgcagc tggaggaatc cggcgctggc ctgctgaagc cttccgagac actgtccctg   60
acctgcgccg tgtacggcgg ctccttctcc ggctactact ggtcctggat ccggcaggct  120
cctggcaagg gcctggagtg gatcggcgag atcgaccact ccggcaccac caactacaac  180
ccttccctga gtcccgggt gaccatctcc gtggagacat ccaagaacca gttctccctg  240
cggctgtcct ccgtgaccgc cgctgactcc gccgtgtact actgcgcctc cagcggctac  300
tgctcccacg gcctgtgccc tcaggaagat                                    330
```

<210> SEQ ID NO 173
<211> LENGTH: 291
<212> TYPE: DNA
<213> ORGANISM: Homo Sapiens

<400> SEQUENCE: 173

```
gacgttgagc tgacccagtc tccttccacc ctgtctgcat ctgtaggaga cagagtcacc   60
atcacttgcc gggccagtca gagtattagt agctggttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tataatagtt atccgtggac g           291
```

<210> SEQ ID NO 174
<211> LENGTH: 97
<212> TYPE: PRT
<213> ORGANISM: Homo Sapiens

<400> SEQUENCE: 174

Asp Val Glu Leu Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Pro Trp
                85                  90                  95

Thr

<210> SEQ ID NO 175
<211> LENGTH: 348
<212> TYPE: DNA
<213> ORGANISM: Homo Sapiens

<400> SEQUENCE: 175
caggtacagc tggtgcagtc tgggggaggc ctggtcaagc ctgggggtc cctgagactc      60 tcctgtgcag cctctggatt caccttcagt agctatagca tgaactgggt ccgccaggct    120
ccagggaagg ggctggagtg ggtctcatcc attagtagta gtagtagtta catatactac    180
gcagactcag tgaagggccg attcaccatc tccagagaca acgccaagaa ctcactgtat    240
ctgcaaatga acagcctgag agccgaggac acggctgtgt attactgtgc gagagggggg    300
gtggctggtc gaaccgaaat ttactactac tactacggta tggacgtc               348

<210> SEQ ID NO 176
<211> LENGTH: 116
<212> TYPE: PRT
<213> ORGANISM: Homo Sapiens

<400> SEQUENCE: 176

Gln Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Val Ala Gly Arg Thr Glu Ile Tyr Tyr Tyr Tyr Tyr
            100                 105                 110

Gly Met Asp Val

<210> SEQ ID NO 177
<211> LENGTH: 699
<212> TYPE: DNA
<213> ORGANISM: Homo Sapiens

<400> SEQUENCE: 177

```
atgggctggt cctgcatcat cctgtttctg gtggccaccg ccaccggcgt gcactccgac      60
atcgagctga cccagtcccc ctccttcctg tccgcctccg tgggcgaccg ggtggccatc     120
acctgccggg cctcccaggg catctccaac tacctggcct ggtatcagca gaagcctggc     180
aaggcccta agctgctgat ctacgccgcc ttcgtgctgc agtccggcgt gccttcccgg     240
ttctccggct ccggcagcgg caccgagttc accctgacca tctccaacct gcagcctgag     300
gacttcgcca cctactactg ccagcagctg aactcctacc ctcgggcctt cggccctggc     360
accaaggtgg acatcaagcg accgtggcc gctccttccg tgttcatctt ccctcccctcc     420
gacgagcagc tgaagtccgg caccgccagc gtggtgtgcc tgctgaacaa cttctacccc     480
cgggaggcca aggtgcagtg gaaggtggac aacgccctgc agagcggcaa ctcccaggaa     540
tccgtcaccg agcaggactc caaggacagc acctactccc tgtcctccac cctgaccctg     600
tccaaggccg actacgagaa gcacaaggtg tacgcctgcg aggtgaccca ccagggcctg     660
tccagccctg tgaccaagtc cttcaaccgg ggcgagtga                            699
```

<210> SEQ ID NO 178
<211> LENGTH: 282
<212> TYPE: DNA
<213> ORGANISM: Homo Sapiens

<400> SEQUENCE: 178

```
ctgtgcgccg actccgccac cctgtccgtg tccggccctc ggagggacgg ccagcactcc      60
tgcggcggca caacatcgg caccaagtcc gtgcactggt atcagcagcg gcctggacag     120
gcccctctgc tggtgctgta ccacgacacc aggcggcctt cccggatccc tgagcggttc     180
tccggctcca actccggcaa caccgctacc ctgaccatct cccgggtgga ggccggcgac     240
gaggccgact actactgcca ggtgtgggac tccaggcggg tg                         282
```

<210> SEQ ID NO 179
<211> LENGTH: 69
<212> TYPE: DNA
<213> ORGANISM: Homo Sapiens

<400> SEQUENCE: 179

```
gacatcgagc tgacccagtc cccctccttc ctgtccgcct ccgtgggcga ccgggtggcc      60
atcacctgc                                                              69
```

<210> SEQ ID NO 180
<211> LENGTH: 33
<212> TYPE: DNA
<213> ORGANISM: Homo Sapiens

<400> SEQUENCE: 180

```
cgggcctccc agggcatctc caactacctg gcc                                   33
```

<210> SEQ ID NO 181
<211> LENGTH: 45
<212> TYPE: DNA
<213> ORGANISM: Homo Sapiens
```

<400> SEQUENCE: 181
tggtatcagc agaagcctgg caaggcccct aagctgctga tctac        45

<210> SEQ ID NO 182
<211> LENGTH: 21
<212> TYPE: DNA
<213> ORGANISM: Homo Sapiens

<400> SEQUENCE: 182
gccgccttcg tgctgcagtc c        21

<210> SEQ ID NO 183
<211> LENGTH: 96
<212> TYPE: DNA
<213> ORGANISM: Homo Sapiens

<400> SEQUENCE: 183
ggcgtgcctt cccggttctc cggctccggc agcggcaccg agttcaccct gaccatctcc        60
aacctgcagc ctgaggactt cgccacctac tactgc        96

<210> SEQ ID NO 184
<211> LENGTH: 27
<212> TYPE: DNA
<213> ORGANISM: Homo Sapiens

<400> SEQUENCE: 184
cagcagctga actcctaccc tcgggcc        27

<210> SEQ ID NO 185
<211> LENGTH: 642
<212> TYPE: DNA
<213> ORGANISM: Homo Sapiens

<400> SEQUENCE: 185
gacattgagt tgacccagtc tccatccttc ctgtctgcat ctgtcggaga cagagtcgcc        60
atcacttgcc gggccagtca gggcattagc aattatttag cctggtatca gcaaaaacca        120
gggaaagccc ctaagctcct gatctatgct gcattcgttt tgcaaagtgg ggtcccatca        180
aggttcagcg gcagtggatc tgggacagaa ttcactctca caatcagtaa cctgcagcct        240
gaagattttg caacttatta ctgtcaacaa cttaatagtt atcctcgcgc tttcggccct        300
gggaccaaag tggatatcaa acgaactgtg gctgcaccat ctgtcttcat cttcccgcca        360
tctgatgagc agttgaaatc tggaactgcc tctgttgtgt gcctgctgaa taacttctat        420
cccagagagg ccaaagtaca gtggaaggtg gataacgccc tccaatcggg taactcccag        480
gagagtgtca cagagcagga cagcaaggac agcacctaca gcctcagcag caccctgacg        540
ctgagcaaag cagactacga gaaacacaaa gtctacgcct gcgaagtcac ccatcagggc        600
ctgagctcgc ccgtcacaaa gagcttcaac aggggagagt ga        642

<210> SEQ ID NO 186
<211> LENGTH: 213
<212> TYPE: PRT
<213> ORGANISM: Homo Sapiens

<400> SEQUENCE: 186

Asp Ile Glu Leu Thr Gln Ser Pro Ser Phe Leu Ser Ala Ser Val Gly
1               5                   10                  15

Asp Arg Val Ala Ile Thr Cys Arg Ala Ser Gln Gly Ile Ser Asn Tyr

```
                    20                  25                  30
Leu Ala Trp Tyr Gln Gln Lys Pro Gly Lys Ala Pro Lys Leu Leu Ile
                35                  40                  45

Tyr Ala Ala Phe Val Leu Gln Ser Gly Val Pro Ser Arg Phe Ser Gly
            50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Leu Asn Ser Tyr Pro Arg
                85                  90                  95

Ala Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu
    210

<210> SEQ ID NO 187
<211> LENGTH: 1356
<212> TYPE: DNA
<213> ORGANISM: Homo Sapiens

<400> SEQUENCE: 187
gaggtgcagc tgttgcagtc tggcgcagga ctgttgaagc cttcggagac cctgtccctc      60
acctgcgctg tctatggtgg gtccttcagt ggatactact ggagttggat ccgccaggcc     120
ccagggaagg gactggagtg gattggggaa atcgatcata gtggaaccac caactacaac     180
ccgtccctca gagtcgggt caccatatca gtagagacat ccaagaacca gttctccctg      240
aggctgagct ctgtgaccgc cgcggactcg gctgtctatt actgtgcgag cagtggatat     300
tgttctcatg gtttatgccc caagaggac tggggccagg gaaccctggt caccgtctcc      360
tcagcctcca ccaagggccc atcggtcttc ccctggcac cctcctccaa gagcacctct      420
gggggcacag cggccctggg ctgcctggtc aaggactact ccccgaacc ggtgacggtg      480 tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc      780 cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
```

```
tccaaagcca aagggcagcc ccgagaacca caggtgtaca ccctgccccc atcccgggat      1080
gagctgacca agaaccaggt cagcctgacc tgcctggtca aaggcttcta tcccagcgac      1140
atcgccgtgg agtgggagag caatgggcag ccggagaaca actacaagac cacgcctccc      1200
gtgctggact ccgacggctc cttcttcctc tacagcaagc tcaccgtgga caagagcagg      1260
tggcagcagg ggaacgtctt ctcatgctcc gtgatgcatg aggctctgca caaccactac      1320
acgcagaaga gcctctccct gtctccgggt aaatga                               1356

<210> SEQ ID NO 188
<211> LENGTH: 451
<212> TYPE: PRT
<213> ORGANISM: Homo Sapiens

<400> SEQUENCE: 188

Glu Val Gln Leu Leu Gln Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ala Pro Gly Lys Gly Leu Glu Trp Ile
        35                  40                  45

Gly Glu Ile Asp His Ser Gly Thr Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Arg Leu Ser Ser Val Thr Ala Ala Asp Ser Ala Val Tyr Tyr Cys Ala
                85                  90                  95

Ser Ser Gly Tyr Cys Ser His Gly Leu Cys Pro Gln Glu Asp Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
```

```
                305                 310                 315                 320
Lys Glu Tyr Lys Cys Lys Val Ser Asn Lys Ala Leu Pro Ala Pro Ile
                    325                 330                 335
Glu Lys Thr Ile Ser Lys Ala Lys Gly Gln Pro Arg Glu Pro Gln Val
                340                 345                 350
Tyr Thr Leu Pro Pro Ser Arg Asp Glu Leu Thr Lys Asn Gln Val Ser
                355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
                420                 425                 430
His Glu Ala Leu His Asn His Tyr Thr Gln Lys Ser Leu Ser Leu Ser
                435                 440                 445
Pro Gly Lys
    450

<210> SEQ ID NO 189
<211> LENGTH: 642
<212> TYPE: DNA
<213> ORGANISM: Homo Sapiens

<400> SEQUENCE: 189
gacatcgagc tgacccagtc cccctccttc ctgtccgcct ccgtgggcga ccgggtggcc      60
atcacctgcc gggcctccca gggcatctcc aactacctgg cctggtatca gcagaagcct     120
ggcaaggccc ctaagctgct gatctacgcc gccttcgtgc tgcagtccgg cgtgccttcc     180
cggttctccg gctccggcag cggcaccgag ttcaccctga ccatctccaa cctgcagcct     240
gaggacttcg ccacctacta ctgccagcag ctgaactcct accctcgggc cttcggccct     300
ggcaccaagg tggacatcaa gggaccgtg ccgctccttc cgtgttcat cttccctccc     360
tccgacgagc agctgaagtc cggcaccgcc agcgtggtgt gcctgctgaa caacttctac     420
ccccgggagg ccaaggtgca gtggaaggtg gacaacgccc tgcagagcgg caactcccag     480
gaatccgtca ccgagcagga ctccaaggac agcacctact ccctgtcctc caccctgacc     540
ctgtccaagg ccgactacga gaagcacaag gtgtacgcct gcgaggtgac ccaccagggc     600
ctgtccagcc ctgtgaccaa gtccttcaac cggggcgagt ga                       642

<210> SEQ ID NO 190
<211> LENGTH: 1356
<212> TYPE: DNA
<213> ORGANISM: Homo Sapiens

<400> SEQUENCE: 190
gaggtgcagc tggaggaatc cggcgctggc ctgctgaagc cttccgagac actgtccctg      60
acctgcgccg tgtacggcgg ctccttctcc ggctactact ggtcctggat ccggcaggct     120
cctggcaagg gcctggagtg gatcggcgag atcgaccact ccggcaccac caactacaac     180
ccttccctga gtcccgggt gaccatctcc gtggagacat ccaagaacca gttctccctg     240
cggctgtcct ccgtgaccgc cgctgactcc gccgtgtact actgcgcctc cagcggctac     300
tgctcccacg gcctgtgccc tcaggaagat tggggccagg gcaccctggt gaccgtgtcc     360
```

```
tccgcctcca ccaagggccc ttccgtgttc cctctggccc cttcctccaa gtccacctcc    420
ggcggcaccg ccgctctggg ctgcctggtg aaggactact ccctgagcc tgtgaccgtg    480
agctggaact ctggcgctct gaccagcggc gtgcacacct tccctgccgt gctgcagtcc    540
tccggcctgt actccctgtc cagcgtggtg acagtgcctt cctcctccct gggcacccag    600
acctacatct gcaacgtgaa ccacaagcct tccaacacca aggtggacaa gcgggtggag    660
cctaagtcct gcgacaagac ccacacctgc cctccctgcc ctgcccctga ctgctgggc    720
ggaccctccg tgttcctgtt ccctcctaag cctaaggaca cctgatgat ctcccggacc    780
cctgaggtga cctgcgtggt ggtggacgtg tcccacgagg atcctgaggt gaagttcaat    840
tggtacgtgg acggcgtgga ggtgcacaac gccaagacca gcctcggga ggaacagtac    900
aactccacct accgggtggt gtccgtgctg accgtgctgc accaggactg gctgaacggc    960
aaggaataca agtgcaaggt ctccaacaag gccgtgcctg cccctatcga aaagaccatc   1020
tccaaggcca agggccagcc tcgcgagcct caggtgtaca ccctgcctcc tagccgggag   1080
gaaatgacca agaatcaggt gtccctgaca tgtctggtga agggcttcta cccttccgat   1140
atcgccgtgg agtgggagtc caacggccag cctgagaaca actacaagac caccccctcct   1200
gtgctggact ccgacggcag cttcttcctg tactccaagc tgaccgtgga caagtcccgg   1260
tggcagcagg gcaacgtgtt ctcctgctcc gtgatgcacg aggccctgca caaccactac   1320
acccagaagt ccctgtccct gtctcctggc aagtga                              1356

<210> SEQ ID NO 191
<211> LENGTH: 1413
<212> TYPE: DNA
<213> ORGANISM: Homo Sapiens

<400> SEQUENCE: 191
atgggctggt cctgcatcat cctgtttctg gtggccaccg ccaccggcgt gcactccgag     60
gtgcagctgg aggaatccgg cgctggcctg ctgaagcctt ccgagacact gtccctgacc    120
tgcgccgtgt acggcggctc cttctccggc tactactggt cctggatccg gcaggctcct    180
ggcaagggcc tggagtggat cggcgagatc gaccactccg gcaccaccaa ctacaaccct    240
tccctgaagt cccgggtgac catctccgtg agacatcca agaaccagtt ctccctgcgg    300
ctgtcctccg tgaccgccgc tgactccgcc gtgtactact gcgcctccag cggctactgc    360
tcccacggcc tgtgccctca ggaagattgg ggccagggca cctggtgac cgtgtcctcc    420
gcctccacca agggcccttc cgtgttccct ctggccccttc ctccaagtc cacctccggc    480
ggcaccgccg ctctgggctg cctggtgaag gactacttcc ctgagcctgt gaccgtgagc    540
tggaactctg gcgctctgac cagcggcgtg cacaccttcc ctgccgtgct gcagtcctcc    600
ggcctgtact ccctgtccag cgtggtgaca gtgccttcct cctccctggg cacccagacc    660
tacatctgca acgtgaacca caagccttcc aacaccaagg tggacaagcg ggtggagcct    720
aagtcctgcg acaagaccca cacctgccct cctgccctg cccctgagct gctgggcgga    780
ccctccgtgt tcctgttccc tcctaagcct aaggacaccc tgatgatctc ccggaccct    840
gaggtgacct gcgtggtggt ggacgtgtcc cacgaggatc tgaggtgaa gttcaattgg    900
tacgtggacg gcgtggaggt gcacaacgcc aagaccaagc tcgggagga acagtacaac    960
tccacctacc gggtggtgtc cgtgctgacc gtgctgcacc aggactggct gaacggcaag   1020
gaatacaagt gcaaggtctc caacaaggcc gtgcctgccc ctatcgaaaa gaccatctcc   1080
aaggccaagg gccagcctcg cgagcctcag gtgtacaccc tgcctcctag ccgggaggaa   1140
```

-continued

```
atgaccaaga atcaggtgtc cctgacatgt ctggtgaagg gcttctaccc ttccgatatc    1200
gccgtggagt gggagtccaa cggccagcct gagaacaact acaagaccac ccctcctgtg    1260
ctggactccg acggcagctt cttcctgtac tccaagctga ccgtggacaa gtcccggtgg    1320
cagcagggca acgtgttctc ctgctccgtg atgcacgagg ccctgcacaa ccactacacc    1380
cagaagtccc tgtccctgtc tcctggcaag tga                                 1413
```

<210> SEQ ID NO 192
<211> LENGTH: 354
<212> TYPE: DNA
<213> ORGANISM: Homo Sapiens

<400> SEQUENCE: 192

```
caggtgcagc tgctggagtc tggcggcgga ctggtgcagc ctggcggctc cctgcggctg     60
tcctgcgccg cctccggctt ctccttcggc gactactgga tgtcctgggt gcggcaggct    120
cctggcaagg gcctggagtg ggtggccgac atcaagcctg acggcagcga caaggactac    180
gtggactccg tgaagggccg gttcaccatc tcccgggaca cgccaagaa ctccctgtac     240 ctgcagatgt cctccctgcg ggcgaggac accgccgtgt actactgcgc cagagactac    300
gtggtggtgg ccccttccca gcctcctaac atccaccctg agtacttcca gaac          354
```

<210> SEQ ID NO 193
<211> LENGTH: 75
<212> TYPE: DNA
<213> ORGANISM: Homo Sapiens

<400> SEQUENCE: 193

```
gaggtgcagc tggaggaatc cggcgctggc ctgctgaagc cttccgagac actgtccctg     60
acctgcgccg tgtac                                                      75
```

<210> SEQ ID NO 194
<211> LENGTH: 30
<212> TYPE: DNA
<213> ORGANISM: Homo Sapiens

<400> SEQUENCE: 194

```
ggcggctcct tctccggcta ctactggtcc                                      30
```

<210> SEQ ID NO 195
<211> LENGTH: 42
<212> TYPE: DNA
<213> ORGANISM: Homo Sapiens

<400> SEQUENCE: 195

```
tggatccggc aggctcctgg caagggcctg gagtggatcg gc                        42
```

<210> SEQ ID NO 196
<211> LENGTH: 48
<212> TYPE: DNA
<213> ORGANISM: Homo Sapiens

<400> SEQUENCE: 196

```
gagatcgacc actccggcac caccaactac aacccttccc tgaagtcc                  48
```

<210> SEQ ID NO 197
<211> LENGTH: 96
<212> TYPE: DNA
<213> ORGANISM: Homo Sapiens -continued

<400> SEQUENCE: 197

```
cgggtgacca tctccgtgga gacatccaag aaccagttct ccctgcggct gtcctccgtg    60
accgccgctg actccgccgt gtactactgc gcctcc                              96
```

<210> SEQ ID NO 198
<211> LENGTH: 39
<212> TYPE: DNA
<213> ORGANISM: Homo Sapiens

<400> SEQUENCE: 198

```
agcggctact gctcccacgg cctgtgccct caggaagat                           39
```

<210> SEQ ID NO 199
<211> LENGTH: 291
<212> TYPE: DNA
<213> ORGANISM: Homo Sapiens

<400> SEQUENCE: 199

```
gacattgagt tgacccagtc tccatccttc ctgtctgcat ctgtcggaga cagagtcgcc    60
atcacttgcc gggccagtca gggcattagc aattatttag cctggtatca gcaaaaacca   120
gggaaagccc ctaagctcct gatctatgct gcattcgttt tgcaaagtgg ggtcccatca   180
aggttcagcg gcagtggatc tgggacagaa ttcactctca caatcagtaa cctgcagcct   240
gaagattttg caacttatta ctgtcaacaa cttaatagtt atcctcgcgc t             291
```

<210> SEQ ID NO 200
<211> LENGTH: 97
<212> TYPE: PRT
<213> ORGANISM: Homo Sapiens

<400> SEQUENCE: 200

```
Asp Ile Glu Leu Thr Gln Ser Pro Ser Phe Leu Ser Ala Ser Val Gly
1               5                   10                  15

Asp Arg Val Ala Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Phe Val Leu Gln Ser Gly Val Pro Ser Arg Phe Ser Gly
    50                  55                  60

Ser Gly Ser Gly Thr Glu Phe Thr Leu Thr Ile Ser Asn Leu Gln Pro
65                  70                  75                  80

Glu Asp Phe Ala Thr Tyr Tyr Cys Gln Gln Leu Asn Ser Tyr Pro Arg
                85                  90                  95

Ala
```

<210> SEQ ID NO 201
<211> LENGTH: 330
<212> TYPE: DNA
<213> ORGANISM: Homo Sapiens

<400> SEQUENCE: 201

```
gaggtgcagc tgttgcagtc tggcgcagga ctgttgaagc cttcggagac cctgtccctc    60
acctgcgctg tctatggtgg gtccttcagt ggatactact ggagttggat ccgccaggcc   120
ccagggaagg gactggagtg gattggggaa atcgatcata gtggaaccac caactacaac   180
ccgtccctca gagtcgggt caccatatca gtagagacat ccaagaacca gttctccctg   240
aggctgagct ctgtgaccgc cgcggactcg gctgtctatt actgtgcgag cagtggatat   300
```

```
tgttctcatg gtttatgccc ccaagaggac                                        330
```

<210> SEQ ID NO 202
<211> LENGTH: 110
<212> TYPE: PRT
<213> ORGANISM: Homo Sapiens

<400> SEQUENCE: 202

```
Glu Val Gln Leu Leu Gln Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ala Pro Gly Lys Gly Leu Glu Trp Ile
        35                  40                  45

Gly Glu Ile Asp His Ser Gly Thr Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Arg Leu Ser Ser Val Thr Ala Ala Asp Ser Ala Val Tyr Tyr Cys Ala
                85                  90                  95

Ser Ser Gly Tyr Cys Ser His Gly Leu Cys Pro Gln Glu Asp
            100                 105                 110
```

<210> SEQ ID NO 203
<211> LENGTH: 330
<212> TYPE: DNA
<213> ORGANISM: Homo Sapiens

<400> SEQUENCE: 203

```
gaggtacagc tggaggagtc tggcgcagga ctgttgaagc cttcggagac cctgtccctc      60
acctgcgctg tctatggtgg gtccttcagt ggatactact ggagttggat ccgccaggcc     120
ccagggaagg gactggagtg gattggggaa atcgatcata gtggaaccac caactacaac     180
ccgtccctca agagtcgggt caccatatca gtagagacat ccaagaacca gttctccctg     240
aggctgagct ctgtgaccgc cgcggactcg gctgtctatt actgtgcgag cagtggatat     300
tgttctcatg gtttatgccc ccaagaggac                                      330
```

<210> SEQ ID NO 204
<211> LENGTH: 110
<212> TYPE: PRT
<213> ORGANISM: Homo Sapiens

<400> SEQUENCE: 204

```
Glu Val Gln Leu Glu Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ala Pro Gly Lys Gly Leu Glu Trp Ile
        35                  40                  45

Gly Glu Ile Asp His Ser Gly Thr Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Arg Leu Ser Ser Val Thr Ala Ala Asp Ser Ala Val Tyr Tyr Cys Ala
                85                  90                  95

Ser Ser Gly Tyr Cys Ser His Gly Leu Cys Pro Gln Glu Asp
```

<210> SEQ ID NO 205
<211> LENGTH: 690
<212> TYPE: DNA
<213> ORGANISM: Homo Sapiens

<400> SEQUENCE: 205

```
atgggctggt cctgcatcat cctgtttctg gtggccaccg ccaccggcgt gcactccctg      60
tgcgccgact ccgccaccct gtccgtgtcc ggccctcgga gggacggcca gcactcctgc     120
ggcggcaaca acatcggcac caagtccgtg cactggtatc agcagcggcc tggacaggcc     180
cctctgctgg tgctgtacca cgacaccagg cggccttccc ggatccctga gcggttctcc     240
ggctccaact ccggcaacac cgctaccctg accatctccc gggtggaggc cggcgacgag     300
gccgactact actgccaggt gtgggactcc aggcgggtgt tcggcggagg aacaaagctg     360
accgtgctgg ccagcctaa ggccgctcct tccgtgaccc tgttccctcc ttcctccgag     420
gaactgcagg ccaacaaggc cacctgtg tgcctgatct ccgacttcta ccctggcgcc     480
gtgaccgtgg cttggaaggc cgactcctcc cctgtgaagg ctggcgtgga gacaaccacc     540
ccttccaagc agtccaacaa caagtacgcc gcctcctcct acctgtccct gaccctgag      600
cagtggaagt cccacaagtc ctacagctgc caggtgaccc acgagggctc caccgtggaa     660
aagaccgtgg cccctaccga gtcctcctga                                     690
```

<210> SEQ ID NO 206
<211> LENGTH: 57
<212> TYPE: DNA
<213> ORGANISM: Artificial Sequence
<220> FEATURE:
<223> OTHER INFORMATION: Polynucleotide

<400> SEQUENCE: 206

```
atgggctggt cctgcatcat cctgtttctg gtggccaccg ccaccggcgt gcactcc        57
```

<210> SEQ ID NO 207
<211> LENGTH: 63
<212> TYPE: DNA
<213> ORGANISM: Homo Sapiens

<400> SEQUENCE: 207

```
ctgtgcgccg actccgccac cctgtccgtg tccggccctc ggagggacgg ccagcactcc     60
tgc                                                                  63
```

<210> SEQ ID NO 208
<211> LENGTH: 33
<212> TYPE: DNA
<213> ORGANISM: Homo Sapiens

<400> SEQUENCE: 208

```
ggcggcaaca acatcggcac caagtccgtg cac                                  33
```

<210> SEQ ID NO 209
<211> LENGTH: 45
<212> TYPE: DNA
<213> ORGANISM: Homo Sapiens

<400> SEQUENCE: 209

```
tggtatcagc agcggcctgg acaggcccct ctgctggtgc tgtac                     45
```

<210> SEQ ID NO 210
<211> LENGTH: 21
<212> TYPE: DNA
<213> ORGANISM: Homo Sapiens

<400> SEQUENCE: 210
cacgacacca ggcggccttc c                                              21

<210> SEQ ID NO 211
<211> LENGTH: 96
<212> TYPE: DNA
<213> ORGANISM: Homo Sapiens

<400> SEQUENCE: 211
cggatccctg agcggttctc cggctccaac tccggcaaca ccgctaccct gaccatctcc    60
cgggtggagg ccggcgacga ggccgactac tactgc                              96

<210> SEQ ID NO 212
<211> LENGTH: 24
<212> TYPE: DNA
<213> ORGANISM: Homo Sapiens

<400> SEQUENCE: 212
caggtgtggg actccaggcg ggtg                                           24

<210> SEQ ID NO 213
<211> LENGTH: 633
<212> TYPE: DNA
<213> ORGANISM: Homo Sapiens

<400> SEQUENCE: 213
ctatgtgctg actcagccac cctcagtgtc agtggcccca ggagagacgg ccagcattcc    60
tgtgggggaa acaacattgg aactaagagt gtccactggt accagcagag gccaggccag   120
gcccctctac tggtcctcta tcatgacacc aggcggccct caaggattcc tgagcgattc   180
tctggctcca actctggaaa cacggccacc ctgaccatca gcagggtcga agccggggat   240
gaggccgact attactgtca ggtgtgggat agtcgaaggg tgttcggcgg agggaccaag   300
ctgaccgtcc taggtcagcc caaggcggcc cctcggtca ctctgttccc gccctcctct   360
gaggagcttc aagccaacaa ggccacactg gtgtgtctca taagtgactt ctacccggga   420
gccgtgacag tggcctggaa ggcagatagc agccccgtca aggcgggagt ggagaccacc   480
acaccctcca acaaagcaa caacaagtac gcggccagca gctacctgag cctgacgcct   540
gagcagtgga agtcccacaa aagctacagc tgccaggtca cgcatgaagg gagcaccgtg   600
gagaagacag tggcccctac agaatcttca tga                                633

<210> SEQ ID NO 214
<211> LENGTH: 210
<212> TYPE: PRT
<213> ORGANISM: Homo Sapiens

<400> SEQUENCE: 214

Leu Cys Ala Asp Ser Ala Thr Leu Ser Val Ser Gly Pro Arg Arg Asp
1               5                   10                  15

Gly Gln His Ser Cys Gly Gly Asn Asn Ile Gly Thr Lys Ser Val His
            20                  25                  30

Trp Tyr Gln Gln Arg Pro Gly Gln Ala Pro Leu Leu Val Leu Tyr His
        35                  40                  45

Asp Thr Arg Arg Pro Ser Arg Ile Pro Glu Arg Phe Ser Gly Ser Asn

```
                    50                  55                  60
Ser Gly Asn Thr Ala Thr Leu Thr Ile Ser Arg Val Glu Ala Gly Asp
 65                  70                  75                  80

Glu Ala Asp Tyr Tyr Cys Gln Val Trp Asp Ser Arg Arg Val Phe Gly
                 85                  90                  95

Gly Gly Thr Lys Leu Thr Val Leu Gly Gln Pro Lys Ala Ala Pro Ser
            100                 105                 110

Val Thr Leu Phe Pro Pro Ser Ser Glu Glu Leu Gln Ala Asn Lys Ala
            115                 120                 125

Thr Leu Val Cys Leu Ile Ser Asp Phe Tyr Pro Gly Ala Val Thr Val
            130                 135                 140

Ala Trp Lys Ala Asp Ser Ser Pro Val Lys Ala Gly Val Glu Thr Thr
145                 150                 155                 160

Thr Pro Ser Lys Gln Ser Asn Asn Lys Tyr Ala Ala Ser Ser Tyr Leu
                165                 170                 175

Ser Leu Thr Pro Glu Gln Trp Lys Ser His Lys Ser Tyr Ser Cys Gln
            180                 185                 190

Val Thr His Glu Gly Ser Thr Val Glu Lys Thr Val Ala Pro Thr Glu
            195                 200                 205

Ser Ser
    210

<210> SEQ ID NO 215
<211> LENGTH: 1371
<212> TYPE: DNA
<213> ORGANISM: Homo Sapiens

<400> SEQUENCE: 215
caggtgcagc tgttggagtc agggggaggc ttggtccagc cggggggggtc cctgagactc      60 tcctgtgcag cctctggatt cagctttggc gactattgga tgagttgggt ccgccaggct     120
ccagggaagg gcctggagtg ggtggccgac ataaagccag atggcagtga caaagactat     180
gtggactctg tgaagggccg attcaccatc tccagagaca cgccaagaa ctcactgtat      240 ctgcaaatga gcagcctgcg aggcgaagac acggctgtct attattgtgc gagagactat     300
gtcgtcgtcg caccatctca accccaaac attcaccctg aatacttcca gaactggggc      360
cagggcaccc tggtcatcgt ctcctcagcc tccaccaagg gcccatcggt cttccccctg     420
gcaccctcct ccaagagcac ctctgggggc acagcggccc tgggctgcct ggtcaaggac     480
tacttccccg aaccggtgac ggtgtcgtgg aactcaggcg ccctgaccag cggcgtgcac     540
accttcccgg ctgtcctaca gtcctcagga ctctactccc tcagcagcgt ggtgaccgtg     600
ccctccagca gcttgggcac ccagacctac atctgcaacg tgaatcacaa gcccagcaac     660
accaaggtgg acaagagagt gagctgtgac aaaactcaca catgcccacc gtgcccagca     720
cctgaactcc tggggggacc gtcagtcttc ctcttccccc caaaacccaa ggacaccctc     780
atgatctccc ggacccctga ggtcacatgc gtggtggtgg acgtgagcca cgaagaccct     840
gaggtcaagt tcaactggta cgtggacggc gtggaggtgc ataatgccaa gacaaagccg     900
cgggaggagc agtacaacag cacgtaccgt gtggtcagcg tcctcaccgt cctgcaccag     960
gactggctga atggcaagga gtacaagtgc aaggtctcca acaaagccct cccagccccc    1020
atcgagaaaa ccatctccaa agccaaaggg cagccccgag aaccacaggt gtacaccctg    1080
cccccatccc gggaggagat gaccaagaac caggtcagcc tgacctgcct ggtcaaaggc    1140
ttctatccca gcgacatcgc cgtggagtgg gagagcaatg ggcagccgga gaacaactac    1200
```

```
aagaccacgc ctcccgtgct ggactccgac ggctccttct tcctctatag caagctcacc   1260
gtggacaaga gcaggtggca gcaggggaac gtcttctcat gctccgtgat gcatgaggct   1320
ctgcacaacc actacacgca gaagagcctc tccctgtctc cgggtaaatg a            1371
```

<210> SEQ ID NO 216
<211> LENGTH: 456
<212> TYPE: PRT
<213> ORGANISM: Homo Sapiens

<400> SEQUENCE: 216

```
Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Gly Asp Tyr
            20                  25                  30

Trp Met Ser Trp Val Arg Gln Ala Pro Gly Lys Gly Leu Glu Trp Val
        35                  40                  45

Ala Asp Ile Lys Pro Asp Gly Ser Asp Lys Asp Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Gly Glu Asp Thr Ala Val Tyr Tyr Cys
                85                  90                  95

Ala Arg Asp Tyr Val Val Ala Pro Ser Gln Pro Pro Asn Ile His
            100                 105                 110

Pro Glu Tyr Phe Gln Asn Trp Gly Gln Gly Thr Leu Val Ile Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Arg Val Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
```

```
                    340                 345                 350
Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 217
<211> LENGTH: 633
<212> TYPE: DNA
<213> ORGANISM: Homo Sapiens

<400> SEQUENCE: 217
ctgtgcgccg actccgccac cctgtccgtg tccggccctc ggagggacgg ccagcactcc      60
tgcggcggca acaacatcgg caccaagtcc gtgcactggt atcagcagcg cctggacag     120 gcccctctgc tggtgctgta ccacgacacc aggcggcctt ccggatccc tgagcggttc     180 tccggctcca actccggcaa caccgctacc ctgaccatct cccgggtgga ggccggcgac     240
gaggccgact actactgcca ggtgtgggac tccaggcggg tgttcggcgg aggaacaaag     300
ctgaccgtgc tgggccagcc taaggccgct ccttccgtga ccctgttccc tccttcctcc     360
gaggaactgc aggccaacaa ggccaccctg gtgtgcctga tctccgactt ctaccctggc     420
gccgtgaccg tggcttggaa ggccgactcc tcccctgtga aggctggcgt ggagacaacc     480
accccttcca gcagtccaa caacaagtac gccgcctcct cctacctgtc cctgaccct      540 gagcagtgga agtcccacaa gtcctacagc tgccaggtga cccacgaggg ctccaccgtg     600
gaaaagaccg tggcccctac cgagtcctcc tga                                 633

<210> SEQ ID NO 218
<211> LENGTH: 1371
<212> TYPE: DNA
<213> ORGANISM: Homo Sapiens

<400> SEQUENCE: 218
caggtgcagc tgctggagtc tggcggcgga ctggtgcagc ctggcggctc cctgcggctg      60
tcctgcgccg cctccggctt ctccttcggc gactactgga tgtcctgggt gcggcaggct     120
cctggcaagg gcctggagtg ggtggccgac atcaagccg acggcagcga caaggactac     180
gtggactccg tgaagggccg gttcaccatc tcccgggaca cgccaagaa ctccctgtac     240 ctgcagatgt cctccctgcg ggcgaggac accgccgtgt actactgcgc cagagactac     300
gtggtggtgg ccccttccca gcctcctaac atccaccctg agtacttcca gaactggggc     360
cagggcaccc tggtgatcgt gtcctccgcc tccaccaagg gccttccgt gttccctctg     420 gccccctcct ccaagtccac ctccggcggc accgccgctc tgggctgcct ggtgaaggac     480
tacttccctg agcctgtgac cgtgtcctgg aactctggcg ccctgaccag cggagtgcac     540
```

```
accttccctg ccgtgctgca gtcctccggc ctgtactccc tgtcctccgt ggtgaccgtg      600
ccttcctcct ccctgggcac ccagacctac atctgcaacg tgaaccacaa gccttccaac      660
accaaggtgg acaagcgggt gtcctgcgac aagacccaca cctgccctcc ctgccctgcc      720
cctgagctgc tgggcggacc ctccgtgttc ctgttccctc ctaagcctaa ggacaccctg      780
atgatctccc ggaccctga ggtgacctgt gtggtggtgg acgtgtccca cgaggatcct       840
gaggtgaagt tcaattggta cgtggacggc gtggaggtgc acaacgctaa gaccaagcct      900
cgggaggaac agtacaactc cacctaccgg gtggtgtctg tgctgaccgt gctgcaccag      960
gactggctga acggcaagga atacaagtgc aaggtctcca acaaggccct gccggctccc     1020
atcgaaaaga ccatctccaa ggccaagggc cagcctcgcg agcctcaggt gtacaccctg     1080
ccccccagcc gggaggaaat gaccaagaac caggtgtccc tgacctgtct ggtgaagggc     1140
ttctacccct tccgatatcgc cgtggagtgg gagtccaacg gccagcctga gaacaactac     1200
aagaccaccc ctcctgtgct ggactccgac ggctccttct tcctgtactc caagctgacc     1260
gtggacaagt cccggtggca gcagggcaac gtgttctcct gctccgtgat gcacgaggcc     1320
ctgcacaacc actcacccca gaagtccctg tccctgagcc ctggcaagtg a              1371
```

<210> SEQ ID NO 219
<211> LENGTH: 1428
<212> TYPE: DNA
<213> ORGANISM: Homo Sapiens

<400> SEQUENCE: 219

```
atgggctggt cctgcatcat cctgtttctg gtggccaccg ccaccggcgt gcactcccag       60
gtgcagctgc tggagtctgg cggcggactg gtgcagcctg gcggctccct gcggctgtcc      120
tgcgccgcct ccggcttctc cttcggcgac tactggatgt cctgggtgcg gcaggctcct      180
ggcaagggcc tggagtgggt ggccgacatc aagcctgacg gcagcgacaa ggactacgtg      240
gactccgtga agggccggtt caccatctcc cgggacaacg ccaagaactc cctgtacctg      300
cagatgtcct ccctgcgggg cgaggacacc gccgtgtact actgcgccag agactacgtg      360
gtggtggccc ttcccagcc tcctaacatc caccctgagt acttccagaa ctggggccag      420
ggcaccctgg tgatcgtgtc ctccgcctcc accaagggcc cttccgtgtt ccctctggcc      480
ccctcctcca gtccaccctc cggcggcacc gccgctctgg gctgcctggt gaaggactac      540
ttccctgagc ctgtgaccgt gtcctggaac tctggcgccc tgaccagcgg agtgcacacc      600
ttccctgccg tgctgcagtc cctccggcctg tactccctgt cctccgtggt gaccgtgcct     660
tcctcctccc tgggcaccca gacctacatc tgcaacgtga accacaagcc ttccaacacc      720
aaggtggaca gcggggtgtc ctgcgacaag acccacacct gccctccctg ccctgccct      780 gagctgctgg gcggaccctc cgtgttcctg ttccctccta agcctaagga caccctgatg      840
atctcccgga ccctgaggt gacctgtgtg tggtggacg tgtcccacga ggatcctgag        900
gtgaagttca attggtacgt ggacggcgtg gaggtgcaca acgctaagac caagcctcgg      960
gaggaacagt acaactccac ctaccgggtg gtgtctgtgc tgaccgtgct gcaccaggac     1020
tggctgaacg gcaaggaata caagtgcaag gtctccaaca aggccctgcc cgctcccatc     1080
gaaaagacca tctccaaggc caagggccag cctcgcgagc ctcaggtgta caccctgccc     1140
ccagccggga ggaaatgac caagaaccag gtgtccctga cctgtctggt gaagggcttc      1200
tacccttccg atatcgccgt ggagtgggag tccaacggcc agcctgagaa caactacaag     1260
accacccctc ctgtgctgga ctccgacggc tccttcttcc tgtactccaa gctgaccgtg     1320
```

```
gacaagtccc ggtggcagca gggcaacgtg ttctcctgct ccgtgatgca cgaggccctg    1380
cacaaccact acacccagaa gtccctgtcc ctgagccctg gcaagtga                 1428
```

<210> SEQ ID NO 220
<211> LENGTH: 57
<212> TYPE: DNA
<213> ORGANISM: Artificial Sequence
<220> FEATURE:
<223> OTHER INFORMATION: Polynucleotide

<400> SEQUENCE: 220

```
atgggatgga gctgtatcat cctcttcttg gtagcaacag ctacaggtgt ccactcc        57
```

<210> SEQ ID NO 221
<211> LENGTH: 75
<212> TYPE: DNA
<213> ORGANISM: Homo Sapiens

<400> SEQUENCE: 221

```
caggtgcagc tgctggagtc tggcggcgga ctggtgcagc ctggcggctc cctgcggctg    60
tcctgcgccg cctcc                                                      75
```

<210> SEQ ID NO 222
<211> LENGTH: 30
<212> TYPE: DNA
<213> ORGANISM: Homo Sapiens

<400> SEQUENCE: 222

```
ggcttctcct tcggcgacta ctggatgtcc                                      30
```

<210> SEQ ID NO 223
<211> LENGTH: 42
<212> TYPE: DNA
<213> ORGANISM: Homo Sapiens

<400> SEQUENCE: 223

```
tgggtgcggc aggctcctgg caagggcctg gagtgggtgg cc                        42
```

<210> SEQ ID NO 224
<211> LENGTH: 51
<212> TYPE: DNA
<213> ORGANISM: Homo Sapiens

<400> SEQUENCE: 224

```
gacatcaagc ctgacggcag cgacaaggac tacgtggact ccgtgaaggg c              51
```

<210> SEQ ID NO 225
<211> LENGTH: 96
<212> TYPE: DNA
<213> ORGANISM: Homo Sapiens

<400> SEQUENCE: 225

```
cggttcacca tctcccggga caacgccaag aactccctgt acctgcagat gtcctccctg    60
cggggcgagg acaccgccgt gtactactgc gccaga                               96
```

<210> SEQ ID NO 226
<211> LENGTH: 60
<212> TYPE: DNA
<213> ORGANISM: Homo Sapiens

<400> SEQUENCE: 226

```
gactacgtgg tggtggcccc ttcccagcct cctaacatcc accctgagta cttccagaac    60
```

<210> SEQ ID NO 227
<211> LENGTH: 282
<212> TYPE: DNA
<213> ORGANISM: Homo Sapiens

<400> SEQUENCE: 227

```
ctatgtgctg actcagccac cctcagtgtc agtggcccca ggagagacgg ccagcattcc    60
tgtggggaa acaacattgg aactaagagt gtccactggt accagcagag gccaggccag    120
gcccctctac tggtcctcta tcatgacacc aggcggccct caaggattcc tgagcgattc    180
tctggctcca actctggaaa cacggccacc ctgaccatca gcagggtcga agccggggat    240
gaggccgact attactgtca ggtgtgggat agtcgaaggg tg                      282
```

<210> SEQ ID NO 228
<211> LENGTH: 94
<212> TYPE: PRT
<213> ORGANISM: Homo Sapiens

<400> SEQUENCE: 228

Leu Cys Ala Asp Ser Ala Thr Leu Ser Val Ser Gly Pro Arg Arg Asp
1               5                   10                  15

Gly Gln His Ser Cys Gly Gly Asn Asn Ile Gly Thr Lys Ser Val His
            20                  25                  30

Trp Tyr Gln Gln Arg Pro Gly Gln Ala Pro Leu Leu Val Leu Tyr His
        35                  40                  45

Asp Thr Arg Arg Pro Ser Arg Ile Pro Glu Arg Phe Ser Gly Ser Asn
    50                  55                  60

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Ser Arg Arg Val
                85                  90

<210> SEQ ID NO 229
<211> LENGTH: 354
<212> TYPE: DNA
<213> ORGANISM: Homo Sapiens

<400> SEQUENCE: 229

```
caggtgcagc tgttggagtc aggggggaggc ttggtccagc cggggggtc cctgagactc    60
tcctgtgcag cctctggatt cagctttggc gactattgga tgagttgggt ccgccaggct    120
ccagggaagg gcctggagtg ggtggccgac ataaagccag atggcagtga caaagactat    180
gtggactctg tgaagggccg attcaccatc tccagagaca acgccaagaa ctcactgtat    240
ctgcaaatga gcagcctgcg aggcgaagac acggctgtct attattgtgc gagagactat    300
gtcgtcgtcg caccatctca accccaaac attcaccctg aatacttcca gaac          354
```

<210> SEQ ID NO 230
<211> LENGTH: 118
<212> TYPE: PRT
<213> ORGANISM: Homo Sapiens

<400> SEQUENCE: 230

Gln Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Gly Asp Tyr
            20                  25                  30

Trp Met Ser Trp Val Arg Gln Ala Pro Gly Lys Gly Leu Glu Trp Val
            35                  40                  45

Ala Asp Ile Lys Pro Asp Gly Ser Asp Lys Asp Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Gly Glu Asp Thr Ala Val Tyr Tyr Cys
                85                  90                  95

Ala Arg Asp Tyr Val Val Val Ala Pro Ser Gln Pro Pro Asn Ile His
            100                 105                 110

Pro Glu Tyr Phe Gln Asn
        115

<210> SEQ ID NO 231
<211> LENGTH: 1356
<212> TYPE: DNA
<213> ORGANISM: Homo Sapiens

<400> SEQUENCE: 231
gaggtacagc tggaggagtc tggcgcagga ctgttgaagc cttcggagac cctgtccctc      60
acctgcgctg tctatggtgg gtccttcagt ggatactact ggagttggat ccgccaggcc     120
ccagggaagg gactggagtg gattggggaa atcgatcata gtggaaccac caactacaac     180
ccgtccctca gagtcgggt caccatatca gtagagacat ccaagaacca gttctccctg     240
aggctgagct ctgtgaccgc cgcggactcg gctgtctatt actgtgcgag cagtggatat     300
tgttctcatg gtttatgccc ccaagaggac tggggccagg gaaccctggt caccgtctcc     360
tcagcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt ccccccaaaa cccaaggaca cctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccgtccag ccccatcga gaaaaccatc    1020
tccaaagcca aagggcagcc ccgagaacca caggtgtaca ccctgccccc atcccgggag    1080
gagatgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaatga                              1356

<210> SEQ ID NO 232
<211> LENGTH: 451
<212> TYPE: PRT
<213> ORGANISM: Homo Sapiens

<400> SEQUENCE: 232

```
Glu Val Gln Leu Glu Glu Ser Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ala Pro Gly Lys Gly Leu Glu Trp Ile
        35                  40                  45

Gly Glu Ile Asp His Ser Gly Thr Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Arg Leu Ser Ser Val Thr Ala Ala Asp Ser Ala Val Tyr Tyr Cys Ala
                85                  90                  95

Ser Ser Gly Tyr Cys Ser His Gly Leu Cys Pro Gln Glu Asp Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Val Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

```
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 233
<211> LENGTH: 20
<212> TYPE: DNA
<213> ORGANISM: Homo Sapiens

<400> SEQUENCE: 233
ggttcgctta ttggggccaa                                               20

<210> SEQ ID NO 234
<211> LENGTH: 20
<212> TYPE: DNA
<213> ORGANISM: Homo Sapiens

<400> SEQUENCE: 234
cggtgtcttc gggtctcagg                                               20

<210> SEQ ID NO 235
<211> LENGTH: 20
<212> TYPE: DNA
<213> ORGANISM: Homo Sapiens

<400> SEQUENCE: 235
ggagggcagt gtagtctgag                                               20

<210> SEQ ID NO 236
<211> LENGTH: 29
<212> TYPE: DNA
<213> ORGANISM: Homo Sapiens

<400> SEQUENCE: 236
cctctacaaa tgtggtatgg ctgattatg                                     29

<210> SEQ ID NO 237
<211> LENGTH: 20
<212> TYPE: DNA
<213> ORGANISM: Homo Sapiens

<400> SEQUENCE: 237
gggaacggtg cattggaacg                                               20

<210> SEQ ID NO 238
<211> LENGTH: 98
<212> TYPE: DNA
<213> ORGANISM: Homo Sapiens
<220> FEATURE:
<221> NAME/KEY: misc_feature
<222> LOCATION: (78)..(78)
<223> OTHER INFORMATION: H = A or C or T
<220> FEATURE:
<221> NAME/KEY: misc_feature
<222> LOCATION: (79)..(79)
<223> OTHER INFORMATION: R = A or G
<220> FEATURE:
<221> NAME/KEY: misc_feature
<222> LOCATION: (81)..(81)
<223> OTHER INFORMATION: Y = C or T
<220> FEATURE:
<221> NAME/KEY: misc_feature
```

```
<222> LOCATION: (82)..(82)
<223> OTHER INFORMATION: S = C or G
<220> FEATURE:
<221> NAME/KEY: misc_feature
<222> LOCATION: (83)..(83)
<223> OTHER INFORMATION: W = A or T
<220> FEATURE:
<221> NAME/KEY: misc_feature
<222> LOCATION: (85)..(85)
<223> OTHER INFORMATION: H = A or C or T
<220> FEATURE:
<221> NAME/KEY: misc_feature
<222> LOCATION: (90)..(90)
<223> OTHER INFORMATION: B = C or G or T

<400> SEQUENCE: 238
cccaagcttg ccgccaccat gggatggagc tgtatcatcc tcttcttggt agcaacagct      60
acaggtgtcc actccgahrt yswghtgacb cagtctcc                              98

<210> SEQ ID NO 239
<211> LENGTH: 39
<212> TYPE: DNA
<213> ORGANISM: Homo Sapiens

<400> SEQUENCE: 239
cccgaattct catgaagatt ctgtaggggc cactgtctt                             39

<210> SEQ ID NO 240
<211> LENGTH: 20
<212> TYPE: DNA
<213> ORGANISM: Homo Sapiens

<400> SEQUENCE: 240
acgccgtcca cgtaccaatt                                                  20

<210> SEQ ID NO 241
<211> LENGTH: 20
<212> TYPE: DNA
<213> ORGANISM: Homo Sapiens

<400> SEQUENCE: 241
aagcccttca ccagacaggt                                                  20

<210> SEQ ID NO 242
<211> LENGTH: 18
<212> TYPE: DNA
<213> ORGANISM: Homo Sapiens

<400> SEQUENCE: 242
tggtggacgt gtcccacg                                                    18

<210> SEQ ID NO 243
<211> LENGTH: 18
<212> TYPE: DNA
<213> ORGANISM: Homo Sapiens

<400> SEQUENCE: 243
ggaagggccc ttggtgga                                                    18

<210> SEQ ID NO 244
<211> LENGTH: 18
<212> TYPE: DNA
<213> ORGANISM: Homo Sapiens

<400> SEQUENCE: 244
```
accgtggccg ctccttcc                                                  18

<210> SEQ ID NO 245
<211> LENGTH: 18
<212> TYPE: DNA
<213> ORGANISM: Homo Sapiens

<400> SEQUENCE: 245
tgcagggcgt tgtccacc                                                  18

<210> SEQ ID NO 246
<211> LENGTH: 18
<212> TYPE: DNA
<213> ORGANISM: Homo Sapiens

<400> SEQUENCE: 246
aggccgctcc ctccgtga                                                  18

<210> SEQ ID NO 247
<211> LENGTH: 19
<212> TYPE: DNA
<213> ORGANISM: Homo Sapiens

<400> SEQUENCE: 247
ttcacagggg aggagtcag                                                 19

<210> SEQ ID NO 248
<211> LENGTH: 645
<212> TYPE: DNA
<213> ORGANISM: Homo Sapiens

<400> SEQUENCE: 248
tcctatgtgc tgactcagcc accctcggtg tcggtgtccc caggacagac ggccaggatc    60
acctgctctg gagatgcatt gccaaagcaa tatacttatt ggtaccagca gaagccaggc   120
caggcccctg tggtggtgat ctataaagac agtgagaggc cctcaggat ccctgagcga    180
ttctctggct ccagctcagg gacaacagtc acggtgacca tcagtggagt ccaggcagaa   240
gacgaggctg actattattg tcaatcagca gacagcagtg gtacttccct ggtgttcggc   300
ggagggacca agctgaccgt cctaggtcag cccaaggctg ccccctcggt cactctgttc   360
ccgccctcct ctgaggagct tcaagccaac aaggccacac tggtgtgtct cataagtgac   420
ttctacccgg gagccgtgac agtggcctgg aaggcagata gcagcccgt caaggcggga    480
gtggagacca ccacccctc caaacaaagc aacaacaagt acgcggccag cagctacctg    540
agcctgacgc ctgagcagtg gaagtcccac aaaagctaca gctgccaggt cacgcatgaa   600
gggagcaccg tggagaagac agtggcccct acagaatctt catag                   645

<210> SEQ ID NO 249
<211> LENGTH: 214
<212> TYPE: PRT
<213> ORGANISM: Homo Sapiens

<400> SEQUENCE: 249

Ser Tyr Val Leu Thr Gln Pro Pro Ser Val Ser Val Ser Pro Gly Gln
1               5                   10                  15

Thr Ala Arg Ile Thr Cys Ser Gly Asp Ala Leu Pro Lys Gln Tyr Thr
            20                  25                  30

Tyr Trp Tyr Gln Gln Lys Pro Gly Gln Ala Pro Val Val Val Ile Tyr
        35                  40                  45

Lys Asp Ser Glu Arg Pro Ser Gly Ile Pro Glu Arg Phe Ser Gly Ser
        50                  55                  60

Ser Ser Gly Thr Thr Val Thr Val Thr Ile Ser Gly Val Gln Ala Glu
 65                  70                  75                  80

Asp Glu Ala Asp Tyr Tyr Cys Gln Ser Ala Asp Ser Ser Gly Thr Ser
                85                  90                  95

Leu Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Ser Ser
        210

<210> SEQ ID NO 250
<211> LENGTH: 1362
<212> TYPE: DNA
<213> ORGANISM: Homo Sapiens

<400> SEQUENCE: 250
gaggtgcagc tggtggagtc tgggggaggc ttggtccagc ctggggggtc cctgagactc     60
tcctgttcag cctctggttt cacctttagt agttattgga tgagctgggt ccgccaggct    120
ccagggaagg ggctggagtg gtcgccaac ataatacaag atggaagtga aaatactat     180 gcggactctg tgaagggccg gctcaccatc tccagagaca cgccaagaa ctcactatat     240 ctgcagatga acagcctgag agtcgacgac acggctgtgt attattgtgc gagaggatat    300
gaggggtgta gtgcaaccag gtgctacctg tactactttg actattgggg cccggggacc    360
ctggtcaccg tctcctcagc ctccaccaag ggcccatcgg tcttccccct ggcaccctcc    420
tccaagagca cctctggggg cacagcggcc ctgggctgcc tggtcaagga ctacttcccc    480
gaaccggtga cggtgtcgtg gaactcaggc gccctgacca gcggcgtgca caccttcccg    540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagagag ttgagcccaa atctggtccc ccatgcccac cttgcccagc acctgaactc    720
ctggggggac cgtcagtctt cctgttcccc ccaaaaccca aggacaccct catgatctcc    780
cggacccctg aggtcacatg cgtggtggtg gacgtgagcc acgaagaccc tgaggtcaag    840
ttcaactggt acgtggacgg cgtggaggtg cataatgcca agacaaagcc gcggaggag    900 cagtacaaca gcacgtaccg tgtggtcagg gtcctcaccg tcctgcacca ggactggctg    960
aatggcaagg agtacaagtg caaggtctcc aacaaagccc tcccggcccc catcgagaaa   1020
accatctcca agccaaaagg gcagccccga gaaccacagg tgtacaccct gcccccatcc   1080
cgggaggaga tgaccaagaa ccaggtcagc ctgacctgcc tggtcaaagg cttctatccc   1140

-continued

```
agcgacatcg ccgtggagtg ggagagcaat gggcagccgg aggacaacta caagaccacg    1200
cctcccgtgc tggactccga cggctccttc ttcctctata gcaagctcac cgtggacaag    1260
agcaggtggc agcaggggaa cgtcttctca tgctccgtga tgcatgaggc tctgcacaac    1320
cactacacgc agaagagcct ctccctgtct ctgggtaaat ga                       1362
```

<210> SEQ ID NO 251
<211> LENGTH: 453
<212> TYPE: PRT
<213> ORGANISM: Homo Sapiens

<400> SEQUENCE: 251

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Ile Gln Asp Gly Ser Glu Lys Tyr Tyr Ala Asp Ser Val
    50                  55                  60

Lys Gly Arg Leu Thr Ile Ser Arg Asp Asn Ala Lys Asn Ser Leu Tyr
65                  70                  75                  80

Leu Gln Met Asn Ser Leu Arg Val Asp Asp Thr Ala Val Tyr Tyr Cys
                85                  90                  95

Ala Arg Gly Tyr Glu Gly Cys Ser Ala Thr Arg Cys Tyr Leu Tyr Tyr
            100                 105                 110

Phe Asp Tyr Trp Gly Pro Gly Thr Leu Val Thr Val Ser Ser Ala Ser
        115                 120                 125

Thr Lys Gly Pro Ser Val Phe Pro Leu Ala Pro Ser Ser Lys Ser Thr
130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Gly Pro Pro Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Arg Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

```
Pro Ile Glu Lys Thr Ile Ser Lys Ala Lys Gly Gln Pro Arg Glu Pro
                340                 345                 350
Gln Val Tyr Thr Leu Pro Pro Ser Arg Glu Glu Met Thr Lys Asn Gln
            355                 360                 365
Val Ser Leu Thr Cys Leu Val Lys Gly Phe Tyr Pro Ser Asp Ile Ala
        370                 375                 380
Val Glu Trp Glu Ser Asn Gly Gln Pro Glu Asn Tyr Lys Thr Thr
385                 390                 395                 400
Pro Pro Val Leu Asp Ser Asp Gly Ser Phe Phe Leu Tyr Ser Lys Leu
                405                 410                 415
Thr Val Asp Lys Ser Arg Trp Gln Gln Gly Asn Val Phe Ser Cys Ser
            420                 425                 430
Val Met His Glu Ala Leu His Asn His Tyr Thr Gln Lys Ser Leu Ser
        435                 440                 445
Leu Ser Leu Gly Lys
    450
```

```
<210> SEQ ID NO 252
<211> LENGTH: 75
<212> TYPE: DNA
<213> ORGANISM: Homo Sapiens

<400> SEQUENCE: 252
caggtgcagc tgttggagtc agggggaggc ttggtccagc cggggggggtc cctgagactc    60 tcctgtgcag cctct                                                    75

<210> SEQ ID NO 253
<211> LENGTH: 30
<212> TYPE: DNA
<213> ORGANISM: Homo Sapiens

<400> SEQUENCE: 253
ggattcagct ttggcgacta ttggatgagt                                    30

<210> SEQ ID NO 254
<211> LENGTH: 18
<212> TYPE: DNA
<213> ORGANISM: Homo Sapiens

<400> SEQUENCE: 254
tgggtccgcc aggctcca                                                 18

<210> SEQ ID NO 255
<211> LENGTH: 75
<212> TYPE: DNA
<213> ORGANISM: Homo Sapiens

<400> SEQUENCE: 255
gggaagggcc tggagtgggt ggccgacata aagccagatg gcagtgacaa agactatgtg    60
gactctgtga agggc                                                    75

<210> SEQ ID NO 256
<211> LENGTH: 96
<212> TYPE: DNA
<213> ORGANISM: Homo Sapiens

<400> SEQUENCE: 256
cgattcacca tctccagaga caacgccaag aactcactgt atctgcaaat gagcagcctg    60
cgaggcgaag acacggctgt ctattattgt gcgaga                             96
```

<210> SEQ ID NO 257
<211> LENGTH: 60
<212> TYPE: DNA
<213> ORGANISM: Homo Sapiens

<400> SEQUENCE: 257
gactatgtcg tcgtcgcacc atctcaaccc ccaaacattc accctgaata cttccagaac    60

<210> SEQ ID NO 258
<211> LENGTH: 63
<212> TYPE: DNA
<213> ORGANISM: Homo Sapiens

<400> SEQUENCE: 258
ctatgtgctg actcagccac cctcagtgtc agtgccccca ggagagacgg ccagcattcc    60
tgt                                                                  63

<210> SEQ ID NO 259
<211> LENGTH: 33
<212> TYPE: DNA
<213> ORGANISM: Homo Sapiens

<400> SEQUENCE: 259
gggggaaaca acattggaac taagagtgtc cac                                 33

<210> SEQ ID NO 260
<211> LENGTH: 45
<212> TYPE: DNA
<213> ORGANISM: Homo Sapiens

<400> SEQUENCE: 260
tggtaccagc agaggccagg ccaggcccct ctactggtcc tctat                    45

<210> SEQ ID NO 261
<211> LENGTH: 21
<212> TYPE: DNA
<213> ORGANISM: Homo Sapiens

<400> SEQUENCE: 261
catgacacca ggcggccctc a                                              21

<210> SEQ ID NO 262
<211> LENGTH: 99
<212> TYPE: DNA
<213> ORGANISM: Homo Sapiens

<400> SEQUENCE: 262
tcaaggattc ctgagcgatt ctctggctcc aactctggaa acacggccac cctgaccatc    60
agcagggtcg aagccgggga tgaggccgac tattactgt                           99

<210> SEQ ID NO 263
<211> LENGTH: 24
<212> TYPE: DNA
<213> ORGANISM: Homo Sapiens

<400> SEQUENCE: 263
caggtgtggg atagtcgaag ggtg                                           24

<210> SEQ ID NO 264
<211> LENGTH: 97
<212> TYPE: DNA

```
<213> ORGANISM: Homo Sapiens
<220> FEATURE:
<221> NAME/KEY: misc_feature
<222> LOCATION: (76)..(76)
<223> OTHER INFORMATION: S = C or G
<220> FEATURE:
<221> NAME/KEY: misc_feature
<222> LOCATION: (81)..(81)
<223> OTHER INFORMATION: R = A or G
<220> FEATURE:
<221> NAME/KEY: misc_feature
<222> LOCATION: (88)..(88)
<223> OTHER INFORMATION: B = C or G or T
<220> FEATURE:
<221> NAME/KEY: misc_feature
<222> LOCATION: (89)..(89)
<223> OTHER INFORMATION: W = A or T
<220> FEATURE:
<221> NAME/KEY: misc_feature
<222> LOCATION: (91)..(91)
<223> OTHER INFORMATION: S = C or G
<220> FEATURE:
<221> NAME/KEY: misc_feature
<222> LOCATION: (96)..(96)
<223> OTHER INFORMATION: D = A or G or T

<400> SEQUENCE: 264
cccaagcttg ccgccaccat gggatggagc tgtatcatcc tcttcttggt agcaacagct      60
acaggtgtcc actccsaggt rcagctgbwg sagtcdg                               97

<210> SEQ ID NO 265
<211> LENGTH: 40
<212> TYPE: DNA
<213> ORGANISM: Homo Sapiens

<400> SEQUENCE: 265
cccgaattct catttacccg gagacaggga gaggctcttc                            40
```